US009738720B2

(12) United States Patent
Bodyak et al.

(10) Patent No.: US 9,738,720 B2
(45) Date of Patent: Aug. 22, 2017

(54) MONOCLONAL ANTIBODIES AGAINST HER2 EPITOPE AND METHODS OF USE THEREOF

(71) Applicant: Mersana Therapeutics, Inc., Cambridge, MA (US)

(72) Inventors: Natalya D. Bodyak, Brookline, MA (US); Michael J. DeVit, Sudbury, MA (US); Eric M. Krauland, Lebanon, NH (US); Timothy B. Lowinger, Carlisle, MA (US); Peter U. Park, Somerville, MA (US); Bianka Prinz, Lebanon, NH (US); Aleksandr V. Yurkovetskiy, Littleton, MA (US)

(73) Assignee: Mersana Therapeutics, Inc., Cambridge, MA (US)

( * ) Notice: Subject to any disclaimer, the term of this patent is extended or adjusted under 35 U.S.C. 154(b) by 0 days.

(21) Appl. No.: 15/344,012

(22) Filed: Nov. 4, 2016

(65) Prior Publication Data

US 2017/0066830 A1 Mar. 9, 2017

Related U.S. Application Data

(62) Division of application No. 14/742,947, filed on Jun. 18, 2015, now Pat. No. 9,555,112.

(60) Provisional application No. 62/013,944, filed on Jun. 18, 2014, provisional application No. 62/034,489, filed on Aug. 7, 2014, provisional application No. 62/147,960, filed on Apr. 15, 2015, provisional application No. 62/149,444, filed on Apr. 17, 2015.

(51) Int. Cl.
| | |
|---|---|
| *A61K 39/00* | (2006.01) |
| *A61K 39/395* | (2006.01) |
| *C07K 16/28* | (2006.01) |
| *C07K 16/32* | (2006.01) |
| *C07K 16/30* | (2006.01) |
| *A61K 47/48* | (2006.01) |
| *A61K 38/08* | (2006.01) |
| *A61K 45/06* | (2006.01) |

(52) U.S. Cl.
CPC .......... *C07K 16/2863* (2013.01); *A61K 38/08* (2013.01); *A61K 45/06* (2013.01); *A61K 47/48384* (2013.01); *A61K 47/48569* (2013.01); *A61K 47/48584* (2013.01); *A61K 47/48692* (2013.01); *C07K 16/30* (2013.01); *C07K 16/32* (2013.01); *A61K 2039/505* (2013.01); *A61K 2039/507* (2013.01); *C07K 2317/21* (2013.01); *C07K 2317/33* (2013.01); *C07K 2317/34* (2013.01); *C07K 2317/565* (2013.01); *C07K 2317/732* (2013.01); *C07K 2317/76* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | |
|---|---|---|
| 8,652,474 B2 | 2/2014 | Harris et al. |
| 8,685,383 B2 | 4/2014 | Yurkovetskiy et al. |
| 8,808,679 B2 | 8/2014 | Yurkovetskiy et al. |
| 8,815,226 B2 | 8/2014 | Yurkovetskiy et al. |
| 8,821,850 B2 | 9/2014 | Yurkovetskiy et al. |
| 9,144,615 B2 | 9/2015 | Yurkovetskiy et al. |
| 2012/0321583 A1 | 12/2012 | Yurkovetskiy et al. |
| 2013/0101546 A1 | 4/2013 | Yurkovetskiy et al. |
| 2013/0195845 A1 | 8/2013 | Fendly et al. |
| 2014/0044704 A1 | 2/2014 | Paton et al. |
| 2014/0086940 A1 | 3/2014 | Bryant |
| 2014/0134127 A1 | 5/2014 | Yurkovetskiy et al. |
| 2014/0186343 A1 | 7/2014 | Harris et al. |
| 2014/0186867 A1 | 7/2014 | Harris et al. |
| 2015/0064130 A1 | 3/2015 | Yurkovetskiy et al. |
| 2015/0104407 A1 | 4/2015 | Yurkovetskiy et al. |
| 2015/0125474 A1 | 5/2015 | Smith et al. |
| 2015/0306240 A1 | 10/2015 | Yurkovetskiy et al. |
| 2015/0314008 A1 | 11/2015 | Yurkovetskiy et al. |
| 2015/0366982 A1 | 12/2015 | Bodyak et al. |

FOREIGN PATENT DOCUMENTS

| | | |
|---|---|---|
| WO | WO 2014200891 A1 | 12/2014 |
| WO | WO 2015104373 A2 | 7/2015 |
| WO | WO 2015104385 A2 | 7/2015 |
| WO | WO 2015115091 A1 | 8/2015 |
| WO | WO 2015155976 A1 | 10/2015 |
| WO | WO 2015162293 A1 | 10/2015 |
| WO | WO 2015164665 A1 | 10/2015 |

OTHER PUBLICATIONS

Aviles et al., MI130004, a New Antibody-Drug Conjugate, Induces Strong, Long-Lasting Antitumor Effect in HER2 Expressing Breast Tumor Models. Annual Meeting of the American Association of Cancer Research, Philadelphia, PA Apr. 18 to Apr. 22, 2015. Abstract 2480.

Bergstrom et al., Potent Promise. Innovations in Pharmaceutical Technology (2014) 49: 16-20.

(Continued)

*Primary Examiner* — Laura B Goddard

(74) *Attorney, Agent, or Firm* — Cooley LLP; Heidi A. Erlacher; Jennifer A. Karmakis

(57) ABSTRACT

This invention provides fully human monoclonal antibodies that recognize HER2. The invention further provides methods of using such monoclonal antibodies in a variety of therapeutic, diagnostic, and prophylactic indications.

30 Claims, 23 Drawing Sheets

(56) References Cited

OTHER PUBLICATIONS

Bergstrom et al., A novel, highly potent HER2-targeted antibody-drug conjugate (ADC) for the treatment of low HER2-expressing tumors and combination with trastuzumab-based regimens in HER2-driven tumors. Annual Meeting of the American Association of Cancer Research, Philadelphia, PA Apr. 18 to Apr. 22, 2015. Abstract #LBA-231.
Bergstrom et al., XMT-1522 induces tumor regressions in pre-clinical models representing HER2-positive and HER2 low-expressing breast cancer. The San Antonio Breast Cancer Symposium, San Antonio, TX, Dec. 8-12, 2015. Abstract # P4-14-28.
Birtalan et al., The functional capacity of the natural amino acids for molecular Recognition. Mol. BioSyst., 2010, 6: 1186-1194.
Bodyak et al., Trastuzumab-dolaflexin, a Highly Potent Fleximer-based Antibody-Drug Conjugate, Demonstrates a Favorable Therapeutic Index in Exploratory Toxicology Studies in Multiple Species. Annual Meeting of the American Association of Cancer Research, Philadelphia, PA Apr. 18 to Apr. 22, 2015. Abstract #641.
Cheng et al., Construction, expression and characterization of the engineered antibody against tumor surface antigen, $p185^{c-erbB-2}$. Cell Research, 2003; 13(1):35-48.
Cho et al., Structure of the extracellular region of HER2 alone and in complex with the Herceptin Fab. Nature, 2003, vol. 421, 756-760.
Fisher et al., Structure of the Complex between HER2 and an Antibody Paratope Formed by Side Chains from Tryptophan and Serine. J. Mol. Biol., (2010) 402, 217-229.
Franklin et al., Insights into ErbB signaling from the structure of the ErbB2-pertuzumab complex. Cancer Cell, 2004, vol. 5, 317-328.
Gianolio et al., Targeting HER2-positive cancer with dolastatin 15 derivatives conjugated to trastuzumab, novel antibody—drug conjugates. Cancer Chemother Pharmacol (2012) 70:439-449.
Goeij et al., HER2 monoclonal antibodies that do not interfere with receptor heterodimerization-mediated signaling induce effective internalization and represent valuable components for rational antibody-drug conjugate design. mAbs, 2014, 6:2, 1-11.
Humphreys et al., Site-specific conjugation of ARX788, an Antibody Drug Conjugate (ADC) targeting HER2, generates a potent and stable targeted therapeutic for multiple cancers. Annual Meeting of the American Association of Cancer Research, Philadelphia, PA Apr. 18 to Apr. 22, 2015.
Jost et al., Structural Basis for Eliciting a Cytotoxic Effect in HER2-Overexpressing Cancer Cells via Binding to the Extracellular Domain of HER2. Structure (2013) 21, 1979-1991.
Klapper et al., A subclass of tumor-inhibitory monoclonal antibodies to ErbB-2/HER2 blocks crosstalk with growth factor receptors. Oncogene, 1997, 14, 2099-2109.
Ko et al., Combination of novel HER2-targeting antibody 1E11 with trastuzumab shows synergistic antitumor activity in HER2-positive gastric cancer. Molecular Oncology, 2015, vol. 9, pp. 398-408.
Lewis Phillips et al., "Targeting HER2-Positive Breast Cancer with Trastuzumab-DM1,an Antibody—Cytotoxic Drug Conjugate." Cancer Research, Nov. 15, 2008, 68:9280-9290.
Li et al., Structural basis for inhibition of the epidermal growth factor receptor by cetuximab. Cancer Cell, 2005, vol. 7, 301-311.
LoRusso et al., Trastuzumab Emtansine: A Unique Antibody-Drug Conjugate in Development for Human Epidermal Growth Factor Receptor 2-Positive Cancer. Clin Cancer Res 2011;17:6437-6447. Published online Oct. 14, 2011.
Palanki et al.; "Development of novel linkers to conjugate pharmacophores to a carrier antibody", Bioorganic & Medicinal Chemistry Letters, vol. 22, No. 13, 2012, pp. 4249-4253.
Smith, et al., ASN004, a Novel 5T4-Targeted Dolaflexin® ADC for the Treatment of Various Cancers. $5^{th}$ World ADC, San Diego, CA, Oct. 27-29, 2014.
Smith, et al., ASN004, a Novel 5T4-Targeted Dolaflexin™ Antibody Drug Conjugate, Causes Complete Regression in Multiple Solid Tumor Models. Annual Meeting of the American Association of Cancer Research, Philadelphia, PA Apr. 18 to Apr. 22, 2015. Abstract #1693.
Spiridon et al., Targeting Multiple Her-2 Epitopes with Monoclonal Antibodies Results in Improved Antigrowth Activity of a Human Breast Cancer Cell Line in Vitro and in Vivo. Clinical Cancer Research 2002, vol. 8, 1720-1730.
Van Der Lee et al., The preclinical profile of the duocarmycin-based HER2-targeting ADC SYD985 predicts for clinical benefit in low HER2-expressing breast cancers. Annual Meeting of the American Association of Cancer Research, Philadelphia, PA Apr. 18 to Apr. 22, 2015. Abstract #5360.
Yip et al., Anti-ErbB-2 monoclonal antibodies and ErbB-2-directed vaccines. Cancer Immunol immunother, 2002, 50: 569-587.
Yurkovetskiy et al., Advantages of polyacetal polymer-based ADCs: Application to low expression targets. Annual Meeting of the American Association of Cancer Research, San Diego, CA Apr. 5 to Apr. 9, 2014. Abstract #2645.
Yurkovetskiy et al.; "Fully Degradable Hydrophilic Polyals for Protein Modification", Biomacromolecules, vol. 6, No. 5, 2005, pp. 2648-2658.
Yurkovetskiy et al., A Polymer-based Antibody-Vinca Drug Conjugate Platform: Characterization and Preclinical Efficacy. Cancer Research, 75(16) OF1-OF8, 2015 (published on-line on Jun. 25, 2015).
Zhou et al., Structural Insights into the Down-regulation of Overexpressed $p185^{her2/neu}$ Protein of Transformed Cells by the Antibody chA21. J. Biol. Chem. 2011, 286:31676-31683.

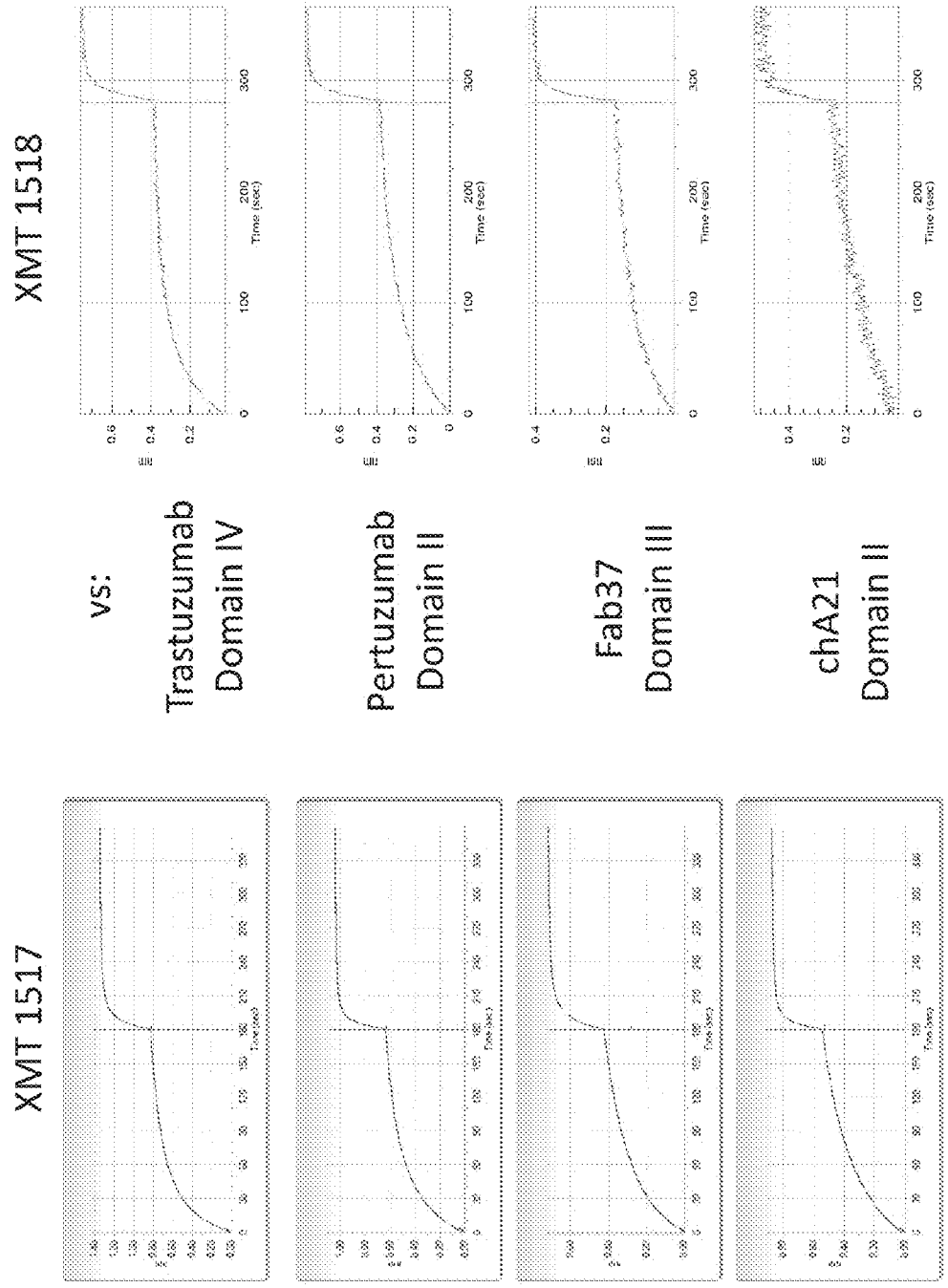

Figure 1b
vs:
Trastuzumab Domain IV
Pertuzumab Domain II
Fab37 Domain III
chA21 Domain I
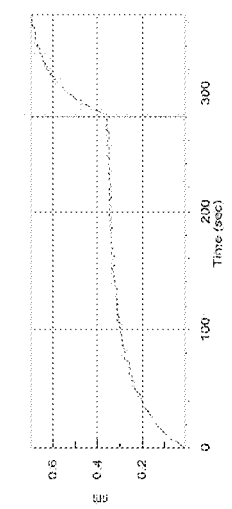
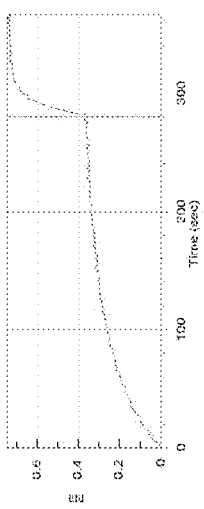
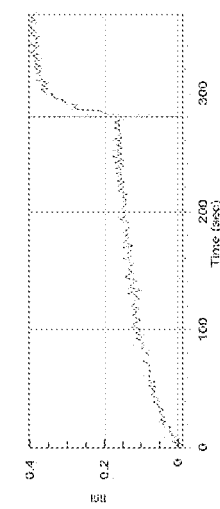
XMT 1520
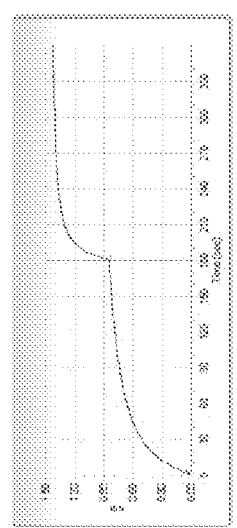
XMT 1519

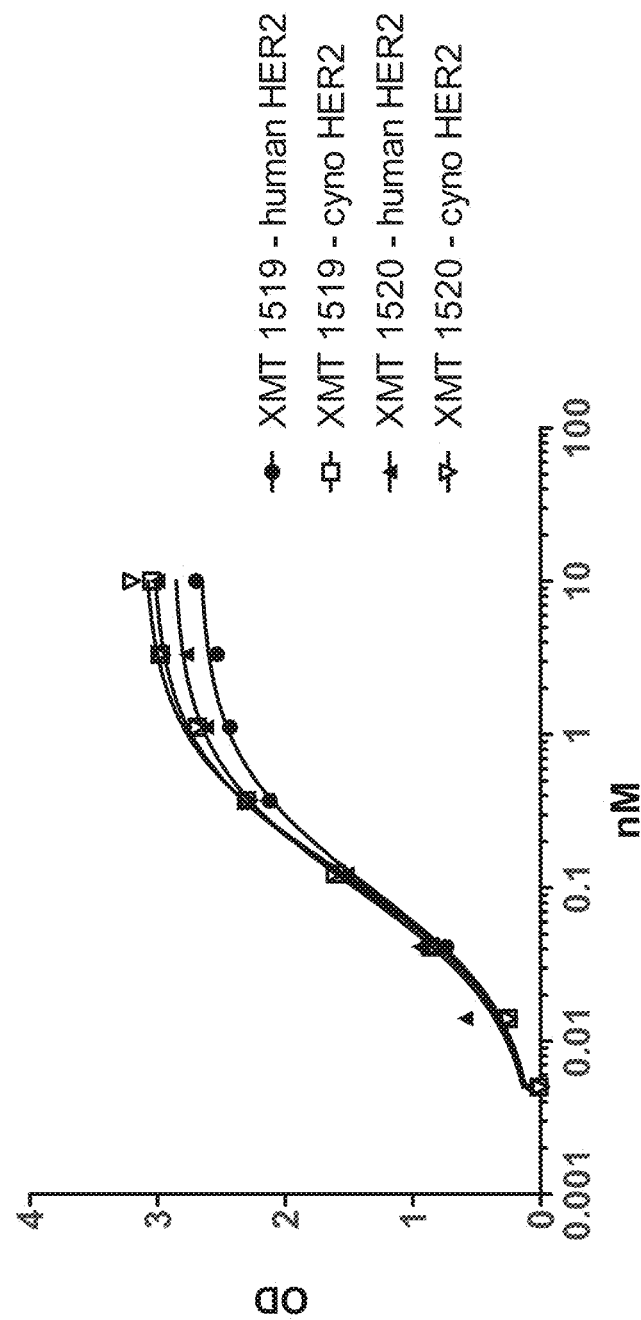

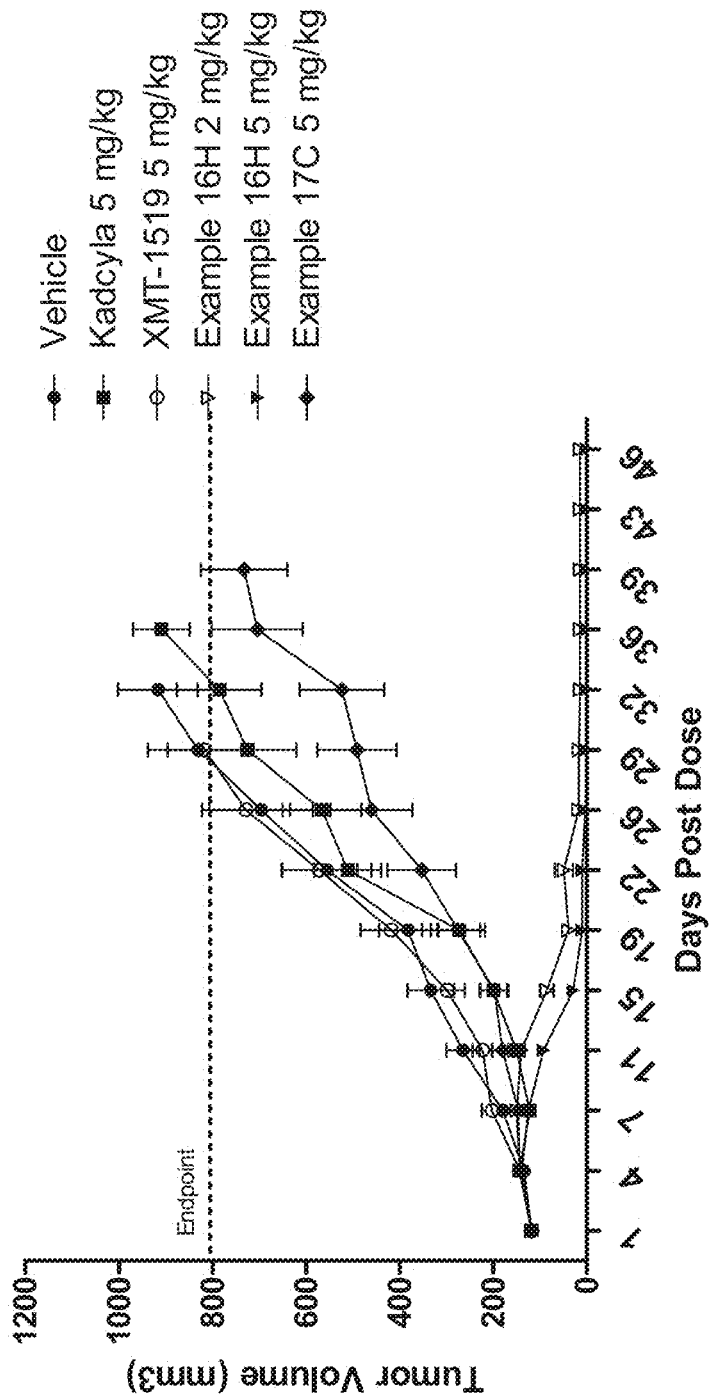

SEQUENCE LISTING

```
<160> NUMBER OF SEQ ID NOS: 47

<210> SEQ ID NO 1
<211> LENGTH: 450
<212> TYPE: PRT
<213> ORGANISM: Artificial Sequence
<220> FEATURE:
<223> OTHER INFORMATION: Synthetic polypeptide

<400> SEQUENCE: 1

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Ala Pro Tyr Tyr Ala Lys Asp Tyr Met Asp Val Trp Gly
            100                 105                 110

Lys Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160
```

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly
    450

<210> SEQ ID NO 2
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 2

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asp
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

```
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Val Ser Tyr Trp
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 3
<211> LENGTH: 450
<212> TYPE: PRT
<213> ORGANISM: Artificial Sequence
<220> FEATURE:
<223> OTHER INFORMATION: Synthetic polypeptide

<400> SEQUENCE: 3

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Gly Ile Trp Trp Asp Gly Ser Asn Glu Lys Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                 90                  95

Ala Lys Glu Ala Pro Tyr Tyr Ala Lys Asp Tyr Met Asp Val Trp Gly
            100                 105                 110

Lys Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205
```

```
Lys Pro Ser Asn Thr Lys Val Asp Lys Lys Val Glu Pro Lys Ser Cys
            210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
            245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
            275                 280                 285
His Asn Ala Lys Thr Lys Pro Arg Glu Glu Gln Tyr Asn Ser Thr Tyr
            290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
            325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
            355                 360                 365
Leu Thr Cys Leu Val Lys Gly Phe Tyr Pro Ser Asp Ile Ala Val Glu
370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
            405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
            435                 440                 445
Pro Gly
    450

<210> SEQ ID NO 4
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 4

Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Asp
            20                  25                  30
Tyr Leu Ala Trp Tyr Gln Gln Lys Pro Gly Gln Ala Pro Arg Leu Leu
            35                  40                  45
Ile Tyr Gly Ala Ser Arg Arg Ala Thr Gly Ile Pro Asp Arg Phe Ser
            50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Val Ser Tyr Trp
            85                  90                  95
Thr Phe Gly Gly Gly Thr Lys Val Glu Ile Lys Arg Thr Val Ala Ala
            100                 105                 110
```

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 5
<211> LENGTH: 446
<212> TYPE: PRT
<213> ORGANISM: Artificial Sequence
<220> FEATURE:
<223> OTHER INFORMATION: Synthetic polypeptide

<400> SEQUENCE: 5

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly His Gly Tyr Phe Asp Leu Trp Gly Arg Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255
```

```
Pro Glu Val Thr Cys Val Val Asp Val Ser His Glu Asp Pro Glu
        260                 265                 270

Val Lys Phe Asn Trp Tyr Val Asp Gly Val Glu Val His Asn Ala Lys
    275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly
            435                 440                 445

<210> SEQ ID NO 6
<211> LENGTH: 215
<212> TYPE: PRT
<213> ORGANISM: Artificial Sequence
<220> FEATURE:
<223> OTHER INFORMATION: Synthetic polypeptide

<400> SEQUENCE: 6

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr His His Ser Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175
```

-continued

```
Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 7
<211> LENGTH: 446
<212> TYPE: PRT
<213> ORGANISM: Artificial Sequence
<220> FEATURE:
<223> OTHER INFORMATION: Synthetic polypeptide

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Arg
            20                  25                  30

Ser Met Asn Trp Val Arg Gln Ala Pro Gly Lys Gly Leu Glu Trp Val
        35                  40                  45

Ser Tyr Ile Ser Ser Asp Ser Arg Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly His Gly Tyr Phe Asp Leu Trp Gly Arg Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320
```

```
Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 8
<211> LENGTH: 215
<212> TYPE: PRT
<213> ORGANISM: Artificial Sequence
<220> FEATURE:
<223> OTHER INFORMATION: Synthetic polypeptide

<400> SEQUENCE: 8

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr His His Ser Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 9
```

```
<211> LENGTH: 121
<212> TYPE: PRT
<213> ORGANISM: Artificial Sequence
<220> FEATURE:
<223> OTHER INFORMATION: Synthetic polypeptide

<400> SEQUENCE: 9

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Glu Ala Pro Tyr Tyr Ala Lys Asp Tyr Met Asp Val Trp Gly
            100                 105                 110

Lys Gly Thr Thr Val Thr Val Ser Ser
        115                 120

<210> SEQ ID NO 10
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 10

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Asp
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Val Ser Tyr Trp
                85                  90                  95

Thr Phe Gly Gly Gly Thr Lys Val Glu Ile Lys
            100                 105

<210> SEQ ID NO 11
<211> LENGTH: 121
<212> TYPE: PRT
<213> ORGANISM: Artificial Sequence
<220> FEATURE:
<223> OTHER INFORMATION: Synthetic polypeptide

<400> SEQUENCE: 11

Gln Val Gln Leu Val Glu Ser Gly Gly Gly Val Val Gln Pro Gly Arg
 1               5                  10                  15

Ser Leu Arg Leu Ser Cys Ala Ser Gly Phe Thr Phe Ser Ser Tyr
            20                  25                  30
```

Gly Met His Trp Val Arg Gln Ala Pro Gly Lys Gly Leu Glu Trp Val
            35                  40                  45

Ala Gly Ile Trp Trp Asp Gly Ser Asn Glu Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Glu Ala Pro Tyr Tyr Ala Lys Asp Tyr Met Asp Val Trp Gly
            100                 105                 110

Lys Gly Thr Thr Val Thr Val Ser Ser
            115                 120

<210> SEQ ID NO 12
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 12

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Asp
            20                  25                  30

Tyr Leu Ala Trp Tyr Gln Gln Lys Pro Gly Gln Ala Pro Arg Leu Leu
        35                  40                  45

Ile Tyr Gly Ala Ser Arg Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Val Ser Tyr Trp
                 85                  90                  95

Thr Phe Gly Gly Gly Thr Lys Val Glu Ile Lys
            100                 105

<210> SEQ ID NO 13
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 13

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
            35                  40                  45

Ser Tyr Ile Ser Ser Ser Ser Ser Thr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly His Gly Tyr Phe Asp Leu Trp Gly Arg Gly Thr Leu
            100                 105                 110

Val Thr Val Ser Ser
        115

<210> SEQ ID NO 14
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 14

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr His His Ser Pro
                85                  90                  95

Leu Thr Phe Gly Gly Gly Thr Lys Val Glu Ile Lys
            100                 105

<210> SEQ ID NO 15
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Arg
            20                  25                  30

Ser Met Asn Trp Val Arg Gln Ala Pro Gly Lys Gly Leu Glu Trp Val
        35                  40                  45

Ser Tyr Ile Ser Ser Asp Ser Arg Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly His Gly Tyr Phe Asp Leu Trp Gly Arg Gly Thr Leu
            100                 105                 110

Val Thr Val Ser Ser
        115

<210> SEQ ID NO 16
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 16

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr His His Ser Pro
                85                  90                  95

Leu Thr Phe Gly Gly Gly Thr Lys Val Glu Ile Lys
                100                 105
```

<210> SEQ ID NO 17
<211> LENGTH: 9
<212> TYPE: PRT
<213> ORGANISM: Artificial Sequence
<220> FEATURE:
<223> OTHER INFORMATION: Synthetic oligopeptide

<400> SEQUENCE: 17

```
Phe Thr Phe Ser Ser Tyr Gly Met His
1               5
```

<210> SEQ ID NO 18
<211> LENGTH: 17
<212> TYPE: PRT
<213> ORGANISM: Artificial Sequence
<220> FEATURE:
<223> OTHER INFORMATION: Synthetic oligopeptide

<400> SEQUENCE: 18

```
Val Ile Trp Tyr Asp Gly Ser Asn Lys Tyr Tyr Ala Asp Ser Val Lys
1               5                   10                  15

Gly
```

<210> SEQ ID NO 19
<211> LENGTH: 12
<212> TYPE: PRT
<213> ORGANISM: Artificial Sequence
<220> FEATURE:
<223> OTHER INFORMATION: Synthetic oligopeptide

<400> SEQUENCE: 19

```
Glu Ala Pro Tyr Tyr Ala Lys Asp Tyr Met Asp Val
1               5                   10
```

<210> SEQ ID NO 20
<211> LENGTH: 12
<212> TYPE: PRT
<213> ORGANISM: Artificial Sequence
<220> FEATURE:
<223> OTHER INFORMATION: Synthetic oligopeptide

<400> SEQUENCE: 20

```
Arg Ala Ser Gln Ser Val Ser Ser Asp Tyr Leu Ala
1               5                   10
```

<210> SEQ ID NO 21
<211> LENGTH: 7
<212> TYPE: PRT

```
<213> ORGANISM: Artificial Sequence
<220> FEATURE:
<223> OTHER INFORMATION: Synthetic oligopeptide

<400> SEQUENCE: 21

Gly Ala Ser Ser Arg Ala Thr
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic oligopeptide

<400> SEQUENCE: 22

Gln Gln Tyr Val Ser Tyr Trp Thr
1               5

<210> SEQ ID NO 23
<211> LENGTH: 17
<212> TYPE: PRT
<213> ORGANISM: Artificial Sequence
<220> FEATURE:
<223> OTHER INFORMATION: Synthetic oligopeptide

<400> SEQUENCE: 23

Gly Ile Trp Trp Asp Gly Ser Asn Glu Lys Tyr Ala Asp Ser Val Lys
1               5                   10                  15

Gly

<210> SEQ ID NO 24
<211> LENGTH: 7
<212> TYPE: PRT
<213> ORGANISM: Artificial Sequence
<220> FEATURE:
<223> OTHER INFORMATION: Synthetic oligopeptide

<400> SEQUENCE: 24

Gly Ala Ser Arg Arg Ala Thr
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic oligopeptide

<400> SEQUENCE: 25

Phe Thr Phe Ser Ser Tyr Ser Met Asn
1               5

<210> SEQ ID NO 26
<211> LENGTH: 17
<212> TYPE: PRT
<213> ORGANISM: Artificial Sequence
<220> FEATURE:
<223> OTHER INFORMATION: Synthetic oligopeptide

<400> SEQUENCE: 26

Tyr Ile Ser Ser Ser Ser Ser Thr Ile Tyr Tyr Ala Asp Ser Val Lys
1               5                   10                  15

Gly
```

```
<210> SEQ ID NO 27
<211> LENGTH: 8
<212> TYPE: PRT
<213> ORGANISM: Artificial Sequence
<220> FEATURE:
<223> OTHER INFORMATION: Synthetic oligopeptide

<400> SEQUENCE: 27

Gly Gly His Gly Tyr Phe Asp Leu
1               5

<210> SEQ ID NO 28
<211> LENGTH: 12
<212> TYPE: PRT
<213> ORGANISM: Artificial Sequence
<220> FEATURE:
<223> OTHER INFORMATION: Synthetic oligopeptide

<400> SEQUENCE: 28

Arg Ala Ser Gln Ser Val Ser Ser Ser Tyr Leu Ala
1               5                   10

<210> SEQ ID NO 29
<211> LENGTH: 9
<212> TYPE: PRT
<213> ORGANISM: Artificial Sequence
<220> FEATURE:
<223> OTHER INFORMATION: Synthetic oligopeptide

<400> SEQUENCE: 29

Gln Gln Tyr His His Ser Pro Leu Thr
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic oligopeptide

<400> SEQUENCE: 30

Phe Thr Phe Ser Gly Arg Ser Met Asn
1               5

<210> SEQ ID NO 31
<211> LENGTH: 17
<212> TYPE: PRT
<213> ORGANISM: Artificial Sequence
<220> FEATURE:
<223> OTHER INFORMATION: Synthetic oligopeptide

<400> SEQUENCE: 31

Tyr Ile Ser Ser Asp Ser Arg Thr Ile Tyr Tyr Ala Asp Ser Val Lys
1               5                   10                  15

Gly

<210> SEQ ID NO 32
<211> LENGTH: 329
<212> TYPE: PRT
<213> ORGANISM: Homo sapiens

<400> SEQUENCE: 32

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 33
<211> LENGTH: 107
<212> TYPE: PRT
<213> ORGANISM: Homo sapiens

<400> SEQUENCE: 33

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
```

```
                 65                  70                  75                  80
Lys His Lys Val Tyr Ala Cys Glu Val Thr His Gln Gly Leu Ser Ser
                85                  90                  95
Pro Val Thr Lys Ser Phe Asn Arg Gly Glu Cys
               100                 105
```

<210> SEQ ID NO 34
<211> LENGTH: 363
<212> TYPE: DNA
<213> ORGANISM: Artificial Sequence
<220> FEATURE:
<223> OTHER INFORMATION: Synthetic polynucleotide

<400> SEQUENCE: 34

| | | | | | |
|---|---|---|---|---|---|
| caggtgcagc | tggtggagtc | tgggggaggc | gtggtccagc | ctgggaggtc | cctgagactc | 60 |
| tcctgtgcag | cgtctggatt | caccttcagt | agctatggca | tgcactgggt | ccgccaggct | 120 |
| ccaggcaagg | ggctggagtg | ggtggcagtt | atatggtatg | atggaagtaa | taaatactat | 180 |
| gcagactccg | tgaagggccg | attcaccatc | tccagagaca | attccaagaa | cacgctgtat | 240 |
| ctgcaaatga | acagcctgag | agccgaggac | acggcggtgt | actactgcgc | caaggaagct | 300 |
| ccctactacg | ctaaagatta | catggacgta | tggggcaagg | gtacaactgt | caccgtctcc | 360 |
| tca | | | | | | 363 |

<210> SEQ ID NO 35
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 35

| | | | | | |
|---|---|---|---|---|---|
| gaaattgtgt | tgacgcagtc | tccaggcacc | ctgtctttgt | ctccagggga | aagagccacc | 60 |
| ctctcctgca | gggccagtca | gagtgttagc | agcgactact | tagcctggta | ccagcagaaa | 120 |
| cctggccagg | ctcccaggct | cctcatctat | ggtgcatcca | gcagggccac | tggcatccca | 180 |
| gacaggttca | gtggcagtgg | gtctgggaca | gacttcactc | tcaccatcag | cagactggag | 240 |
| cctgaagatt | ttgcagtgta | ttactgtcag | cagtacgtca | gttactggac | ttttggcgga | 300 |
| gggaccaagg | ttgagatcaa | a | | | | 321 |

<210> SEQ ID NO 36
<211> LENGTH: 351
<212> TYPE: DNA
<213> ORGANISM: Artificial Sequence
<220> FEATURE:
<223> OTHER INFORMATION: Synthetic polynucleotide

<400> SEQUENCE: 36

| | | | | | |
|---|---|---|---|---|---|
| gaggtgcagc | tggtggagtc | tgggggaggc | ttggtacagc | ctgggggtc  | cctgagactc | 60 |
| tcctgtgcag | cctctggatt | caccttcagt | agctatagca | tgaactgggt | ccgccaggct | 120 |
| ccagggaagg | ggctggagtg | ggtttcatac | attagtagta | gtagtagtac | catatactac | 180 |
| gcagactctg | tgaagggccg | attcaccatc | tccagagaca | atgccaagaa | ctcactgtat | 240 |
| ctgcaaatga | acagcctgag | agctgaggac | acggcggtgt | actactgcgc | cagaggtgga | 300 |
| cacggatatt | tcgacctatg | ggggagaggt | accttggtca | ccgtctcctc | a | 351 |

<210> SEQ ID NO 37
<211> LENGTH: 324

```
<212> TYPE: DNA
<213> ORGANISM: Artificial Sequence
<220> FEATURE:
<223> OTHER INFORMATION: Synthetic polynucleotide

<400> SEQUENCE: 37
gaaattgtgt tgacgcagtc tccaggcacc ctgtctttgt ctccagggga aagagccacc     60
ctctcctgca gggccagtca gagtgttagc agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtaccacc acagtcctct cacttttggc    300
ggagggacca aggttgagat caaa                                           324

<210> SEQ ID NO 38
<211> LENGTH: 1255
<212> TYPE: PRT
<213> ORGANISM: Homo sapiens

<400> SEQUENCE: 38

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
```

```
                    275                 280                 285
Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
                340                 345                 350

Val Arg Ala Val Thr Ser Ala Asn Ile Gln Glu Phe Ala Gly Cys Lys
            355                 360                 365

Lys Ile Phe Gly Ser Leu Ala Phe Leu Pro Glu Ser Phe Asp Gly Asp
        370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
                420                 425                 430

Gly Arg Ile Leu His Asn Gly Ala Tyr Ser Leu Thr Leu Gln Gly Leu
            435                 440                 445

Gly Ile Ser Trp Leu Gly Leu Arg Ser Leu Arg Glu Leu Gly Ser Gly
        450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
                500                 505                 510

Gln Leu Cys Ala Arg Gly His Cys Trp Gly Pro Gly Pro Thr Gln Cys
            515                 520                 525

Val Asn Cys Ser Gln Phe Leu Arg Gly Gln Glu Cys Val Glu Glu Cys
        530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
                580                 585                 590

Pro Pro Phe Cys Val Ala Arg Cys Pro Ser Gly Val Lys Pro Asp Leu
            595                 600                 605

Ser Tyr Met Pro Ile Trp Lys Phe Pro Asp Glu Glu Gly Ala Cys Gln
        610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Leu Gly Val Val Phe Gly
                660                 665                 670

Ile Leu Ile Lys Arg Arg Gln Gln Lys Ile Arg Lys Tyr Thr Met Arg
            675                 680                 685

Arg Leu Leu Gln Glu Thr Glu Leu Val Glu Pro Leu Thr Pro Ser Gly
        690                 695                 700
```

-continued

```
Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
    850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
    930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
        995                 1000                1005

Leu Glu Asp Asp Asp Met Gly Asp Leu Val Asp Ala Glu Glu Tyr
    1010                1015                1020

Leu Val Pro Gln Gln Gly Phe Phe Cys Pro Asp Pro Ala Pro Gly
    1025                1030                1035

Ala Gly Gly Met Val His His Arg His Arg Ser Ser Ser Thr Arg
    1040                1045                1050

Ser Gly Gly Gly Asp Leu Thr Leu Gly Leu Glu Pro Ser Glu Glu
    1055                1060                1065

Glu Ala Pro Arg Ser Pro Leu Ala Pro Ser Glu Gly Ala Gly Ser
    1070                1075                1080

Asp Val Phe Asp Gly Asp Leu Gly Met Gly Ala Ala Lys Gly Leu
    1085                1090                1095

Gln Ser Leu Pro Thr His Asp Pro Ser Pro Leu Gln Arg Tyr Ser
    1100                1105                1110
```

-continued

```
Glu Asp Pro Thr Val Pro Leu Pro Ser Glu Thr Asp Gly Tyr Val
    1115                1120                1125

Ala Pro Leu Thr Cys Ser Pro Gln Pro Glu Tyr Val Asn Gln Pro
    1130                1135                1140

Asp Val Arg Pro Gln Pro Pro Ser Pro Arg Glu Gly Pro Leu Pro
    1145                1150                1155

Ala Ala Arg Pro Ala Gly Ala Thr Leu Glu Arg Pro Lys Thr Leu
    1160                1165                1170

Ser Pro Gly Lys Asn Gly Val Val Lys Asp Val Phe Ala Phe Gly
    1175                1180                1185

Gly Ala Val Glu Asn Pro Glu Tyr Leu Thr Pro Gln Gly Gly Ala
    1190                1195                1200

Ala Pro Gln Pro His Pro Pro Pro Ala Phe Ser Pro Ala Phe Asp
    1205                1210                1215

Asn Leu Tyr Tyr Trp Asp Gln Asp Pro Pro Glu Arg Gly Ala Pro
    1220                1225                1230

Pro Ser Thr Phe Lys Gly Thr Pro Thr Ala Glu Asn Pro Glu Tyr
    1235                1240                1245

Leu Gly Leu Asp Val Pro Val
    1250                1255

<210> SEQ ID NO 39
<211> LENGTH: 630
<212> TYPE: PRT
<213> ORGANISM: Homo sapiens

<400> SEQUENCE: 39

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
                20                  25                  30

Val Val Gln Gly Asn Leu Glu Leu Thr Tyr Leu Pro Thr Asn Ala Ser
            35                  40                  45

Leu Ser Phe Leu Gln Asp Ile Gln Glu Val Gln Gly Tyr Val Leu Ile
        50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
    130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
            180                 185                 190

Leu Thr Arg Thr Val Cys Ala Gly Gly Cys Ala Arg Cys Lys Gly Pro
        195                 200                 205

Leu Pro Thr Asp Cys Cys His Glu Gln Cys Ala Ala Gly Cys Thr Gly
    210                 215                 220
```

```
Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
            245                 250                 255

Phe Glu Ser Met Pro Asn Pro Glu Gly Arg Tyr Thr Phe Gly Ala Ser
            260                 265                 270

Cys Val Thr Ala Cys Pro Tyr Asn Tyr Leu Ser Thr Asp Val Gly Ser
            275                 280                 285

Cys Thr Leu Val Cys Pro Leu His Asn Gln Glu Val Thr Ala Glu Asp
            290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
                325                 330                 335

Ala Asn Ile Gln Glu Phe Ala Gly Cys Lys Lys Ile Phe Gly Ser Leu
            340                 345                 350

Ala Phe Leu Pro Glu Ser Phe Asp Gly Asp Pro Ala Ser Asn Thr Ala
            355                 360                 365

Pro Leu Gln Pro Glu Gln Leu Gln Val Phe Glu Thr Leu Glu Glu Ile
370                 375                 380

Thr Gly Tyr Leu Tyr Ile Ser Ala Trp Pro Asp Ser Leu Pro Asp Leu
385                 390                 395                 400

Ser Val Phe Gln Asn Leu Gln Val Ile Arg Gly Arg Ile Leu His Asn
            405                 410                 415

Gly Ala Tyr Ser Leu Thr Leu Gln Gly Leu Gly Ile Ser Trp Leu Gly
            420                 425                 430

Leu Arg Ser Leu Arg Glu Leu Gly Ser Gly Leu Ala Leu Ile His His
            435                 440                 445

Asn Thr His Leu Cys Phe Val His Thr Val Pro Trp Asp Gln Leu Phe
450                 455                 460

Arg Asn Pro His Gln Ala Leu Leu His Thr Ala Asn Arg Pro Glu Asp
465                 470                 475                 480

Glu Cys Val Gly Glu Gly Leu Ala Cys His Gln Leu Cys Ala Arg Gly
            485                 490                 495

His Cys Trp Gly Pro Gly Pro Thr Gln Cys Val Asn Cys Ser Gln Phe
            500                 505                 510

Leu Arg Gly Gln Glu Cys Val Glu Glu Cys Arg Val Leu Gln Gly Leu
            515                 520                 525

Pro Arg Glu Tyr Val Asn Ala Arg His Cys Leu Pro Cys His Pro Glu
530                 535                 540

Cys Gln Pro Gln Asn Gly Ser Val Thr Cys Phe Gly Pro Glu Ala Asp
545                 550                 555                 560

Gln Cys Val Ala Cys Ala His Tyr Lys Asp Pro Pro Phe Cys Val Ala
            565                 570                 575

Arg Cys Pro Ser Gly Val Lys Pro Asp Leu Ser Tyr Met Pro Ile Trp
            580                 585                 590

Lys Phe Pro Asp Glu Glu Gly Ala Cys Gln Pro Cys Pro Ile Asn Cys
            595                 600                 605

Thr His Ser Cys Val Asp Leu Asp Asp Lys Gly Cys Pro Ala Glu Gln
            610                 615                 620

Arg Ala Ser Pro Leu Thr
625                 630
```

<210> SEQ ID NO 40
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 40

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 41
<211> LENGTH: 449
<212> TYPE: PRT
<213> ORGANISM: Artificial Sequence
<220> FEATURE:
<223> OTHER INFORMATION: Synthetic polypeptide

<400> SEQUENCE: 41

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

Ser Arg Trp Gly Gly Asp Gly Phe Tyr Ala Met Asp Tyr Trp Gly Gln
            100                 105                 110

Gly Thr Leu Val Thr Val Ser Ala Ser Thr Lys Gly Pro Ser Val
    115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 42
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 42

-continued

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 43
<211> LENGTH: 448
<212> TYPE: PRT
<213> ORGANISM: Artificial Sequence
<220> FEATURE:
<223> OTHER INFORMATION: Synthetic polypeptide

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 44
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Ile Trp Trp Ser
                20                  25                  30

Trp Ile His Trp Val Arg Gln Ala Pro Gly Lys Gly Leu Glu Trp Val
            35                  40                  45

Ala Ser Ile Ser Pro Ser Ser Gly Trp Thr Ser Tyr Ala Asp Ser Val
        50                  55                  60

```
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Trp Trp Ser Ser Ala Met Asp Tyr Trp Gly Gln Gly Thr Leu
            100                 105                 110

Val Thr Val Ser Ser
            115

<210> SEQ ID NO 45
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 45

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Val Ser Ser Ala
             20                  25                  30

Val Ala Trp Tyr Gln Gln Lys Pro Gly Lys Ala Pro Lys Leu Leu Ile
         35                  40                  45

Tyr Ser Ala Ser Ser Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Trp Trp Trp Trp Pro Ser
                 85                  90                  95

Thr Phe Gly Gln Gly Thr Lys Val Glu Ile Lys
            100                 105

<210> SEQ ID NO 46
<211> LENGTH: 120
<212> TYPE: PRT
<213> ORGANISM: Artificial Sequence
<220> FEATURE:
<223> OTHER INFORMATION: Synthetic polypeptide

<400> SEQUENCE: 46

Glu Val Gln Leu Gln Gln Ser Gly Pro Glu Val Val Lys Thr Gly Ala
 1               5                  10                  15

Ser Val Lys Ile Ser Cys Lys Ala Ser Gly Tyr Ser Phe Thr Gly Tyr
             20                  25                  30

Phe Ile Asn Trp Val Lys Lys Asn Ser Gly Lys Ser Pro Glu Trp Ile
         35                  40                  45

Gly His Ile Ser Ser Ser Tyr Ala Thr Ser Thr Tyr Asn Gln Lys Phe
 50                  55                  60

Lys Asn Lys Ala Ala Phe Thr Val Asp Thr Ser Ser Ser Thr Ala Phe
 65                  70                  75                  80

Met Gln Leu Asn Ser Leu Thr Ser Glu Asp Ser Ala Val Tyr Tyr Cys
                 85                  90                  95

Val Arg Ser Gly Asn Tyr Glu Glu Tyr Ala Met Asp Tyr Trp Gly Gln
            100                 105                 110

Gly Thr Ser Val Thr Val Ser Ser
            115                 120

<210> SEQ ID NO 47
```

-continued

```
<211> LENGTH: 113
<212> TYPE: PRT
<213> ORGANISM: Artificial Sequence
<220> FEATURE:
<223> OTHER INFORMATION: Synthetic polypeptide

<400> SEQUENCE: 47

Asp Ile Val Leu Thr Gln Thr Pro Ser Ser Leu Pro Val Ser Val Gly
1               5                   10                  15

Glu Lys Val Thr Met Thr Cys Lys Ser Ser Gln Thr Leu Leu Tyr Ser
            20                  25                  30

Asn Asn Gln Lys Asn Tyr Leu Ala Trp Tyr Gln Gln Lys Pro Gly Gln
        35                  40                  45

Ser Pro Lys Leu Leu Ile Ser Trp Ala Phe Thr Arg Lys Ser Gly Val
    50                  55                  60

Pro Asp Arg Phe Thr Gly Ser Gly Ser Gly Thr Asp Phe Thr Leu Thr
65                  70                  75                  80

Ile Gly Ser Val Lys Ala Glu Asp Leu Ala Val Tyr Tyr Cys Gln Gln
                85                  90                  95

Tyr Ser Asn Tyr Pro Trp Thr Phe Gly Gly Gly Thr Arg Leu Glu Ile
                100                 105                 110

Lys
```

MONOCLONAL ANTIBODIES AGAINST HER2 EPITOPE AND METHODS OF USE THEREOF

RELATED APPLICATIONS

This application is a divisional application of U.S. application Ser. No. 14/742,947, filed Jun. 18, 2015, which claims priority to, and the benefit of, U.S. provisional application Nos. 62/013,944, filed Jun. 18, 2014; 62/034,489, filed Aug. 7, 2014; 62/147,960, filed Apr. 15, 2015; and 62/149,444, filed Apr. 17, 2015, under 35 USC §119(e). The contents of each of these applications are hereby incorporated by reference in their entireties.

INCORPORATION OF SEQUENCE LISTING

The contents of the text file named "MRSN-012001US_SeqList_ST25.txt", which was created on Aug. 19, 2015 and is 73 KB in size, are hereby incorporated by reference in their entireties.

FIELD OF THE INVENTION

This invention relates generally to the generation of monoclonal antibodies that recognize human HER2 receptor, to monoclonal antibodies that recognize specific HER2 epitopes within the extracellular domain of the human HER2 receptor, and to methods of using these monoclonal antibodies as therapeutics and/or diagnostics.

BACKGROUND OF THE INVENTION

Members of the ErbB family of receptor tyrosine kinases are important mediators of cell growth, differentiation and survival. The receptor family includes four distinct members, including epidermal growth factor receptor (EGFR or ErbB1), HER2 (ErbB2 or p185$^{neu}$), HER3 (ErbB3) and HER4 (ErbB4 or tyro2). Both homo- and heterodimers are formed by the four members of the EGFR family, with HER2 being the preferred and most potent dimerization partner for other ErbB receptors (Graus-Porta et al., Embo 3 1997; 16:1647-1655; Tao et al., J Cell Sci 2008; 121:3207-3217). HER2 has no known ligand, but can be activated via homodimerization when overexpressed, or by heterodimerization with other, ligand occupied ErbB receptors.

The HER2 gene (also known as HER2/neu and ErbB2 gene) is amplified in 20-30% of early-stage breast cancers, which makes it overexpress epidermal growth factor (EGF) receptors in the cell membrane (Bange, et al., Nature Medicine 7 (5): 548-552). Besides breast cancer, HER2 expression has also been associated with other human carcinoma types, including non-small cell lung cancer, ovarian cancer, gastric cancer, prostate cancer, bladder cancer, colon cancer, esophageal cancer and squamous cell carcinoma of the head & neck (Garcia de Palazzo et al., Int J Biol Markers 1993; 8:233-239; Ross et al., Oncologist 2003; 8:307-325; Osman et al., J Urol 2005; 174:2174-2177; Kapitanovic et al., Gastroenterology 1997; 112:1103-1113; Turken et al., Neoplasma 2003; 50:257-261; and Oshima et al., Int J Biol Markers 2001; 16:250-254).

Trastuzumab (Herceptin®) is a recombinant, humanized monoclonal antibody directed against domain IV of the HER2 protein, thereby blocking ligand-independent HER2 homodimerization, and to a lesser extend heterodimerization of HER2 with other family members in cells with high HER2 overexpression (Cho et al., Nature 2003; 421:756-760 and Wehrman et al., Proc Natl Acad Sci USA 2006; 103: 19063-19068). Herceptin® has been approved both for first-line and adjuvant treatment of HER2 overexpressing metastatic breast cancer, either in combination with chemotherapy, or as a single agent following one or more chemotherapy regimens. Trastuzumab has been found to be effective only in 20-50% of HER2 overexpressing breast tumor patients and many of the initial responders show relapse after a few months (Dinh et al., Clin Adv Hematol Oncol 2007; 5:707-717).

Pertuzumab (Omnitar/Perjeta® also called 2C4) is another humanized monoclonal antibody directed against domain II of the HER2 protein, resulting in inhibition of ligand-induced heterodimerization (i.e., HER2 dimerizing with another member of the ErbB family to which a ligand has bound); a mechanism reported to not strictly require high HER2 expression levels (Franklin et al., Cancer Cell 2004; 5:317-328.). Pertuzumab is approved for the treatment of HER2-positive metastatic breast cancer, in combination with trastuzumab and docetaxel.

A HER2 antibody drug conjugate (ADC), Trastuzumab emtansine (ado-trastuzumab emtansine, Kadcyla®) is an antibody-drug conjugate consisting of the monoclonal antibody trastuzumab (Herceptin) linked to the cytotoxic agent mertansine (DM1). Kadcyla as a single agent, has been approved for the treatment of patients with HER2-positive (HER2+), metastatic breast cancer (MBC) who previously received trastuzumab and a taxane, separately or in combination.

While many factors are involved in selecting a suitable antibody for HER2 targeted therapy, it is typically an advantage for an ADC approach if the HER2-antibody complex efficiently internalizes upon antibody binding. As compared to EGFR, however, internalization of HER2 is impaired.

The complex mechanisms regulating the function of HER2 warrant further research on new and optimized therapeutic strategies against this proto-oncogene.

Accordingly, there exists a need for therapies that target the biological activities of HER2.

SUMMARY OF THE INVENTION

The present invention provides monoclonal antibodies that specifically recognize HER2, also known as (ErbB2, p185$^{neu}$, and/or HER2/neu). The antibodies disclosed herein are capable of and useful in modulating, e.g., blocking, inhibiting, reducing, antagonizing, neutralizing or otherwise interfering with PI3K-Akt pathway which promotes cell survival by reducing levels of phosphorylated AKT. The antibodies disclosed herein are also capable of and useful in modulating, e.g., blocking, inhibiting, reducing, antagonizing, neutralizing or otherwise interfering with ligand-independent homodimerization and/or heterodimerization of HER2. Antibodies disclosed herein also include antibodies that bind soluble HER2.

The antibodies of the present invention exhibit HER2 binding characteristics that differ from antibodies described in the art. Particularly, the antibodies disclosed herein bind to a different epitopes of HER2, in that they cross-block each other but not trastuzumab, pertuzumab, Fab37 or chA21 from binding to HER2. Further, as opposed to the known antibodies, the antibodies disclosed herein can internalize efficiently into HER2-expressing cells without promoting cell proliferation.

The antibodies disclosed herein are fully human monoclonal antibodies that bind to novel epitopes and/or have other favorable properties for therapeutic use. Exemplary properties include, but are not limited to, favorable binding characteristics to cancer cells expressing human HER2 at high or low levels, specific binding to recombinant human and cynomolgus monkey HER2, efficient internalization upon binding to HER2, high capacity for killing cancer cells expressing high or low levels of HER2 when administered as an antibody drug conjugate (ADC), no substantial agonistic effect on the proliferation of HER2-expressing cancer cells, and provide for effective antibody-dependent cellular cytotoxicity (ADCC)-mediated killing of HER2-expressing cells, as well as any combination of the foregoing properties.

The antibodies disclosed herein also include an isolated antibody or antigen binding fragment thereof that specifically binds to an epitope of the human HER2 receptor that includes residues 452 to 531 of the extracellular domain of the human HER2 receptor, for example, residues 474 to 553 of SEQ ID NO: 38 or residues 452 to 531 of SEQ ID NO: 39.

The antibodies disclosed herein include an isolated antibody or an antigen binding fragment thereof that binds at least a portion of the N-terminus of domain IV of human HER2 receptor but does not cross-compete with an antibody that binds to epitope 4D5 of the human HER2 receptor. For example, the antibodies or antigen binding fragments thereof described herein do not cross-compete with trastuzumab for binding to the human HER2 receptor, as trastuzumab is known to bind epitope 4D5 of the human HER2 receptor. As used herein, the term epitope 4D5 of the human HER2 receptor refers to amino acid residues 529 to 627 of the extracellular domain of the human HER2 receptor, for example residues 551 to 649 of SEQ ID NO: 38 or residues 529 to 627 of SEQ ID NO: 39. In some embodiments, the isolated antibody or antigen binding fragment thereof also binds at least one epitope on cynomolgus monkey HER2 receptor.

The antibodies disclosed herein also include an isolated antibody or antigen binding fragment thereof that specifically binds to an epitope of the human HER2 receptor that includes residues 452 to 500 of the extracellular domain of the human HER2 receptor, for example, residues 474 to 522 of SEQ ID NO: 38 or residues 452 to 500 of SEQ ID NO: 39.

The antibodies disclosed herein also include an isolated antibody or antigen binding fragment thereof that specifically binds to an epitope of the human HER2 receptor that includes at least one of amino acid residue selected from the group consisting of amino acid residues E521, L525 and R530 of the extracellular domain of the human HER2 receptor, e.g., residues 543, 547, and 552 of SEQ ID NO: 38, and residues 521, 525, and 530 of SEQ ID NO: 39. For example, the antibodies disclosed herein include an isolated antibody or antigen binding fragment thereof that specifically binds to an epitope of the extracellular domain of the human HER2 receptor that includes at least two amino acid residues selected from the group consisting of amino acid residues E521, L525 and R530 of the extracellular domain of the human HER2 receptor. The antibodies disclosed herein also include an isolated antibody or antigen binding fragment thereof that specifically binds to an epitope of the human HER2 receptor that includes at least amino acid residues E521, L525 and R530 of the extracellular domain of the human HER2 receptor. In some embodiments, any or all of these isolated antibodies or antigen binding fragments thereof also bind at least one epitope on cynomolgus monkey HER2 receptor.

The antibodies disclosed herein also include an isolated antibody or an antigen binding fragment thereof that binds to at least a portion of domain III and at least a portion of the N-terminus of domain IV of human HER2 receptor but does not cross-compete with Fab37 monoclonal antibody or an antibody that binds to epitope 4D5 of the human HER2 receptor. For example, the antibodies or antigen binding fragments thereof described herein do not cross-compete with the Fab37 monoclonal antibody and/or trastuzumab for binding to the human HER2 receptor. In some embodiments, the isolated antibody or antigen binding fragment thereof also binds at least one epitope on cynomolgus monkey HER2 receptor.

The antibodies disclosed herein also include an isolated antibody or antigen binding fragment thereof that specifically binds to an epitope of the human HER2 receptor that includes residues 520 to 531 of the extracellular domain of the human HER2 receptor, for example, residues 542 to 553 of SEQ ID NO: 38 or residues 520 to 531 of SEQ ID NO: 39.

The antibodies disclosed herein also include an isolated antibody or antigen binding fragment thereof that specifically binds to an epitope of the human HER2 receptor that includes at least one amino acid residue selected from the group consisting of residues C453, H456, H473, N476, R495, G496, H497 and W499 of the extracellular domain of the human HER2 receptor, e.g., residues 475, 478, 495, 498, 517, 518, 519, and 521 of SEQ ID NO: 38 or residues 453, 456, 473, 476, 495, 496, 497 and 499 of SEQ ID NO: 39. For example, the antibodies disclosed herein include an isolated antibody or antigen binding fragment thereof that specifically binds to an epitope of the extracellular domain of the human HER2 receptor that includes at least two amino acid residues selected from the group consisting of amino acid residues C453, H456, H473, N476, R495, G496, H497 and W499 of the extracellular domain of the human HER2 receptor. For example, the antibodies disclosed herein include an isolated antibody or antigen binding fragment thereof that specifically binds to an epitope of the extracellular domain of the human HER2 receptor that includes at least three amino acid residues selected from the group consisting of amino acid residues C453, H456, H473, N476, R495, G496, H497 and W499 of the extracellular domain of the human HER2 receptor. For example, the antibodies disclosed herein include an isolated antibody or antigen binding fragment thereof that specifically binds to an epitope of the extracellular domain of the human HER2 receptor that includes at least four amino acid residues selected from the group consisting of amino acid residues C453, H456, H473, N476, R495, G496, H497 and W499 of the extracellular domain of the human HER2 receptor. For example, the antibodies disclosed herein include an isolated antibody or antigen binding fragment thereof that specifically binds to an epitope of the extracellular domain of the human HER2 receptor that includes at least five amino acid residues selected from the group consisting of amino acid residues C453, H456, H473, N476, R495, G496, H497 and W499 of the extracellular domain of the human HER2 receptor. For example, the antibodies disclosed herein include an isolated antibody or antigen binding fragment thereof that specifically binds to an epitope of the extracellular domain of the human HER2 receptor that includes at least six amino acid residues selected from the group consisting of amino acid residues C453, H456, H473, N476, R495, G496, H497 and W499 of the extracellular domain of the human HER2 receptor. For example, the antibodies disclosed herein include an isolated antibody or antigen binding fragment thereof that specifically binds to an epitope of the extracellular domain of the human HER2 receptor that includes at least amino acid residues C453, H456, H473, N476, R495, G496, H497 and W499 of the extracellular domain of the human HER2 receptor. In some embodiments, any or all of these isolated antibodies or antigen binding fragments thereof also bind at least one epitope on cynomolgus monkey HER2 receptor.

The antibodies disclosed herein also include an isolated antibody or antigen binding fragment thereof that specifically binds to an epitope of the human HER2 receptor that includes at least one amino acid residue selected from the group consisting of residues C453, H473, N476, R495, H497 and W499 of the extracellular domain of the human HER2 receptor, e.g., residues 475, 495, 498, 517, 519, and 521 of SEQ ID NO: 38 or residues 453, 473, 476, 495, 497 and 499 of SEQ ID NO: 39. For example, the antibodies disclosed herein include an isolated antibody or antigen binding fragment thereof that specifically binds to an epitope of the extracellular domain of the human HER2 receptor that includes at least two amino acid residues selected from the group consisting of amino acid residues C453, H473, N476, R495, H497 and W499 of the extracellular domain of the human HER2 receptor. For example, the antibodies disclosed herein include an isolated antibody or antigen binding fragment thereof that specifically binds to an epitope of the extracellular domain of the human HER2 receptor that includes at least three amino acid residues selected from the group consisting of amino acid residues C453, H473, N476, R495, H497 and W499 of the extracellular domain of the human HER2 receptor. For example, the antibodies disclosed herein include an isolated antibody or antigen binding fragment thereof that specifically binds to an epitope of the extracellular domain of the human HER2 receptor that includes at least four amino acid residues selected from the group consisting of amino acid residues C453, H473, N476, R495, H497 and W499 of the extracellular domain of the human HER2 receptor. For example, the antibodies disclosed herein include an isolated antibody or antigen binding fragment thereof that specifically binds to an epitope of the extracellular domain of the human HER2 receptor that includes at least five amino acid residues selected from the group consisting of amino acid residues C453, H473, N476, R495, H497 and W499 of the extracellular domain of the human HER2 receptor. For example, the antibodies disclosed herein include an isolated antibody or antigen binding fragment thereof that specifically binds to an epitope of the extracellular domain of the human HER2 receptor that includes at least six amino acid residues selected from the group consisting of amino acid residues C453, H473, N476, R495, H497 and W499 of the extracellular domain of the human HER2 receptor. For example, the antibodies disclosed herein include an isolated antibody or antigen binding fragment thereof that specifically binds to an epitope of the extracellular domain of the human HER2 receptor that includes at least amino acid residues C453, H473, N476, R495, H497 and W499 of the extracellular domain of the human HER2 receptor. In some embodiments, any or all of these isolated antibodies or antigen binding fragments thereof also bind at least one epitope on cynomolgus monkey HER2 receptor.

These and other aspects of the invention are described in further detail below.

Exemplary monoclonal antibodies disclosed herein include, for example, the XMT 1517 antibody, the XMT 1518 antibody, the XMT 1519 antibody and the XMT 1520 antibody described herein. Alternatively, the monoclonal antibody is an antibody that cross block each other but do not bind to the same epitope as trastuzumab, pertuzumab, Fab37 or chA21 (that bind to specific epitopes on domain IV, domain II, domain III and domain I of HER2 respectively) or biosimilars thereof. These antibodies are respectively referred to herein as "HER2" antibodies. HER2 antibodies include fully human monoclonal antibodies, as well as humanized monoclonal antibodies and chimeric antibodies. These antibodies show specificity for human HER2, and they have been shown to modulate, e.g., block, inhibit, reduce, antagonize, neutralize or otherwise interfere with the PI3K-Akt pathway which promotes cell survival by reducing levels of phosphorylated AKT. These antibodies internalize from the cell surface of HER2-expressing cells at a rate that is the same or substantially similar to the rate at which trastuzumab or a biosimilar thereof internalizes. For example, these antibodies and antigen binding fragments have a rate of internalization that is about 50% of the total surface bound at time 0 being internalized by 4 hours.

The antibodies disclosed herein contain a heavy chain having an amino acid sequence at least 90%, 91%, 92%, 93%, 94%, 95%, 96%, 97% 98%, 99% or more identical to a sequence selected from the group consisting of SEQ ID NOs: 1, 3, 5, and 7 and a light chain having an amino acid sequence at least 90%, 91%, 92%, 93%, 94%, 95%, 96%, 97% 98%, 99% or more identical to a sequence selected from the group consisting of SEQ ID NOs: 2, 4, 6, and 8.

The antibodies disclosed herein contain a combination of heavy chain and light chain amino acid sequences selected from the group consisting of (i) a heavy chain amino acid sequence at least 90%, 91%, 92%, 93%, 94%, 95%, 96%, 97% 98%, 99% or more identical to the amino acid sequence of SEQ ID NO: 1 and a light chain amino acid sequence at least 90%, 91%, 92%, 93%, 94%, 95%, 96%, 97% 98%, 99% or more identical to the amino acid sequence of SEQ ID NO: 2; (ii) a heavy chain amino acid sequence at least 90%, 91%, 92%, 93%, 94%, 95%, 96%, 97% 98%, 99% or more identical to the amino acid sequence of SEQ ID NO: 3 and a light chain amino acid sequence at least 90%, 91%, 92%, 93%, 94%, 95%, 96%, 97% 98%, 99% or more identical to the amino acid sequence of SEQ ID NO: 4; (iii) a heavy chain amino acid sequence at least 90%, 91%, 92%, 93%, 94%, 95%, 96%, 97% 98%, 99% or more identical to the amino acid sequence of SEQ ID NO: 5 and a light chain amino acid sequence at least 90%, 91%, 92%, 93%, 94%, 95%, 96%, 97% 98%, 99% or more identical to the amino acid sequence of SEQ ID NO: 6; and (iv) a heavy chain amino acid sequence at least 90%, 91%, 92%, 93%, 94%, 95%, 96%, 97% 98%, 99% or more identical to the amino acid sequence of SEQ ID NO: 7 and a light chain amino acid sequence at least 90%, 91%, 92%, 93%, 94%, 95%, 96%, 97% 98%, 99% or more identical to the amino acid sequence of SEQ ID NO: 8.

In some embodiments, the antibodies disclosed herein contain a heavy chain amino acid sequence at least 90%, 91%, 92%, 93%, 94%, 95%, 96%, 97% 98%, 99% or more identical to the amino acid sequence of SEQ ID NO: 1 and a light chain amino acid sequence at least 90%, 91%, 92%, 93%, 94%, 95%, 96%, 97% 98%, 99% or more identical to the amino acid sequence of SEQ ID NO: 2.

In some embodiments, the antibodies disclosed herein contain a heavy chain amino acid sequence at least 90%, 91%, 92%, 93%, 94%, 95%, 96%, 97% 98%, 99% or more identical to the amino acid sequence of SEQ ID NO: 3 and a light chain amino acid sequence at least 90%, 91%, 92%, 93%, 94%, 95%, 96%, 97% 98%, 99% or more identical to the amino acid sequence of SEQ ID NO: 4.

In some embodiments, the antibodies disclosed herein contain a heavy chain amino acid sequence at least 90%, 91%, 92%, 93%, 94%, 95%, 96%, 97% 98%, 99% or more identical to the amino acid sequence of SEQ ID NO: 5 and a light chain amino acid sequence at least 90%, 91%, 92%, 93%, 94%, 95%, 96%, 97% 98%, 99% or more identical to the amino acid sequence of SEQ ID NO: 6.

In some embodiments, the antibodies disclosed herein contain a heavy chain amino acid sequence at least 90%, 91%, 92%, 93%, 94%, 95%, 96%, 97% 98%, 99% or more identical to the amino acid sequence of SEQ ID NO: 7 and a light chain amino acid sequence at least 90%, 91%, 92%, 93%, 94%, 95%, 96%, 97% 98%, 99% or more identical to the amino acid sequence of SEQ ID NO: 8.

The antibodies disclosed herein contain a heavy chain having an amino acid sequence selected from the group consisting of SEQ ID NOs: 1, 3, 5, and 7 and a light chain having an amino acid sequence selected from the group consisting of SEQ ID NOs: 2, 4, 6, and 8 respectively.

The antibodies disclosed herein contain a combination of heavy chain and light chain amino acid sequences selected from the group consisting of (i) the heavy chain amino acid sequence of SEQ ID NO: 1 and the light chain amino acid sequence of SEQ ID NO: 2; (ii) the heavy chain amino acid sequence of SEQ ID NO: 3 and the light chain amino acid sequence of SEQ ID NO: 4; (iii) the heavy chain amino acid sequence of SEQ ID NO: 5 and the light chain amino acid sequence of SEQ ID NO: 6; and (iv) the heavy chain amino acid sequence of SEQ ID NO: 7 and the light chain amino acid sequence of SEQ ID NO: 8.

In some embodiments, the antibodies disclosed herein contain the heavy chain amino acid sequence of SEQ ID NO: 1 and the light chain amino acid sequence of SEQ ID NO: 2.

In some embodiments, the antibodies disclosed herein contain the heavy chain amino acid sequence of SEQ ID NO: 3 and the light chain amino acid sequence of SEQ ID NO: 4.

In some embodiments, the antibodies disclosed herein contain the heavy chain amino acid sequence of SEQ ID NO: 5 and the light chain amino acid sequence of SEQ ID NO: 6.

In some embodiments, the antibodies disclosed herein contain the heavy chain amino acid sequence of SEQ ID NO: 7 and the light chain amino acid sequence of SEQ ID NO: 8.

The antibodies disclosed herein contain a heavy chain variable region having an amino acid sequence at least 90%, 91%, 92%, 93%, 94%, 95%, 96%, 97% 98%, 99% or more identical to a sequence selected from the group consisting of SEQ ID NOs: 9, 11, 13, and 15 and a light chain variable region having an amino acid sequence at least 90%, 91%, 92%, 93%, 94%, 95%, 96%, 97% 98%, 99% or more identical to a sequence selected from the group consisting of SEQ ID NOs: 10, 12, 14, and 16.

The antibodies disclosed herein contain a combination of heavy chain variable region and light chain variable region amino acid sequences selected from the group consisting of (i) a heavy chain variable region amino acid sequence at least 90%, 91%, 92%, 93%, 94%, 95%, 96%, 97% 98%, 99% or more identical to the amino acid sequence of SEQ ID NO: 9 and a light chain variable region amino acid sequence at least 90%, 91%, 92%, 93%, 94%, 95%, 96%, 97% 98%, 99% or more identical to the amino acid sequence of SEQ ID NO: 10; (ii) a heavy chain variable region amino acid sequence at least 90%, 91%, 92%, 93%, 94%, 95%, 96%, 97% 98%, 99% or more identical to the amino acid sequence of SEQ ID NO: 11 and a light chain variable region amino acid sequence at least 90%, 91%, 92%, 93%, 94%, 95%, 96%, 97% 98%, 99% or more identical to the amino acid sequence of SEQ ID NO: 12; (iii) a heavy chain variable region amino acid sequence at least 90%, 91%, 92%, 93%, 94%, 95%, 96%, 97% 98%, 99% or more identical to the amino acid sequence of SEQ ID NO: 13 and a light chain variable region amino acid sequence at least 90%, 91%, 92%, 93%, 94%, 95%, 96%, 97% 98%, 99% or more identical to the amino acid sequence of SEQ ID NO: 14; and (iv) a heavy chain variable region amino acid sequence at least 90%, 91%, 92%, 93%, 94%, 95%, 96%, 97% 98%, 99% or more identical to the amino acid sequence of SEQ ID NO: 15 and a light variable region chain amino acid sequence at least 90%, 91%, 92%, 93%, 94%, 95%, 96%, 97% 98%, 99% or more identical to the amino acid sequence of SEQ ID NO: 16.

In some embodiments, the antibodies disclosed herein contain a heavy chain variable region amino acid sequence at least 90%, 91%, 92%, 93%, 94%, 95%, 96%, 97% 98%, 99% or more identical to the amino acid sequence of SEQ ID NO: 9 and a light chain variable region amino acid sequence at least 90%, 91%, 92%, 93%, 94%, 95%, 96%, 97% 98%, 99% or more identical to the amino acid sequence of SEQ ID NO: 10.

In some embodiments, the antibodies disclosed herein contain a heavy chain variable region amino acid sequence at least 90%, 91%, 92%, 93%, 94%, 95%, 96%, 97% 98%, 99% or more identical to the amino acid sequence of SEQ ID NO: 11 and a light chain variable region amino acid sequence at least 90%, 91%, 92%, 93%, 94%, 95%, 96%, 97% 98%, 99% or more identical to the amino acid sequence of SEQ ID NO: 12.

In some embodiments, the antibodies disclosed herein contain a heavy chain variable region amino acid sequence at least 90%, 91%, 92%, 93%, 94%, 95%, 96%, 97% 98%, 99% or more identical to the amino acid sequence of SEQ ID NO: 13 and a light chain variable region amino acid sequence at least 90%, 91%, 92%, 93%, 94%, 95%, 96%, 97% 98%, 99% or more identical to the amino acid sequence of SEQ ID NO: 14.

In some embodiments, the antibodies disclosed herein contain a heavy chain variable region amino acid sequence at least 90%, 91%, 92%, 93%, 94%, 95%, 96%, 97% 98%, 99% or more identical to the amino acid sequence of SEQ ID NO: 15 and a light variable region chain amino acid sequence at least 90%, 91%, 92%, 93%, 94%, 95%, 96%, 97% 98%, 99% or more identical to the amino acid sequence of SEQ ID NO: 16.

The antibodies disclosed herein contain a heavy chain variable region an amino acid sequence selected from the group consisting of SEQ ID NOs: 9, 11, 13, and 15 and a light chain variable region having an amino acid sequence selected from the group consisting of SEQ ID NOs: 10, 12, 14, and 16.

The antibodies disclosed herein contain a combination of heavy chain variable region and light chain variable region amino acid sequences selected from the group consisting of (i) the heavy chain variable region amino acid sequence of SEQ ID NO: 9 and the light chain variable region amino acid sequence of SEQ ID NO: 10; (ii) the heavy chain variable region amino acid sequence of SEQ ID NO: 11 and the light chain variable region amino acid sequence of SEQ ID NO: 12; (iii) the heavy chain variable region amino acid sequence of SEQ ID NO: 13 and the light chain variable region amino acid sequence of SEQ ID NO: 14; and (iv) the heavy chain variable region amino acid sequence of SEQ ID NO: 15 and the light chain variable region amino acid sequence of SEQ ID NO: 16.

In some embodiments, the antibodies disclosed herein contain the heavy chain variable region amino acid sequence of SEQ ID NO: 9 and the light chain variable region amino acid sequence of SEQ ID NO: 10.

In some embodiments, the antibodies disclosed herein contain the heavy chain variable region amino acid sequence of SEQ ID NO: 11 and the light chain variable region amino acid sequence of SEQ ID NO: 12.

In some embodiments, the antibody disclosed herein contain a heavy chain variable region an amino acid sequence of SEQ ID NO: 13, and a light chain variable region having an amino acid sequence of SEQ ID NO: 14.

In some embodiments, the antibodies disclosed herein contain the heavy chain variable region amino acid sequence of SEQ ID NO: 15 and the light chain variable region amino acid sequence of SEQ ID NO: 16.

The three heavy chain CDRs of the antibodies disclosed herein include a heavy chain complementarity determining region 1 (CDRH1) that includes an amino acid sequence at least 90%, 91%, 92%, 93%, 94%, 95%, 96%, 97% 98%, 99% or more identical to a sequence selected from the group consisting of SEQ ID NOs: 17, 25, and 30; a heavy chain complementarity determining region 2 (CDRH2) that includes an amino acid sequence at least 90%, 91%, 92%, 93%, 94%, 95%, 96%, 97% 98%, 99% or more identical to a sequence selected from the group consisting of SEQ ID NOs: 18, 23, 26, and 31; and a heavy chain complementarity determining region 3 (CDRH3) that includes an amino acid sequence at least 90%, 91%, 92%, 93%, 94%, 95%, 96%, 97% 98%, 99% or more identical to a sequence selected from the group consisting of SEQ ID NOs: 19 and 27.

The three light chain CDRs of the antibodies disclosed herein include a light chain complementarity determining region 1 (CDRL1) that includes an amino acid sequence at least 90%, 91%, 92%, 93%, 94%, 95%, 96%, 97% 98%, 99% or more identical to a sequence selected from the group consisting of SEQ ID NOs: 20 and 28; a light chain complementarity determining region 2 (CDRL2) that includes an amino acid sequence at least 90%, 91%, 92%, 93%, 94%, 95%, 96%, 97% 98%, 99% or more identical to a sequence selected from the group consisting of SEQ ID NOs: 21 and 24; and a light chain complementarity determining region 3 (CDRL3) that includes an amino acid sequence at least 90%, 91%, 92%, 93%, 94%, 95%, 96%, 97% 98%, 99% or more identical to a sequence selected from the group consisting of SEQ ID NOs: 22 and 29.

The antibodies include a combination of heavy chain CDR and light chain CDR sequences that include a CDRH1 that includes an amino acid sequence at least 90%, 91%, 92%, 93%, 94%, 95%, 96%, 97% 98%, 99% or more identical to a sequence selected from the group consisting of SEQ ID NOs: 17, 25, and 30; a CDRH2 that includes an amino acid sequence at least 90%, 91%, 92%, 93%, 94%, 95%, 96%, 97% 98%, 99% or more identical to a sequence selected from the group consisting of SEQ ID NOs: 18, 23, 26, and 31; a CDRH3 that includes an amino acid sequence at least 90%, 91%, 92%, 93%, 94%, 95%, 96%, 97% 98%, 99% or more identical to a sequence selected from the group consisting of SEQ ID NOs: 19 and 27; a CDRL1 that includes an amino acid sequence at least 90%, 91%, 92%, 93%, 94%, 95%, 96%, 97% 98%, 99% or more identical to a sequence selected from the group consisting of SEQ ID NOs: 20 and 28; a CDRL2 that includes an amino acid sequence at least 90%, 91%, 92%, 93%, 94%, 95%, 96%, 97% 98%, 99% or more identical to a sequence selected from the group consisting of SEQ ID NOs: 21 and 24; and a CDRL3 that includes an amino acid sequence at least 90%, 91%, 92%, 93%, 94%, 95%, 96%, 97% 98%, 99% or more identical to a sequence selected from the group consisting of SEQ ID NOs: 22 and 29.

The three heavy chain CDRs of the antibodies disclosed herein include a CDRH1 that includes an amino acid sequence selected from the group consisting of SEQ ID NOs: 17, 25, and 30; a CDRH2 that includes an amino acid sequence selected from the group consisting of SEQ ID NOs: 18, 23, 26, and 31; and a CDRH3 that includes an amino acid sequence selected from the group consisting of SEQ ID NOs: 19 and 27.

The three light chain CDRs of the antibodies disclosed herein include a CDRL1 that includes an amino acid sequence selected from the group consisting of SEQ ID NOs: 20 and 28; a CDRL2 that includes an amino acid sequence selected from the group consisting of SEQ ID NOs: 21 and 24; and a CDRL3 that includes an amino acid sequence selected from the group consisting of SEQ ID NOs: 22 and 29.

The antibodies disclosed herein include a combination of heavy chain CDR and light chain CDR sequences that include a CDHR1 that includes an amino acid sequence selected from the group consisting of SEQ ID NOs: 17, 25, and 30; a CDRH2 that includes an amino acid sequence selected from the group consisting of SEQ ID NOs: 18, 23, 26, and 31; a CDRH3 that includes an amino acid sequence selected from the group consisting of SEQ ID NOs: 19 and 27; a CDRL1 that includes an amino acid sequence selected from the group consisting of SEQ ID NOs: 20 and 28; a CDRL2 that includes an amino acid sequence selected from the group consisting of SEQ ID NOs: 21 and 24; and a CDRL3 that includes an amino acid sequence selected from the group consisting of SEQ ID NOs: 22 and 29.

The antibodies disclosed herein contain a combination of heavy chain complementarity determining region and light chain complementarity determining region amino acid sequences selected from the group consisting of (i) the CDRH1 amino acid sequence of SEQ ID NO: 17, the CDRH2 amino acid sequence of SEQ ID NO: 18, the CDRH3 amino acid sequence of SEQ ID NO: 19, the CDRL1 amino acid sequence of SEQ ID NO: 20, the CDRL2 amino acid sequence of SEQ ID NO: 21, and the CDRL3 amino acid sequence of SEQ ID NO: 22; (ii) the CDRH1 amino acid sequence of SEQ ID NO: 17, the CDRH2 amino acid sequence of SEQ ID NO: 23, the CDRH3 amino acid sequence of SEQ ID NO: 19, the CDRL1 amino acid sequence of SEQ ID NO: 20, the CDRL2 amino acid sequence of SEQ ID NO: 24, and the CDRL3 amino acid sequence of SEQ ID NO: 22; (iii) the CDRH1 amino acid sequence of SEQ ID NO: 25, the CDRH2 amino acid sequence of SEQ ID NO: 26, the CDRH3 amino acid sequence of SEQ ID NO: 27, the CDRL1 amino acid sequence of SEQ ID NO: 28, the CDRL2 amino acid sequence of SEQ ID NO: 21, and the CDRL3 amino acid sequence of SEQ ID NO: 29; and (iv) the CDRH1 amino acid sequence of SEQ ID NO: 30, the CDRH2 amino acid sequence of SEQ ID NO: 31, the CDRH3 amino acid sequence of SEQ ID NO: 27, the CDRL1 amino acid sequence of SEQ ID NO: 28, the CDRL2 amino acid sequence of SEQ ID NO: 21, and the CDRL3 amino acid sequence of SEQ ID NO: 29.

In some embodiments, the antibodies disclosed herein contain the CDRH1 amino acid sequence of SEQ ID NO: 17, the CDRH2 amino acid sequence of SEQ ID NO: 18, the CDRH3 amino acid sequence of SEQ ID NO: 19, the CDRL1 amino acid sequence of SEQ ID NO: 20, the CDRL2 amino acid sequence of SEQ ID NO: 21, and the CDRL3 amino acid sequence of SEQ ID NO: 22.

In some embodiments, the antibodies disclosed herein contain the CDRH1 amino acid sequence of SEQ ID NO: 17, the CDRH2 amino acid sequence of SEQ ID NO: 23, the CDRH3 amino acid sequence of SEQ ID NO: 19, the CDRL1 amino acid sequence of SEQ ID NO: 20, the CDRL2 amino acid sequence of SEQ ID NO: 24, and the CDRL3 amino acid sequence of SEQ ID NO: 22.

In some embodiments, the antibodies disclosed herein contain the CDRH1 amino acid sequence of SEQ ID NO: 25, the CDRH2 amino acid sequence of SEQ ID NO: 26, the CDRH3 amino acid sequence of SEQ ID NO: 27, the CDRL1 amino acid sequence of SEQ ID NO: 28, the CDRL2 amino acid sequence of SEQ ID NO: 21, and the CDRL3 amino acid sequence of SEQ ID NO: 29.

In some embodiments, the antibodies disclosed herein contain the CDRH1 amino acid sequence of SEQ ID NO: 30, the CDRH2 amino acid sequence of SEQ ID NO: 31, the CDRH3 amino acid sequence of SEQ ID NO: 27, the CDRL1 amino acid sequence of SEQ ID NO: 28, the CDRL2 amino acid sequence of SEQ ID NO: 21, and the CDRL3 amino acid sequence of SEQ ID NO: 29.

In some embodiments, the HER2 antibody disclosed herein also includes an agent conjugated to the antibody. In some embodiments, the agent is a therapeutic agent. In some embodiments, the agent is an antineoplastic agent. In some embodiments, the agent is a toxin or fragment thereof. In some embodiments the agent is (a) an auristatin compound; (b) a calicheamicin compound; (c) a duocarmycin compound; (d) SN38, (e) a pyrrolobenzodiazepine; (f) a vinca compound; (g) a tubulysin compound; (h) a non-natural camptothecin compound; (i) a maytansinoid compound; (j) a DNA binding drug; (k) a kinase inhibitor; (l) a MEK inhibitor; (m) a KSP inhibitor; (n) a topoisomerase inhibitor; and analogs thereof or analogues thereof. In some embodiments, the agent is conjugated to the HER2 antibody via a linker. In some embodiments, the linker is a cleavable linker. In some embodiments, the linker is a non-cleavable linker. In some embodiments, the agent is any of the toxins described herein.

In one aspect, the HER2 antibody conjugate described herein includes an isolated HER2 antibody or antigen binding fragment thereof connected directly or indirectly to one or more therapeutic or diagnostic agents (D). In some embodiments, the HER2 antibody conjugate also includes one or more polymeric scaffolds connected to the antibody or antigen binding fragment thereof, wherein each of the one or more D is independently connected to the antibody or antigen binding fragment thereof via the one or more polymeric scaffolds.

In some embodiments, each of the one or more polymeric scaffolds that are connected to the isolated HER2 antibody or antigen binding fragment thereof, independently, comprises poly(1-hydroxymethylethylene hydroxymethyl-formal) (PHF) having a molecular weight ranging from about 2 kDa to about 40 kDa.

In some embodiments, each of the one or more polymeric scaffolds independently is of Formula (Ic):

(Ic)

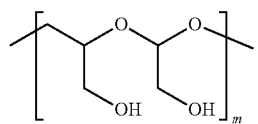

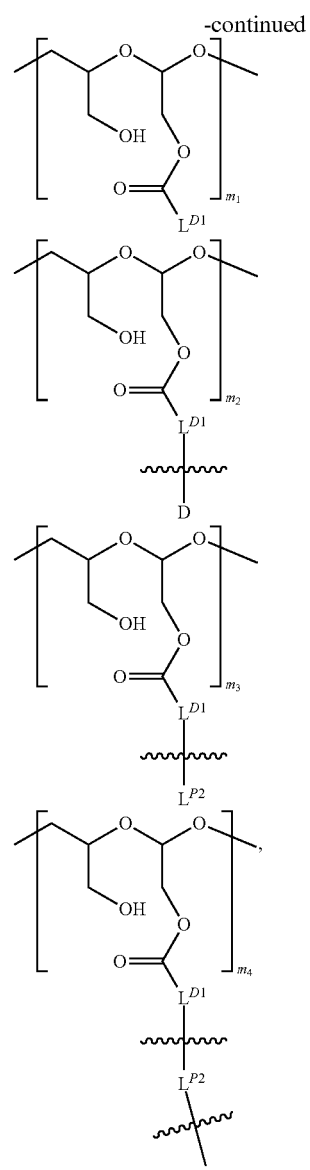

wherein:
$L^{D1}$ is a carbonyl-containing moiety;
each occurrence of

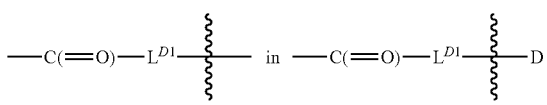

is independently a first linker that contains a biodegradable bond so that when the bond is broken, D is released in an active form for its intended therapeutic effect; and the

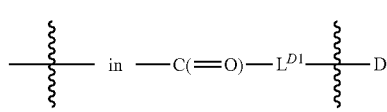

between $L^{D1}$ and D denotes direct or indirect attachment of D to $L^{D1}$;

each occurrence of

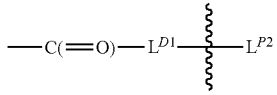

is independently a second linker not yet connected to the isolated antibody or antigen binding fragment thereof, in which $L^{P2}$ is a moiety containing a functional group that is yet to form a covalent bond with a functional group of the isolated antibody or antigen binding fragment thereof, and the

between $L^{D1}$ and $L^{P2}$ denotes direct or indirect attachment of $L^{P2}$ to $L^{D1}$, and each occurrence of the second linker is distinct from each occurrence of the first linker;
each occurrence of

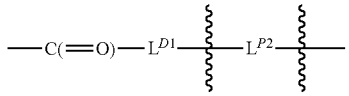

is independently a third linker that connects each D-carrying polymeric scaffold to the isolated antibody or antigen binding fragment thereof, in which the terminal

attached to $L^{P2}$ denotes direct or indirect attachment of $L^{P2}$ to the isolated antibody or antigen binding fragment thereof upon formation of a covalent bond between a functional group of $L^{P2}$ and a functional group of the isolated antibody or antigen binding fragment thereof; and each occurrence of the third linker is distinct from each occurrence of the first linker;
m is an integer from 1 to about 300,
$m_1$ is an integer from 1 to about 140,
$m_2$ is an integer from 1 to about 40,
$m_3$ is an integer from 0 to about 18,
$m_4$ is an integer from 1 to about 10;
the sum of m, $m_1$, $m_2$, $m_3$, and $m_4$ ranges from about 15 to about 300; and
the total number of $L^{P2}$ connected to the isolated antibody or antigen binding fragment thereof is 10 or less.

The conjugate described herein can include one or more of the following features:

For example, in Formula (Ic), the isolated HER2 antibody or antigen-binding fragment thereof has a molecular weight of 40 kDa or greater (e.g., 60 kDa or greater, 80 kDa or greater, 100 kDa or greater, 120 kDa or greater, 140 kDa or greater, 160 kDa or greater, 180 kDa or greater, or 200 kDa or greater, or about 40-200 kDa, 40-180 kDa, 40-140 kDa, 60-200 kDa, 60-180 kDa, 60-140 kDa, 80-200 kDa, 80-180 kDa, 80-140 kDa, 100-200 kDa, 100-180 kDa, 100-140 kDa, or 140-150 kDa). In some embodiments, the isolated HER2 antibody or antigen-binding fragment thereof if any antibody or antigen-binding fragment of the disclosure, including, by way of non-limiting example, the XMT 1517 antibody, the XMT 1518 antibody, the XMT 1519 antibody and the XMT 1520 antibody described herein.

For example, in Formula (Ic), $m_1$ is an integer from 1 to about 120 (e.g., about 1-90) and/or $m_3$ is an integer from 1 to about 10 (e.g., about 1-8).

For example, when the PHF in Formula (Ic) has a molecular weight ranging from about 6 kDa to about 20 kDa (i.e., the sum of m, $m_1$, $m_2$, $m_3$, and $m_4$ ranging from about 45 to about 150), $m_2$ is an integer from 2 to about 20, $m_3$ is an integer from 0 to about 9, $m_4$ is an integer from 1 to about 10, and/or $m_1$ is an integer from 1 to about 75 (e.g., $m_1$ being about 4-45).

For example, when the PHF in Formula (Ic) has a molecular weight ranging from about 8 kDa to about 15 kDa (i.e., the sum of m, $m_1$, $m_2$, $m_3$, and $m_4$ ranging from about 60 to about 110), $m_2$ is an integer from 2 to about 15, $m_3$ is an integer from 0 to about 7, $m_4$ is an integer from 1 to about 10, and/or $m_1$ is an integer from 1 to about 55 (e.g., $m_1$ being about 4-30).

For example, when the PHF in Formula (Ic) has a molecular weight ranging from about 2 kDa to about 20 kDa (i.e., the sum of m, $m_1$, $m_2$, $m_3$, and $m_4$ ranging from about 15 to about 150), $m_2$ is an integer from 1 to about 20, $m_3$ is an integer from 0 to about 10 (e.g., $m_3$ ranging from 0 to about 9), $m_4$ is an integer from 1 to about 8, and/or $m_1$ is an integer from 1 to about 70, and the total number of $L^{P2}$ connected to the isolated antibody or antigen binding fragment thereof ranges from about 2 to about 8 (e.g., about 2, 3, 4, 5, 6, 7, or 8).

For example, when the PHF in Formula (Ic) has a molecular weight ranging from about 3 kDa to about 15 kDa (i.e., the sum of m, $m_1$, $m_2$, $m_3$, and $m_4$ ranging from about 20 to about 110), $m_2$ is an integer from 2 to about 15, $m_3$ is an integer from 0 to about 8 (e.g., $m_3$ ranging from 0 to about 7), $m_4$ is an integer from 1 to about 8, and/or $m_1$ is an integer from 2 to about 50, and the total number of $L^{P2}$ connected to the isolated antibody or antigen binding fragment thereof ranges from about 2 to about 8 (e.g., about 2, 3, 4, 5, 6, 7, or 8).

For example, when the PHF in Formula (Ic) has a molecular weight ranging from about 5 kDa to about 10 kDa, (i.e. the sum of m, $m_1$, $m_2$, $m_3$ and $m_4$ ranges from about 40 to about 75), $m_2$ is an integer from about 2 to about 10 (e.g., $m_2$ being about 3-10), $m_3$ is an integer from 0 to about 5 (e.g., $m_3$ ranging from 0 to about 4), $m_4$ is an integer from 1 to about 8 (e.g., $m_4$ ranging from 1 to about 5), and/or $m_1$ is an integer from about 2 to about 35 (e.g., $m_1$ being about 5-35), and the total number of $L^{P2}$ connected to the isolated antibody or antigen binding fragment thereof ranges from about 2 to about 8 (e.g., about 2, 3, 4, 5, 6, 7, or 8).

For example, each occurrence of D independently is a therapeutic agent having a molecular weight of ≤5 kDa.

For example, each occurrence of D independently is an anti-cancer drug, for example, selected from vinca alkaloids, auristatins, tubulysins, duocarmycins, non-natural camptothecin compounds, maytansinoids, calicheamicin compounds, topoisomerase inhibitors, DNA binding drugs, kinase inhibitors, MEK inhibitors, KSP inhibitors, and analogs thereof.

For example, each
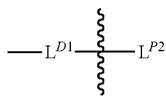
when not connected to the isolated antibody or antigen-binding fragment thereof, independently comprises a terminal group $W^P$, in which each $W^P$ independently is:
(1)
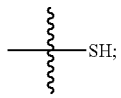
(2)
(3)
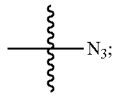
(4)
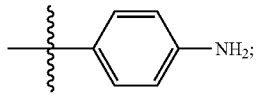
(5)
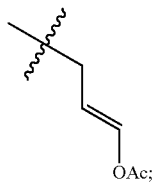
(6)
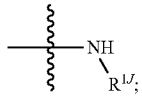
(7)
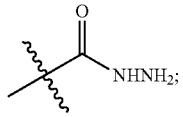
(8)
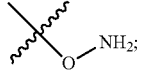
(9)
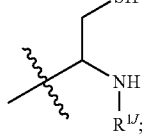
(10)
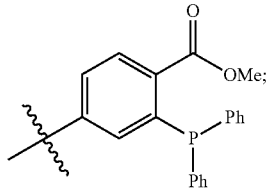
(11)
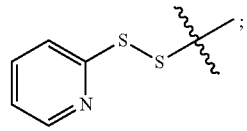
(12)
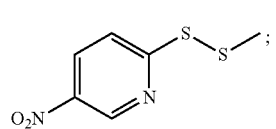
(13)
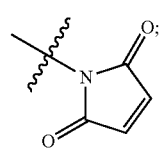
(14)
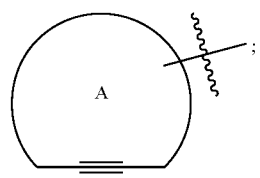
(15)
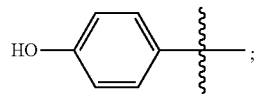
(16)
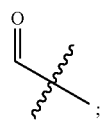
(17)
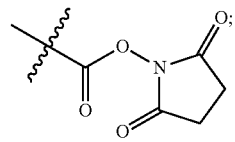
(18)
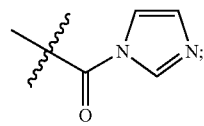
(19)
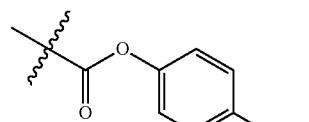
(20)
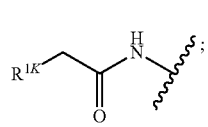
(21)
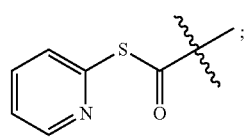

-continued (22)

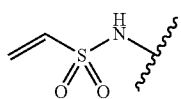 or;

(23)

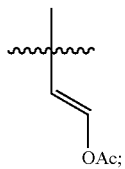

in which $R^{1K}$ is a leaving group (e.g., halide or RC(O)O— in which R is hydrogen, an aliphatic, heteroaliphatic, carbocyclic, or heterocycloalkyl moiety), $R^{1A}$ is a sulfur protecting group, and ring A is cycloalkyl or heterocycloalkyl, and $R^{1J}$ is hydrogen, an aliphatic, heteroaliphatic, carbocyclic, or heterocycloalkyl moiety.

For example, each $R^{1A}$ independently is

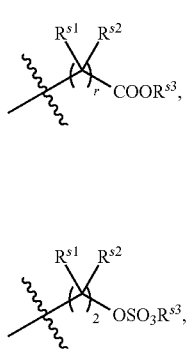 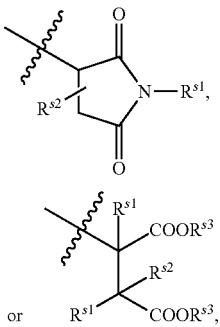

in which r is 1 or 2 and each of $R^{s1}$, $R^{s2}$, and $R^{s3}$ is hydrogen, an aliphatic, heteroaliphatic, carbocyclic, or heterocycloalkyl moiety.

For example, the functional group of $L^{P2}$ that is yet to form a covalent bond with a functional group of the isolated antibody or antigen binding fragment thereof is selected from —$SR^p$, —S—S-LG,

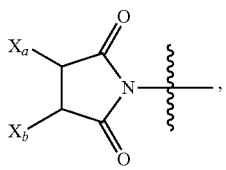

and halo, in which LG is a leaving group, $R^p$ is H or a sulfur protecting group, and one of $X_a$ and $X_b$ is H and the other is a water-soluble maleimido blocking moiety, or $X_a$ and $X_b$, together with the carbon atoms to which they are attached for a carbon-carbon double bond. For example, the functional group of $L^{P2}$ that is yet to form a covalent bond is a functional group that is not reacted with a functional group of the isolated antibody or antigen binding fragment thereof, e.g.,

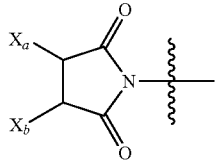

as the functional group of $L^{P2}$, in which one of $X_a$ and $X_b$ is H and the other is a water-soluble maleimido blocking moiety, or $X_a$ and $X_b$.

For example, $L^{D1}$ comprises —X—$(CH_2)_v$—C(=O)— with X directly connected to the carbonyl group of

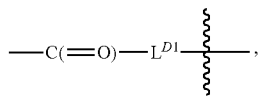

in which X is $CH_2$, O, or NH, and v is an integer from 1 to 6.

For example, each occurrence of

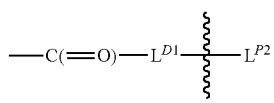

is independently —C(=O)—X—$(CH_2)_v$—C(=O)—NH—$(CH_2)_u$—NH—C(=O)—$(CH_2)_w$—$(OCH_2)_x$—NHC(=O)—$(CH_2)_y$-M, in which X is $CH_2$, O, or NH, each of v, u, w, x and y independently is an integer from 1 to 6, and M is

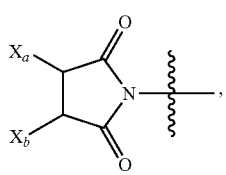

wherein one of $X_a$ and $X_b$ is H and the other is a water-soluble maleimido blocking moiety, or $X_a$ and $X_b$, together with the carbon atoms to which they are attached for a carbon-carbon double bond.

For example, each of v, u, w, x and y is 2.

For example, the ratio between D and the isolated HER2 antibody or antigen-binding fragment thereof is about 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1, 6; 1, 5:1, 4:1, 3:1, 2:1 or 1:1.

For example, the ratio between D and the isolated HER2 antibody or antigen-binding fragment thereof is about 20:1, 15:1, 10:1, 5:1, 2:1 or 1:1.

For example, the ratio between D and the isolated HER2 antibody or antigen-binding fragment thereof is about 16:1, 15:1, 14:1, 13:1, 12:1, 11:1 or 10:1.

For example, the ratio between D and the isolated HER2 antibody or antigen-binding fragment thereof is about 15:1, 14:1, 13:1, 12:1 or 11:1.

For example, the ratio between D and the isolated HER2 antibody or antigen-binding fragment thereof is about 15:1, 14:1, 13:1 or 12:1.

For example, the ratio between the D and the isolated HER2 antibody or antigen-binding fragment thereof is about 6:1, 5:1, 4:1, 3:1, 2:1 or 1:1.

For example, each of the one or more D-carrying polymeric scaffolds independently is of Formula (Id):

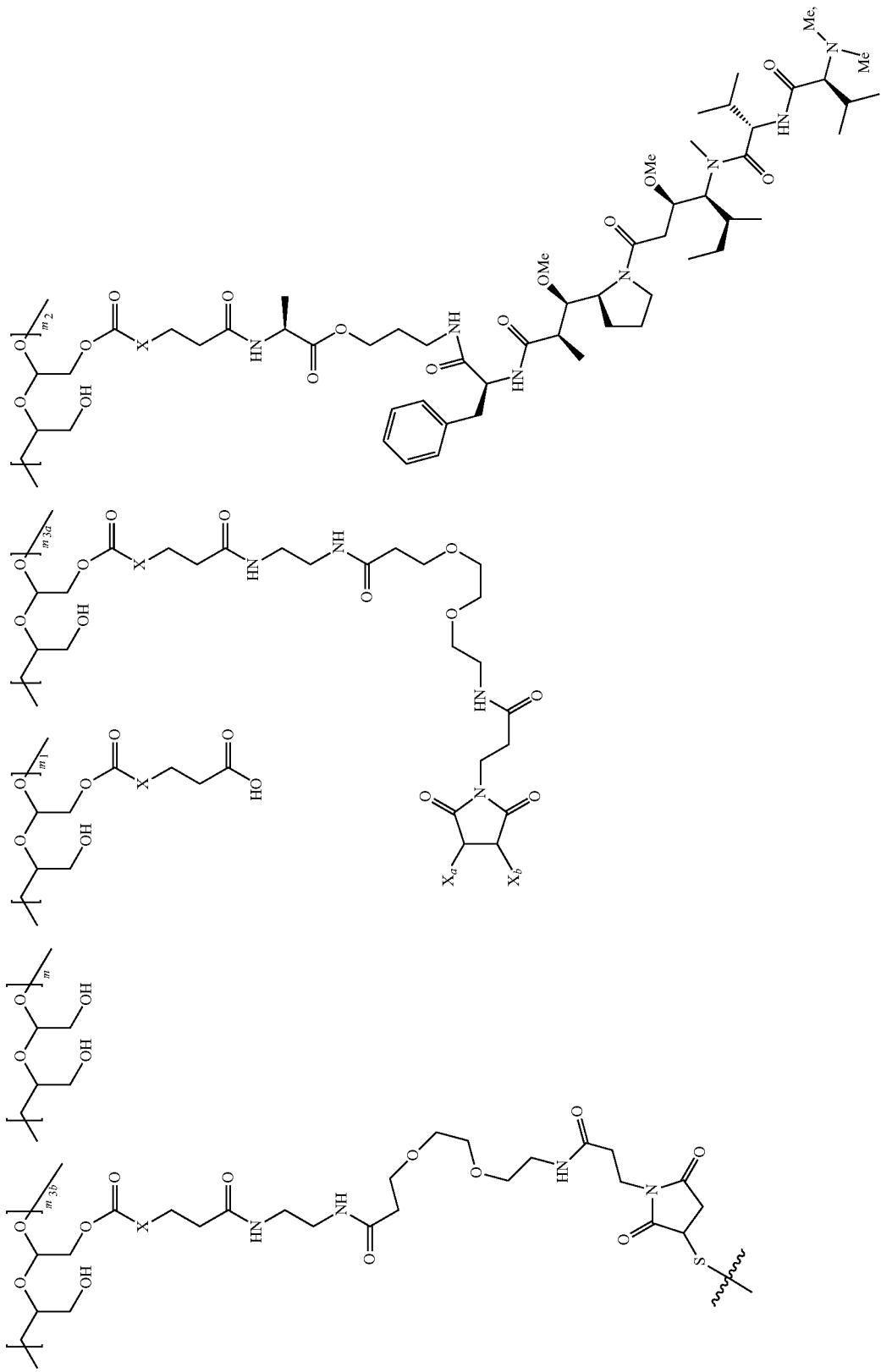

wherein:
m$_{3a}$ is an integer from 0 to about 17,
m$_{3b}$ is an integer from 1 to about 8, and
the terminal

denotes the direct attachment of the one or more polymeric scaffolds to the isolated HER2 antibody or antigen-binding fragment thereof having a molecular weight of 40 kDa or greater.

The scaffold of Formula (Id) can include one or more of the following features:

The sum of m$_{3a}$ and m$_{3b}$ is between 1 and 18.

When the PHF in Formula (Id) has a molecular weight ranging from about 2 kDa to about 40 kDa, the sum of m, m$_1$, m$_2$, m$_{3a}$ and m$_{3b}$ ranges from about 15 to about 300, m$_1$ is an integer from 1 to about 140, m$_2$ is an integer from 1 to about 40, m$_{3a}$ is an integer from 0 to about 17, m$_{3b}$ is an integer from 1 to about 8, the sum of m$_{3a}$ and m$_{3b}$ ranges from 1 and about 18, and the ratio between the PHF and the isolated HER2 antibody or antigen-binding fragment thereof is 10 or less.

When the PHF in Formula (Id) has a molecular weight ranging from about 2 kDa to about 20 kDa, the sum of m, m$_1$, m$_2$, m$_{3a}$ and m$_{3b}$ ranges from about 15 to about 150, m$_1$ is an integer from 1 to about 70, m$_2$ is an integer from 1 to about 20, m$_{3a}$ is an integer from 0 to about 9, m$_{3b}$ is an integer from 1 to about 8, the sum of m$_{3a}$ and m$_{3b}$ ranges from 1 and about 10, and the ratio between the PHF and the isolated HER2 antibody or antigen-binding fragment thereof is an integer from 2 to about 8.

When the PHF in Formula (Id) has a molecular weight ranging from about 3 kDa to about 15 kDa, the sum of m, m$_1$, m$_2$, m$_{3a}$ and m$_{3b}$ ranges from about 20 to about 110, m$_1$ is an integer from 2 to about 50, m$_2$ is an integer from 2 to about 15, m$_{3a}$ is an integer from 0 to about 7, m$_{3b}$ is an integer from 1 to about 8, the sum of m$_{3a}$ and m$_{3b}$ ranges from 1 and about 8; and the ratio between the PHF and the isolated HER2 antibody or antigen-binding fragment thereof is an integer from 2 to about 8 (e.g., from about 2 to about 6 or from about 2 to about 4).

When the PHF in Formula (Id) has a molecular weight ranging from about 5 kDa to about 10 kDa, the sum of m, m$_1$, m$_2$, m$_{3a}$ and m$_{3b}$ ranges from about 40 to about 75, m$_1$ is an integer from about 2 to about 35, m$_2$ is an integer from about 2 to about 10, m$_{3a}$ is an integer from 0 to about 4, m$_{3b}$ is an integer from 1 to about 5, the sum of m$_{3a}$ and m$_{3b}$ ranges from 1 and about 5; and the ratio between the PHF and the isolated HER2 antibody or antigen-binding fragment thereof is an integer from 2 to about 8 (e.g., from about 2 to about 6 or from about 2 to about 4).

In certain embodiments, the ratio between auristatin F hydroxylpropyl amide ("AF HPA") and the isolated HER2 antibody or antigen-binding fragment thereof can be about 30:1, 29:1, 28:1, 27:1, 26:1, 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1 or 6:1.

In certain embodiments, the ratio between AF HPA and the isolated HER2 antibody or antigen-binding fragment thereof can be about 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1 or 6:1.

In other embodiments, the ratio between AF HPA and the isolated HER2 antibody or antigen-binding fragment thereof can be about 20:1, 19:1, 18:1, 17:1, 16:1, 15:1, 14:1, 13:1, 12:1, 11:1, 10:1, 9:1, 8:1, 7:1 or 6:1.

In some embodiments, the ratio between AF HPA and isolated HER2 antibody or antigen-binding fragment thereof can be about 16:1, 15:1, 14:1, 13:1, 12:1, 11:1 or 10:1.

In some embodiments, the ratio between AF HPA and isolated HER2 antibody or antigen-binding fragment thereof can be about 15:1, 14:1, 13:1, 12:1 or 11:1.

In some embodiments, the ratio between AF HPA and isolated HER2 antibody or antigen-binding fragment thereof can be about 15:1, 14:1, 13:1 or 12:1.

In certain embodiments, the ratio between PHF and isolated HER2 antibody or antigen-binding fragment thereof can be about 10:1, 9:1, 8:1, 7:1, 6:1, 5:1, 4:1, 3:1, 2:1 or 1:1.

In certain embodiments, the ratio between PHF and isolated HER2 antibody or antigen-binding fragment thereof can be about 8:1, 7:1, 6:1, 5:1, 4:1, 3:1 or 2:1.

In other embodiments, the ratio between PHF and isolated HER2 antibody or antigen-binding fragment thereof can be about 6:1, 5:1, 4:1, 3:1, 2:1 or 1:1.

In other embodiments, the ratio between PHF and isolated HER2 antibody or antigen-binding fragment thereof can be about 6:1, 5:1, 4:1, 3:1 or 2:1.

In other embodiments, the ratio between PHF and isolated HER2 antibody or antigen-binding fragment thereof can be about 6:1, 5:1, 4:1 or 3:1.

In some embodiments, the ratio between PHF and isolated HER2 antibody or antigen-binding fragment thereof can be about 5:1, 4:1 or 3:1.

In some embodiments, the ratio between PHF and isolated HER2 antibody or antigen-binding fragment thereof can be about 4:1, 3:1 or 2:1.

The water-soluble maleimido blocking moieties (e.g., X$_a$ or X$_b$) are moieties that can be covalently attached to one of the two olefin carbon atoms upon reaction of the maleimido group with a thiol-containing compound of Formula (II):

$$R_{90}-(CH_2)_d-SH \quad (II)$$

wherein:
R$_{90}$ is NHR$_{91}$, OH, COOR$_{93}$, CH(NHR$_{91}$)COOR$_{93}$ or a substituted phenyl group;
R$_{93}$ is hydrogen or C$_{1-4}$ alkyl;
R$_{91}$ is hydrogen, CH$_3$ or CH$_3$CO and
d is an integer from 1 to 3.

In one embodiment, the water-soluble maleimido blocking compound of Formula (II) can be cysteine, N-acetyl cysteine, cysteine methyl ester, N-methyl cysteine, 2-mercaptoethanol, 3-mercaptopropanoic acid, 2-mercaptoacetic acid, mercaptomethanol (i.e., HOCH$_2$SH), benzyl thiol in which phenyl is substituted with one or more hydrophilic substituents, or 3-aminopropane-1-thiol. The one or more hydrophilic substituents on phenyl comprise OH, SH, methoxy, ethoxy, COOH, CHO, COC$_{1-4}$ alkyl, NH$_2$, F, cyano, SO$_3$H, PO$_3$H, and the like.

In another aspect, the water-soluble maleimido blocking group is —S—(CH$_2$)$_d$—R$_{90}$, in which,
R$_{90}$ is OH, COOH, or CH(NHR$_{91}$)COOR$_{93}$;
R$_{93}$ is hydrogen or CH$_3$;
R$_{91}$ is hydrogen or CH$_3$CO; and
d is 1 or 2.

In another embodiment, the water-soluble maleimido blocking group is —S—CH$_2$—CH(NH$_2$)COOH.

In certain embodiments, the conjugate described herein comprises one or more D-carrying PHF, each of which independently is of Formula (If), wherein the PHF has a molecular weight ranging from about 2 kDa to about 40 kDa:

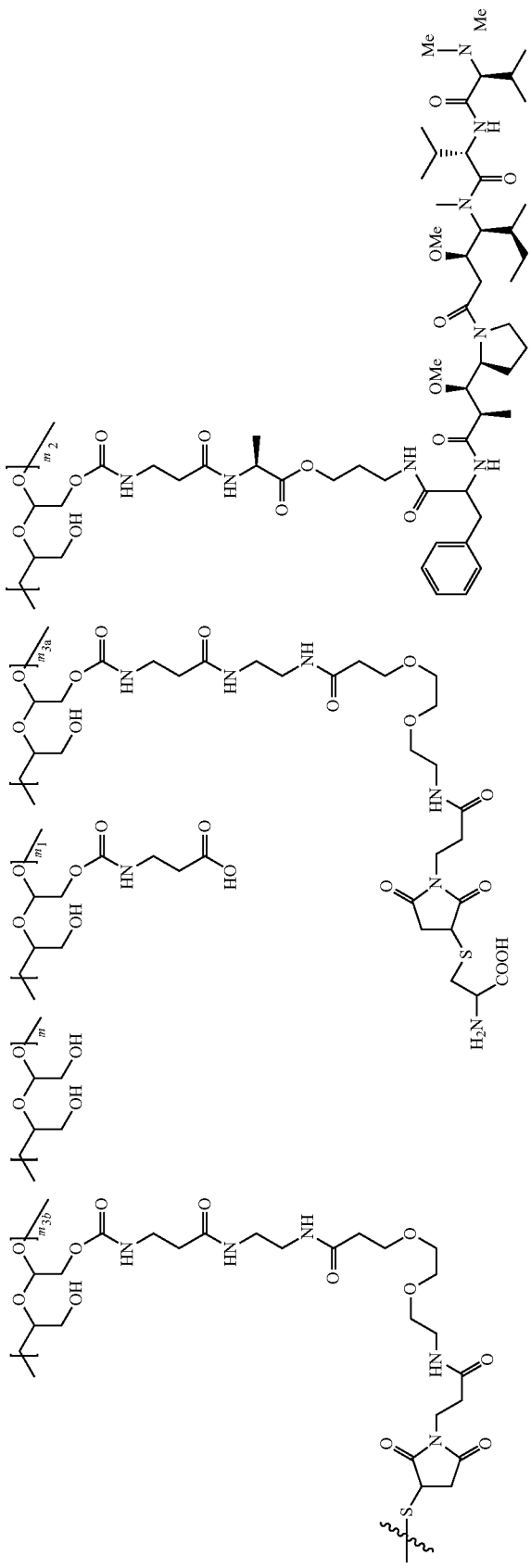

wherein:
    m is an integer from 1 to about 300,
    $m_1$ is an integer from 1 to about 140,
    $m_2$ is an integer from 1 to about 40,
    $m_{3a}$ is an integer from 0 to about 17,
    $m_{3b}$ is an integer from 1 to about 8;
    the sum of $m_{3a}$ and $m_{3b}$ ranges from 1 and about 18;
    the sum of m, $m_1$, $m_2$, $m_{3a}$, and $m_{3b}$ ranges from about 15 to about 300;
    the terminal

denotes the attachment of one or more PHF polymeric scaffolds to the isolated antibody or antigen binding fragment thereof that specifically binds to an epitope of the human HER2 receptor and comprises a variable heavy chain complementarity determining region 1 (CDRH1) comprising the amino acid sequence FTFSSYSMN (SEQ ID NO: 25); a variable heavy chain complementarity determining region 2 (CDRH2) comprising the amino acid sequence YISSSSSTIYYADSVKG (SEQ ID NO: 26); a variable heavy chain complementarity determining region 3 (CDRH3) comprising the amino acid sequence GGH-GYFDL (SEQ ID NO: 27); a variable light chain complementarity determining region 1 (CDRL1) comprising the amino acid sequence RASQSVSSSYLA (SEQ ID NO: 28); a variable light chain complementarity determining region 2 (CDRL2) comprising the amino acid sequence GASSRAT (SEQ ID NO: 21); and a variable light chain complementarity determining region 3 (CDRL3) comprising the amino acid sequence QQYHHSPLT (SEQ ID NO: 29); and
    the ratio between the PHF and the antibody is 10 or less.
    The scaffold of Formula (If) can include one or more of the following features:
    When the PHF in Formula (If) has a molecular weight ranging from about 2 kDa to about 20 kDa, the sum of m, $m_1$, $m_2$, $m_{3a}$ and $m_{3b}$ ranges from about 15 to about 150, $m_1$ is an integer from 1 to about 70, $m_2$ is an integer from 1 to about 20, $m_{3a}$ is an integer from 0 to about 9, $m_{3b}$ is an integer from 1 to about 8, the sum of $m_{3a}$ and $m_{3b}$ ranges from 1 and about 10, and the ratio between the PHF and the antibody is an integer from 2 to about 8.
    When the PHF in Formula (If) has a molecular weight ranging from about 3 kDa to about 15 kDa, the sum of m, $m_1$, $m_2$, $m_{3a}$ and $m_{3b}$ ranges from about 20 to about 110, $m_1$ is an integer from 2 to about 50, $m_2$ is an integer from 2 to about 15, $m_{3a}$ is an integer from 0 to about 7, $m_{3b}$ is an integer from 1 to about 8, the sum of $m_{3a}$ and $m_{3b}$ ranges from 1 and about 8; and the ratio between the PHF and the antibody is an integer from 2 to about 8 (e.g., from about 2 to about 6 or from about 2 to about 4).

When the PHF in Formula (If) has a molecular weight ranging from about 5 kDa to about 10 kDa, the sum of m, $m_1$, $m_2$, $m_{3a}$ and $m_{3b}$ ranges from about 40 to about 75, $m_1$ is an integer from about 2 to about 35, $m_2$ is an integer from about 2 to about 10, $m_{3a}$ is an integer from 0 to about 4, $m_{3b}$ is an integer from 1 to about 5, the sum of $m_{3a}$ and $m_{3b}$ ranges from 1 and about 5; and the ratio between the PHF and the antibody is an integer from 2 to about 8 (e.g., from about 2 to about 6 or from about 2 to about 4).

In certain embodiments, the ratio between auristatin F hydroxylpropyl amide ("AF HPA") and the antibody can be about 30:1, 29:1, 28:1, 27:1, 26:1, 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1 or 6:1.

In certain embodiments, the ratio between AF HPA and the antibody can be about 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1 or 6:1.

In other embodiments, the ratio between AF HPA and the antibody can be about 20:1, 19:1, 18:1, 17:1, 16:1, 15:1, 14:1, 13:1, 12:1, 11:1, 10:1, 9:1, 8:1, 7:1 or 6:1.

In some embodiments, the ratio between AF HPA and the antibody can be about 16:1, 15:1, 14:1, 13:1, 12:1, 11:1 or 10:1.

In some embodiments, the ratio between AF and the antibody can be about 15:1, 14:1, 13:1, 12:1 or 11:1.

In some embodiments, the ratio between AF HPA and the antibody can be about 15:1, 14:1, 13:1 or 12:1.

In certain embodiments, the ratio between PHF and the antibody can be about 10:1, 9:1, 8:1, 7:1, 6:1, 5:1, 4:1, 3:1, 2:1 or 1:1.

In certain embodiments, the ratio between PHF and the antibody can be about 8:1, 7:1, 6:1, 5:1, 4:1, 3:1 or 2:1.

In other embodiments, the ratio between PHF and the antibody can be about 6:1, 5:1, 4:1, 3:1, 2:1 or 1:1.

In other embodiments, the ratio between PHF and the antibody can be about 6:1, 5:1, 4:1, 3:1 or 2:1.

In other embodiments, the ratio between PHF and the antibody can be about 6:1, 5:1, 4:1 or 3:1.

In some embodiments, the ratio between PHF and the antibody can be about 5:1, 4:1 or 3:1.

In some embodiments, the ratio between PHF and the antibody can be about 4:1, 3:1 or 2:1.

In another aspect, the conjugate described herein is of Formula (Ib):

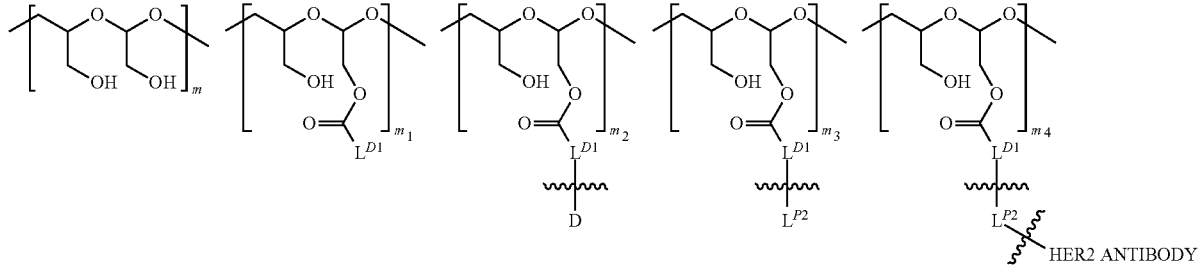

(Ib)

$m_1$, $m_2$, $m_{3a}$ and $m_{3b}$ ranges from about 20 to about 110, $m_1$ is an integer from 2 to about 50, $m_2$ is an integer from 2 to about 15, $m_{3a}$ is an integer from 0 to about 7, $m_{3b}$ is an wherein:
    HER2 ANTIBODY denotes the isolated HER2 antibody or antigen-binding fragment thereof described herein;

between $L^{P2}$ and HER2 ANTIBODY denotes direct or indirect attachment of HER2 ANTIBODY to $L^{P2}$, each occurrence of HER2 ANTIBODY independently has a molecular weight of less than 200 kDa, m is an integer from 1 to about 2200,
$m_1$ is an integer from 1 to about 660,
$m_2$ is an integer from 3 to about 300,
$m_3$ is an integer from 0 to about 110,
$m_4$ is an integer from 1 to about 60; and
the sum of m, $m_1$, $m_2$, $m_3$ and $m_4$ ranges from about 150 to about 2200.

In Formula (Ib), $m_1$ is an integer from about 10 to about 660 (e.g., about 10-250).

When the PHF in Formula (Ib) has a molecular weight ranging from about 50 kDa to about 100 kDa (i.e., the sum of m, $m_1$, $m_2$, $m_3$, and $m_4$ ranging from about 370 to about 740), $m_2$ is an integer from 5 to about 100, $m_3$ is an integer from 1 to about 40, $m_4$ is an integer from 1 to about 20, and/or $m_1$ is an integer from 1 to about 220 (e.g., $m_1$ being about 15-80).

In Formula (Ib), each HER2 ANTIBODY independently has a molecular weight of 120 kDa or less, 80 kDa or less, 70 kDa or less, 60 kDa or less, 50 kDa or less, 40 kDa or less, 30 kDa or less, 20 kDa or less or 10 kDa or less, or about 4 kDa to 80 kDa (e.g., 4-20 kDa, 20-30 kDa, or 30-70 kDa).

Another aspect of the invention features a method of preparing a conjugate described herein. The method includes reacting the isolated antibody or antigen-binding fragment thereof with a polymeric scaffold of Formula (Ia) such that the conjugate is formed:

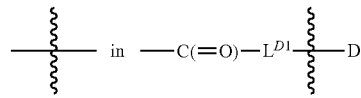

between $L^{D1}$ and D denotes direct or indirect attachment of D to $L^{D1}$;

each occurrence of

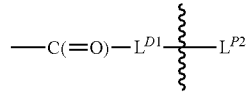

is independently a second linker not yet connected to the isolated antibody or antigen-binding fragment thereof, in which $L^{P2}$ is a moiety containing a functional group that is yet to form a covalent bond with a functional group of the isolated antibody or antigen-binding fragment thereof, and the

between $L^{D1}$ and $L^{P2}$ denotes direct or indirect attachment of $L^{P2}$ to $L^{D1}$, and each occurrence of the second linker is distinct from each occurrence of the first linker;

m is an integer from 1 to about 300,
$m_1$ is an integer from 1 to about 140,
$m_2$ is an integer from 1 to about 40,
$m_3$ is an integer from 1 to about 18, and

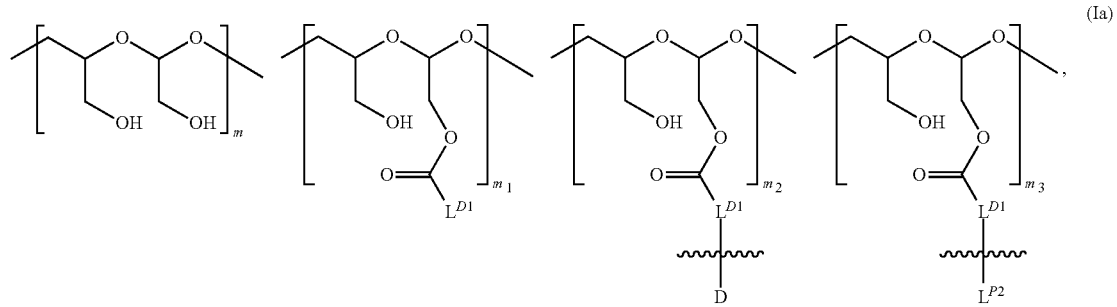

wherein:

$L^{D1}$ is a carbonyl-containing moiety;

each occurrence of

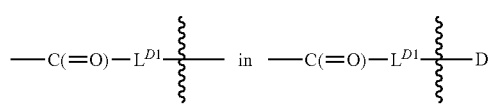

is independently a first linker that contains a biodegradable bond so that when the bond is broken, D is released in an active form for its intended therapeutic effect; and the the sum of m, $m_1$, $m_2$ and $m_3$ ranges from about 15 to about 300.

In the formulae for polymeric scaffolds disclosed herein, the disconnection or gap between the polyacetal units indicates that the units can be connected to each other in any order. In other words, the appending groups that contain, e.g., D, $L^{P2}$, and the isolated antibody or antigen-binding fragment thereof, can be randomly distributed along the polymer backbone.

The present invention also provides methods of treating, preventing, delaying the progression of or otherwise ameliorating a symptom of one or more pathologies associated with aberrant HER2 expression, function and/or activation or alleviating a symptom associated with such pathologies, by administering a monoclonal antibody, fragment thereof, and/or conjugate thereof disclosed herein to a subject in which such treatment or prevention is desired. The subject to be treated is, e.g., human. The monoclonal antibody, fragment thereof, and/or conjugate thereof is administered in an amount sufficient to treat, prevent or alleviate a symptom associated with the pathology.

The present invention also provides methods of treating, preventing, delaying the progression of or otherwise ameliorating a symptom of one or more pathologies associated with HER2 expression, function and/or activation or alleviating a symptom associated with such pathologies, by administering a monoclonal antibody, fragment thereof, and/or conjugate thereof disclosed herein to a subject in which such treatment or prevention is desired. The subject to be treated is, e.g., human. The monoclonal antibody, fragment thereof, and/or conjugate thereof is administered in an amount sufficient to treat, prevent or alleviate a symptom associated with the pathology.

Pathologies treated and/or prevented using the monoclonal antibodies, fragments thereof, and/or conjugates thereof disclosed herein include, for example, a cancer. For example, the antibodies, fragments thereof, and/or conjugates thereof disclosed herein are useful in treating, preventing, delaying the progression of or otherwise ameliorating a symptom of a cancer selected from the group consisting of anal cancer, astrocytoma, leukemia, lymphoma, head and neck cancer, liver cancer, testicular cancer, cervical cancer, sarcoma, hemangioma, esophageal cancer, eye cancer, laryngeal cancer, mouth cancer, mesothelioma, skin cancer, myeloma, oral cancer, rectal cancer, throat cancer, bladder cancer, breast cancer, uterine cancer, ovarian cancer, prostate cancer, lung cancer, non-small cell lung cancer (NSCLC), colon cancer, pancreatic cancer, renal cancer, and gastric cancer.

In some embodiments, the antibodies or antigen binding fragments thereof and/or PBRM-polymer-drug conjugates thereof disclosed herein are useful in treating, preventing, the delaying the progression of or otherwise ameliorating a symptom of breast cancer.

In some embodiments, the antibodies or antigen binding fragments thereof and/or PBRM-polymer-drug conjugates thereof disclosed herein are useful in treating, preventing, the delaying the progression of or otherwise ameliorating a symptom of gastric cancer.

In some embodiments, the antibodies or antigen binding fragments thereof and/or PBRM-polymer-drug conjugates thereof disclosed herein are useful in treating, preventing, the delaying the progression of or otherwise ameliorating a symptom of non-small cell lung cancer (NSCLC).

In some embodiments, the antibodies or antigen binding fragments thereof and/or PBRM-polymer-drug conjugates thereof disclosed herein are useful in treating, preventing, the delaying the progression of or otherwise ameliorating a symptom of ovarian cancer.

In some embodiments, the Her2 antibody or antigen binding fragment thereof used in treating, preventing, delaying the progression of or otherwise ameliorating a symptom of a cancer (e.g., a cancer selected from the group consisting of anal cancer, astrocytoma, leukemia, lymphoma, head and neck cancer, liver cancer, testicular cancer, cervical cancer, sarcoma, hemangioma, esophageal cancer, eye cancer, laryngeal cancer, mouth cancer, mesothelioma, skin cancer, myeloma, oral cancer, rectal cancer, throat cancer, bladder cancer, breast cancer, uterine cancer, ovarian cancer, prostate cancer, lung cancer, non-small cell lung cancer (NSCLC), colon cancer, pancreatic cancer, renal cancer, and gastric cancer) competes for binding to the same epitope of Her-2 with an antibody comprising (1) heavy chain variable region CDRH1 comprising the amino acid sequence FTFSSYSMN (SEQ ID NO: 25); CDRH2 comprising the amino acid sequence YISSSSSTIYYADSVKG (SEQ ID NO: 26); CDRH3 comprising the amino acid sequence GGHGYFDL (SEQ ID NO: 27); and light chain variable region CDRL1 comprising the amino acid sequence RASQSVSSSYLA (SEQ ID NO: 28); CDRL2 comprising the amino acid sequence GASSRAT (SEQ ID NO: 21) and CDRL3 comprising the amino acid sequence QQYHHSPLT (SEQ ID NO: 29); (2) heavy chain variable region CDRH1 comprising the amino acid sequence FTFSGRSMN (SEQ ID NO: 30); CDRH2 comprising the amino acid sequence YISSDSRTIYYADSVKG (SEQ ID NO: 31); CDRH3 comprising the amino acid sequence GGHGYFDL (SEQ ID NO: 27); light chain variable region CDRL1 comprising the amino acid sequence RASQSVSSSYLA (SEQ ID NO: 28); CDRL2 comprising the amino acid sequence GASSRAT (SEQ ID NO: 21); and CDRL3 comprising the amino acid sequence QQYHHSPLT (SEQ ID NO: 29); (3) heavy chain variable region CDRH1 comprising the amino acid sequence FTFSSYGMH (SEQ ID NO: 17); CDRH2 comprising the amino acid sequence VIWYDGSNKYYADSVKG (SEQ ID NO: 18); CDRH3 comprising the amino acid sequence EAPYYAKDYMDV (SEQ ID NO: 19), and light chain variable region CDRL1 comprising the amino acid sequence RASQSVSSDYLA (SEQ ID NO: 20); CDRL2 comprising the amino acid sequence GASSRAT (SEQ ID NO: 21); and CDRL3 comprising the amino acid sequence QQYVSYWT (SEQ ID NO: 22); or (4) heavy chain variable region CDRH1 comprising the amino acid sequence FTFSSYGMH (SEQ ID NO: 17); CDRH2 comprising the amino acid sequence GIWWDGSNEKYADSVKG (SEQ ID NO: 23); CDRH3 comprising the amino acid sequence EAPYYAKDYMDV (SEQ ID NO: 19); and light chain variable region CDRL1 comprising the amino acid sequence RASQSVSSDYLA (SEQ ID NO: 20); CDRL2 comprising the amino acid sequence GASRRAT (SEQ ID NO: 24); and CDRL3 comprising the amino acid sequence QQYVSYWT (SEQ ID NO: 22).

In another embodiment, the Her2 antibody or antigen binding fragment thereof used in treating, preventing, delaying the progression of or otherwise ameliorating a symptom of a cancer (e.g., a cancer selected from the group consisting of anal cancer, astrocytoma, leukemia, lymphoma, head and neck cancer, liver cancer, testicular cancer, cervical cancer, sarcoma, hemangioma, esophageal cancer, eye cancer, laryngeal cancer, mouth cancer, mesothelioma, skin cancer, myeloma, oral cancer, rectal cancer, throat cancer, bladder cancer, breast cancer, uterine cancer, ovarian cancer, prostate cancer, lung cancer, non-small cell lung cancer (NSCLC), colon cancer, pancreatic cancer, renal cancer, and gastric cancer) competes for binding to the same epitope of Her-2 with an antibody comprising (1) heavy chain variable region CDRH1 comprising the amino acid sequence FTFSSYSMN (SEQ ID NO: 25); CDRH2 comprising the amino acid sequence YISSSSSTIYYADSVKG (SEQ ID NO: 26); CDRH3 comprising the amino acid sequence GGHGYFDL (SEQ ID NO: 27); and light chain variable region CDRL1 comprising the amino acid sequence RASQSVSSSYLA (SEQ ID NO: 28); CDRL2 comprising the amino acid sequence GASSRAT (SEQ ID NO: 21) and CDRL3 comprising the amino acid sequence QQYHHSPLT (SEQ ID NO: 29); (2) heavy chain variable region CDRH1 comprising the amino acid sequence FTFSGRSMN (SEQ ID NO: 30); CDRH2 comprising the amino acid sequence YISSDSRTIYYADSVKG (SEQ ID NO: 31); CDRH3 comprising the amino acid sequence GGHGYFDL (SEQ ID NO: 27); light chain variable region CDRL1 comprising the amino acid sequence RASQSVSSSYLA (SEQ ID NO: 28); CDRL2 comprising the amino acid sequence GASSRAT (SEQ ID NO: 21); and CDRL3 comprising the amino acid sequence QQYHHSPLT (SEQ ID NO: 29); (3) heavy chain variable region CDRH1 comprising the amino acid sequence FTFSSYGMH (SEQ ID NO: 17); CDRH2 comprising the amino acid sequence VIWYDGSNKYYADSVKG (SEQ ID NO: 18); CDRH3 comprising the amino acid sequence EAPYYAKDYMDV (SEQ ID NO: 19), and light chain variable region CDRL1 comprising the amino acid sequence RASQSVSSDYLA (SEQ ID NO: 20); CDRL2 comprising the amino acid sequence GASSRAT (SEQ ID NO: 21); and CDRL3 comprising the amino acid sequence QQYVSYWT (SEQ ID NO: 22); or (4) heavy chain variable region CDRH1 comprising the amino acid sequence FTFSSYGMH (SEQ ID NO: 17); CDRH2 comprising the amino acid sequence GIWWDGSNEKYADSVKG (SEQ ID NO: 23); CDRH3 comprising the amino acid sequence EAPYYAKDYMDV (SEQ ID NO: 19); and light chain variable region CDRL1 comprising the amino acid sequence RASQSVSSDYLA (SEQ ID NO: 20); CDRL2 comprising the amino acid sequence GASRRAT (SEQ ID NO: 24); and CDRL3 comprising the amino acid sequence QQYVSYWT (SEQ ID NO: 22), wherein the Her2 antibody or antigen binding fragment thereof is conjugated directly or indirectly with at least one therapeutic agent, wherein the therapeutic agent is a small molecule having a molecular weight≤about 5 kDa, ≤about 4 kDa, ≤about 3 kDa, ≤about 1.5 kDa, or ≤about 1 kDa. The invention also provides kits and/or methods for identifying or otherwise refining, e.g., stratifying, a patient population suitable for therapeutic administration of a HER2 antibody or antigen binding fragment thereof and/or PBRM-polymer-drug conjugates thereof disclosed herein by identifying patients having low expression of HER2 prior to treatment with a HER2 antibody or antigen binding fragment thereof, and/or conjugates thereof disclosed herein. Low HER2 expression represents those patients having less than or equal to 100,000, less than or equal to 90,000, or less than or equal to 80,000 HER2 molecules per cell, for example, as measured per cell in a test cell population. The level of HER2 expression, i.e., number of HER2 molecules per cell, can be measured using any art-recognized method, including, but not limited to using the cell-based viability assays shown in the working examples provided herein (see e.g., Example 18).

The invention also provides kits and/or methods for identifying or otherwise refining, e.g., stratifying, a patient population suitable for therapeutic administration of a HER2 antibody or antigen binding fragment thereof, and/or conjugates thereof disclosed herein by identifying the HER2 score of subject prior to treatment with a HER2 antibody or antigen binding fragment thereof, and/or conjugates thereof disclosed herein. In some embodiments, the subject is identified as having a scoring of 1+ or 2+ for HER2 expression. In some embodiments, the subject is identified as having a scoring of 1+ or 2+ for HER2 expression as detected by immunohistochemistry (IHC) analysis performed on a test cell population, and wherein the HER2 gene is not amplified in the test cell population. In some embodiments, the test cell population is derived from fresh, unfrozen tissue from a biopsy sample. In some embodiments, the test cell population is derived from a frozen tissue from a biopsy sample.

The IHC test measures the amount of HER2 receptor protein on the surface of cells in a cancer tissue sample, e.g., a breast cancer tissue sample or a gastric cancer sample, and assigns the detected level of cell surface HER2 receptor a HER2 score of 0, 1+, 2+ or 3+. If the subject's HER2 score is in the range of 0 to 1+, the cancer is deemed to be "HER2 negative." If the score is 2+, the cancer is referred to as "borderline," and a score of 3+ signifies that the cancer is "HER2 positive."

In some embodiments, the subject is identified as having a scoring of 1+ or 2+ for HER2 expression and is refractory to chemotherapy, including standard, front-line chemotherapeutic agents. As used herein, the term subject includes humans and other mammals. In some embodiments, the subject is identified as having a scoring of 1+ or 2+ for HER2 expression and is suffering from breast cancer, gastric cancer, non-small cell lung cancer (NSCLC), or ovarian cancer.

In some embodiments, the antibodies or antigen binding fragments thereof and/or PBRM-polymer-drug conjugates disclosed herein are useful in treating, preventing, the delaying the progression of or otherwise ameliorating a symptom of breast cancer in patients who have HER2 IHC 1+ or HER2 IHC 2+ without gene amplification, e.g., FISH− (or fluorescence in situ hybridization negative).

In some embodiments, the antibodies or antigen binding fragments thereof and/or PBRM-polymer-drug conjugates disclosed herein are useful in treating, preventing, the delaying the progression of or otherwise ameliorating a symptom of breast cancer in patients who have advanced HER2 positive breast cancer and who have received prior treatment with Kadcyla.

In some embodiments, the antibodies or antigen binding fragments thereof and/or PBRM-polymer-drug conjugates disclosed herein are useful in treating, preventing, the delaying the progression of or otherwise ameliorating a symptom of breast cancer in patients who have advanced HER2 positive breast cancer and who have not previously received prior treatment with Kadcyla.

In some embodiments, the antibodies or antigen binding fragments thereof and/or PBRM-polymer-drug conjugates disclosed herein are useful in treating, preventing, the delaying the progression of or otherwise ameliorating a symptom of gastric cancer in patients who have HER2 IHC 1+ or HER2 IHC 2+ without gene amplification, e.g., FISH−.

In some embodiments, the antibodies or antigen binding fragments thereof and/or PBRM-polymer-drug conjugates disclosed herein are useful in treating, preventing, the delaying the progression of or otherwise ameliorating a symptom of non-small cell lung cancer (NSCLC) in patients who have HER2 IHC 2+, HER2 IHC 3+, any HER2 gene amplification or mutation status.

In some embodiments, the subject is refractory to chemotherapy, including standard, front-line chemotherapeutic agents. In some embodiments, the subject is resistant to treatment with Kadcyla.

A HER2 antibody or antigen binding fragment thereof and/or conjugated HER2 antibody or antigen binding fragment thereof used in any of the embodiments of the methods and uses provided herein can be administered at any stage of the disease. For example, such a HER2 antibody and/or conjugated HER2 antibody can be administered to a patient suffering cancer of any stage, from early to metastatic.

A HER2 antibody and/or conjugated HER2 antibody used in any of the embodiments of these methods and uses can be administered either alone or in combination with one or more chemotherapeutic agents or other agents. In some embodiments, the agent is any of the toxins described herein. In some embodiments, the agent is (1) HER2 inhibitors, (2) EGFR inhibitors (e.g., tyrosine kinase inhibitors or targeted anti-EGFR antibodies), (3) BRAF inhibitors, (4) ALK inhibitors, (5) hormone receptor inhibitors, (6) mTOR inhibitors, (7) VEGF inhibitors, or (8) cancer vaccines. In some embodiments, the agent is a standard, first line chemotherapeutic agent, such as, for example, trastuzumab, pertuzumab, ado-trastuzumab emtansine (Kadcyla), lapatinib, anastrozole, letrozole, exemestane, everolimus, fulvestrant, tamoxifen, toremifene, megestrol acetate, fluoxymesterone, ethinyl estradiol, paclitaxel, capecitabine, gemcitabine, eribulin, vinorelbine, cyclophosphamide, carboplatin, docetaxel, albumin-bound paclitaxel, cisplatin, epirubicin, ixabepilone, doxorubicin, fluorouracil, oxaliplatin, fluoropyrimidine, irinotecan, ramucirumab, mitomycin, leucovorin, cetuximab, bevacizumab, erlotinib, afatinib, crizotinib, permetrexed, ceritinib, etoposide, vinblastine, vincristine, ifosfamid, liposomal doxorubicin, topotecan, altretamine, melphalan or leuprolide acetate. In some embodiments, the second agent is Kadcyla.

In some embodiments, the agent is at least a second antibody or antigen binding fragment thereof that specifically binds HER2. In some embodiments, the HER2 antibody and/or conjugated HER2 antibody are administered in combination with a HER2 antibody, a HER2 dimerization inhibitor antibody or a combination of a HER2 antibody and a HER2 dimerization inhibitor antibody, such as, for example, trastuzumab or pertuzumab or a combination thereof. In some embodiments, the HER2 antibody and/or conjugated HER2 antibody are administered in combination with a biosimilar of trastuzumab or a biosimilar of pertuzumab or a combination thereof.

These combinations of HER2 antibodies and/or conjugated HER2 antibodies are useful in treating pathologies such as, for example, a cancer. For example, these combinations of HER2 antibodies and/or conjugated HER2 antibodies, e.g., a HER2 antibody or antigen binding fragment thereof and/or conjugated HER2 antibodies (e.g., HER2 antibody-polymer-drug conjugates) disclosed herein in combination with trastuzumab, pertuzumab or both trastuzumab and pertuzumab or a biosimilar of trastuzumab, a biosimilar of pertuzumab or both biosimilars, are useful in treating, preventing, delaying the progression of or otherwise ameliorating a symptom of a cancer (e.g., a cancer selected from the group consisting of anal cancer, astrocytoma, leukemia, lymphoma, head and neck cancer, liver cancer, testicular cancer, cervical cancer, sarcoma, hemangioma, esophageal cancer, eye cancer, laryngeal cancer, mouth cancer, mesothelioma, skin cancer, myeloma, oral cancer, rectal cancer, throat cancer, bladder cancer, breast cancer, uterine cancer, ovarian cancer, prostate cancer, lung cancer, non-small cell lung cancer (NSCLC), colon cancer, pancreatic cancer, renal cancer, and gastric cancer).

These combinations are also useful for increasing the degradation of HER2 when a HER2-expressing cell is contacted with these combinations. The level of HER2 degradation is detected using any art-recognized method for detecting HER2 degradation, including, but not limited to detecting levels of HER2 degradation in the presence and absence of a combination of HER2 antibodies (or biosimilars thereof) as shown in the working examples provided herein (see e.g., Example 14). For example, the level of HER2 degradation is determined using western analysis of the lysates of HER2-expressing cells that have been treated with a combination of HER2 antibodies, as compared to the level of HER2 degradation in HER2-expressing cells that have not been treated with a combination of HER2 antibodies.

In some embodiments, the HER2 antibody and/or conjugated HER2 antibody and additional agent(s) are formulated into a single therapeutic composition, and the HER2 antibody and/or conjugated HER2 antibody and additional agent are administered simultaneously. Alternatively, the HER2 antibody and/or conjugated HER2 antibody and additional agent are separate from each other, e.g., each is formulated into a separate therapeutic composition, and HER2 antibody and/or conjugated HER2 antibody and the additional agent are administered simultaneously, or HER2 antibody and/or conjugated HER2 antibody and the additional agent are administered at different times during a treatment regimen. For example, the HER2 antibody and/or conjugated HER2 antibody is administered prior to the administration of the additional agent, the HER2 antibody and/or conjugated HER2 antibody is administered subsequent to the administration of the additional agent, or the HER2 antibody and/or conjugated HER2 antibody and the additional agent are administered in an alternating fashion. As described herein, the HER2 antibody and/or conjugated HER2 antibody and additional agent are administered in single doses or in multiple doses.

Pharmaceutical compositions according to the invention can include an antibody, fragment thereof, and/or conjugate thereof disclosed herein and a suitable carrier. These pharmaceutical compositions can be included in kits, such as, for example, diagnostic kits.

One skilled in the art will appreciate that the antibodies disclosed herein have a variety of uses. For example, the proteins disclosed herein are used as therapeutic agents. The antibodies disclosed herein are also used as reagents in diagnostic kits or as diagnostic tools, or these antibodies can be used in competition assays to generate therapeutic reagents.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. In the case of conflict, the present specification, including definitions, will control. In addition, the materials, methods and examples are illustrative only and are not intended to be limiting.

Other features and advantages of the invention will be apparent from the following detailed description and claims.

BRIEF DESCRIPTION OF THE FIGURES

FIG. 1a shows the epitope binning for the antibodies XMT 1517 and XMT 1518 by Octet Red384 Epitope Binning.

FIG. 1b shows the epitope binning for the antibodies XMT 1519 and XMT 1520 by Octet Red384 Epitope Binning.

FIG. 3b shows binding affinities of antibodies XMT 1519, XMT 1520 to recombinant human HER2 and cynomolgus monkey HER2.

FIG. 20 illustrates the anti-tumor efficacy of Kadcyla, Example 16H, XMT 1519-(EG2-MI-(10 kDa PHF-BA-(AF-HPA-Ala))) and Example 17C, rituximab-(EG2-MI-(10 kDa PHF-BA-(AF-HPA-Ala))) as measured in a BT474 mouse tumor xenograft model.

DETAILED DESCRIPTION

Figure 2:
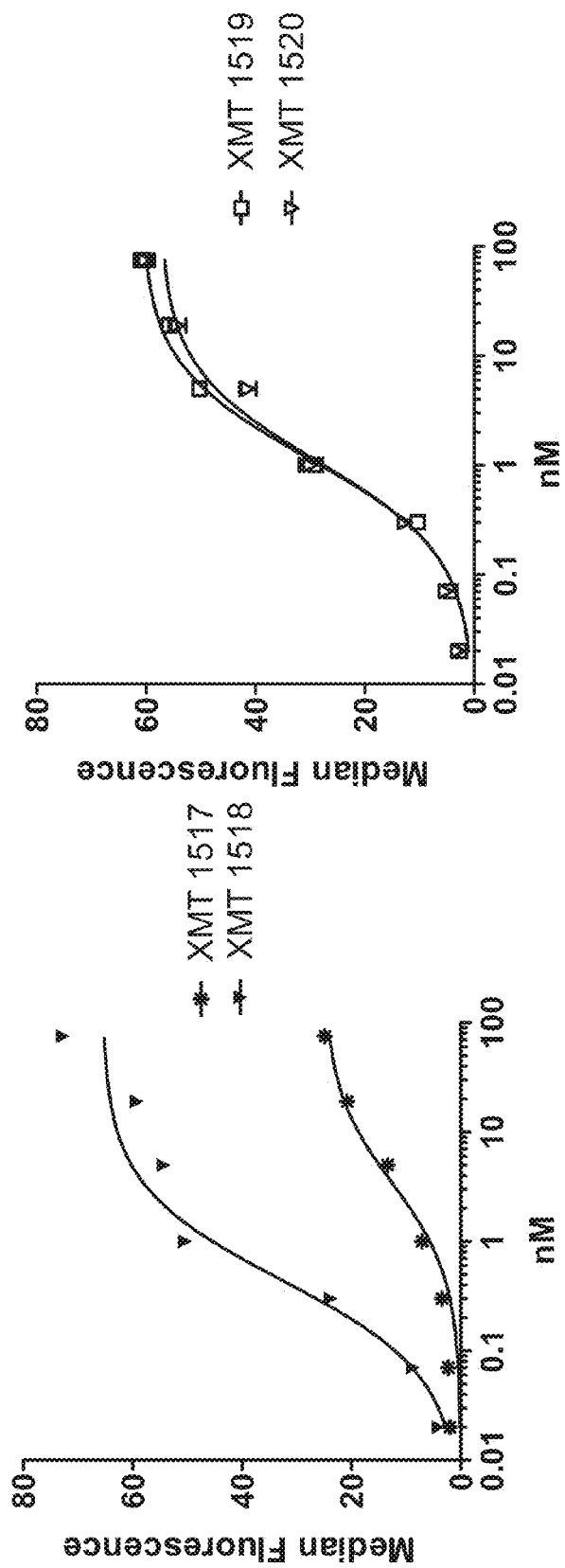
FIG. 2 shows the cell surface binding of antibodies XMT 1517, XMT 1518, XMT 1519 and XMT 1520 to JIMT-1 cells.

The present invention provides monoclonal antibodies that specifically bind the human HER2 in soluble form, or membrane bound (i.e., when expressed on a cell surface). The invention further provides monoclonal antibodies that specifically bind HER2. HER2. These antibodies are collectively referred to herein as "HER2" antibodies.

The antibodies of the present invention bind to a HER2 epitope with an equilibrium dissociation constant ($K_d$ or $K_D$) of ≤1 µM, e.g., 100 nM, preferably 10 nM, and more preferably ≤1 nM. For example, the HER2 antibodies provided herein exhibit a $K_d$ in the range approximately between ≤1 nM to about 1 pM.

The HER2 antibodies disclosed herein serve to modulate, block, inhibit, reduce, antagonize, neutralize or otherwise interfere with the functional activity of HER2. HER2. Functional activities of HER2 include for example, modulation of PI3K-Akt pathway activity. For example, the HER2 antibodies completely or partially inhibit HER2 functional activity by partially or completely modulating, blocking, inhibiting, reducing antagonizing, neutralizing, or otherwise interfering with PI3K-Akt pathway activity. PI3K-Akt pathway activity is assessed using any art-recognized method for detecting PI3K-Akt pathway activity, including, but not limited to detecting levels of phosphorylated Akt in the presence and absence of an antibody or antigen binding fragment disclosed herein.

The HER2 antibodies are considered to completely modulate, block, inhibit, reduce, antagonize, neutralize or otherwise interfere with HER2 functional activity when the level of HER2 functional activity in the presence of the HER2 antibody is decreased by at least 95%, e.g., by 96%, 97%, 98%, 99% or 100% as compared to the level of HER2 functional activity in the absence of binding with a HER2 antibody described herein. The HER2 antibodies are considered to partially modulate, block, inhibit, reduce, antagonize, neutralize or otherwise interfere with HER2 functional activity when the level of HER2 activity in the presence of the HER2 antibody is decreased by less than 95%, e.g., 10%, 20%, 25%, 30%, 40%, 50%, 60%, 75%, 80%, 85% or 90% as compared to the level of HER2 activity in the absence of binding with a HER2 antibody described herein.

DEFINITIONS

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the terms "HER2" (also known as ErbB-2, NEU, HER-2, and CD340), when used herein, refers to human epidermal growth factor receptor 2 (SwissProt P04626) and includes any variants, isoforms and species homologs of HER2 which are naturally expressed by cells, including tumor cells, or are expressed on cells transfected with the HER2 gene. Species homologs include rhesus monkey HER2 (macaca mulatta; Genbank accession No. GI:109114897). These terms are synonymous and may be used interchangeably.

As used herein, the term "HER2 antibody" or "anti-HER2 antibody" is an antibody which binds specifically to the antigen HER2.

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" "or directed against" is meant that the antibody reacts with one or more antigenic determinants of the desired antigen and does not react with other polypeptides or binds at much lower affinity ($K_d > 10^{-6}$). Antibodies include, but are not limited to, polyclonal, monoclonal, chimeric, dAb (domain antibody), single chain, $F_{ab}$, $F_{ab'}$ and $F_{(ab')2}$ fragments, scFvs, and an $F_{ab}$ expression library.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "monoclonal antibody" (mAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. mAbs contain an antigen binding site capable of immunoreacting with a particular epitope of the antigen characterized by a unique binding affinity for it.

In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

The terms "fragment," "antibody fragment," "antigen-binding fragment," and "antigen binding fragment" are used As used interchangeably herein, unless otherwise specified.

As used herein, the term "epitope" includes any protein determinant capable of specific binding to an immunoglobulin or fragment thereof, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is $\leq 1$ µM; e.g., $\leq 100$ nM, preferably $\leq 10$ nM and more preferably $\leq 1$ nM.

When used herein in the context of two or more antibodies, the term "competes with" or "cross-competes with" indicates that the two or more antibodies compete for binding to HER2, e.g., compete for HER2 binding in the assay described in Examples 5 or 8. An antibody "blocks" or "cross-blocks" one or more other antibodies from binding to HER2 if the antibody competes with the one or more other antibodies 25% or more, with 25%-74% representing "partial block" and 75%-400% representing "full block", preferably as determined using the assay of Examples 5 and 8. For some pairs of antibodies, competition or blocking in the assay of the Examples 5 or 8 is only observed when one antibody is coated on the plate and the other is used to compete, and not vice versa. Unless otherwise defined or negated by context, the terms "competes with", "cross-competes with", "blocks" or "cross-blocks" when used herein is also intended to cover such pairs of antibodies.

As used herein an antibody which "inhibits HER dimerization" shall mean an antibody which inhibits, or interferes with, formation of a HER dimer. Preferably, such an antibody binds to HER2 at the heterodimeric binding site thereof. In one embodiment the dimerization inhibiting antibody herein is pertuzumab or MAb 2C4. Other examples of antibodies which inhibit HER dimerization include antibodies which bind to EGFR and inhibit dimerization thereof with one or more other HER receptors, such as, for example EGFR monoclonal antibody 806, MAb 806, which binds to activated or "untethered" EGFR (see Johns et al., J. Biol. Chem. 279(29):30375-30384 (2004)); antibodies which bind to HER3 and inhibit dimerization thereof with one or more other HER receptors; and antibodies which bind to HER4 and inhibit dimerization thereof with one or more other HER receptors.

The term "HER2 dimerization inhibitor" as used herein shall mean an agent that inhibits formation of a dimer or heterodimer comprising HER2.

As used herein, the term "internalization", when used in the context of a HER2 antibody includes any mechanism by which the antibody is internalized into a HER2-expressing cell from the cell-surface and/or from surrounding medium, e.g., via endocytosis.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to HER2, when the equilibrium dissociation constant ($K_d$ or $K_D$) is ≤1 µM, preferably ≤100 nM, more preferably ≤10 nM, and most preferably ≤100 pM to about 1 pM, as measured by assays such as radioligand binding assays or similar assays known to those skilled in the art.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence. Polynucleotides in accordance with the invention include the nucleic acid sequences of SEQ ID NOs: 34 and 36, as well as nucleic acid molecules encoding the heavy chain immunoglobulin molecules presented in SEQ ID NOs: 1, 3, 5, and 7, and the nucleic acid sequences of SEQ ID NOs: 35 and 37, as well as nucleic acid molecules encoding the light chain immunoglobulin molecules represented in SEQ ID NOs: 2, 4, 6, and 8.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Polypeptides in accordance with the invention comprise the heavy chain immunoglobulin molecules represented in SEQ ID NOs: 1, 3, 5, and 7, and the light chain immunoglobulin molecules represented in SEQ ID NOs: 2, 4, 6, and 8 as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences which are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means a polymeric boron of nucleotides of at least 10 bases in length, either ribonucleotides or deoxyribonucleotides or a modified form of either type of nucleotide. The term includes single and double stranded forms of DNA.

The term "oligonucleotide" referred to herein includes naturally occurring, and modified nucleotides linked together by naturally occurring, and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g., for probes, although oligonucleotides may be double stranded, e.g., for use in the construction of a gene mutant. Oligonucleotides disclosed herein are either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes Oligonucleotides linkages such as phosphorothioate, phosphorodithioate, phosphoroselerloate, phosphorodiselenoate, phosphoroanilothioate, phoshoraniladate, phosphoronmidate, and the like. See e.g., LaPlanche et al. Nucl. Acids Res. 14:9081 (1986); Stec et al. J. Am. Chem. Soc. 106:6077 (1984), Stein et al. Nucl. Acids Res. 16:3209 (1988), Zon et al. Anti Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990). An oligonucleotide can include a label for detection, if desired.

The term "selectively hybridize" referred to herein means to detectably and specifically bind. Polynucleotides, oligonucleotides and fragments thereof in accordance with the invention selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments disclosed herein and a nucleic acid sequence of interest will be at least 80%, and more typically with preferably increasing homologies of at least 85%, 90%, 95%, 99%, and 100%. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M.O., in Atlas of Protein Sequence and Structure, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program. The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman Adv. Appl. Math. 2:482 (1981), by the homology alignment algorithm of Needleman and Wunsch J. Mol. Biol. 48:443 (1970), by the search for similarity method of Pearson and Lipman Proc. Natl. Acad. Sci. (U.S.A.) 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages), or by inspection, and the best alignment (i.e., resulting in the highest percentage of homology over the comparison window) generated by the various methods is selected.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See Immunology—A Synthesis (2nd Edition, E. S. Golub and D. R. Gren, Eds., Sinauer Associates, Sunderland7 Mass. (1991)). Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end the left-hand direction of double-stranded polynucleotide sequences is referred to as the 5' direction. The direction of 5' to 3' addition of nascent RNA transcripts is referred to as the transcription direction sequence regions on the DNA strand having the same sequence as the RNA and which are 5' to the 5' end of the RNA transcript are referred to as "upstream sequences", sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity.

Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991).

The term "polypeptide fragment" as used herein refers to a polypeptide that has an amino terminal and/or carboxy-terminal deletion, but where the remaining amino acid sequence is identical to the corresponding positions in the naturally-occurring sequence deduced, for example, from a full length cDNA sequence. Fragments typically are at least 5, 6, 8 or 10 amino acids long, preferably at least 14 amino acids long' more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence and which has specific binding to HER2 under suitable binding conditions. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

Peptide analogs are commonly used in the pharmaceutical industry as non-peptide drugs with properties analogous to those of the template peptide. These types of non-peptide compound are termed "peptide mimetics" or "peptidomimetics". Fauchere, J. Adv. Drug Res. 15:29 (1986), Veber and Freidinger TINS p.392 (1985); and Evans et al. J. Med. Chem. 30:1229 (1987). Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: $-CH_2NH-$, $-CH_2S-$, $-CH_2-CH_2-$, $-CH=CH-$(cis and trans), $-COCH_2-$, $CH(OH)CH_2-$, and $-CH_2SO-$, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch Ann. Rev. Biochem. 61:387 (1992)); for example, by adding internal cysteine residues capable of forming intramolecular disulfide bridges which cyclize the peptide.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{131}I$), fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

Other chemistry terms herein are used according to conventional usage in the art, as exemplified by The McGraw-Hill Dictionary of Chemical Terms (Parker, S., Ed., McGraw-Hill, San Francisco (1985)).

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present.

Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The use of the articles "a", "an", and "the" in both the following description and claims are to be construed to cover both the singular and the plural, unless otherwise indicated herein or clearly contradicted by context. The terms "comprising", "having", "being of" as in "being of a chemical formula", "including", and "containing" are to be construed as open terms (i.e., meaning "including but not limited to") unless otherwise noted. For example, a polymeric scaffold of a certain formula includes all the monomer units shown in the formula and may also include additional monomer units not shown in the formula. Additionally whenever "comprising" or another open-ended term is used in an embodiment, it is to be understood that the same embodiment can be more narrowly claimed using the intermediate term "consisting essentially of" or the closed term "consisting of."

The term "about", "approximately", or "approximate", when used in connection with a numerical value, means that a collection or range of values is included. For example, "about X" includes a range of values that are ±20%, ±10%, ±5%, ±2%, ±1%, ±0.5%, ±0.2%, or ±0.1% of X, where X is a numerical value. In one embodiment, the term "about" refers to a range of values which are 5% more or less than the specified value. In another embodiment, the term "about" refers to a range of values which are 2% more or less than the specified value. In another embodiment, the term "about" refers to a range of values which are 1% more or less than the specified value.

Recitation of ranges of values are merely intended to serve as a shorthand method of referring individually to each separate value falling within the range, unless otherwise indicated herein, and each separate value is incorporated into the specification as if it were individually recited herein. A range used herein, unless otherwise specified, includes the two limits of the range. For example, the expressions "x being an integer between 1 and 6" and "x being an integer of 1 to 6" both mean "x being 1, 2, 3, 4, 5, or 6", i.e., the terms "between X and Y" and "range from X to Y, are inclusive of X and Y and the integers there between.

All methods described herein can be performed in any suitable order unless otherwise indicated herein or otherwise clearly contradicted by context. The use of any and all examples, or exemplary language (e.g., "such as") provided herein, is intended merely to better illustrate the invention and is not to be construed as a limitation on the scope of the claims unless explicitly otherwise claimed. No language in the specification is to be construed as indicating that any non-claimed element is essential to what is claimed.

"Protein based recognition-molecule" or "PBRM" refers to a molecule that recognizes and binds to a cell surface marker or receptor such as, a transmembrane protein, surface immobilized protein, or protoglycan. Examples of PBRMs include but are not limited to, the XMT 1517 antibody, the XMT 1518 antibody, the XMT 1519 antibody and the XMT 1520 antibody described herein, as we all as other antibodies (e.g., Trastuzumab, Cetuximab, Rituximab, Bevacizumab, Epratuzumab, Veltuzumab, Labetuzumab, B7-H4, B7-H3, CAl25, CD33, CXCR2, EGFR, FGFR1, FGFR2, FGFR3, FGFR4, HER2, NaPi2b, c-Met, MUC-1, NOTCH1, NOTCH2, NOTCH3, NOTCH4, PD-L1-and-anti-5T4), and antibodies or antigen binding fragments thereof described herein) or peptides (LHRH receptor targeting peptides, EC-1 peptide), lipocalins, such as, for example, anticalins, proteins such as, for example, interferons, lymphokines, growth factors, colony stimulating factors, and the like, peptides or peptide mimics, and the like. The protein based recognition molecule, in addition to targeting the modified polymer conjugate to a specific cell, tissue or location, may also have certain therapeutic effect such as antiproliferative (cytostatic and/or cytotoxic) activity against a target cell or pathway. The protein based recognition molecule comprises or may be engineered to comprise at least one chemically reactive group such as, —COOH, primary amine, secondary amine —NHR, —SH, or a chemically reactive amino acid moiety or side chains such as, for example, tyrosine, histidine, cysteine, or lysine.

"Biocompatible" as used herein is intended to describe compounds that exert minimal destructive or host response effects while in contact with body fluids or living cells or tissues. Thus a biocompatible group, as used herein, refers to an aliphatic, cycloalkyl, heteroaliphatic, heterocycloalkyl, aryl, or heteroaryl moiety, which falls within the definition of the term biocompatible, as defined above and herein. The term "Biocompatibility" as used herein, is also taken to mean that the compounds exhibit minimal interactions with recognition proteins, e.g., naturally occurring antibodies, cell proteins, cells and other components of biological systems, unless such interactions are specifically desirable. Thus, substances and functional groups specifically intended to cause the above minimal interactions, e.g., drugs and prodrugs, are considered to be biocompatible. Preferably (with exception of compounds intended to be cytotoxic, such as, e.g., antineoplastic agents), compounds are "biocompatible" if their addition to normal cells in vitro, at concentrations similar to the intended systemic in vivo concentrations, results in less than or equal to 1% cell death during the time equivalent to the half-life of the compound in vivo (e.g., the period of time required for 50% of the compound administered in vivo to be eliminated/cleared), and their administration in vivo induces minimal and medically acceptable inflammation, foreign body reaction, immunotoxicity, chemical toxicity and/or other such adverse effects. In the above sentence, the term "normal cells" refers to cells that are not intended to be destroyed or otherwise significantly affected by the compound being tested.

"Biodegradable": As used herein, "biodegradable" polymers are polymers that are susceptible to biological processing in vivo. As used herein, "biodegradable" compounds or moieties are those that, when taken up by cells, can be broken down by the lysosomal or other chemical machinery or by hydrolysis into components that the cells can either reuse or dispose of without significant toxic effect on the cells. The term "biocleavable" as used herein has the same meaning of "biodegradable". The degradation fragments preferably induce little or no organ or cell overload or pathological processes caused by such overload or other adverse effects in vivo. Examples of biodegradation processes include enzymatic and non-enzymatic hydrolysis, oxidation and reduction. Suitable conditions for non-enzymatic hydrolysis of the biodegradable protein-polymer-drug conjugates (or their components, e.g., the biodegradable polymeric carrier and the linkers between the carrier and the antibody or the drug molecule) described herein, for example, include exposure of the biodegradable conjugates to water at a temperature and a pH of lysosomal intracellular compartment. Biodegradation of some protein-polymer-drug conjugates (or their components, e.g., the biodegradable polymeric carrier and the linkers between the carrier and the antibody or the drug molecule), can also be enhanced extracellularly, e.g., in low pH regions of the animal body, e.g., an inflamed area, in the close vicinity of activated macrophages or other cells releasing degradation facilitating factors. In certain preferred embodiments, the effective size of the polymer carrier at pH-7.5 does not detectably change over 1 to 7 days, and remains within 50% of the original polymer size for at least several weeks. At pH-5, on the other hand, the polymer carrier preferably detectably degrades over 1 to 5 days, and is completely transformed into low molecular weight fragments within a two-week to several-month time frame. Polymer integrity in such tests can be measured, for example, by size exclusion HPLC. Although faster degradation may be in some cases preferable, in general it may be more desirable that the polymer degrades in cells with the rate that does not exceed the rate of metabolization or excretion of polymer fragments by the cells. In preferred embodiments, the polymers and polymer biodegradation byproducts are biocompatible.

"Maleimido blocking compound": as used herein refers to a compound that can react with maleimide to convert it to succinimide and "maleimido blocking moiety" refers to the chemical moiety attached to the succinimide upon conversion. In certain embodiments, the maleimido blocking compound is a compound having a terminal thiol group for reacting with the maleimide. In one embodiment, the maleimido blocking compound is cysteine, N-acetyl cysteine, cysteine methyl ester, N-methyl cysteine, 2-mercaptoethanol, 3-mercaptopropanoic acid, 2-mercaptoacetic acid, mercaptomethanol (i.e., $HOCH_2SH$), benzyl thiol in which phenyl is substituted with one or more hydrophilic substituents, or 3-aminopropane-1-thiol.

"Hydrophilic": The term "hydrophilic" as it relates to substituents, e.g., on the polymer monomeric units or on a maleimido blocking moiety to render them hydrophilic or water soluble, does not essentially differ from the common meaning of this term in the art, and denotes chemical moieties which contain ionizable, polar, or polarizable atoms, or which otherwise may be solvated by water molecules. Thus a hydrophilic group, as used herein, refers to an aliphatic, cycloalkyl, heteroaliphatic, heterocycloalkyl, aryl or heteroaryl moiety, which falls within the definition of the term hydrophilic, as defined above. Examples of particular hydrophilic organic moieties which are suitable include, without limitation, aliphatic or heteroaliphatic groups comprising a chain of atoms in a range of between about one and twelve atoms, hydroxyl, hydroxyalkyl, amine, carboxyl, amide, carboxylic ester, thioester, aldehyde, nitryl, isonitryl, nitroso, hydroxylamine, mercaptoalkyl, heterocycle, carbamates, carboxylic acids and their salts, sulfonic acids and their salts, sulfonic acid esters, phosphoric acids and their salts, phosphate esters, polyglycol ethers, polyamines, polycarboxylates, polyesters and polythioesters. In certain embodiments, hydrophilic substituents comprise a carboxyl group (COOH), an aldehyde group (CHO), a ketone group ($COC_{1-4}$ alkyl), a methylol ($CH_2OH$) or a glycol (for example, $CHOH-CH_2OH$ or $CH-(CH_2OH)_2$), $NH_2$, F, cyano, $SO_3H$, $PO_3H$, and the like.

The term "hydrophilic" as it relates to the polymers disclosed herein generally does not differ from usage of this term in the art, and denotes polymers comprising hydrophilic functional groups as defined above. In a preferred embodiment, hydrophilic polymer is a water-soluble polymer. Hydrophilicity of the polymer can be directly measured through determination of hydration energy, or determined through investigation between two liquid phases, or by chromatography on solid phases with known hydrophobicity, such as, for example, C4 or C18.

"Polymeric Carrier": The term polymeric carrier, as used herein, refers to a polymer or a modified polymer, which is suitable for covalently attaching to or can be covalently attached to one or more drug molecules with a designated linker and/or one or more PBRMs with a designated linker.

"Physiological conditions": The phrase "physiological conditions", as used herein, relates to the range of chemical (e.g., pH, ionic strength) and biochemical (e.g., enzyme concentrations) conditions likely to be encountered in the extracellular fluids of living tissues. For most normal tissues, the physiological pH ranges from about 7.0 to 7.4. Circulating blood plasma and normal interstitial liquid represent typical examples of normal physiological conditions.

"Drug": As used herein, the term "drug" refers to a compound which is biologically active and provides a desired physiological effect following administration to a subject in need thereof (e.g., an active pharmaceutical ingredient).

"Cytotoxic": As used herein the term "cytotoxic" means toxic to cells or a selected cell population (e.g., cancer cells). The toxic effect may result in cell death and/or lysis. In certain instances, the toxic effect may be a sublethal destructive effect on the cell, e.g., slowing or arresting cell growth. In order to achieve a cytotoxic effect, the drug or prodrug may be selected from a group consisting of a DNA damaging agent, a microtubule disrupting agent, or a cytotoxic protein or polypeptide, amongst others.

"Cytostatic": As used herein the term "cytostatic" refers to a drug or other compound which inhibits or stops cell growth and/or multiplication.

"Small molecule": As used herein, the term "small molecule" refers to molecules, whether naturally-occurring or artificially created (e.g., via chemical synthesis) that have a relatively low molecular weight. Preferred small molecules are biologically active in that they produce a local or systemic effect in animals, preferably mammals, more preferably humans. In certain preferred embodiments, the small molecule is a drug and the small molecule is referred to as "drug molecule" or "drug" or "therapeutic agent". In certain embodiments, the drug molecule has MW less than or equal to about 5 kDa. In other embodiments, the drug molecule has MW less than or equal to about 1.5 kDa. In embodiments, the drug molecule is selected from vinca alkaloids, auristatins, duocarmycins, tubuly sins, non-natural camptothecin compounds, topoisomerase inhibitors, DNA binding drugs, kinase inhibitors, MEK inhibitors, KSP inhibitors, calicheamicins, SN38, pyrrolobenzodiazepines, and analogs thereof. Preferably, though not necessarily, the drug is one that has already been deemed safe and effective for use by an appropriate governmental agency or body, e.g., the FDA. For example, drugs for human use listed by the FDA under 21 C.F.R. §§330.5, 331 through 361, and 440 through 460; drugs for veterinary use listed by the FDA under 21 C.F.R. §§500 through 589, incorporated herein by reference, are all considered suitable for use with the present hydrophilic polymers.

"Drug derivative" or "modified drug" or the like as used herein, refers to a compound that comprises the drug molecule intended to be delivered by the conjugate disclosed herein and a functional group capable of attaching the drug molecule to the polymeric carrier.

"Active form" as used herein refers to a form of a compound that exhibits intended pharmaceutical efficacy in vivo or in vitro. In particular, when a drug molecule intended to be delivered by the conjugate disclosed herein is released from the conjugate, the active form can be the drug itself or its derivatives, which exhibit the intended therapeutic properties. The release of the drug from the conjugate can be achieved by cleavage of a biodegradable bond of the linker which attaches the drug to the polymeric carrier. The active drug derivatives accordingly can comprise a portion of the linker.

"PHF" refers to poly(1-hydroxymethylethylene hydroxymethyl-formal).

As used herein, the terms "polymer unit", "monomeric unit", "monomer", "monomer unit", "unit" all refer to a repeatable structural unit in a polymer.

As used herein, "molecular weight" or "MW" of a polymer or polymeric carrier/scaffold or polymer conjugates refers to the weight average molecular weight of the unmodified polymer unless otherwise specified.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

The present invention is intended to include all isomers of the compound, which refers to and includes, optical isomers, and tautomeric isomers, where optical isomers include enantiomers and diastereomers, chiral isomers and non-chiral isomers, and the optical isomers include isolated optical isomers as well as mixtures of optical isomers including racemic and non-racemic mixtures; where an isomer may be in isolated form or in a mixture with one or more other isomers.

HER2 Antibodies

Monoclonal antibodies disclosed herein have the ability to inhibit HER2-mediated PI3K-Akt pathway activity.

Exemplary antibodies disclosed herein include, for example, the XMT 1517 antibody, the XMT 1518 antibody, the XMT 1519 antibody, and the XMT 1520 antibody. These antibodies show specificity for human HER2 and they have been shown to inhibit the functional activity of HER2 in vitro.

Each of the HER2 monoclonal antibodies described herein includes a heavy chain (HC), heavy chain variable region (VH), light chain (LC), and a light chain variable region (VL), as shown in the amino acid and corresponding nucleic acid sequences presented below. The variable heavy chain region and variable light chain region for each antibody are shaded in the amino acid sequences below. The complementarity determining regions (CDRs) of the heavy chain and the light chain are underlined in the amino acid sequences presented below. The amino acids encompassing the complementarity determining regions (CDR) are as defined by E. A. Kabat et al. (See Kabat, E. A., et al., Sequences of Protein of immunological interest, Fifth Edition, US Department of Health and Human Services, US Government Printing Office (1991)).

>XMT 1517 Heavy Chain Amino Acid Sequence (Heavy chain variable region (SEQ ID NO: 9) + IgG1 Heavy chain constant region (SEQ ID NO: 32))
(SEQ ID NO: 1)
QVQLVESGGGVVQPGRSLRLSCAASG<u>FTFSSYGMH</u>WVRQAPGKGLEWVA <u>VIWYDGSNKYYADSVKG</u>RFTISRDNSKNTLYLQMNSLRAEDTAVYYCAK <u>EAPYYAKDYMDV</u>WGKGTTVTVSSASTKGPSVFPLAPSSKSTSGGTAALG

CLVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSVF

LFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKA

KGQPREPQVYTLPPSRDELTKNQVSLTCLVKGFYPSDIAVEWESNGQPE

NNYKTTPPVLDSDGSFFLYSKLTVDKSRWQQGNVFSCSVMHEALHNHYT

QKSLSLSPG*

CDRH1:
(SEQ ID NO: 17)
FTFSSYGMH

CDRH2:
(SEQ ID NO: 18)
VIWYDGSNKYYADSVKG

CDRH3:
(SEQ ID NO: 19)
EAPYYAKDYMDV

>XMT 1517 Heavy Chain variable region nucleic acid sequence
(SEQ ID NO: 34)
CAGGTGCAGCTGGTGGAGTCTGGGGGAGGCGTGGTCCAGCCTGGGAGGT

CCCTGAGACTCTCCTGTGCAGCGTCTGGATTCACCTTCAGTAGCTATGG

CATGCACTGGGTCCGCCAGGCTCCAGGCAAGGGGCTGGAGTGGGIGGCA

GTTATATGGTATGATGGAAGTAATAAATACTATGCAGACTCCGTGAAGG

GCCGATTCACCATCTCCAGAGACAATTCCAAGAACACGCTGTATCTGCA

AATGAACAGCCTGAGAGCCGAGGACACGGCGGTGTACTACTGCGCCAAG

GAAGCTCCCTACTACGCTAAAGATTACATGGACGTATGGGGCAAGGGTA

CAACTGTCACCGTCTCCTCA

>XMT 1517 Light Chain Amino Acid Sequence (Light chain variable region (SEQ ID NO: 10) + Light chain constant region (SEQ ID NO: 33))
(SEQ ID NO: 2)
EIVLTQSPGTLSLSPGERATLSC<u>RASQSVSSDYLA</u>WYQQKPGQAPRLLI Y<u>GASSRAT</u>GIPDRFSGSGSGTDFTLTISRLEPEDFAVYYC<u>QQYVSYWT</u>F

GGGTKVEIKRTVAAPSVFIFPPSDEQLKSGTASVVCLLNNFYPREAKVQ

-continued
WKVDNALQSGNSQESVIEQDSKDSTYSLSSTLTLSKADYEKHKVYACEV

THQGLSSPVTKSFNRGEC

CDRL1:
(SEQ ID NO: 20)
RASQSVSSDYLA

CDRL2:
(SEQ ID NO: 21)
GASSRAT

CDRL3:
(SEQ ID NO: 22)
QQYVSYWT

>XMT 1517 Light Chain variable region nucleic acid sequence
(SEQ ID NO: 35)
GAAATTGTGTTGACGCAGTCTCCAGGCACCCTGTCTTTGTCTCCAGGGG

AAAGAGCCACCCTCTCCTGCAGGGCCAGTCAGAGTGTTAGCAGCGACTA

CTTAGCCTGGTACCAGCAGAAACCTGGCCAGGCTCCCAGGCTCCTCATC

TATGGTGCATCCAGCAGGGCCACTGGCATCCCAGACAGGTTCAGTGGCA

GTGGGTCTGGGACAGACTTCACTCTCACCATCAGCAGACTGGAGCCTGA

AGATTTTGCAGTGTATTACTGTCAGCAGTACGTCAGTTACTGGACTTTT

GGCGGAGGGACCAAGGTTGAGATCAAA

>XMT 1518 Heavy Chain Amino Acid Sequence (Heavy chain variable region (SEQ ID NO: 11) + IgG1 Heavy chain constant (SEQ ID NO: 32))
(SEQ ID NO: 3)
QVQLVESGGGVVQPGRSLRLSCAASG<u>FTFSSYGMH</u>WVRQAPGKGLEWVA <u>GIWWDGSNEKYADSVKG</u>RFTISRDNSKNTLYLQMNSLRAEDTAVYYCAK <u>EAPYYAKDYMDV</u>WGKGTTVTVSSASTKGPSVFPLAPSSKSTSGGTAALG

CLVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSVF

LFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKA

KGQPREPQVYTLPPSRDELTKNQVSLTCLVKGFYPSDIAVEWESNGQPE

NNYKTTPPVLDSDGSFFLYSKLTVDKSRWQQGNVFSCSVMHEALHNHYT

QKSLSLSPG*

CDRH1:
(SEQ ID NO: 17)
FTFSSYGMH

CDRH2:
(SEQ ID NO: 23)
GIWWDGSNEKYADSVKG

CDRH3:
(SEQ ID NO: 19)
EAPYYAKDYMDV

>XMT 1518 Light Chain Amino Acid Sequence (Light chain variable region (SEQ ID NO: 12) + Light chain constant (SEQ ID NO: 33))
(SEQ ID NO: 4)
EIVLTQSPGTLSLSPGERATLSC<u>RASQSVSSDYLA</u>WYQQKPGQAPRLLI Y<u>GASRRAT</u>GIPDRFSGSGSGTDFTLTISRLEPEDFAVYYC<u>QQYVSYWT</u>F

GGGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

CDRL1:
(SEQ ID NO: 20)
RASQSVSSDYLA

CDRL2:
(SEQ ID NO: 24)
GASRRAT

CDRL3:
(SEQ ID NO: 22)
QQYVSYWT

>XMT 1519 Heavy Chain Amino Acid Sequence (Heavy chain variable region (SEQ ID NO: 13) + IgG1 Heavy chain constant region (SEQ ID NO: 32))
(SEQ ID NO: 5)
EVQLVESGGGLVQPGGSLRLSCAASG<u>FTFSSYSMN</u>WVRQAPGKGLEWVS <u>YISSSSSTIYYADSVKG</u>RFTISRDNAKNSLYLQMNSLRAEDTAVYYCAR <u>GGHGYFDL</u>WGRGTLVTVSSASTKGPSVFPLAPSSKSTSGGTAALGCLVK

DYFPEPVTVSWNSGALTSGVHTFPAVLQSSGLYSLSSVVTVPSSSLGTQ

TYICNVNHKPSNTKVDKKVEPKSCDKTHTCPPCPAPELLGGPSVFLFPP

KPKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQP

REPQVYTLPPSRDELTKNQVSLTCLVKGFYPSDIAVEWESNGQPENNYK

TTPPVLDSDGSFFLYSKLTVDKSRWQQGNVFSCSVMHEALHNHYTQKSL

SLSPG*

CDRH1:
(SEQ ID NO: 25)
FTFSSYSMN

CDRH2:
(SEQ ID NO: 26)
YISSSSSTIYYADSVKG

CDRH3:
(SEQ ID NO: 27)
GGHGYFDL

>XMT 1519 Heavy Chain variable region nucleic acid sequence
(SEQ ID NO: 36)
GAGGTGCAGCTGGTGGAGTCTGGGGGAGGCTTGGTACAGCCTGGGGGT

CCCTGAGACTCTCCTGTGCAGCCTCTGGATTCACCTTCAGTAGCTATAG

CATGAACTGGGTCCGCCAGGCTCCAGGGAAGGGGCTGGAGTGGGTTTCA

TACATTAGTAGTAGTAGTAGTACCATATACTACGCAGACTCTGTGAAGG

GCCGATTCACCATCTCCAGAGACAATGCCAAGAACTCACTGTATCTGCA

AATGAACAGCCTGAGAGCTGAGGACACGGCGGTGTACTACTGCGCCAGA

GGTGGACACGGATATTTCGACCTATGGGGGAGAGGTACCTTGGTCACCG

TCTCCTCA

>XMT 1519 Light Chain Amino Acid Sequence (Light chain variable region (SEQ ID NO: 14) + Light chain constant region (SEQ ID NO: 33))
(SEQ ID NO: 6)
EIVLTQSPGTLSLSPGERATLSC<u>RASQSVSSSYLA</u>WYQQKPGQAPRLLI

Y<u>GASSRAT</u>GIPDRFSGSGSGTDFTLTISRLEPEDFAVYYC<u>QQYHHSPLT</u>

FGGGTKVEIKRTVAAPSVFIFPPSDEQLKSGTASVVCLLNNFYPREAKV

QWKVDNALQSGNSQESVIEQDSKDSTYSLSSTLTLSKADYEKHKVYACE

VTHQGLSSPVTKSFNRGEC

CDRL1:
(SEQ ID NO: 28)
RASQSVSSSYLA

CDRL2:
(SEQ ID NO: 21)
GASSRAT

CDRL3:
(SEQ ID NO: 29)
QQYHHSPLT

>XMT 1519 Light Chain variable region nucleic acid sequence
(SEQ ID NO: 37)
GAAATTGTGTTGACGCAGTCTCCAGGCACCCTGTCTTTGTCTCCAGGGG

AAAGAGCCACCCTCTCCTGCAGGGCCAGTCAGAGTGTTAGCAGCAGCTA

CTTAGCCTGGTACCAGCAGAAACCTGGCCAGGCTCCCAGGCTCCTCATC

TATGGTGCATCCAGCAGGGCCACTGGCATCCCAGACAGGTTCAGTGGCA

GTGGGTCTGGGACAGACTTCACTCTCACCATCAGCAGACTGGAGCCTGA

AGATTTTGCAGTGTATTACTGTCAGCAGTACCACCACAGTCCTCTCACT

TTTGGCGGAGGGACCAAGGTTGAGATCAAA

>XMT 1520 Heavy Chain Amino Acid Sequence (Heavy chain variable region (SEQ ID NO: 15) + IgG1 Heavy chain constant region (SEQ ID NO: 32))
(SEQ ID NO: 7)
EVQLVESGGGLVQPGGSLRLSCAASG<u>FTFSGRSMN</u>WVRQAPGKGLEWVS <u>YISSDSRTIYYADSVKG</u>RFTISRDNAKNSLYLQMNSLRAEDTAVYYCAR <u>GGHGYFDL</u>WGRGTLVTVSSASTKGPSVFPLAPSSKSTSGGTAALGCLVK

DYFPEPVTVSWNSGALTSGVHTFPAVLQSSGLYSLSSVVTVPSSSLGTQ

TYICNVNHKPSNTKVDKKVEPKSCDKTHTCPPCPAPELLGGPSVFLFPP

KPKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQP

REPQVYTLPPSRDELTKNQVSLTCLVKGFYPSDIAVEWESNGQPENNYK

TTPPVLDSDGSFFLYSKLTVDKSRWQQGNVFSCSVMHEALHNHYTQKSL

SLSPG*

CDRH1:
(SEQ ID NO: 30)
FTFSGRSMN

CDRH2:
(SEQ ID NO: 31)
YISSDSRTIYYADSVKG

CDRH3:
(SEQ ID NO: 27)
GGHGYFDL

>XMT 1520 Light Chain Amino Acid Sequence (Light chain variable region (SEQ ID NO: 16) + Light chain constant region (SEQ ID NO: 33))
(SEQ ID NO: 8)
EIVLTQSPGTLSLSPGERATLSC<u>RASQSVSSSYLA</u>WYQQKPGQAPRLLI

Y<u>GASSRAT</u>GIPDRFSGSGSGTDFTLTISRLEPEDFAVYYC<u>QQYHHSPLT</u>

FGGGTKVEIKRTVAAPSVFIFPPSDEQLKSGTASVVCLLNNFYPREAKV

```
QWKVDNALQSGNSQESVTEQDSKDSTYSLSSTLTLSKADYEKHKVYACE

VTHQGLSSPVTKSFNRGEC

CDRL1:
                                            (SEQ ID NO: 28)
RASQSVSSSYLA

CDRL2:
                                            (SEQ ID NO: 21)
GASSRAT

CDRL3:
                                            (SEQ ID NO: 29)
QQYHHSPLT
```

Also included in the invention are antibodies and antigen binding fragments thereof that bind to the same epitope or cross compete for binding to the same epitope as the antibodies and antigen binding fragments thereof described herein. For example, antibodies and antigen binding fragments disclosed herein specifically bind to HER2, wherein the antibody or fragment binds to an epitope that includes one or more amino acid residues on human HER2 (e.g., GenBank Accession No. P04626.1).

Antibodies and antigen binding fragments thereof disclosed herein specifically bind to an epitope on the full-length human HER2 receptor comprising the amino acid sequence:

```
                                                        (SEQ ID NO: 38)
   1    MELAALCRWG  LLLALLPPGA  ASTQVCTGTD  MKLRLPASPE  THLDMLRHLY

51    QGCQVVQGNL  ELTYLPTNAS  LSFLQDIQEV  QGYVLIAHNQ  VRQVPLQRLR

101    IVRGTQLFED  NYALAVLDNG  DPLNNTTPVT  GASPGGLREL  QLRSLTEILK

151    GGVLIQRNPQ  LCYQDTILWK  DIFHKNNQLA  LTLIDTNRSR  ACHPCSPMCK

201    GSRCWGESSE  DCQSLTRTVC  AGGCARCKGP  LPTDCCHEQC  AAGCTGPKHS

251    DCLACLHFNH  SGICELHCPA  LVTYNTDTFE  SMPNPEGRYT  FGASCVTACP

301    YNYLSTDVGS  CTLVCPLHNQ  EVTAEDGTQR  CEKCSKPCAR  VCYGLGMEHL

351    REVRAVTSAN  IQEFAGCKKI  FGSLAFLPES  FDGDPASNTA  PLQPEQLQVF

401    ETLEEITGYL  YISAWPDSLP  DLSVFQNLQV  IRGRILHNGA  YSLTLQGLGI

451    SWLGLRSLRE  LGSGLALIHH  NTHLCFVHTV  PWDQLFRNPH  QALLHTANRP

501    EDECVGEGLA  CHQLCARGHC  WGPGPTQCVN  CSQFLRGQEC  VEECRVLQGL

551    PREYVNARHC  LPCHPECQPQ  NGSVTCFGPE  ADQCVACAHY  KDPPFCVARC

601    PSGVKPDLSY  MPIWKFPDEE  GACQPCPINC  THSCVDLDDK  GCPAEQRASP

651    LTSIISAVVG  ILLVVVLGVV  FGILIKRRQQ  KIRKYTMRRL  LQETELVEPL

701    TPSGAMPNQA  QMRILKETEL  RKVKVLGSGA  FGTVYKGIWI  PDGENVKIPV

751    AIKVLRENTS  PKANKEILDE  AYVMAGVGSP  YVSRLLGICL  TSTVQLVTQL

801    MPYGCLLDHV  RENRGRLGSQ  DLLNWCMQIA  KGMSYLEDVR  LVHRDLAARN

851    VLVKSPNHVK  ITDFGLARLL  DIDETEYHAD  GGKVPIKWMA  LESILRRRFT

901    HQSDVWSYGV  TVWELMTFGA  KPYDGIPARE  IPDLLEKGER  LPQPPICTID

951    VYMIMVKCWM  IDSECRPRFR  ELVSEFSRMA  RDPQRFVVIQ  NEDLGPASPL

1001    DSTFYRSLLE  DDDMGDLVDA  EEYLVPQQGF  FCPDPAPGAG  GMVHHRHRSS

1051    STRSGGGDLT  LGLEPSEEEA  PRSPLAPSEG  AGSDVFDGDL  GMGAAKGLQS

1101    LPTHDPSPLQ  RYSEDPTVPL  PSETDGYVAP  LTCSPQPEYV  NQPDVRPQPP

1151    SPREGPLPAA  RPAGATLERP  KTLSPGKNGV  VKDVFAFGGA  VENPEYLTPQ

1201    GGAAPQPHPP  PAFSPAFDNL  YYWDQDPPER  GAPPSTFKGT  PTAENPEYLG

1251    LDVPV
```

Antibodies and antigen binding fragments thereof disclosed herein specifically bind to an epitope on the extracellular domain (ECD) of the human HER2 receptor comprising the amino acid sequence:

```
                                                         (SEQ ID NO: 39)
  1  TQVCTGTDMK LRLPASPETH LDMLRHLYQG CQVVQGNLEL TYLPTNASLS

51  FLQDIQEVQG YVLIAHNQVR QVPLQRLRIV RGTQLFEDNY ALAVLDNGDP

101  LNNTTPVTGA SPGGLRELQL RSLTEILKGG VLIQRNPQLC YQDTILWKDI

151  FHKNNQLALT LIDTNRSRAC HPCSPMCKGS RCWGESSEDC QSLTRTVCAG

201  GCARCKGPLP TDCCHEQCAA GCTGPKHSDC LACLHFNHSG ICELHCPALV

251  TYNTDTFESM PNPEGRYTFG ASCVTACPYN YLSTDVGSCT LVCPLHNQEV

301  TAEDGTQRCE KCSKPCARVC YGLGMEHLRE VRAVTSANIQ EFAGCKKIFG

351  SLAFLPESFD GDPASNTAPL QPEQLQVFET LEEITGYLYI SAWPDSLPDL

401  SVFQNLQVIR GRILHNGAYS LTLQGLGISW LGLRSLRELG SGLALIHHNT

451  HLCFVHTVPW DQLFRNPHQA LLHTANRPED ECVGEGLACH QLCARGHCWG

501  PGPTQCVNCS QFLRGQECVE ECRVLQGLPR EYVNARHCLP CHPECQPQNG

551  SVTCFGPEAD QCVACAHYKD PPFCVARCPS GVKPDLSYMP IWKFPDEEGA

601  CQPCPINCTH SCVDLDDKGC PAEQRASPLT
```

Those skilled in the art will recognize that it is possible to determine, without undue experimentation, if a monoclonal antibody has the same specificity as a monoclonal antibody disclosed herein (e.g., XMT 1517, XMT 1518, XMT 1519, and XMT 1520) by ascertaining whether the former prevents the latter from binding to a natural binding partner or other molecule known to be associated with HER2. If the monoclonal antibody being tested competes with the monoclonal antibody disclosed herein, as shown by a decrease in binding by the monoclonal antibody disclosed herein, then the two monoclonal antibodies bind to the same, or a closely related, epitope.

An alternative method for determining whether a monoclonal antibody has the specificity of monoclonal antibody disclosed herein is to pre-incubate the monoclonal antibody disclosed herein with soluble HER2 (with which it is normally reactive), and then add the monoclonal antibody being tested to determine if the monoclonal antibody being tested is inhibited in its ability to bind HER2. If the monoclonal antibody being tested is inhibited then, in all likelihood, it has the same, or functionally equivalent, epitopic specificity as the monoclonal antibody disclosed herein.

Screening of monoclonal antibodies disclosed herein, can be also carried out, e.g., by measuring HER2-mediated PI3K-Akt pathway activity, and determining whether the test monoclonal antibody is able to modulate, block, inhibit, reduce, antagonize, neutralize or otherwise interfere with PI3K-Akt pathway activity.

HER2 antibodies are generated, for example, using the methods described in the Examples provided herein. Alternatively or in addition, various procedures known within the art may be used for the production of monoclonal antibodies directed against HER2, or against derivatives, fragments, analogs homologs or orthologs thereof. (See, for example, Antibodies: A Laboratory Manual, Harlow E, and Lane D, 1988, Cold Spring Harbor Laboratory Press, Cold Spring Harbor, N.Y., incorporated herein by reference). Fully human antibodies are antibody molecules in which the entire sequence of both the light chain and the heavy chain, including the CDRs, arise from human genes. Such antibodies are termed "human antibodies" or "fully human antibodies" herein. Human monoclonal antibodies are prepared, for example, using the procedures described in the Examples provided below. Human monoclonal antibodies can be also prepared by using the trioma technique; the human B-cell hybridoma technique (see Kozbor, et al., 1983 Immunol Today 4: 72); and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

Antibodies are purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

Monoclonal antibodies that modulate, block, inhibit, reduce, antagonize, neutralize or otherwise interfere with HER2 mediated PI3K-Akt pathway activity are generated, e.g., by immunizing an animal with membrane bound and/or soluble HER2, such as, for example, murine, rat or human HER2 or an immunogenic fragment, derivative or variant thereof. Alternatively, the animal is immunized with cells transfected with a vector containing a nucleic acid molecule encoding HER2 such that HER2 is expressed and associated with the surface of the transfected cells. Alternatively, the antibodies are obtained by screening a library that contains antibody or antigen binding domain sequences for binding to HER2. This library is prepared, e.g., in bacteriophage as protein or peptide fusions to a bacteriophage coat protein that is expressed on the surface of assembled phage particles and the encoding DNA sequences contained within the phage particles (i.e., "phage displayed library"). Hybridomas resulting from myeloma/B cell fusions are then screened for reactivity to HER2. Additionally, the antibodies by selected from, and optionally optimized in, yeast antibody display libraries and yeast library presentation systems as described in, e.g.: Blaise L, Wehnert A, Steukers M P, van den Beucken T, Hoogenboom H R, Hufton S E. Construction and diversification of yeast cell surface displayed libraries by yeast mating: application to the affinity maturation of Fab antibody fragments. Gene. 2004 Nov. 24; 342(2):211-8; Boder E T, Wittrup K D. Yeast surface display for screening combinatorial polypeptide libraries. Nat Biotechnol. 1997 June; 15(6):553-7; Kuroda K, Ueda M. Cell surface engineering of yeast for applications in white biotechnology. Biotechnol Lett. 2011 January; 33(1):1-9. doi: 10.1007/s10529-010-0403-9. Review; Lauer T M, Agrawal N J, Chennamsetty N, Egodage K, Helk B, Trout B L. Developability index: a rapid in silico tool for the screening of antibody aggregation propensity. J Pharm Sci. 2012 January; 101(1):102-15; Orcutt K. D. and Wittrup K. D. (2010), 207-233 doi: 10.1007/978-3-642-01144-3_15; Rakestraw J A, Aird D, Aha P M, Baynes B M, Lipovsek D. Secretion-and-capture cell-surface display for selection of target-binding proteins. Protein Eng Des Sel. 2011 June; 24(6): 525-30; U.S. Pat. No. 8,258,082; U.S. Pat. No. 6,300,064; U.S. Pat. No. 6,696,248; U.S. Pat. No. 6,165,718; U.S. Pat. No. 6,500,644; U.S. Pat. No. 6,291,158; U.S. Pat. No. 6,291,159; U.S. Pat. No. 6,096,551; U.S. Pat. No. 6,368,805; U.S. Pat. No. 6,500,644. Exemplary yeast library presentation systems are described in, e.g., WO2008118476; WO2009/036379; WO2010105256; and WO2012009568. In certain embodiments, such yeast antibody display libraries or yeast library presentation systems are designed to mimic or reflect the diversity characteristic of the human preimmune antibody repertoire. In certain embodiments such yeast antibody display library diversity or yeast library presentation system diversity is generated in silico. In certain embodiments such yeast antibody display libraries or yeast library presentation systems comprise *Saccharomyces* yeast cells, such as *Saccharomyces Cerevisiae* cells. In certain embodiments such yeast antibody display libraries or yeast library presentation systems comprise Pichia cells.

Monoclonal antibodies are prepared, for example, using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (MA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Moreover, in therapeutic applications of monoclonal antibodies, it is important to identify antibodies having a high degree of specificity and a high binding affinity for the target antigen.

After the desired hybridoma cells are identified, the clones can be subcloned by limiting dilution procedures and grown by standard methods. (See Goding, Monoclonal Antibodies: Principles and Practice, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxyapatite chromatography, gel electrophoresis, dialysis, or affinity chromatography.

Monoclonal antibodies can also be made by recombinant DNA methods, such as those described in U.S. Pat. No. 4,816,567. DNA encoding the monoclonal antibodies disclosed herein can be readily isolated and sequenced using conventional procedures (e.g., by using oligonucleotide probes that are capable of binding specifically to genes encoding the heavy and light chains of murine antibodies). The hybridoma cells disclosed herein serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody disclosed herein, or can be substituted for the variable domains of one antigen-combining site of an antibody disclosed herein to create a chimeric bivalent antibody.

Monoclonal antibodies disclosed herein include fully human antibodies or humanized antibodies. These antibodies are suitable for administration to humans without engendering an immune response by the human against the administered immunoglobulin.

A humanized or fully human HER2 antibody is generated, for example, using the procedures described in the Examples provided below.

In other, alternative methods, a HER2 antibody is developed, for example, using phage-display methods using antibodies containing only human sequences. Such approaches are well-known in the art, e.g., in WO92/01047 and U.S. Pat. No. 6,521,404, which are hereby incorporated by reference. In this approach, a combinatorial library of phage carrying random pairs of light and heavy chains are screened using natural or recombinant source of HER2 or fragments thereof. In another approach, a HER2 antibody can be produced by a process wherein at least one step of the process includes immunizing a transgenic, non-human animal with human HER2 protein. In this approach, some of the endogenous heavy and/or kappa light chain loci of this xenogenic non-human animal have been disabled and are incapable of the rearrangement required to generate genes encoding immunoglobulins in response to an antigen. In addition, at least one human heavy chain locus and at least one human light chain locus have been stably transfected into the animal. Thus, in response to an administered antigen, the human loci rearrange to provide genes encoding human variable regions immunospecific for the antigen. Upon immunization, therefore, the xenomouse produces B-cells that secrete fully human immunoglobulins.

A variety of techniques are well-known in the art for producing xenogenic non-human animals. For example, see U.S. Pat. No. 6,075,181 and U.S. Pat. No. 6,150,584, which is hereby incorporated by reference in its entirety. This general strategy was demonstrated in connection with generation of the first XenoMouse™ strains as published in 1994. See Green et al. Nature Genetics 7:13-21 (1994), which is hereby incorporated by reference in its entirety. See also, U.S. Pat. Nos. 6,162,963, 6,150,584, 6,114,598, 6,075, 181, and 5,939,598 and Japanese Patent Nos. 3 068 180 B2, 3 068 506 B2, and 3 068 507 B2 and European Patent No., EP 0 463 151 B1 and International Patent Applications No. WO 94/02602, WO 96/34096, WO 98/24893, WO 00/76310 and related family members.

In an alternative approach, others have utilized a "mini-locus" approach in which an exogenous Ig locus is mimicked through the inclusion of pieces (individual genes) from the Ig locus. Thus, one or more VH genes, one or more $D_H$ genes, one or more $J_H$ genes, a mu constant region, and a second constant region (preferably a gamma constant region) are formed into a construct for insertion into an animal. See e.g., U.S. Pat. Nos. 5,545,806; 5,545,807; 5,591,669; 5,612,205; 5,625,825; 5,625,126; 5,633,425; 5,643,763; 5,661,016; 5,721,367; 5,770,429; 5,789,215; 5,789,650; 5,814,318; 5,877; 397; 5,874,299; 6,023,010; and 6,255,458; and European Patent No. 0 546 073 B1; and International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and related family members.

Generation of human antibodies from mice in which, through microcell fusion, large pieces of chromosomes, or entire chromosomes, have been introduced, has also been demonstrated. See European Patent Application Nos. 773 288 and 843 961.

Human anti-mouse antibody (HAMA) responses have led the industry to prepare chimeric or otherwise humanized antibodies. While chimeric antibodies have a human constant region and a immune variable region, it is expected that certain human anti-chimeric antibody (HACA) responses will be observed, particularly in chronic or multi-dose utilizations of the antibody. Thus, it would be desirable to provide fully human antibodies against HER2 in order to vitiate or otherwise mitigate concerns and/or effects of HAMA or HACA response.

The production of antibodies with reduced immunogenicity is also accomplished via humanization, chimerization and display techniques using appropriate libraries. It will be appreciated that murine antibodies or antibodies from other species can be humanized or primatized using techniques well known in the art. See e.g., Winter and Harris Immunol Today 14:43 46 (1993) and Wright et al. Crit, Reviews in Immunol. 12125-168 (1992). The antibody of interest may be engineered by recombinant DNA techniques to substitute the CH1, CH2, CH3, hinge domains, and/or the framework domain with the corresponding human sequence (See WO 92102190 and U.S. Pat. Nos. 5,530,101; 5,585,089; 5,693, 761; 5,693,792; 5,714,350; and 5,777,085). Also, the use of Ig cDNA for construction of chimeric immunoglobulin genes is known in the art (Liu et al. P.N.A.S. 84:3439 (1987) and J. Immunol. 139:3521 (1987)). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) Sequences of Proteins of immunological Interest, N.I.H. publication no. 91-3242. Human C region genes are readily available from known clones. The choice of isotype will be guided by the desired effecter functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

Antibody fragments, such as Fv, F(ab')$_2$ and Fab may be prepared by cleavage of the intact protein, e.g., by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g., SV-40 early promoter, (Okayama et al. Mol. Cell. Bio. 3:280 (1983)), Rous sarcoma virus LTR (Gorman et al. P.N.A.S. 79:6777 (1982)), and moloney murine leukemia virus LTR (Grosschedl et al. Cell 41:885 (1985)). Also, as will be appreciated, native Ig promoters and the like may be used.

Further, human antibodies or antibodies from other species can be generated through display type technologies, including, without limitation, phage display, retroviral display, ribosomal display, and other techniques, using techniques well known in the art and the resulting molecules can be subjected to additional maturation, such as affinity maturation, as such techniques are well known in the art. Wright et al. Crit, Reviews in Immunol. 12125-168 (1992), Hanes and Plückthun PNAS USA 94:4937-4942 (1997) (ribosomal display), Parmley and Smith Gene 73:305-318 (1988) (phage display), Scott, TIBS, vol. 17:241-245 (1992), Cwirla et al. PNAS USA 87:6378-6382 (1990), Russel et al. Nucl. Acids Research 21:1081-1085 (1993), Hoganboom et al. Immunol. Reviews 130:43-68 (1992), Chiswell and McCafferty TIBTECH; 10:80-8A (1992), and U.S. Pat. No. 5,733,743. If display technologies are utilized to produce antibodies that are not human, such antibodies can be humanized as described above.

Using these techniques, antibodies can be generated to HER2 expressing cells, soluble forms of HER2, epitopes or peptides thereof, and expression libraries thereto (See e.g., U.S. Pat. No. 5,703,057) which can thereafter be screened as described above for the activities described herein.

The HER2 antibodies disclosed herein can be expressed by a vector containing a DNA segment encoding the single chain antibody described above.

These can include vectors, liposomes, naked DNA, adjuvant-assisted DNA, gene gun, catheters, etc. Vectors include chemical conjugates such as described in WO 93/64701, which has targeting moiety (e.g., a ligand to a cellular surface receptor), and a nucleic acid binding moiety (e.g., polylysine), viral vector (e.g., a DNA or RNA viral vector), fusion proteins such as described in PCT/US 95/02140 (WO 95/22618) which is a fusion protein containing a target moiety (e.g., an antibody specific for a target cell) and a nucleic acid binding moiety (e.g., a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as orthopox or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl. Acad. Sci USA 87:1149 (1990), Adenovirus Vectors (see LeGal LaSalle et al., Science, 259:988 (1993); Davidson, et al., Nat. Genet 3:219 (1993); Yang, et al., J. Virol. 69:2004 (1995) and Adeno-associated Virus Vectors (see Kaplitt, M. G. et al., Nat. Genet. 8:148 (1994).

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g., infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g., adenovirus, HSV) to a desired location. Additionally, the particles can be delivered by intracerebroventricular (icy) infusion using a minipump infusion system, such as a SynchroMed Infusion System. A method based on bulk flow, termed convection, has also proven effective at delivering large molecules to extended areas of the brain and may be useful in delivering the vector to the target cell. (See Bobo et al., Proc. Natl. Acad. Sci. USA 91:2076-2080 (1994); Morrison et al., Am. J. Physiol. 266:292-305 (1994)). Other methods that can be used include catheters, intravenous, parenteral, intraperitoneal and subcutaneous injection, and oral or other known routes of administration.

These vectors can be used to express large quantities of antibodies that can be used in a variety of ways. For example, to detect the presence of HER2 in a sample. The antibody can also be used to try to bind to and disrupt HER2-related signaling.

Techniques can be adapted for the production of single-chain antibodies specific to an antigenic protein disclosed herein (see e.g., U.S. Pat. No. 4,946,778). In addition, methods can be adapted for the construction of $F_{ab}$ expression libraries (see e.g., Huse, et al., 1989 Science 246: 1275-1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

The invention also includes $F_v$, $F_{ab}$, $F_{ab'}$ and $F_{(ab')2}$ anti-HER2 fragments or anti-HER2 fragments, single chain anti-HER2 antibodies, multispecific antibodies in which at least one arm binds HER2, and heteroconjugate anti-HER2 antibodies.

Bispecific antibodies are antibodies that have binding specificities for at least two different antigens. In the present case, one of the binding specificities is for HER2. The second binding target is any other antigen, including a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies can be prepared as full length antibodies or antibody fragments (e.g., F(ab')$_2$ bispecific antibodies). Techniques for generating bispecific antibodies from antibody fragments have been described in the literature. For example, bispecific antibodies can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from E. coli and chemically coupled to form bispecific antibodies. Shalaby et al., J. Exp. Med. 175:217-225 (1992) describe the production of a fully humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994).

Antibodies with more than two valencies are contemplated. For example, trispecific antibodies can be prepared. Tutt et al., J. Immunol. 147:60 (1991).

Exemplary bispecific antibodies can bind to two different epitopes, at least one of which originates in the protein antigen disclosed herein. Alternatively, an anti-antigenic arm of an immunoglobulin molecule can be combined with an arm which binds to a triggering molecule on a leukocyte such as a T-cell receptor molecule (e.g., CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

Heteroconjugate antibodies are also within the scope of the present invention. Heteroconjugate antibodies are composed of two covalently joined antibodies. Such antibodies have, for example, been proposed to target immune system cells to unwanted cells (see U.S. Pat. No. 4,676,980), and for treatment of HIV infection (see WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

It can be desirable to modify the antibody disclosed herein with respect to effector function, so as to enhance, e.g., the effectiveness of the antibody in treating diseases and disorders associated with aberrant HER2 expression and/or activity. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)).

HER2 Antibody Conjugates:

The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies disclosed herein. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238:1098 (1987).

Preferred linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat.#21651G); (iv) Sulfo-LC-SPDP (sulfosuccinimidyl 6 [3-(2-pyridyldithio)-propianamide] hexanoate (Pierce Chem. Co. Cat.#2165-G); and (v) sulfo-NHS (N-hydroxysulfo-succinimide: Pierce Chem. Co., Cat.#24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NETS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction.

In one aspect, the conjugate described herein includes an isolated HER2 antibody or antigen-binding fragment thereof connected directly or indirectly to one or more D-carrying polymeric scaffolds independently comprising poly(1-hydroxymethylethylene hydroxymethyl-formal) (PHF) having a molecular weight ranging from about 2 kDa to about 40 kDa, wherein each of the one or more D-carrying polymeric scaffolds independently is of Formula (Ic):

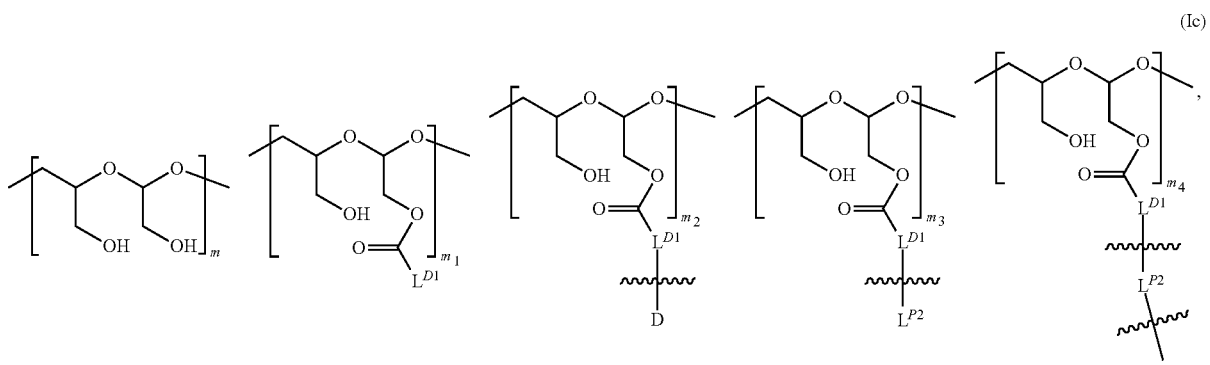

(Ic)

wherein:

each occurrence of D, independently, is a therapeutic or diagnostic agent;

$L^{D1}$ is a carbonyl-containing moiety;

each occurrence of

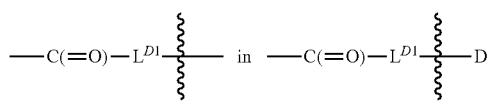

is independently a first linker that contains a biodegradable bond so that when the bond is broken, D is released in an active form for its intended therapeutic effect; and the

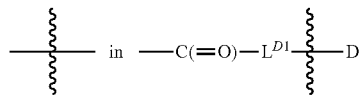

between $L^{D1}$ and D denotes direct or indirect attachment of D to $L^{D1}$;

each occurrence of

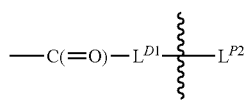

is independently a second linker not yet connected to the isolated HER2 antibody or antigen-binding fragment thereof, in which $L^{P2}$ is a moiety containing a functional group that is yet to form a covalent bond with a functional group of the isolated antibody or antigen-binding fragment thereof, and the

between $L^{D1}$ and $L^{P2}$ denotes direct or indirect attachment of $L^{P2}$ to $L^{D1}$, and each occurrence of the second linker is distinct from each occurrence of the first linker;

each occurrence of

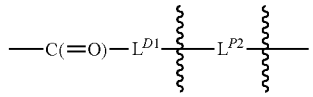

is independently a third linker that connects each D-carrying polymeric scaffold to the isolated antibody or antigen-binding fragment thereof, in which the terminal

attached to $L^{P2}$ denotes direct or indirect attachment of $L^{P2}$ to the isolated antibody or antigen-binding fragment thereof upon formation of a covalent bond between a functional group of $L^{P2}$ and a functional group of the isolated antibody or antigen-binding fragment thereof; and each occurrence of the third linker is distinct from each occurrence of the first linker;

m is an integer from 1 to about 300, $m_1$ is an integer from 1 to about 140, $m_2$ is an integer from 1 to about 40, $m_3$ is an integer from 0 to about 18, $m_4$ is an integer from 1 to about 10;

the sum of m, $m_1$, $m_2$, $m_3$, and $m_4$ ranges from about 15 to about 300; and the total number of $L^{P2}$ attached to the isolated antibody or antigen-binding fragment thereof is 10 or less.

The conjugate may include one or more of the following features.

For example, in Formula (Ic), $m_1$ is an integer from 1 to about 120 (e.g., about 1-90) and/or $m_3$ is an integer from 1 to about 10 (e.g., about 1-8).

For example, when the PHF in Formula (Ic) has a molecular weight ranging from about 6 kDa to about 20 kDa (i.e., the sum of m, $m_1$, $m_2$, $m_3$, and $m_4$ ranging from about 45 to about 150), $m_2$ is an integer from 2 to about 20, $m_3$ is an integer from 0 to about 9, $m_4$ is an integer from 1 to about 10, and/or $m_1$ is an integer from 1 to about 75 (e.g., $m_1$ being about 4-45).

For example, when the PHF in Formula (Ic) has a molecular weight ranging from about 8 kDa to about 15 kDa (i.e., the sum of m, $m_1$, $m_2$, $m_3$, and $m_4$ ranging from about 60 to about 110), $m_2$ is an integer from 2 to about 15, $m_3$ is an integer from 0 to about 7, $m_4$ is an integer from 1 to about 10, and/or $m_1$ is an integer from 1 to about 55 (e.g., $m_1$ being about 4-30).

For example, when the PHF in Formula (Ic) has a molecular weight ranging from about 2 kDa to about 20 kDa (i.e., the sum of m, $m_1$, $m_2$, $m_3$, and $m_4$ ranging from about 15 to about 150), $m_2$ is an integer from 1 to about 20, $m_3$ is an integer from 0 to about 10 (e.g., $m_3$ ranging from 0 to about 9), $m_4$ is an integer from 1 to about 8, and/or $m_1$ is an integer from 1 to about 70, and the total number of $L^{P2}$ connected to the isolated antibody or antigen binding fragment thereof ranges from about 2 to about 8 (e.g., about 2, 3, 4, 5, 6, 7, or 8).

For example, when the PHF in Formula (Ic) has a molecular weight ranging from about 3 kDa to about 15 kDa (i.e., the sum of m, $m_1$, $m_2$, $m_3$, and $m_4$ ranging from about 20 to about 110), $m_2$ is an integer from 2 to about 15, $m_3$ is an integer from 0 to about 8 (e.g., $m_3$ ranging from 0 to about 7), $m_4$ is an integer from 1 to about 8, and/or $m_1$ is an integer from 2 to about 50, and the total number of $L^{P2}$ connected to the isolated antibody or antigen binding fragment thereof ranges from about 2 to about 8 (e.g., about 2, 3, 4, 5, 6, 7, or 8).

For example, when the PHF in Formula (Ic) has a molecular weight ranging from about 5 kDa to about 10 kDa, (i.e. the sum of m, $m_1$, $m_2$, $m_3$ and $m_4$ ranges from about 40 to about 75), $m_2$ is an integer from about 2 to about 10 (e.g., $m_2$ being about 3-10), $m_3$ is an integer from 0 to about 5 (e.g., $m_3$ ranging from 0 to about 4), $m_4$ is an integer from 1 to about 8 (e.g., $m_4$ ranging from 1 to about 5), and/or $m_1$ is an integer from about 2 to about 35 (e.g., $m_1$ being about 5-35), and the total number of $L^{P2}$ connected to the isolated antibody or antigen binding fragment thereof ranges from about 2 to about 8 (e.g., about 2, 3, 4, 5, 6, 7, or 8).

For example, when the PHF has a molecular weight ranging from 2 kDa to 40 kDa, (e.g., about 6-20 kDa or about 8-15 kDa, about 2-20 kDa, or about 3-15 kDa, or about 5-10 kDa), the number of drugs per PHF (e.g., $m_2$) is an integer from 1 to about 40 (e.g., about 1-20, or about 2-15 or about 3-10 or about 2-10). This scaffold can be used, for example, for conjugating the isolated antibody or antigen-binding fragment thereof having a molecular weight of 40 kDa or greater (e.g., 60 kDa or greater; 80 kDa or greater; 100 kDa or greater; 120 kDa or greater; 140 kDa or greater; 160 kDa or greater, 180 kDa or greater, or 200 kDa or greater, or about 40-200 kDa, 40-180 kDa, 40-140 kDa, 60-200 kDa, 60-180 kDa, 60-140 kDa, 80-200 kDa, 80-180 kDa, 80-140 kDa, 100-200 kDa, 100-180 kDa, 100-140 kDa or 140-150 kDa). In this embodiment, the ratio of the isolated antibody or antigen-binding fragment thereof to PHF is between about 1:1 and about 1:10, between about 1:1 and about 1:9, between about 1:1 and about 1:8, between about 1:1 and about 1:7, between about 1:1 and about 1:6, between about 1:1 and about 1:5, between about 1:1 and about 1:4, between about 1:1 and about 1:3, between about 1:1 and about 1:2, between about 1:2 and about 1:4, between about 1:2 and about 1:3, between about 1:3 and about 1:4, or between about 1:3 and about 1:5.

For example, when the PHF has a molecular weight ranging from 2 kDa to 40 kDa, (e.g., about 6-20 kDa or about 8-15 kDa, about 2-20 kDa, or about 3-15 kDa, or about 5-10 kDa), the number of drugs per PHF (e.g., $m_2$) is an integer from 1 to about 40 (e.g., about 1-20, or about 2-15 or about 3-10 or about 2-10). This scaffold can be used, for example, for conjugating the isolated antibody or antigen-binding fragment thereof having a molecular weight of 140 kDa to 180 kDa or of 140 kDa to 150 kDa. In this embodiment, the ratio of the isolated antibody or antigen-binding fragment thereof to PHF is between about 1:1 and about 1:10, between about 1:1 and about 1:9, between about 1:1 and about 1:8, between about 1:1 and about 1:7, between about 1:1 and about 1:6, between about 1:1 and about 1:5, between about 1:1 and about 1:4, between about 1:1 and about 1:3, between about 1:1 and about 1:2, between about 1:2 and about 1:4, between about 1:2 and about 1:3, between about 1:3 and about 1:4, or between about 1:3 and about 1:5.

The isolated antibody or antigen-binding fragment thereof in this molecular weight range, include but are not limited to, for example, full length antibodies, such as, IgG, IgM.

For example, when the PHF has a molecular weight ranging from 2 kDa to 40 kDa, the number of drugs per PHF (e.g., $m_2$) is an integer from 1 to about 40 (e.g., about 1-20 or about 2-15 or about 3-10 or about 2-10). This scaffold can be used, for example, for conjugating the isolated antibody or antigen-binding fragment thereof having a molecular weight of 60 kDa to 120 kDa. In this embodiment, the ratio of the isolated antibody or antigen-binding fragment thereof to PHF is between about 1:1 and about 1:10, between about 1:1 and about 1:9, between about 1:1 and about 1:8, between about 1:1 and about 1:7, between about 1:1 and about 1:6, between about 1:1 and about 1:5, between about 1:1 and about 1:4, between about 1:1 and about 1:3, between about 1:1 and about 1:2, between about 1:2 and about 1:4, between about 1:2 and about 1:3, between about 1:3 and about 1:4, or between about 1:3 and about 1:5.

The isolated antibodies or antigen-binding fragments thereof in this molecular weight range, include but are not limited to, for example, antibody fragments such as, for example, Fab2 and camelids.

In certain embodiment, D is a therapeutic agent. In certain embodiments, the therapeutic agent is a small molecule having a molecular weight≤about 5 kDa, ≤about 4 kDa, ≤about 3 kDa, ≤about 1.5 kDa, or ≤about 1 kDa.

In certain embodiments, the therapeutic agent has an $IC_{50}$ of about less than 1 nM.

In another embodiment, the therapeutic agent has an $IC_{50}$ of about greater than 1 nM, for example, the therapeutic agent has an $IC_{50}$ of about 1 to 50 nM.

Some therapeutic agents having an $IC_{50}$ of greater than about 1 nM (e.g., "less potent drugs") are unsuitable for conjugation with an antibody using art-recognized conjugation techniques. Without wishing to be bound by theory, such therapeutic agents have a potency that is insufficient for use in targeted antibody-drug conjugates using conventional techniques as sufficient copies of the drug (i.e., more than 8) cannot be conjugated using art-recognized techniques without resulting in diminished pharmacokinetic and physiochemical properties of the conjugate. However sufficiently high loadings of these less potent drugs can be achieved using the conjugation strategies described herein thereby resulting in high loadings of the therapeutic agent while maintaining the desirable pharmacokinetic and physiochemical properties. Thus, the invention also relates to an antibody-polymer-drug conjugate which includes the isolated antibody or antigen-binding fragment thereof, PHF and at least eight therapeutic agent moieties, where D is auristatin, Dolastatin, monomethylauristatin E (MMAE), monomethylauristatin F (MMAF), auristatin F, AF HPA, phenylenediamine (AFP).

For example, the duocarmycin or analogs thereof is duocarmycin A, duocarmycin B1, duocarmycin B2, duocarmycin C1, duocarmycin C2, duocarmycin D, duocarmycin SA, CC-1065, adozelesin, bizelesin, or carzelesin.

Other examples of D include those described in, for example, US Application Publication No. 2013-0101546 and U.S. Pat. No. 8,815,226; and co-pending applications with U.S. Ser. No. 14/512,316 filed Oct. 10, 2014, 61/988, 011 filed May 2, 2014, and 62/010,972 filed Jun. 11, 2014; the disclosure of each of which is incorporated herein in its entirety.

In some embodiments, the number of D-carrying polymeric scaffolds that can be conjugated to an antibody is limited by the number of free cysteine residues. In some embodiments, free cysteine residues are introduced into the antibody amino acid sequence by the methods described herein. Exemplary conjugates disclosed herein can include antibodies that have 1, 2, 3, or 4 engineered cysteine amino acids (Lyon, R. et al (2012) Methods in Enzym. 502:123-138). In some embodiments, one or more free cysteine residues are already present in an antibody, without the use of engineering, in which case the existing free cysteine residues may be used to conjugate the antibody to a D-carrying polymeric scaffold. In some embodiments, an antibody is exposed to reducing conditions prior to conjugation of the antibody in order to generate one or more free cysteine residues.

In certain embodiments, in the conjugate described herein, the D-carrying polymeric scaffold of Formula (Ic) is of Formula (Ie):

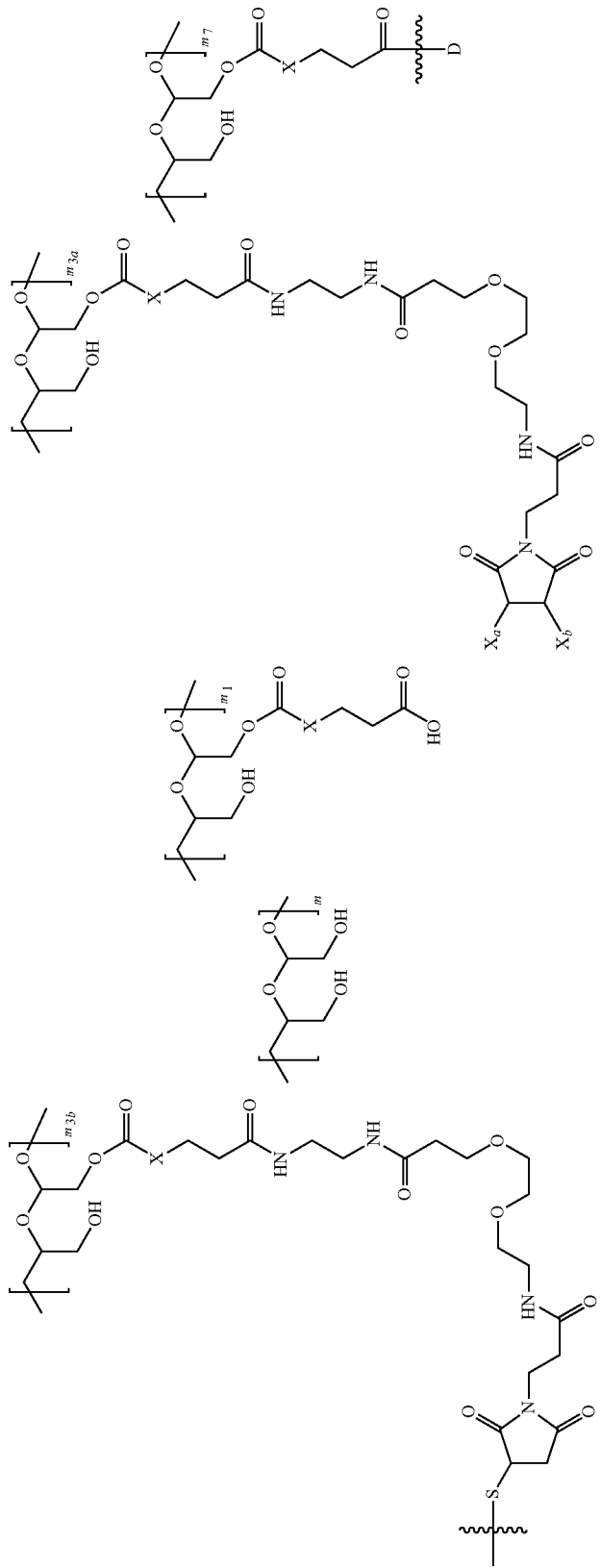

wherein, the PHF has a molecular weight ranging from about 2 kDa to about 40 kDa;

each occurrence of D independently is a therapeutic agent having a molecular weight of ≤5 kDa, and the

between D and the carbonyl group denotes direct or indirect attachment of D to the carbonyl group, X is $CH_2$, O, or NH;

one of $X_a$ and $X_b$ is H and the other is a water-soluble maleimido blocking moiety, or $X_a$ and $X_b$, together with the carbon atoms to which they are attached for a carbon-carbon double bond, $m_1$ is an integer from 1 to about 140, $m_7$ is an integer from 1 to about 40, and the sum of $m_1$ and $m_7$ is about 2 to about 180 m is an integer from 1 to about 300, $m_{3a}$ is an integer from 0 to about 17, $m_{3b}$ is an integer from 1 to about 8, and the sum of $m_{3a}$ and $m_{3b}$ is between 1 and 18, and the sum of m, $m_1$, $m_7$, $m_{3a}$, and $m_{3b}$ ranges from about 15 to about 300.

In certain embodiments, in the conjugate described herein, the D-carrying polymeric scaffold of Formula (Ie) is of Formula (Id):

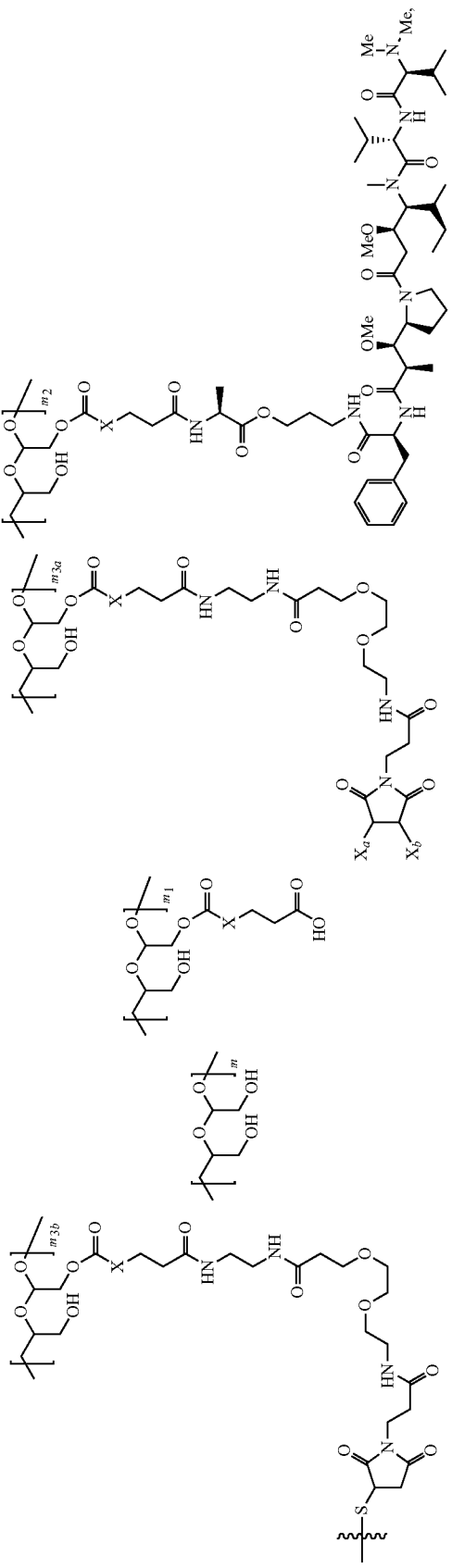

wherein:
one of $X_a$ and $X_b$ is H and the other is a water-soluble maleimido blocking moiety, or $X_a$ and $X_b$, together with the carbon atoms to which they are attached for a carbon-carbon double bond;

$m_{3a}$ is an integer from 0 to about 17, $m_{3b}$ is an integer from 1 to about 8, and the sum of $m_{3a}$ and $m_{3b}$ is between 1 and 18, and the sum of m, $m_1$, $m_2$, $m_{3a}$, and $m_{3b}$ ranges from about 15 to about 300.

For example, the ratio between $m_2$ and $m_{3b}$ is greater than 1:1 and less than or equal to 10:1.

For example, the ratio between $m_2$ and $m_{3b}$ is about 9:1, 8:1, 7:1, 6:1, 5:1, 4:1, 3:1, or 2:1.

For example, the ratio between $m_2$ and $m_{3b}$ is between 2:1 and 8:1.

For example, the ratio between $m_2$ and $m_{3b}$ is about 8:1, 7:1, 6:1, 5:1, 4:1, 3:1, or 2:1.

For example, the ratio between $m_2$ and $m_{3b}$ is between 2:1 and 4:1.

For example, the ratio between $m_2$ and $m_{3b}$ is about 4:1, 3:1, or 2:1.

For example, the ratio between $m_2$ and $m_{3b}$ is about 3:1 and 5:1.

For example, the ratio between $m_2$ and $m_{3b}$ is about 3:1, 4:1 or 5:1.

For example, when the PHF in Formula (Id) has a molecular weight ranging from about 2 kDa to about 20 kDa, the sum of m, $m_1$, $m_2$, $m_{3a}$ and $m_{3b}$ ranges from about 15 to about 150, $m_1$ is an integer from 1 to about 70, $m_2$ is an integer from 1 to about 20, $m_{3a}$ is an integer from 0 to about 9, $m_{3b}$ is an integer from 1 to about 8 and the ratio between the PHF and the isolated HER2 antibody or antigen-binding fragment thereof is an integer from 2 to about 8.

For example, when the PHF in Formula (Id) has a molecular weight ranging from about 3 kDa to about 15 kDa, the sum of m, $m_1$, $m_2$, $m_{3a}$ and $m_{3b}$ ranges from about 20 to about 110, $m_1$ is an integer from 2 to about 50, $m_2$ is an integer from 2 to about 15, $m_{3a}$ is an integer from 0 to about 7, $m_{3b}$ is an integer from 1 to about 8 and the ratio between the PHF and the isolated HER2 antibody or antigen-binding fragment thereof is an integer from 2 to about 8 (e.g., an integer from 2 to about 6 or an integer from 2 to about 4).

For example, when the PHF in Formula (Id) has a molecular weight ranging from about 5 kDa to about 10 kDa, the sum of m, $m_1$, $m_2$, $m_{3a}$ and $m_{3b}$ ranges from about 40 to about 75, $m_1$ is an integer from about 2 to about 35, $m_2$ is an integer from about 2 to about 10, $m_{3a}$ is an integer from 0 to about 4, $m_{3b}$ is an integer from 1 to about 5 and the ratio between the PHF and the isolated HER2 antibody or antigen-binding fragment thereof is an integer from 2 to about 8 (e.g., an integer from 2 to about 6 or an integer from 2 to about 4).

For example, the water-soluble maleimido blocking moieties are moieties that can be covalently attached to one of the two olefin carbon atoms upon reaction of the maleimido group with a thiol-containing compound of Formula (II):

$$R_{90}-(CH_2)_d-SH \quad (II)$$

wherein:
$R_{90}$ is $NHR_{91}$, OH, $COOR_{93}$, $CH(NHR_{91})COOR_{93}$ or a substituted phenyl group;

$R_{93}$ is hydrogen or $C_{1-4}$ alkyl;

$R_{91}$ is hydrogen, $CH_3$ or $CH_3CO$ and d is an integer from 1 to 3.

For example, the water-soluble maleimido blocking compound of Formula (II) can be cysteine, N-acetyl cysteine, cysteine methyl ester, N-methyl cysteine, 2-mercaptoethanol, 3-mercaptopropanoic acid, 2-mercaptoacetic acid, mercaptomethanol (i.e., $HOCH_2SH$), benzyl thiol in which phenyl is substituted with one or more hydrophilic substituents, or 3-aminopropane-1-thiol. The one or more hydrophilic substituents on phenyl comprise OH, SH, methoxy, ethoxy, COOH, CHO, $COC_{1-4}$ alkyl, $NH_2$, F, cyano, $SO_3H$, $PO_3H$, and the like.

For example, the water-soluble maleimido blocking group is $-S-(CH_2)_d-R_{90}$, in which, $R_{90}$ is OH, COOH, or $CH(NHR_{91})COOR_{93}$;

$R_{93}$ is hydrogen or $CH_3$;

$R_{91}$ is hydrogen or $CH_3CO$; and d is 1 or 2.

For example, the water-soluble maleimido blocking group is $-S-CH_2-CH(NH_2)COOH$.

For example, when the PHF has a molecular weight ranging from 2 kDa to 40 kDa, (e.g., about 2-20 kDa, or about 3-15 kDa, or about 5-10 kDa), the number of drugs per PHF (e.g., $m_2$) is an integer from 1 to about 40 (e.g., about 1-20 or about 2-15 or about 3-10 or about 2-10). This scaffold can be used, for example, for conjugating an isolated antibody or antigen-binding fragment thereof having a molecular weight of 40 kDa or greater (e.g., 60 kDa or greater; 80 kDa or greater; or 100 kDa or greater; 120 kDa or greater; 140 kDa or greater; 160 kDa or greater, 180 kDa or greater, or 200 kDa or greater, or about 40-200 kDa, 40-180 kDa, 40-140 kDa, 60-200 kDa, 60-180 kDa, 60-140 kDa, 80-200 kDa, 80-180 kDa, 80-140 kDa, 100-200 kDa, 100-180 kDa, 100-140 kDa or 140-150 kDa). In this embodiment, the ratio of the isolated antibody or antigen-binding fragment thereof to PHF is between about 1:1 and about 1:10, between about 1:1 and about 1:9, between about 1:1 and about 1:8, between about 1:1 and about 1:7, between about 1:1 and about 1:6, between about 1:1 and about 1:5, between about 1:1 and about 1:4, between about 1:1 and about 1:3, between about 1:1 and about 1:2, between about 1:2 and about 1:8, between about 1:2 and about 1:6, between about 1:2 and about 1:5, between about 1:2 and about 1:4, between about 1:2 and about 1:3, between about 1:3 and about 1:4, or between about 1:3 and about 1:5.

For example, when the PHF has a molecular weight ranging from 2 kDa to 40 kDa, (e.g., about 2-20 kDa, or about 3-15 kDa, or about 5-10 kDa), the number of drugs per PHF (e.g., $m_2$) is an integer from 1 to about 40 (e.g., about 1-20 or about 2-15 or about 3-10 or about 2-10). This scaffold can be used, for example, for conjugating an isolated antibody or antigen-binding fragment having a molecular weight of 140 kDa to 180 kDa or of 140 kDa to 150 kDa. In this embodiment the ratio of the isolated antibody or antigen-binding fragment thereof to PHF is between about 1:1 and about 1:10, between about 1:1 and about 1:9, between about 1:1 and about 1:8, between about 1:1 and about 1:7, between about 1:1 and about 1:6, between about 1:1 and about 1:5, between about 1:1 and about 1:4, between about 1:1 and about 1:3, between about 1:1 and about 1:2, between about 1:2 and about 1:8, between about 1:2 and about 1:6, between about 1:2 and about 1:5, between about 1:2 and about 1:4, between about 1:2 and about 1:3, between about 1:3 and about 1:4, or between about 1:3 and about 1:5.

The isolated antibodies or antigen-binding fragments in this molecular weight range, include but are not limited to, for example, full length antibodies, such as, IgG, IgM.

For example, when the PHF has a molecular weight ranging from 2 kDa to 40 kDa (e.g., about 2-20 kDa, or about 3-15 kDa, or about 5-10 kDa), the number of drugs per PHF (e.g., $m_2$) is an integer from 1 to about 40, (e.g., about 1-20 or about 2-15 or about 3-10 or 2-10). This scaffold can be used, for example, for conjugating an isolated antibody or antigen-binding fragment having a molecular weight of 60 kDa to 120 kDa. In this embodiment the ratio of the isolated antibody or antigen-binding fragment thereof to PHF is between about 1:1 and about 1:10, between about 1:1 and about 1:9, between about 1:1 and about 1:8, between about 1:1 and about 1:7, between about 1:1 and about 1:6, between about 1:1 and about 1:5, between about 1:1 and about 1:4, between about 1:1 and about 1:3, between about 1:1 and about 1:2, between about 1:2 and about 1:8, between about 1:2 and about 1:6, between about 1:2 and about 1:5, between about 1:2 and about 1:4, between about 1:2 and about 1:3, between about 1:3 and about 1:4, or between about 1:3 and about 1:5.

The isolated antibodies or antigen-binding fragments in this molecular weight range, include but are not limited to, for example, antibody fragments such as, for example Fab2, scFcFv and camelids.

For example, when the PHF has a molecular weight ranging from 2 kDa to 40 kDa, (e.g., about 2-20 kDa, or about 3-15 kDa, or about 5-10 kDa), the number of drugs per PHF (e.g., $m_2$) is an integer from 1 to about 40 (e.g., about 1-20 or about 2-15 or about 3-10 or 2-10). This scaffold can be used, for example, for conjugating the isolated antibody or antigen-binding fragment thereof having a molecular weight of 40 kDa to 80 kDa. In this embodiment the ratio of the isolated antibody or antigen-binding fragment thereof to PHF is between about 1:1 and about 1:10, between about 1:1 and about 1:9, between about 1:1 and about 1:8, between about 1:1 and about 1:7, between about 1:1 and about 1:6, between about 1:1 and about 1:5, between about 1:1 and about 1:4, between about 1:1 and about 1:3, between about 1:1 and about 1:2, between about 1:2 and about 1:8, between about 1:2 and about 1:6, between about 1:2 and about 1:5, between about 1:2 and about 1:4, between about 1:2 and about 1:3, between about 1:3 and about 1:4, or between about 1:3 and about 1:5.

The isolated antibodies or antigen-binding fragments in this molecular weight range, i.e., about 40 kDa to about 80 kDa, include but are not limited to, for example, antibody fragments such as, for example, Fabs.

In certain embodiments, in the conjugate described herein, the D-carrying polymeric scaffold of Formula (Ie) is of Formula (If), wherein the polymer is PHF that has a molecular weight ranging from about 2 kDa to about 40 kDa:

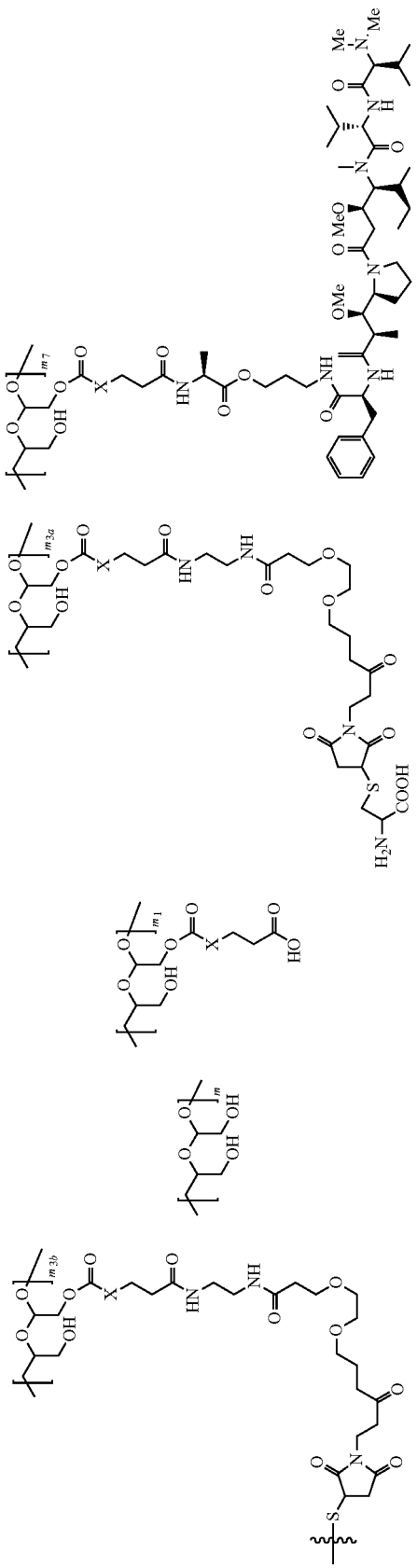

wherein:
m is an integer from 1 to about 300,
$m_1$ is an integer from 1 to about 140,
$m_2$ is an integer from 1 to about 40,
$m_{3a}$ is an integer from 0 to about 17,
$m_{3b}$ is an integer from 1 to about 8;
the sum of $m_{3a}$ and $m_{3b}$ ranges from 1 and about 18;
the sum of m, $m_1$, $m_2$, $m_{3a}$, and $m_3$b ranges from about 15 to about 300;
the terminal

denotes the attachment of one or more polymeric scaffolds to the isolated antibody or antigen binding fragment thereof that specifically binds to an epitope of the human HER2 receptor and comprises a variable heavy chain complementarity determining region 1 (CDRH1) comprising the amino acid sequence FTFSSYSMN (SEQ ID NO: 25); a variable heavy chain complementarity determining region 2 (CDRH2) comprising the amino acid sequence YISSSSSTI-YYADSVKG (SEQ ID NO: 26); a variable heavy chain complementarity determining region 3 (CDRH3) comprising the amino acid sequence GGHGYFDL (SEQ ID NO: 27); a variable light chain complementarity determining region 1 (CDRL1) comprising the amino acid sequence RASQSVSSSYLA (SEQ ID NO: 28); a variable light chain complementarity determining region 2 (CDRL2) comprising the amino acid sequence GASSRAT (SEQ ID NO: 21); and a variable light chain complementarity determining region 3 (CDRL3) comprising the amino acid sequence QQYHH-SPLT (SEQ ID NO: 29); and the ratio between the PHF and the antibody is 10 or less.

The scaffold of Formula (If) can include one or more of the following features:

When the PHF in Formula (If) has a molecular weight ranging from about 2 kDa to about 20 kDa, the sum of m, $m_1$, $m_2$, $m_{3a}$ and $m_{3b}$ ranges from about 15 to about 150, $m_1$ is an integer from 1 to about 70, $m_2$ is an integer from 1 to about 20, $m_{3a}$ is an integer from 0 to about 9, $m_{3b}$ is an integer from 1 to about 8, the sum of $m_{3a}$ and $m_{3b}$ ranges from 1 and about 10, and the ratio between the PHF and antibody is an integer from 2 to about 8.

When the PHF in Formula (If) has a molecular weight ranging from about 3 kDa to about 15 kDa, the sum of m, $m_1$, $m_2$, $m_{3a}$ and $m_{3b}$ ranges from about 20 to about 110, $m_1$ is an integer from 2 to about 50, $m_2$ is an integer from 2 to about 15, $m_{3a}$ is an integer from 0 to about 7, $m_{3b}$ is an integer from 1 to about 8, the sum of $m_{3a}$ and $m_{3b}$ ranges from 1 and about 8; and the ratio between the PHF and antibody is an integer from 2 to about 8 (e.g., from about 2 to about 6 or from about 2 to about 4).

When the PHF in Formula (If) has a molecular weight ranging from about 5 kDa to about 10 kDa, the sum of m, $m_1$, $m_2$, $m_{3a}$ and $m_{3b}$ ranges from about 40 to about 75, $m_1$ is an integer from about 2 to about 35, $m_2$ is an integer from about 2 to about 10, $m_{3a}$ is an integer from 0 to about 4, $m_{3b}$ is an integer from 1 to about 5, the sum of $m_{3a}$ and $m_{3b}$ ranges from 1 and about 5; and the ratio between the PHF and antibody is an integer from 2 to about 8 (e.g., from about 2 to about 6 or from about 2 to about 4).

In certain embodiments, the ratio between auristatin F hydroxylpropyl amide ("AF HPA") and the antibody can be about 30:1, 29:1, 28:1, 27:1, 26:1, 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1 or 6:1.

In certain embodiments, the ratio between AF HPA and the antibody can be about 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1 or 6:1.

In other embodiments, the ratio between AF HPA and the antibody can be about 20:1, 19:1, 18:1, 17:1, 16:1, 15:1, 14:1, 13:1, 12:1, 11:1, 10:1, 9:1, 8:1, 7:1 or 6:1.

In some embodiments, the ratio between AF HPA and the antibody can be about 16:1, 15:1, 14:1, 13:1, 12:1, 11:1 or 10:1.

In some embodiments, the ratio between AF and the antibody can be about 15:1, 14:1, 13:1, 12:1 or 11:1.

In some embodiments, the ratio between AF HPA and the antibody can be about 15:1, 14:1, 13:1 or 12:1.

In certain embodiments, the ratio between PHF and the antibody can be about 10:1, 9:1, 8:1, 7:1, 6:1, 5:1, 4:1, 3:1, 2:1 or 1:1.

In certain embodiments, the ratio between PHF and the antibody can be about 8:1, 7:1, 6:1, 5:1, 4:1, 3:1 or 2:1.

In other embodiments, the ratio between PHF and the antibody can be about 6:1, 5:1, 4:1, 3:1, 2:1 or 1:1.

In other embodiments, the ratio between PHF and the antibody can be about 6:1, 5:1, 4:1, 3:1 or 2:1.

In other embodiments, the ratio between PHF and the antibody can be about 6:1, 5:1, 4:1 or 3:1.

In some embodiments, the ratio between PHF and the antibody can be about 5:1, 4:1 or 3:1.

In some embodiments, the ratio between PHF and the antibody can be about 4:1, 3:1 or 2:1.

The isolated antibodies or antigen-binding fragments in this molecular weight range, include but are not limited to, for example, antibody fragments, such as, Fabs.

Other embodiments of antibody-polymer drug conjugates are those described in, for example, U.S. Pat. No. 8,815,226; and U.S. Ser. No. 14/512,316 filed Oct. 10, 2014, and 61/988,011 filed May 2, 2014; the disclosure of each of which is incorporated herein in its entirety.

This invention also relates to a drug derivative so modified that it can be directly conjugated to an antibody or antigen-binding fragment thereof absent a polymeric carrier, and the drug-antibody conjugates thereof.

In some embodiments, the antibody-drug conjugates include an antibody or antigen-binding fragment thereof conjugated, i.e. covalently attached, to the drug moiety. In some embodiments, the antibody or antigen-binding fragment thereof is covalently attached to the drug moiety through a linker, e.g., a non-polymeric linker.

The drug moiety (D) of the antibody-drug conjugates (ADC) may include any compound, moiety or group that has a cytotoxic or cytostatic effect as defined herein. In certain embodiments, an antibody-drug conjugate (ADC) comprises an antibody (Ab) which targets a tumor cell, a drug moiety (D), and a linker moiety (L) that attaches Ab to D. In some embodiments, the antibody is attached to the linker moiety (L) through one or more amino acid residues, such as lysine and/or cysteine.

In certain embodiments the ADC has Formula (Ig):

$$Ab\text{-}(L\text{-}D)_p \qquad (Ig),$$

where p is 1 to about 20.

In some embodiments, the number of drug moieties that can be conjugated to an antibody is limited by the number of free cysteine residues. In some embodiments, free cysteine residues are introduced into the antibody amino acid sequence by the methods described herein. Exemplary ADC of Formula Ig include, but are not limited to, antibodies that have 1, 2, 3, or 4 engineered cysteine amino acids (Lyon, R. et al (2012) Methods in Enzym. 502:123-138). In some embodiments, one or more free cysteine residues are already present in an antibody, without the use of engineering, in which case the existing free cysteine residues may be used to conjugate the antibody to a drug. In some embodiments, an antibody is exposed to reducing conditions prior to conjugation of the antibody in order to generate one or more free cysteine residues.

In some embodiments the "Linker" (L) is a bifunctional or multifunctional moiety that can be used to link one or more drug moieties (D) to an antibody (Ab) to form an antibody-drug conjugate (ADC) of Formula Ig. In some embodiments, antibody-drug conjugates (ADC) can be prepared using a Linker having reactive functionalities for covalently attaching to the drug and to the antibody. For example, in some embodiments, a cysteine thiol of an antibody (Ab) can form a bond with a reactive functional group of a linker or a drug-linker intermediate to make an ADC.

In one aspect, a linker has a functionality that is capable of reacting with a free cysteine present on an antibody to form a covalent bond. Nonlimiting exemplary such reactive functionalities include maleimide, haloacetamides, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates, and isothiocyanates. See, e.g., the conjugation method at page 766 of Klussman, et al (2004), Bioconjugate Chemistry 15(4):765-773, and the Examples herein.

In some embodiments, a linker has a functionality that is capable of reacting with an electrophilic group present on an antibody. Exemplary such electrophilic groups include, but are not limited to, aldehyde and ketone carbonyl groups. In some embodiments, a heteroatom of the reactive functionality of the linker can react with an electrophilic group on an antibody and form a covalent bond to an antibody unit. Nonlimiting exemplary such reactive functionalities include, but are not limited to, hydrazide, oxime, amino, hydrazine, thiosemicarbazone, hydrazine carboxylate, and arylhydrazide.

A linker may comprise one or more linker components. Exemplary linker components include 6-maleimidocaproyl ("MC"), maleimidopropanoyl ("MP"), valine-citrulline ("val-cit" or "vc"), alanine-phenylalanine ("ala-phe"), p-aminobenzyloxycarbonyl (a "PAB"), N-Succinimidyl 4-(2-pyridylthio) pentanoate ("SPP"), and 4-(N-maleimidomethyl)cyclohexane-1 carboxylate ("MCC"). Various linker components are known in the art, some of which are described below.

A linker may be a "cleavable linker," facilitating release of a drug. Nonlimiting exemplary cleavable linkers include acid-labile linkers (e.g., comprising hydrazone), protease-sensitive (e.g., peptidase-sensitive) linkers, photolabile linkers, or disulfide-containing linkers (Chari et al., Cancer Research 52:127-131 (1992); U.S. Pat. No. 5,208,020).

In certain embodiments, a linker has the following Formula (IIg):

-A$_a$-W$_w$—Y$_y$  (IIg)

wherein:
A is a "stretcher unit", and a is an integer from 0 to 1;
W is an "amino acid unit", and w is an integer from 0 to 12;
Y is a "spacer unit", and y is an integer 0, 1, or 2. An ADC comprising the linker of Formula (IIg) has the Formula I(A):

Ab-(Aa-Ww-Yy-D)p, wherein Ab, D, and p are defined as above for Formula (Ig). Exemplary embodiments of such linkers are described in U.S. Pat. No. 7,498,298, which is incorporated herein by reference in its entirety.

In some embodiments, a linker component comprises a "stretcher unit" (A) that links an antibody to another linker component or to a drug moiety. Nonlimiting exemplary stretcher units are shown below (wherein the wavy line indicates sites of covalent attachment to an antibody, drug, or additional linker components):

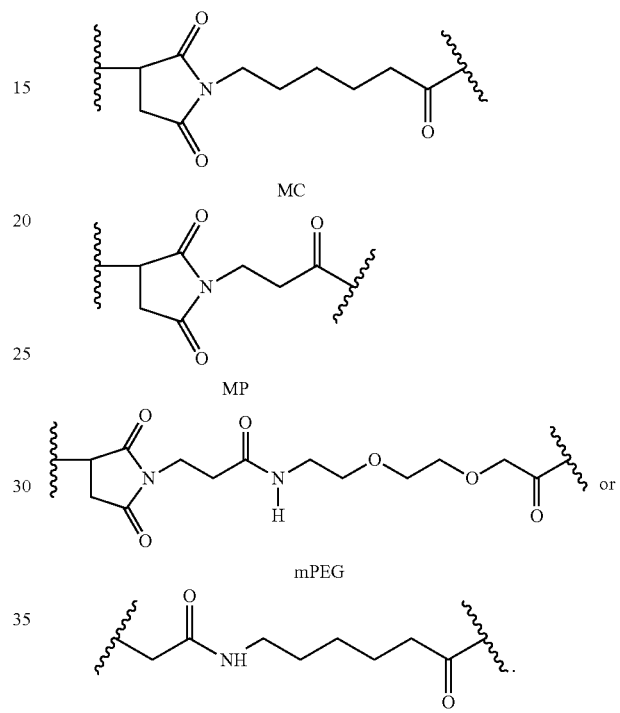

In some embodiments, a linker component comprises an "amino acid unit" (W). In some such embodiments, the amino acid unit allows for cleavage of the linker by a protease, thereby facilitating release of the drug from the immunoconjugate upon exposure to intracellular proteases, such as lysosomal enzymes (Doronina et al. (2003) Nat. Biotechnol. 21:778-784). Exemplary amino acid units include, but are not limited to, dipeptides, tripeptides, tetrapeptides, and pentapeptides. Exemplary dipeptides include, but are not limited to, valine-citrulline (vc or val-cit), alanine-phenylalanine (af or ala-phe); phenylalanine-lysine (fk or phe-lys); phenylalanine-homolysine (phe-homolys); and N-methyl-valine-citrulline (Me-val-cit). Exemplary tripeptides include, but are not limited to, glycine-valine-citrulline (gly-val-cit) and glycine-glycine-glycine (gly-gly-gly). An amino acid unit may comprise amino acid residues that occur naturally and/or minor amino acids and/or non-naturally occurring amino acid analogs, such as citrulline. Amino acid units can be designed and optimized for enzymatic cleavage by a particular enzyme, for example, a tumor-associated protease, cathepsin B, C and D, or a plasmin protease.

Typically, peptide-type linkers can be prepared by forming a peptide bond between two or more amino acids and/or peptide fragments. Such peptide bonds can be prepared, for example, according to a liquid phase synthesis method (e.g., E. Schrider and K. Lubke (1965) "The Peptides", volume 1, pp 76-136, Academic Press).

In some embodiments, a linker component comprises a "spacer" unit that links the antibody to a drug moiety, either directly or through a stretcher unit and/or an amino acid unit. A spacer unit may be "self-immolative" or a "non-self-immolative." A "non-self-immolative" spacer unit is one in which part or all of the spacer unit remains bound to the drug moiety upon cleavage of the ADC. Examples of non-self-immolative spacer units include, but are not limited to, a glycine spacer unit and a glycine-glycine spacer unit. In some embodiments, enzymatic cleavage of an ADC containing a glycine-glycine spacer unit by a tumor-cell associated protease results in release of a glycine-glycine-drug moiety from the remainder of the ADC. In some such embodiments, the glycine-glycine-drug moiety is subjected to a hydrolysis step in the tumor cell, thus cleaving the glycine-glycine spacer unit from the drug moiety.

A "self-immolative" spacer unit allows for release of the drug moiety. In certain embodiments, a spacer unit of a linker comprises a p-aminobenzyl unit. In some such embodiments, a p-aminobenzyl alcohol is attached to an amino acid unit via an amide bond, and a carbamate, methylcarbamate, or carbonate is made between the benzyl alcohol and the drug (Hamann et al. (2005) Expert Opin. Ther. Patents (2005) 15:1087-1103). In some embodiments, the spacer unit comprises p-aminobenzyloxycarbonyl (PAB). In some embodiments, an ADC comprising a self-immolative linker has the structure:

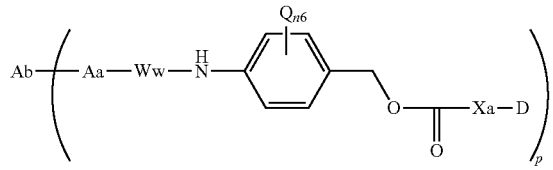

wherein:
Q is —$C_1$-C8 alkyl, —O—($C_1$-$C_8$ alkyl), halogen, nitro, or cyano;
$n_6$ is an integer from 0 to 4;
$X_a$ may be one or more additional spacer units or may be absent; and
p in an integer from 1 to about 20.

In some embodiments, p in an integer from 1 to 10, 1 to 7, 1 to 5, or 1 to 4. Nonlimiting exemplary $X_a$ spacer units include:

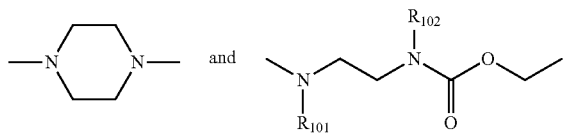

wherein $R_{101}$ and $R_{102}$ are independently selected from H and $C_1$-$C_6$ alkyl. In some embodiments, $R_{101}$ and $R_{102}$ are each —$CH_3$.

Other examples of self-immolative spacers include, but are not limited to, aromatic compounds that are electronically similar to the PAB group, such as 2-aminoimidazol-5-methanol derivatives (U.S. Pat. No. 7,375,078; Hay et al. (1999) Bioorg. Med. Chem. Lett. 9:2237) and ortho- or para-aminobenzylacetals. In some embodiments, spacers can be used that undergo cyclization upon amide bond hydrolysis, such as substituted and unsubstituted 4-aminobutyric acid amides (Rodrigues et al (1995) Chemistry Biology 2:223), appropriately substituted bicyclo[2.2.1] and bicyclo[2.2.2] ring systems (Storm et al (1972) J. Amer. Chem. Soc. 94:5815) and 2-aminophenylpropionic acid amides (Amsberry, et al (1990) J. Org. Chem. 55:5867). Linkage of a drug to the α-carbon of a glycine residue is another example of a self-immolative spacer that may be useful in ADC (Kingsbury et al (1984) J. Med. Chem. 27:1447).

In some embodiments, linker L may be a dendritic type linker for covalent attachment of more than one drug moiety to an antibody through a branching, multifunctional linker moiety (Sun et al (2002) Bioorganic & Medicinal Chemistry Letters 12:2213-2215; Sun et al (2003) Bioorganic & Medicinal Chemistry 11:1761-1768). Dendritic linkers can increase the molar ratio of drug to antibody, i.e. loading, which is related to the potency of the ADC. Thus, where an antibody bears only one reactive cysteine thiol group, a multitude of drug moieties may be attached through a dendritic linker.

Nonlimiting exemplary linkers are shown below for ADCs of Formula (Ig):

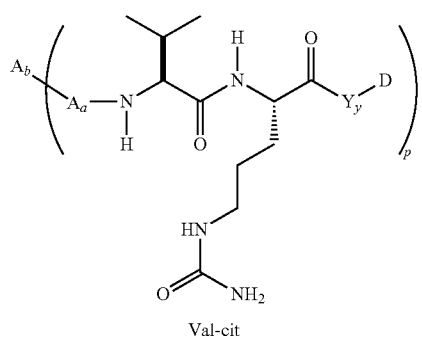

Val-cit

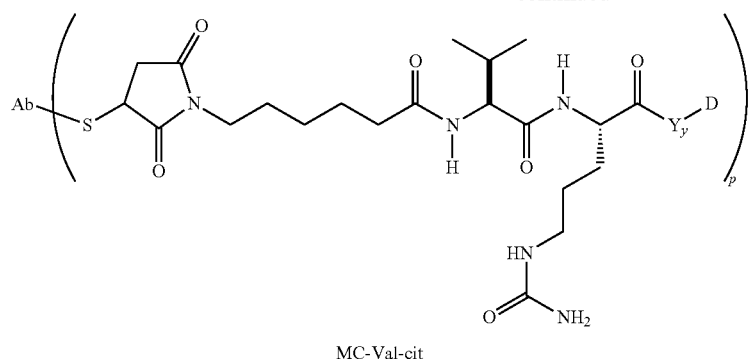
MC-Val-cit
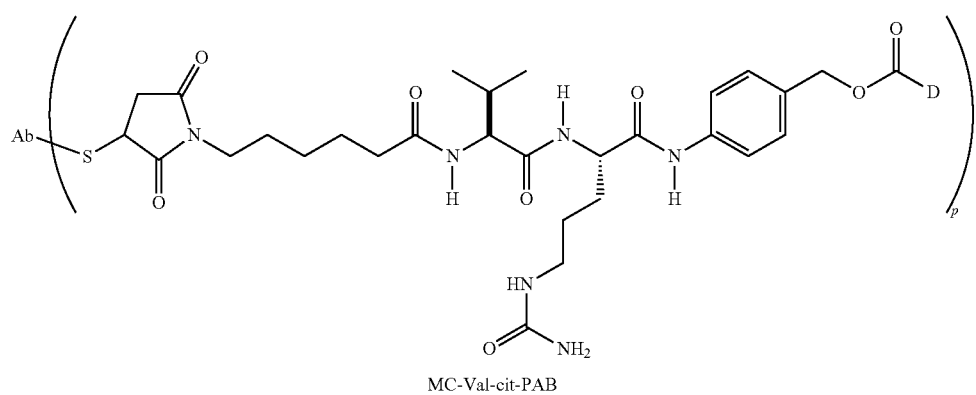
MC-Val-cit-PAB
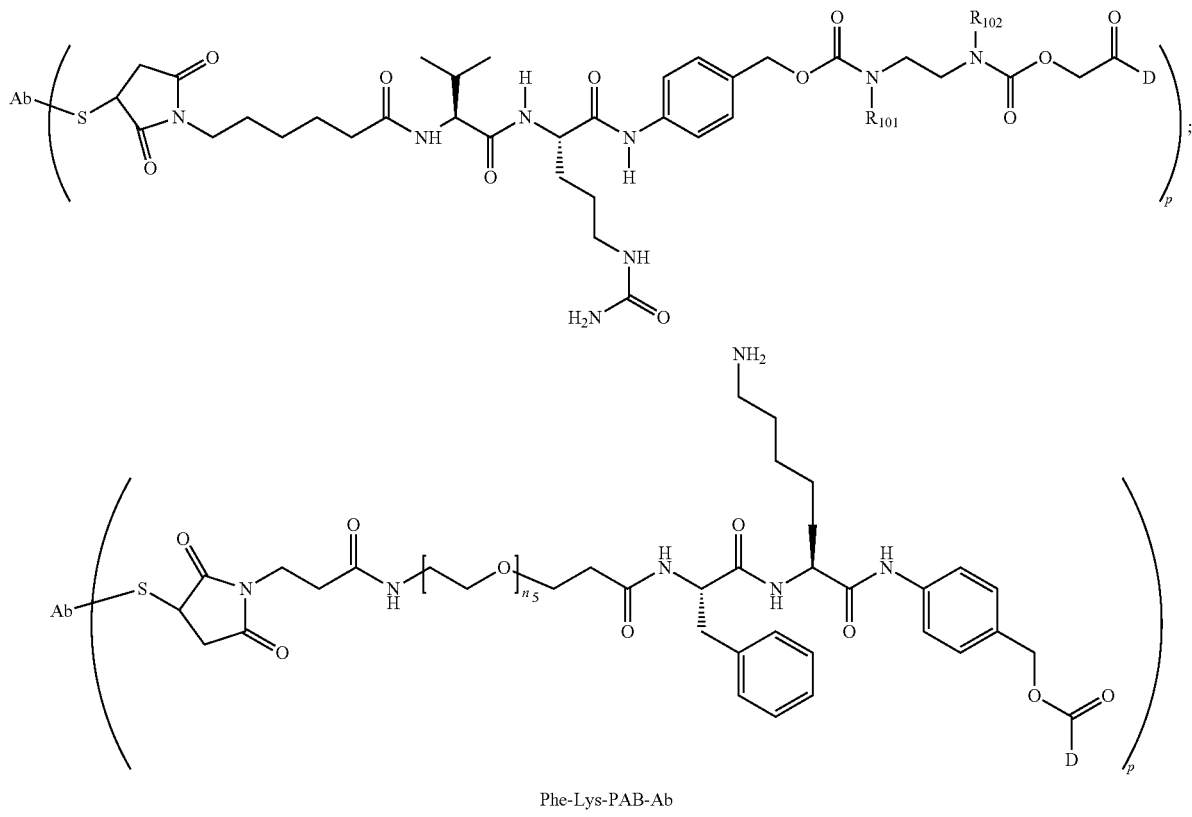
Phe-Lys-PAB-Ab wherein $R_{101}$ and $R_{102}$ are independently selected from H and $C_1$-$C_6$ alkyl;

$n_5$ is an integer from 0 to 12.

In some embodiments, n is an integer 2 to 10. In some embodiments, n is an integer from 4 to 8.

In some embodiments, $R_{101}$ and $R_{102}$ are each —$CH_3$.

Further nonlimiting exemplary ADCs include the structures:

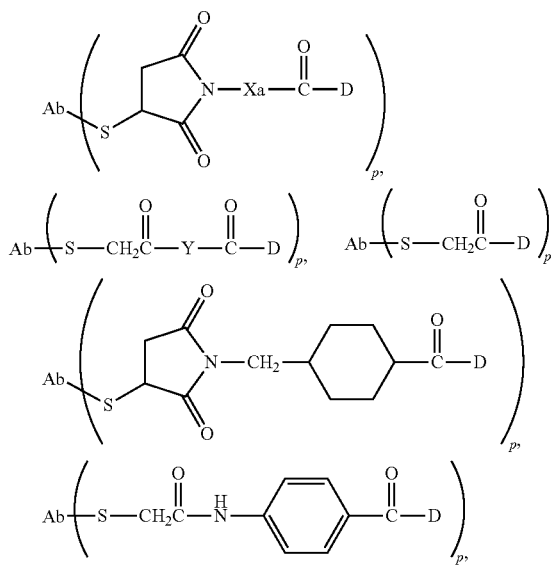

wherein Xa is:

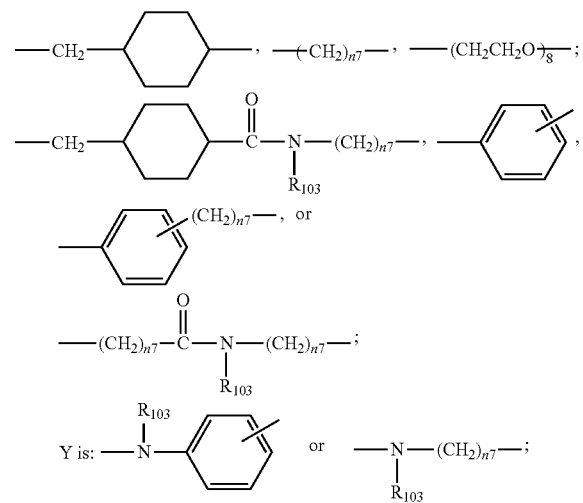

each $R_{103}$ is independently H or $C_1$-$C_6$ alkyl; and n7 is an integer from 1 to 12.

In some embodiments, a linker is substituted with groups that modulate solubility and/or reactivity. As a nonlimiting example, a charged substituent such as sulfonate (—$SO_3^-$) or ammonium may increase water solubility of the linker reagent and facilitate the coupling reaction of the linker reagent with the antibody and/or the drug moiety, or facilitate the coupling reaction of Ab-L (antibody-linker intermediate) with D, or D-L (drug-linker intermediate) with Ab, depending on the synthetic route employed to prepare the ADC. In some embodiments, a portion of the linker is coupled to the antibody and a portion of the linker is coupled to the drug, and then the Ab-(linker portion)$^a$ is coupled to drug-(linker portion)$^b$ to form the ADC of Formula Ig.

The compounds disclosed herein expressly contemplate, but are not limited to, ADC prepared with the following linker reagents: bis-maleimido-trioxyethylene glycol (BMPEO), N-(β-maleimidopropyloxy)-N-hydroxy succinimide ester (BMPS), N-(ε-maleimidocaproyloxy) succinimide ester (EMCS), N-[γ-maleimidobutyryloxy]succinimide ester (GMBS), 1,6-hexane-bis-vinylsulfone (HBVS), succinimidyl 4-(N-maleimidomethyl)cyclohexane-1-carboxy-(6-amidocaproate) (LC-SMCC), m-maleimidobenzoyl-N-hydroxysuccinimide ester (MBS), 4-(4-N-Maleimidophenyl)butyric acid hydrazide (MPBH), succinimidyl 3-(bromoacetamido)propionate (SBAP), succinimidyl iodoacetate (SIA), succinimidyl (4-iodoacetyl) aminobenzoate (SIAB), N-succinimidyl-3-(2-pyridyldithio) propionate (SPDP), N-succinimidyl-4-(2-pyridylthio)pentanoate (SPP), succinimidyl 4-(N-maleimidomethyl)cyclohexane-1-carboxylate (SMCC), succinimidyl 4-(p-maleimidophenyl)butyrate (SMPB), succinimidyl 6-[(β-maleimidopropionamido)hexanoate] (SMPH), iminothiolane (IT), sulfo-EMCS, sulfo-GMBS, sulfo-KMUS, sulfo-MBS, sulfo-SIAB, sulfo-SMCC, and sulfo-SMPB, and succinimidyl-(4-vinyl sulfone)benzoate (SVSB), and including bis-maleimide reagents: dithiobis-maleimidoethane (DTME), 1,4-Bismaleimidobutane (BMB), 1,4 Bismaleimidyl-2,3-dihydroxybutane (BMDB), bismaleimidohexane (BMH), bismaleimidoethane (BMOE), BM(PEG)$_2$ (shown below), and BM(PEG)$_3$ (shown below); bifunctional derivatives of imidoesters (such as dimethyl adipimidate HCl), active esters (such as disuccinimidyl suberate), aldehydes (such as glutaraldehyde), bis-azido compounds (such as bis-(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). In some embodiments, bis-maleimide reagents allow the attachment of the thiol group of a cysteine in the antibody to a thiol-containing drug moiety, linker, or linker-drug intermediate. Other functional groups that are reactive with thiol groups include, but are not limited to, iodoacetamide, bromoacetamide, vinyl pyridine, disulfide, pyridyl disulfide, isocyanate, and isothiocyanate.

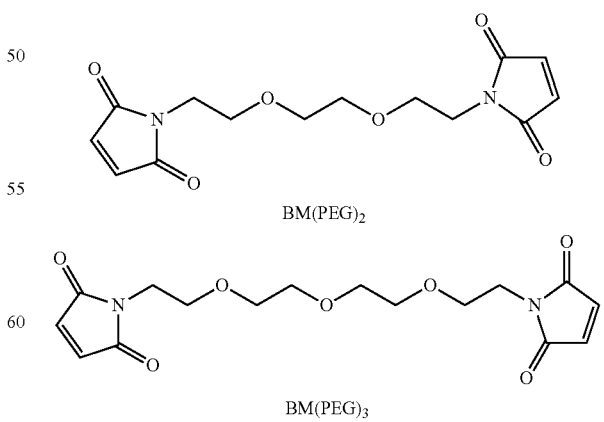

Certain useful linker reagents can be obtained from various commercial sources, such as Pierce Biotechnology, Inc.

(Rockford, Ill.), Molecular Biosciences Inc. (Boulder, Colo.), or synthesized in accordance with procedures described in the art; for example, in Toki et al (2002) J. Org. Chem. 67:1866-1872; Dubowchik, et al. (1997) Tetrahedron Letters, 38:5257-60; Walker, M. A. (1995) J. Org. Chem. 60:5352-5355; Frisch et al (1996) Bioconjugate Chem. 7:180-186; U.S. Pat. No. 6,214,345; WO 02/088172; US 2003130189; US2003096743; WO 03/026577; WO 03/043583; and WO 04/032828.

Carbon-14-labeled 1-isothiocyanatobenzyl-3-methyldiethylene triaminepentaacetic acid (MX-DTPA) is an exemplary chelating agent for conjugation of radionucleotide to the antibody. See, e.g., WO 94/11026.

Methods of Making HER2 Antibody Conjugates:

In certain embodiments, the conjugates are formed in several steps. These steps include (1) modifying a polymer so that it contains a functional group that can react with a functional group of the drug or its derivative; (2) reacting the modified polymer with the drug or its derivative so that the drug is linked to the polymer; (3) modifying the polymer-drug conjugate so that the polymer contains a functional group that can react with a functional group of the isolated antibody or antigen-binding fragment thereof or its derivative; and (4) reacting the modified polymer-drug conjugate with the antibody or antigen-binding fragment thereof to form the conjugate disclosed herein. Step (3) may be omitted if the modified polymer produced by step (1) contains a functional group that can react with a functional group of the antibody or antigen-binding fragment thereof.

In another embodiment the conjugates are formed in several steps: (1) modifying a polymer so that it contains a functional group that can react with a functional group of a first drug or its derivative; (2) reacting the modified polymer with the first drug or its derivative so that the first drug is linked to the polymer; (3) modifying the polymer-drug conjugate so that it contains a different functional group that can react with a functional group of a second drug or its derivative (4) reacting the modified polymer-drug conjugate with the second drug or its derivative so that the second drug is linked to the polymer-drug conjugate; (5) modifying the polymer-drug conjugate containing 2 different drugs so that the polymer contains a functional group that can react with a functional group of the antibody or antigen-binding fragment thereof; and (6) reacting the modified polymer-drug conjugate of step (5) with the isolated antibody or antigen-binding fragment thereof or its derivative to form the conjugate disclosed herein. Steps (5) and (6) may be repeated if 2 different isolated antibodies or antigen-binding fragments thereof or their derivatives are to be conjugated to form a polymer-drug conjugate comprising two different drugs and two different antibodies or antigen-binding fragments thereof.

In yet another embodiment, the conjugates are formed in several steps. These steps include (1) modifying a polymer so that it contains a functional group that can react with a functional group of the drug or its derivative; (2) further modifying the polymer so that it also contains a functional group that can react with a functional group of the antibody or antigen-binding fragment thereof; (3) reacting the modified polymer with the drug or its derivative so that the drug is linked to the polymer; and (4) reacting the modified polymer-drug conjugate with the antibody or antigen-binding fragment thereof to form the conjugate disclosed herein. The sequence of steps (1) and (2) or that of steps (3) and (4) can be reversed. Further either step (1) or (2) may be omitted if the modified polymer contains a functional group that can react with both a functional group of the drug or its derivatives and a functional group of the antibody or antigen-binding fragment thereof.

In another embodiment the conjugates are formed in several steps: (1) modifying a polymer so that it contains a functional group that can react with a functional group of a first drug or its derivative; (2) further modifying a polymer so that it contains a functional group that can react with a functional group of the antibody or antigen-binding fragment thereof; (3) reacting the modified polymer with the first drug or its derivative so that the first drug is linked to the polymer; (4) modifying the polymer-drug conjugate so that it contains a different functional group that can react with a functional group of a second drug or its derivative (5) reacting the modified polymer-drug conjugate with the second drug or its derivative so that the second drug is linked to the polymer-drug conjugate; (6) reacting the modified polymer-drug conjugate containing 2 different drugs so that the polymer with the isolated antibody or antigen-binding fragment thereof or its derivative to form the conjugate disclosed herein. Step (6) may be repeated if 2 different isolated antibodies or antigen-binding fragments thereof or their derivatives are to be conjugated to form a polymer-drug conjugate comprising two different drugs and two different antibodies or antigen-binding fragment thereof. Step (4) may be carried out after step (1) so that the modified polymer contains two different functional groups that can react with two different drugs or their derivatives. In this embodiment, the modified polymer containing two different functional group that can react with two different drugs or their derivatives can be further modified so that it contains a functional group that can react with a functional group of the antibody or antigen-binding fragment thereof; prior to the reaction of the modified polymer with either the two different drugs (step (3) and step (5) or antibody or antigen-binding fragment thereof (step (6).

In certain exemplary embodiments, the conjugates disclosed herein find use in biomedical applications, such as drug delivery and tissue engineering, and the polymeric carrier is biocompatible and biodegradable. In certain embodiments, the carrier is a soluble polymer, nanoparticle, gel, liposome, micelle, suture, implant, etc. In certain embodiments, the term "soluble polymer" encompasses biodegradable biocompatible polymer such as a polyal (e.g., hydrophilic polyacetal or polyketal). In certain other embodiments, the carrier is a fully synthetic, semi-synthetic or naturally-occurring polymer. In certain other embodiments, the carrier is hydrophilic. Examples of suitable polymeric carrier for producing the conjugates disclosed herein are described in U.S. Pat. No. 8,815,226, the content of which is hereby incorporated by reference in its entirety.

In one embodiment, the polymeric carrier comprises units of Formula (IV):

wherein X' indicates the substituent for the hydroxyl group of the polymer backbone. As shown in Formula (IV) and the other formulae described herein, each polyacetal unit has a single hydroxyl group attached to the glycerol moiety of the unit and an X' group attached to the glycolaldehyde moiety of the unit. This is for convenience only and it should be construed that the polymer having units of Formula (IV) and other formulae described herein can contain a random distribution of units having a X' group (or another substituent such as a linker comprising a maleimide terminus) attached to the glycolaldehyde moiety of the units and those having a single X' group (or another substituent such as a linker comprising a maleimide terminus) attached to the glycerol moiety of the units as well as units having two X' groups (or other substituents such as a linker comprising a maleimide terminus) with one attached to the glycolaldehyde moiety and the other attached to the glycerol moiety of the units.

In one embodiment, biodegradable biocompatible polyals suitable for practicing the present invention have a molecular weight of between about 0.5 and about 300 kDa. For example, the biodegradable biocompatible polyals have a molecular weight of between about 1 and about 300 kDa (e.g., between about 1 and about 200 kDa, between about 2 and about 300 kDa, between about 2 and about 200 kDa, between about 5 and about 100 kDa, between about 10 and about 70 kDa, between about 20 and about 50 kDa, between about 20 and about 300 kDa, between about 40 and about 150 kDa, between about 50 and about 100 kDa, between about 2 and about 40 kDa, between about 6 and about 20 kDa, or between about 8 and about 15 kDa). For example, the biodegradable biocompatible polyal used for the polymer scaffold or conjugate disclosed herein is PHF having a molecular weight of between about 2 and about 40 kDa (e.g., about 2-20 kDa, 3-15 kDa, or 5-10 kDa.)

Methods for preparing polymer carriers (e.g., biocompatible, biodegradable polymer carriers) suitable for conjugation to modifiers are known in the art. For example, synthetic guidance can be found in U.S. Pat. Nos. 5,811,510; 5,863,990; 5,958,398; 7,838,619; 7,790,150; and 8,685,383. The skilled practitioner will know how to adapt these methods to make polymer carriers for use in the practice of the invention.

In one embodiment, a method for forming the biodegradable biocompatible polyal conjugates of the present invention comprises a process by which a suitable polysaccharide is combined with an efficient amount of a glycol-specific oxidizing agent to form an aldehyde intermediate. The aldehyde intermediate, which is a polyal itself, may then be reduced to the corresponding polyol, succinylated, and coupled with one or more suitable modifiers to form a biodegradable biocompatible polyal conjugate comprising succinamide-containing linkages.

In another preferred embodiment, fully synthetic biodegradable biocompatible polyals for used in the present invention can be prepared by reacting a suitable initiator with a suitable precursor compound.

For example, fully synthetic polyals may be prepared by condensation of vinyl ethers with protected substituted diols. Other methods, such as cycle opening polymerization, may be used, in which the method efficacy may depend on the degree of substitution and bulkiness of the protective groups.

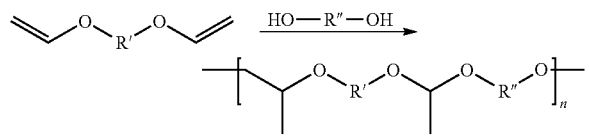

One of ordinary skill in the art will appreciate that solvent systems, catalysts and other factors may be optimized to obtain high molecular weight products.

In certain embodiments, the carrier is PHF.

In embodiments, the polymer carrier is PHF having a polydispersity index (PDI) of ≤1.5, e.g., <1.4, <1.3, <1.2 or <1.1.

For example, for conjugating the isolated antibody or antigen-binding fragment thereof having a molecular weight of 40 kDa to 200 kDa, the polymeric carrier of the scaffold is a polyacetal, e.g., a PHF having a molecular weight (i.e., MW of the unmodified PHF) ranging from about 2 kDa to about 40 kDa (e.g., about 2-20 kDa, or about 3-15 kDa, or about 5-10 kDa).

For example, for conjugating the antibody or antigen-binding fragment thereof having a molecular weight of 40 kDa to 80 kDa, the polymeric carrier of the scaffold disclosed herein is a polyacetal, e.g., a PHF having a molecular weight (i.e., MW of the unmodified PHF) ranging from about 2 kDa to about 40 kDa (e.g., about 2-20 kDa, or about 3-15 kDa, or about 5-10 kDa). For example the PHF has a molecular weight of about 5 kDa, 6 kDa, 7 kDa, 8 kDa, 9 kDa, 10 kDa, 11 kDa, 12 kDa, 13 kDa, 14 kDa, or 15 kDa.

The antibody or antigen-binding fragment thereof in this molecular weight range, includes but are not limited to, for example, antibody fragments, such as, for example, Fabs.

For example, for conjugating the antibody or antigen-binding fragment thereof having a molecular weight of 60 kDa to 120 kDa, the polymeric carrier of the scaffold disclosed herein is a polyacetal, e.g., a PHF having a molecular weight (i.e., MW of the unmodified PHF) ranging from about 2 kDa to about 40 kDa (e.g., about 2-20 kDa, or about 3-15 kDa, or about 5-10 kDa). For example the PHF has a molecular weight of about 5 kDa, 6 kDa, 7 kDa, 8 kDa, 9 kDa, 10 kDa, 11 kDa, 12 kDa, 13 kDa, 14 kDa, or 15 kDa.

The antibody or antigen-binding fragment thereof in this molecular weight range, includes but are not limited to, for example, camelids, Fab2, scFvFc, and the like.

For example, for conjugating the antibody or antigen-binding fragment thereof having a molecular weight of 140 kDa to 180 kDa or of 140 kDa to 150 kDa, the polymeric carrier of the scaffold disclosed herein is a polyacetal, e.g., a PHF having a molecular weight (i.e., MW of the unmodified PHF) ranging from about 2 kDa to about 40 kDa (e.g., about 2-20 kDa, or about 3-15 kDa, or about 5-10 kDa). For example the PHF has a molecular weight of about 5 kDa, 6 kDa, 7 kDa, 8 kDa, 9 kDa, 10 kDa, 11 kDa, 12 kDa, 13 kDa, 14 kDa, or 15 kDa.

The antibody or antigen-binding fragment thereof in this molecular weight range, includes but are not limited to, for example, full length antibodies, such as, IgG, IgM.

The biodegradable biocompatible conjugates disclosed herein can be prepared to meet desired requirements of biodegradability and hydrophilicity. For example, under physiological conditions, a balance between biodegradability and stability can be reached. For instance, it is known that molecules with molecular weights beyond a certain threshold (generally, above 40-100 kDa, depending on the physical shape of the molecule) are not excreted through kidneys, as small molecules are, and can be cleared from the body only through uptake by cells and degradation in intracellular compartments, most notably lysosomes. This observation exemplifies how functionally stable yet biodegradable materials may be designed by modulating their stability under general physiological conditions (pH=7.5±0.5) and at lysosomal pH (pH near 5). For example, hydrolysis of acetal and ketal groups is known to be catalyzed by acids, therefore polyals will be in general less stable in acidic lysosomal environment than, for example, in blood plasma. One can design a test to compare polymer degradation profile at, for example, pH=5 and pH=7.5 at 37° C. in aqueous media, and thus to determine the expected balance of polymer stability in normal physiological environment and in the "digestive" lysosomal compartment after uptake by cells. Polymer integrity in such tests can be measured, for example, by size exclusion HPLC. One skilled on the art can select other suitable methods for studying various fragments of the degraded conjugates disclosed herein.

In many cases, it will be preferable that at pH=7.5 the effective size of the polymer will not detectably change over 1 to 7 days, and remain within 50% from the original for at least several weeks. At pH=5, on the other hand, the polymer should preferably detectably degrade over 1 to 5 days, and be completely transformed into low molecular weight fragments within a two-week to several-month time frame. Although faster degradation may be in some cases preferable, in general it may be more desirable that the polymer degrades in cells with the rate that does not exceed the rate of metabolization or excretion of polymer fragments by the cells. Accordingly, in certain embodiments, the conjugates of the present invention are expected to be biodegradable, in particular upon uptake by cells, and relatively "inert" in relation to biological systems. The products of carrier degradation are preferably uncharged and do not significantly shift the pH of the environment. It is proposed that the abundance of alcohol groups may provide low rate of polymer recognition by cell receptors, particularly of phagocytes. The polymer backbones of the present invention generally contain few, if any, antigenic determinants (characteristic, for example, for some polysaccharides and polypeptides) and generally do not comprise rigid structures capable of engaging in "key-and-lock" type interactions in vivo unless the latter are desirable. Thus, the soluble, crosslinked and solid conjugates disclosed herein are predicted to have low toxicity and bioadhesivity, which makes them suitable for several biomedical applications.

In certain embodiments of the present invention, the biodegradable biocompatible conjugates can form linear or branched structures. For example, the biodegradable biocompatible polyal conjugates of the present invention can be chiral (optically active). Optionally, the biodegradable biocompatible polyal conjugates of the present invention can be scalemic.

In certain embodiments, the conjugates disclosed herein are water-soluble. In certain embodiments, the conjugates disclosed herein are water-insoluble. In certain embodiments, the inventive conjugate is in a solid form. In certain embodiments, the conjugates disclosed herein are colloids. In certain embodiments, the conjugates disclosed herein are in particle form. In certain embodiments, the conjugates disclosed herein are in gel form.

Scheme 1 below shows a synthetic scheme of making a polymeric drug scaffold disclosed herein. In one embodiment, the conjugates are formed in several steps: (1) the polymer, PHF is modified to contain a COOH moiety (e.g., —C(O)—X—$(CH_2)_2$—COOH); (2) the polymer is then further modified so that it contains a maleimido moiety (e.g., EG2-MI) that can react with a functional group of a PBRM; (3) the modified polymer, containing two different functional groups, is reacted with a functional group of a drug or its derivative (e.g., AF-HPA-Ala) to form a polymer-drug conjugate; (4) the disulfide bonds of a PBRM are reduced; (5) the reduced PBRM is then reacted with the polymer-drug conjugate to form the protein-polymer-drug conjugate; and (6) the remaining maleimido moieties are optionally reacted with a maleimido blocking compound (e.g., cysteine).

In another embodiment the order of steps (2) and (3) can be reversed as depicted in the right side route in Scheme 1 below.

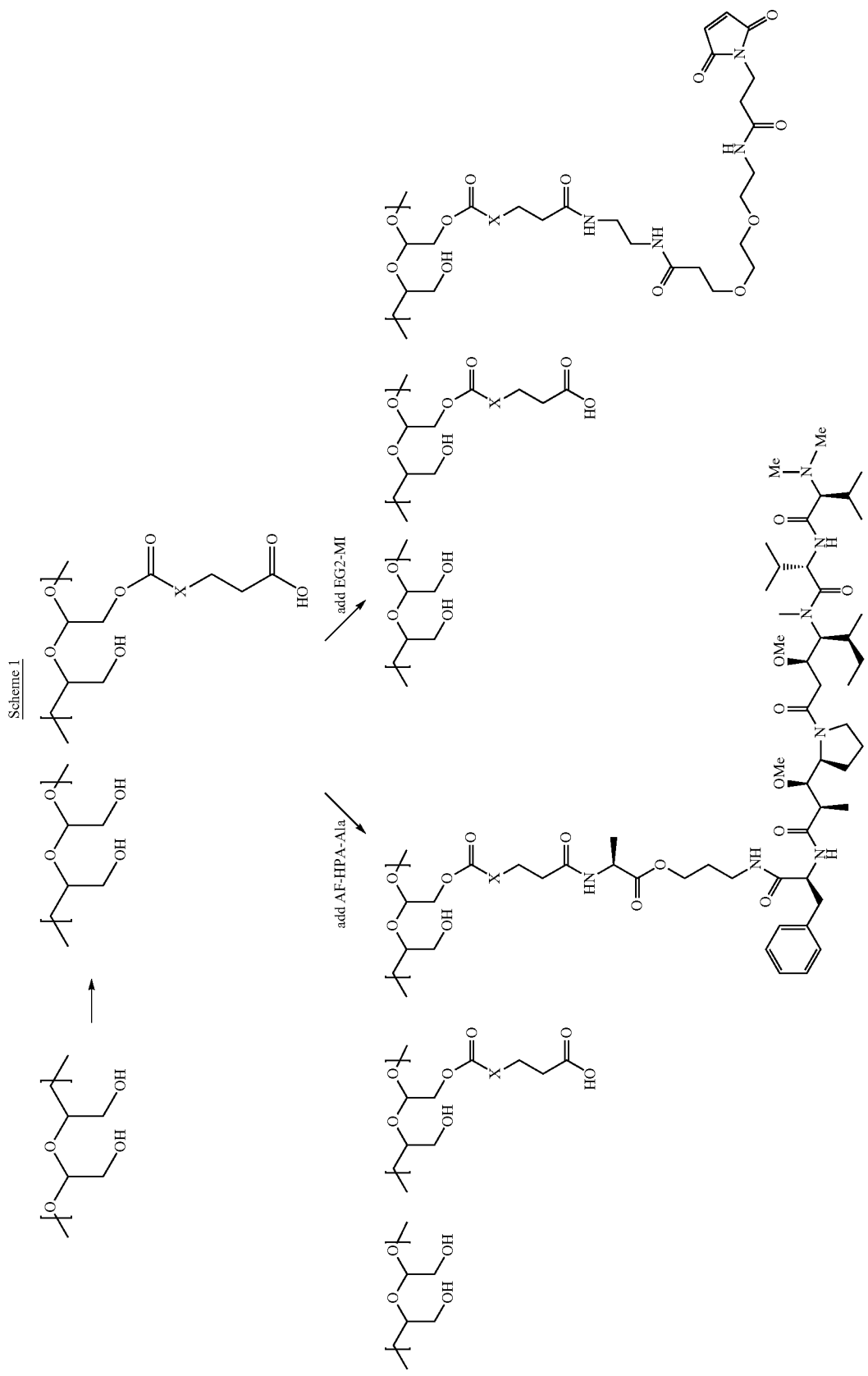

-continued
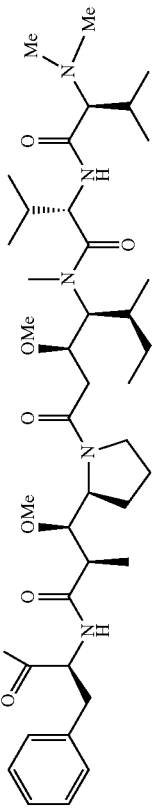
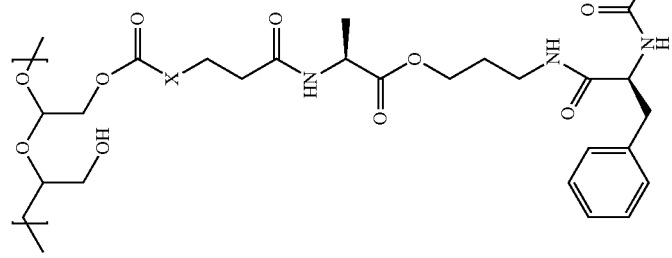
add AF-HPA-Ala
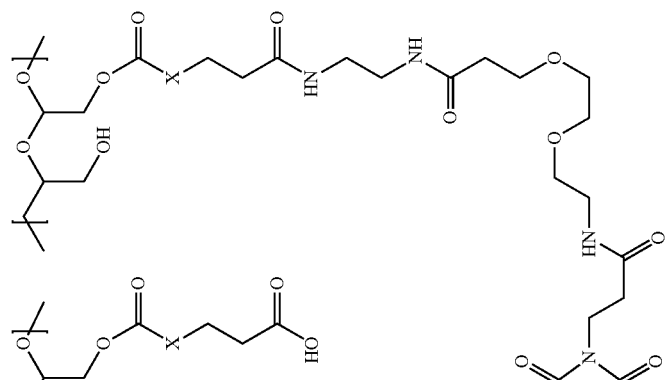
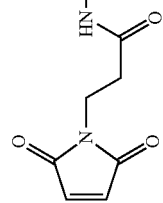
add EG2-MI
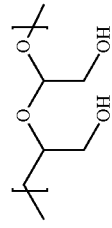

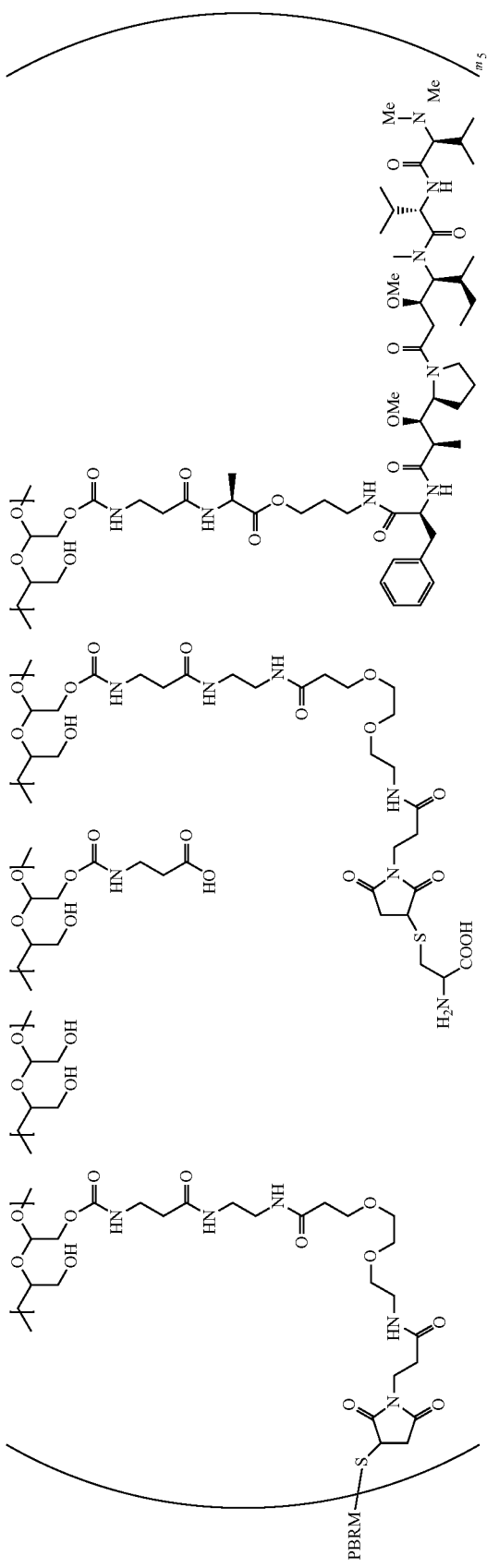

In yet another embodiment, steps (2) and (3) above are carried out simultaneously as depicted in Scheme 2 below.

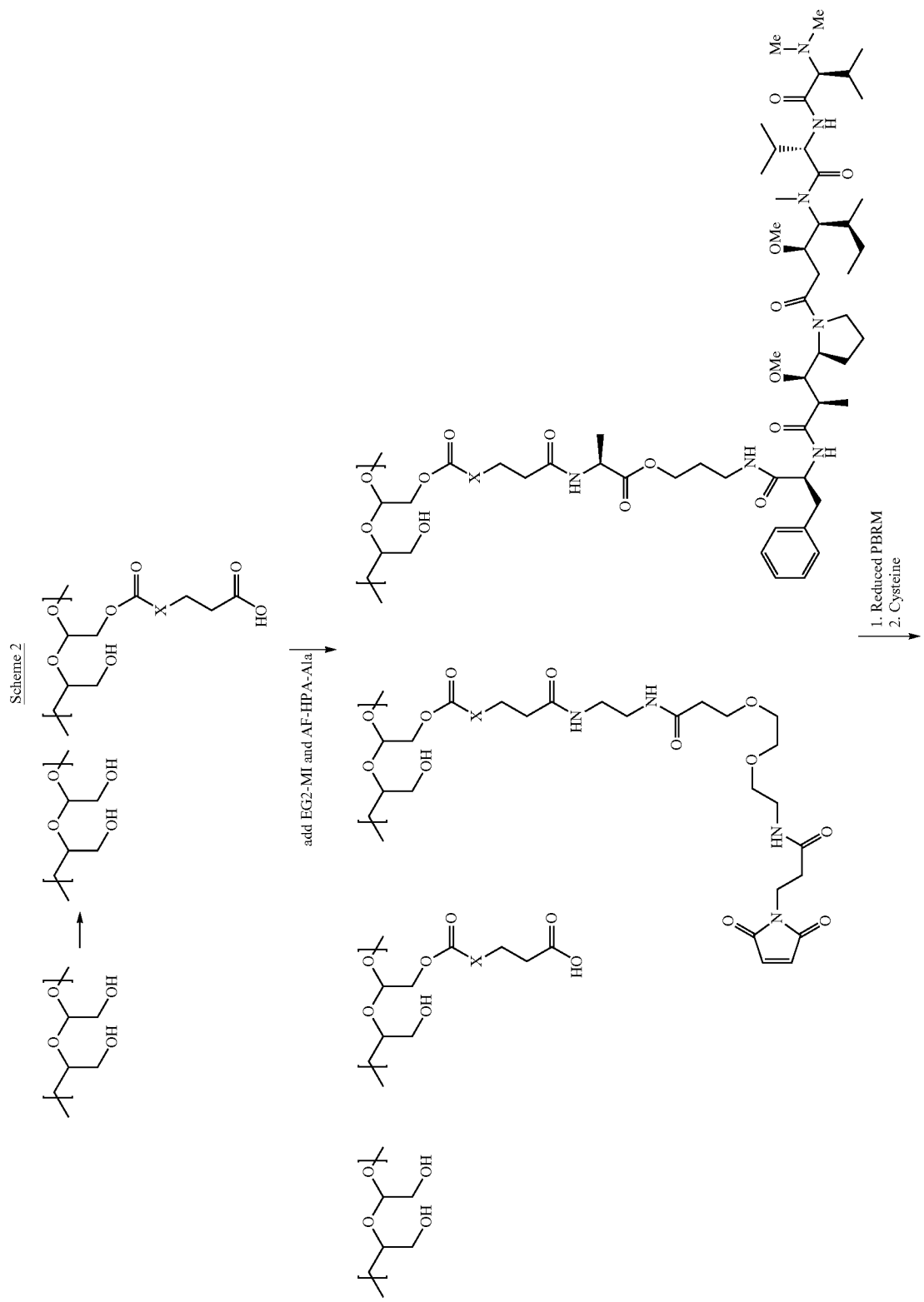

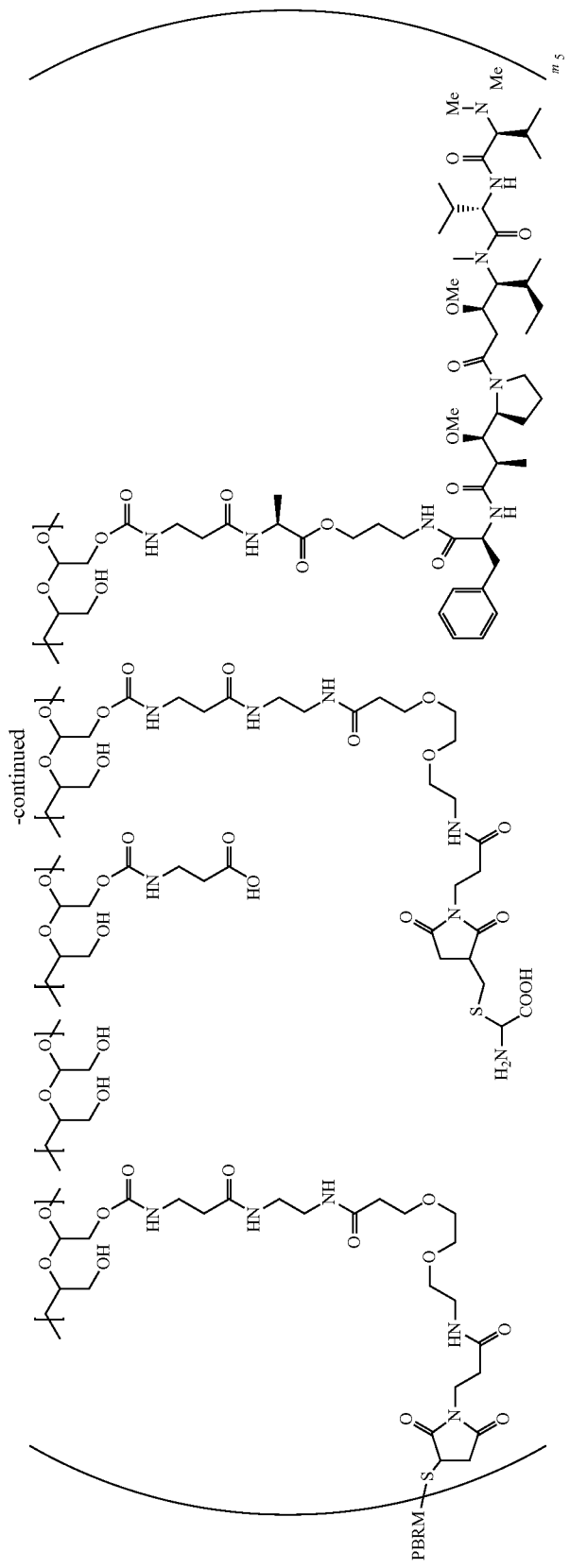

Use of Antibodies Against HER2

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

In one embodiment, antibodies, fragments thereof, and/or conjugates thereof disclosed herein may be used as therapeutic agents. Such agents will generally be employed to diagnose, prognose, monitor, treat, alleviate, prevent, and/or delay the progression of a disease or pathology associated with, e.g., an aberrant HER2 activity and/or expression in a subject. A therapeutic regimen is carried out by identifying a subject, e.g., a human patient suffering from (or at risk of developing) a disease or disorder associated with aberrant HER2 activity and/or expression, e.g., a cancer, using standard methods. An antibody preparation, preferably one having high specificity and high affinity for its target antigen, is administered to the subject and will generally have an effect due to its binding with the target. Administration of the antibody may abrogate or inhibit or interfere with the signaling function of the target. Administration of the antibody may abrogate or inhibit or interfere with the binding of the target with an endogenous ligand to which it naturally binds. For example, the antibody binds to the target and modulates, blocks, inhibits, reduces, antagonizes, neutralizes, or otherwise interferes with HER2 activity and/or expression.

Diseases or disorders related to aberrant HER2 activity and/or expression include but not limited to cancer. The target cancer can be anal, astrocytoma, leukemia, lymphoma, head and neck, liver, testicular, cervical, sarcoma, hemangioma, esophageal, eye, laryngeal, mouth, mesothelioma, skin, myeloma, oral, rectal, throat, bladder, breast, uterus, ovary, prostate, lung, colon, pancreas, renal, or gastric cancer.

In another aspect, diseases or disorders are cancer selected from the group consisting of breast cancer, gastric cancer, non-small cell lung cancer (NSCLC), and ovarian cancer.

Generally, alleviation or treatment of a disease or disorder involves the lessening of one or more symptoms or medical problems associated with the disease or disorder. For example, in the case of cancer, the therapeutically effective amount of the drug can accomplish one or a combination of the following: reduce the number of cancer cells; reduce the tumor size; inhibit (i.e., to decrease to some extent and/or stop) cancer cell infiltration into peripheral organs; inhibit tumor metastasis; inhibit, to some extent, tumor growth; and/or relieve to some extent one or more of the symptoms associated with the cancer. In some embodiments, a composition disclosed herein can be used to prevent the onset or reoccurrence of the disease or disorder in a subject.

A therapeutically effective amount of an antibody, fragment thereof, and/or conjugate thereof disclosed herein relates generally to the amount needed to achieve a therapeutic objective. As noted above, this may be a binding interaction between the antibody and its target antigen that, in certain cases, interferes with the functioning of the target. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment, and/or conjugates thereof disclosed herein may be, by way of nonlimiting example, from about 0.1 mg/kg body weight to about 50 mg/kg body weight, from about 0.1 mg/kg body weight to about 100 mg/kg body weight or from about 0.1 mg/kg body weight to about 150 mg/kg body weight. Common dosing frequencies may range, for example, from twice daily to once a month (e.g., once daily, once weekly; once every other week; once every 3 weeks or monthly). For example, conjugates of XMT 1519 disclosed herein, such as XMT 1519-(EG2-MI-(PHF-BA-(AF-HPA-Ala))) conjugate or XMT 1519-(EG2-MI-(10 kDa PHF-BA-(AF-HPA-Ala))) conjugate can be administered (e.g., as a single dose weekly, every 2 weeks, every 3 weeks, or monthly) at about 0.1 mg/kg to about 20 mg/kg (e.g., 0.2 mg/kg, 0.5 mg/kg, 0.67 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, or 20 mg/kg). For example, conjugates of XMT 1519 disclosed herein, such as XMT 1519-(EG2-MI-(PHF-BA-(AF-HPA-Ala))) conjugate or XMT 1519-(EG2-MI-(10 kDa PHF-BA-(AF-HPA-Ala))) conjugate can be administered (e.g., as a single dose weekly, every 2 weeks, every 3 weeks, or monthly) at about 0.1 mg/kg to about 20 mg/kg (e.g., 0.2 mg/kg, 0.5 mg/kg, 0.67 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, or 20 mg/kg) for treating low HER2-expressing breast or low HER2-expressing gastric cancer.

Efficaciousness of treatment is determined in association with any known method for diagnosing or treating the particular HER2-related disorder. Alleviation of one or more symptoms of the HER2-related disorder indicates that the antibody confers a clinical benefit.

Methods for the screening of antibodies that possess the desired specificity include, but are not limited to, enzyme linked immunosorbent assay (ELISA) and other immunologically mediated techniques known within the art.

In another embodiment, antibodies directed against HER2 may be used in methods known within the art relating to the localization and/or quantitation of HER2 (e.g., for use in measuring levels of HER2 within appropriate physiological samples, for use in diagnostic methods, for use in imaging the protein, and the like). In a given embodiment, antibodies specific to HER2, or derivative, fragment, analog or homolog thereof, that contain the antibody derived antigen binding domain, are utilized as pharmacologically active compounds (referred to hereinafter as "Therapeutics").

In another embodiment, an antibody specific for HER2 be used to isolate a HER2 polypeptide, by standard techniques, such as immunoaffinity, chromatography or immunoprecipitation. Antibodies directed against HER2 protein (or a fragment thereof) can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

In yet another embodiment, an antibody according to the invention can be used as an agent for detecting the presence of HER2 protein (or a fragment thereof) in a sample. In some embodiments, the antibody contains a detectable label. Antibodies are polyclonal, or more preferably, monoclonal. An intact antibody, or a fragment thereof (e.g., $F_{ab}$, scFv, or $F_{(ab)2}$) is used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method disclosed herein can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

Therapeutic Administration and Formulations of HER2 Antibodies

The antibodies, derivatives, fragments, analogs and homologs thereof, and/or conjugates thereof disclosed herein (also referred to herein as "active compounds"), can be incorporated into pharmaceutical compositions suitable for administration. Principles and considerations involved in preparing such compositions, as well as guidance in the choice of components are provided, for example, in Remington's Pharmaceutical Sciences: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Such compositions typically comprise the antibody, fragments thereof, and/or conjugates thereof and a pharmaceutically acceptable carrier. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)).

As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated.

The formulations to be used for in vivo administration must be sterile. This is readily accomplished by filtration through sterile filtration membranes.

A pharmaceutical composition disclosed herein is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a sustained/controlled release formulations, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

For example, the active ingredients can be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nano-capsules) or in macroemulsions.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods.

The materials can also be obtained commercially from Alza Corporation and Nova Pharmaceuticals, Inc. Liposomal suspensions (including liposomes targeted to infected cells with monoclonal antibodies to viral antigens) and can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms disclosed herein are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

In one embodiment, the active compounds are administered in combination therapy, i.e., combined with other agents, e.g., therapeutic agents, that are useful for treating pathological conditions or disorders, such as various forms of cancer, autoimmune disorders and inflammatory diseases. The term "in combination" in this context means that the agents are given substantially contemporaneously, either simultaneously or sequentially. If given sequentially, at the onset of administration of the second compound, the first of the two compounds is preferably still detectable at effective concentrations at the site of treatment.

For example, the combination therapy can include one or more antibodies, fragments thereof, and/or conjugates thereof disclosed herein coformulated with, and/or coadministered with, one or more additional antibodies e.g., a HER2 antibody, a HER2 dimerization inhibitor antibody or a combination of a HER2 antibody and a HER2 dimerization inhibitor antibody, such as, for example, trastuzumab, pertuzumab or a combination of trastuzumab and pertuzumab, or a biosimilar of trastuzumab and/or pertuzumab or combinations of biosimilars.

For example, the combination therapy can include one or more antibodies, fragments thereof, and/or conjugates thereof disclosed herein coformulated with, and/or coadministered with, one or more additional therapeutic agents, e.g., a taxane (paclitaxel or docetaxel), an anthracycline (doxorubicin or epirubicin), cyclophosphamide, capecitabine, tamoxifen, letrozole, carboplatin, gemcitabine, cisplatin, erlotinib, irinotecan, fluorouracil, or oxaliplatin. Such combination therapies may advantageously utilize lower dosages of the administered therapeutic agents, thus avoiding possible toxicities or complications associated with the various monotherapies.

In some embodiments, the additional therapeutic agent(s) used in combination with an antibody, fragment thereof, and/or conjugate thereof disclosed herein are those agents that interfere at different stages in an immune and/or inflammatory response. In one embodiment, one or more antibodies described herein may be coformulated with, and/or coadministered with, one or more additional agents.

Diagnostic and Prophylactic Formulations

The HER2 antibody, antigen-binding fragment thereof and/or conjugate thereof disclosed herein are used in diagnostic and prophylactic formulations. In one embodiment, a HER2 antibody, antigen-binding fragment thereof and/or conjugate thereof disclosed herein is administered to patients that are at risk of developing one or more of the aforementioned diseases, such as for example, without limitation, cancer. A patient's or organ's predisposition to one or more of the aforementioned indications can be determined using genotypic, serological or biochemical markers.

In another embodiment of the invention, a HER2 antibody, antigen-binding fragment thereof and/or conjugate thereof disclosed herein is administered to human individuals diagnosed with a clinical indication associated with one or more of the aforementioned diseases, such as for example, without limitation, cancer. Upon diagnosis, a HER2 antibody, antigen-binding fragment thereof and/or conjugate thereof disclosed herein is administered to mitigate or reverse the effects of the clinical indication associated with one or more of the aforementioned diseases.

In another embodiment of the invention, a method for identifying a breast cancer patient amenable to treatment with the conjugates disclosed herein, comprise measuring the status of certain characteristics in a tumor sample obtained from the patient, and identifying the patient for treatment based on the status of certain characteristics in the tumor sample.

Antibodies disclosed herein are also useful in the detection of HER2 in patient samples and accordingly are useful as diagnostics. For example, HER2 antibodies disclosed herein are used in in vitro assays, e.g., ELISA, to detect HER2 levels in a patient sample.

In one embodiment, a HER2 antibody disclosed herein is immobilized on a solid support (e.g., the well(s) of a microtiter plate). The immobilized antibody serves as a capture antibody for any HER2 that may be present in a test sample. Prior to contacting the immobilized antibody with a patient sample, the solid support is rinsed and treated with a blocking agent such as milk protein or albumin to prevent nonspecific adsorption of the analyte.

Subsequently the wells are treated with a test sample suspected of containing the antigen, or with a solution containing a standard amount of the antigen. Such a sample is, e.g., a serum sample from a subject suspected of having levels of circulating antigen considered to be diagnostic of a pathology. After rinsing away the test sample or standard, the solid support is treated with a second antibody that is detectably labeled. The labeled second antibody serves as a detecting antibody. The level of detectable label is measured, and the concentration of HER2 antigen in the test sample is determined by comparison with a standard curve developed from the standard samples.

It will be appreciated that based on the results obtained using the HER2 antibodies disclosed herein in an in vitro diagnostic assay, it is possible to stage a disease in a subject based on expression levels of the HER2 antigen. For a given disease, samples of blood are taken from subjects diagnosed as being at various stages in the progression of the disease, and/or at various points in the therapeutic treatment of the disease. Using a population of samples that provides statistically significant results for each stage of progression or therapy, a range of concentrations of the antigen that may be considered characteristic of each stage is designated.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

The following working examples are illustrative of the linkers, drug molecules and PBRM, and methods for preparing same. These are not intended to be limiting and it will be readily understood by one of skill in the art that other reagents or methods may be utilized.

Abbreviations

The following abbreviations are used in the reaction schemes and synthetic examples, which follow. This list is not meant to be an all-inclusive list of abbreviations used in the application as additional standard abbreviations, which are readily understood by those skilled in the art of organic synthesis, can also be used in the synthetic schemes and examples.

AF-HPA Auristatin F-hydroxypropylamide
BSA Bovine serum albumin
DMEM Dulbecco's Modified Eagle's medium
FBS Fetal bovine serum
HRP Horseradish peroxidase
PBS Phosphate buffered saline, 0.9% NaCl
TMB 3,3',5,5'-tetramethylbenzidine
General Information Kadcyla® (ado-trastuzumab emtansine) for injection manufactured by Genentech was purchased.

CDRs were identified by the Kabat numbering scheme.

Tumor growth inhibition (% TGI) was defined as the percent difference in median tumor volumes (MTVs) between treated and control groups.

Treatment efficacy was determined from the incidence and magnitude of regression responses of the tumor size observed during the study. Treatment may cause partial regression (PR) or complete regression (CR) of the tumor in an animal. In a PR response, the tumor volume was 50% or less of its Day 1 volume for three consecutive measurements during the course of the study, and equal to or greater than 13.5 mm$^3$ for one or more of these three measurements. In a CR response, the tumor volume was less than 13.5 mm3 for three consecutive measurements during the course of the study. An animal with a CR response at the termination of a study was additionally classified as a tumor-free survivor (TFS). Animals were monitored for regression responses.

HPLC purification was performed on a Phenomenex Gemini 5 μm 110 Å, 250×10 mm, 5 micron, semi-preparation column.

SEC was performed on a Tosoh Biosciences TSK gel G5000 column (7.8 mm×30 cm, 10 um) or Superose 12 column (GE Healthcare).

WCX was performed on ProPac WCX-10 (94 mm×250 mm) column (ThermoFisher).

Whenever possible the drug content of the conjugates was determined spectrophotometrically otherwise LC/MS or $^1$H-NMR was performed for quantitative determination of the drug content.

The protein content of the protein-polymer-drug conjugates was determined spectrophotometrically at 280 nm or by ELISA.

The molecular weights of the polymer conjugates (reported as the apparent weight average molecular weights or peak molecular weights) were determined by SEC with either polysaccharide or protein molecular weight standards. More specifically, for the polymer or polymer-drug conjugates, polysaccharide molecular weights standard were used, and for protein-drug-polymer conjugates, protein standards are used. Unless specifically indicated the reported polymer carrier molecular weight is the weight average molecular weight of PHF; and the polymer-drug conjugate molecular weight and the protein-polymer-drug conjugates is the peak molecular weight. The HER2-polymer-drug conjugates have a peak molecular weight of about 170 kDa to about 230 kDa. The polymer and polymer conjugates synthesized/measured typically have a polydispersity ≤1.5.

Her2-polymer-drug conjugates were separated from residual unreacted drug-polymer conjugates by extensive diafiltration. If necessary, additional purification by size exclusion chromatography and/or WCX chromatography was conducted to remove any aggregated Her2-polymer-drug conjugates. In general, the Her2-polymer-drug conjugates typically contained <5% (w/w, e.g., <2% w/w) aggregated fraction as determined by SEC; <0.5% (w/w, e.g., <0.1% w/w) free (unconjugated) drug as determined by RP-HPLC or LC-MS/MS; <1% (w/w) of free polymer-drug conjugate as determined by SEC and/or RP-HPLC and <2% (w/w, e.g., <1% w/w) unconjugated Her2 as determined by HIC-HPLC and/or WCX HPLC. Reduced or partially reduced antibodies were prepared using procedures described in the literature, see, for example, Francisco et al., Blood 102 (4): 1458-1465 (2003). The total drug (conjugated and unconjugated) concentration was determined by LC-MS/MS.

General Procedures

General Procedure A. Conjugation of Colymer with Linker or Drug

In general, the conjugation of the polymer (PHF-BA or PHF-GA) with an amine-containing linker, such as, for example, EG2-maleimide or an amine-containing linker drug, such as, for example, AF-HPA-Ala, HPA-Ala, is conducted in an aqueous or 10-90% organic/aqueous solvent mixture in the presence of an activating agent, such as, for example EDC.HCl. Typical organic solvents, include, but are not limited to, water miscible solvents, such as, for example, DMSO, DMF, DMA, NMP and ACN. To accelerate the coupling, a co-activator, such as, for example, NHS, is added. The polymer is first mixed with the amino-containing compound followed by addition of the co-activator (NHS) and then the addition of the activator (EDC.HCl). The reaction is conducted at 0-10° C., pH 4.5 to 7.5 for 1 h to 24 hours at ambient temperature. The resulting polymer conjugated product is purified by diafiltration or by SEC. The product is concentrated to 2-50 mg/mL, the pH is adjusted to 4.5 to 6.5 to insure drug-polymer linker stability and the conjugate is stored frozen at −20 to −80° C. until further use.

The conjugation of the polymer with the amine-containing linker or drug can conducted sequentially, in any order, or simultaneously.

General Procedure B. Partial Selective Reduction of Protein (HER2 Antibody)

The partial selective reduction of the inter-chain disulfide groups or unpaired disulfide in the relevant HER2 antibody prior to conjugation with the polymer-drug conjugate is achieved by using a reducing agent, such as, for example, TCEP, DTT or β-mercaptoethanol. When the reduction is performed with an excess of the reducing agent, the reducing agent is removed prior to conjugation by SEC. The degree of conversion of the HER2 disulfide groups into reactive sulfhydryl groups depends on the stoichiometry of HER2, reducing agent, pH, temperature and/or duration of the reaction. When some but not all of the disulfide groups in the PBRM are reduced, the reduced PBRM is a partially reduced HER2.

General Procedure C. Conjugation of Partially Reduced HER2 with Polymer Drug Conjugate The conjugation of the partially reduced PBRM to the polymer-drug conjugate is conducted under neutral or slightly basic conditions (pH 6.5-8.5) at PBRM concentrations of 1-10 mg/mL and polymer-drug conjugate concentration of 0.5-10 mg/mL. The polymer-drug conjugate is typically used in 1-5.0 fold excess relative to the desired protein-polymer-drug conjugate stoichiometry. When the PBRM is conjugated to the maleimido group of the polymer-drug conjugate, the conjugation is optionally terminated by the addition of a water-soluble maleimido blocking compound, such as, for example, N-acetyl cysteine, cysteine methyl ester, N-methyl cysteine, 2-mercaptoethanol, 3-mercaptopropanoic acid, 2-mercaptoacetic acid, mercaptomethanol (i.e., $HOCH_2SH$), benzyl thiol, and the like.

The resulting HER2-polymer-drug conjugate is typically purified by diafiltration to remove any unconjugated polymer-drug conjugate, unconjugated drug and small molecule impurities. Alternatively or additionally, appropriate chromatographic separation procedures such as, for example, size-exclusion chromatography, hydrophobic interaction chromatography, ion chromatography such as, for example, WCX chromatography; reversed phase chromatography, hydroxyl apatite chromatography, affinity chromatography or combination thereof may be used to purify the HER2-polymer-drug conjugate. The resulting purified HER2-polymer-drug conjugate is typically formulated in a buffer at pH 5.0-6.5.

Example 1: FACS Selection for HER2 Antibodies

Two of the HER2 antibodies disclosed herein, XMT 1517 and XMT 1519, were selected using the procedure described below. Eight naïve human synthetic yeast libraries each of ~$10^9$ diversity were propagated as described previously (see, for example, WO 2009036379; WO2010105256; WO2012/009568; and Xu et al., Protein Eng Des Sel. 2013 October; 26(10):663-70). For the first two rounds of selection, a magnetic bead sorting technique utilizing the Miltenyi MACs system was performed, as described (Siegel et al., J Immunol Methods. 2004 March; 286(1-2):141-53). Briefly, yeast cells (~$10^{10}$ cells/library) were incubated with 3 ml of 200 nM biotinylated monomeric HER2 antigen or 10 nM biotinylated HER2-Fc fusion antigen for 15 min at room temperature in FACS wash buffer PBS with 0.1% BSA (biotinylations were done using the EZ-Link Sulfo-NHS-Biotinylation Kit, Thermo Scientific, Cat.#21425). After washing once with 50 ml ice-cold wash buffer, the cell pellet was resuspended in 40 mL wash buffer, and 500 µl Streptavidin MicroBeads (Miltenyi Biotec, Bergisch Gladbach, Germany. Cat.#130-048-101) were added to the yeast and incubated for 15 min at 4° C. Next, the yeast were pelleted, resuspended in 5 mL wash buffer, and loaded onto a MACS LS column (Miltenyi Biotec, Bergisch Gladbach, Germany. Cat.#130-042-401). After the 5 mL was loaded, the column was washed 3 times with 3 ml FACS wash buffer. The column was then removed from the magnetic field, and the yeast were eluted with 5 mL of growth media and then grown overnight. The following three rounds of sorting were performed using flow cytometry. Approximately $1\times10^8$ yeast were pelleted, washed three times with wash buffer, and incubated with 200 nM, 100 or 10 biotinylated HER2 for 10 min at room temperature respectively. Yeast were then washed twice and stained with goat anti-human $F(ab')_2$ kappa-FITC diluted 1:100 (Southern Biotech, Birmingham, Ala., Cat.#2062-02) and either streptavidin-Alexa Fluor 633 (Life Technologies, Grand Island, N.Y., Cat.#521375) diluted 1:500, or Extravidin-phycoerthyrin (Sigma-Aldrich, St Louis, Cat.# E4011) diluted 1:50, secondary reagents for 15 min at 4° C. After washing twice with ice-cold wash buffer, the cell pellets were resuspended in 0.4 mL wash buffer and transferred to strainer-capped sort tubes. Sorting was performed using a FACS ARIA sorter (BD Biosciences) and sort gates were determined to select only HER2 binding clones for two rounds and the third round was a negative sort to decrease reagent binders. After the final round of sorting, yeast were plated and individual colonies were picked for characterization.

Example 2: Affinity Maturation of HER2 Antibodies

The affinity matured HER2 antibodies disclosed herein, XMT 1518 and XMT 1520, were made using the procedure described below. A Round 5 binding population was used for a light chain batch diversification (LCBD). Heavy chain plasmids were extracted and transformed into a light chain library with a diversity of $1\times10^6$. Selections were performed as described above with one round of MACS sorting and two rounds of FACS sorting using 10 nM or 1 nM biotinylated antigen for respective rounds.

Further affinity maturation was performed on the best clones from the LCBD. Each of the CDRH3 of the heavy chains from these clones were individually recombined into a premade library with variants of a diversity of $1\times10^8$ and selections were performed as described above. Affinity pressures were applied by incubating the antigen antibody yeast complex with parental Fab for different amounts of time to select for the highest affinity antibodies.

A third round of affinity maturation included error prone PCR of the heavy chain and the light chain. Selections were performed similar to previous cycles using FACS sorting for all three rounds and with increased times for Fab pressure.

Example 3: Antibody Production and Purification

Yeast clones were grown to saturation and then induced for 48 h at 30° C. with shaking. After induction, yeast cells were pelleted and the supernatants were harvested for purification. IgGs were purified using a Protein A column and eluted with acetic acid, pH 2.0. Fab fragments were generated by papain digestion and purified over KappaSelect (GE Healthcare LifeSciences, Cat.#17-5458-01).

Mammalian expression of IgG was done by sub-cloning antibodies into new expression vector follow by transient transfection and expression in HEK. Briefly, expression vectors containing the antibody of interest are transfected by complexing with a transfection reagent followed by exposure to HEK cells for one hour followed by dilution of culture media to a final density of 4 million cells per mL. The cells are then cultured for 7 days with fresh feed media every 48 hours. After 7 days, the supernatant is collected following centrifugation and purification was performed using protein A and if necessary a CHT column purification added to reach >95% monomer.

Example 4: Affinity Measurements of HER2 Antibodies

The affinity for the HER2 antibodies was determined by measuring their $K_D$ by ForteBio or MSD-SET. ForteBio affinity measurements were performed generally as previously described (Estep et al., MAbs. 2013 March-April; 5(2):270-8). Briefly, ForteBio affinity measurements were performed by loading IgGs on-line onto AHQ sensors. Sensors were equilibrated off-line in assay buffer for 30 min and then monitored on-line for 60 seconds for baseline establishment. Sensors with loaded IgGs were exposed to 100 nM antigen for 5 minutes, afterwards they were transferred to assay buffer for 5 min for off-rate measurement. Kinetics were analyzed using the 1:1 binding model.

Equilibrium affinity measurements performed as previously described (Estep et al., 2013). Solution equilibrium titrations (SET) were performed in PBS+0.1% IgG-Free BSA (PBSF) with antigen held constant at 50 pM and incubated with 3- to 5-fold serial dilutions of antibody starting at 10 nM. Antibodies (20 nM in PBS) were coated onto standard bind MSD-ECL plates overnight at 4° C. or room temperature for 30 min. Plates were then blocked for 30 min with shaking at 700 rpm, followed by three washes with wash buffer (PBSF+0.05% Tween 20). SET samples were applied and incubated on the plates for 150 s with shaking at 700 rpm followed by one wash. Antigen captured on a plate was detected with 250 ng/mL sulfotag-labeled streptavidin in PBSF by incubation on the plate for 3 min. The plates were washed three times with wash buffer and then read on the MSD Sector Imager 2400 instrument using 1× Read Buffer T with surfactant. The percent free antigen was plotted as a function of titrated antibody in Prism and fit to a quadratic equation to extract the $K_D$. To improve throughput, liquid handling robots were used throughout MSD-SET experiments, including SET sample preparation. Table I gives the results for the ForteBio and MSD-SET affinity measurements

TABLE I

| Test Antibody | $K_D$ (M) (ForteBio)[1] | $k_{on}$ (1/M/s) (ForteBio)[1] | $k_{off}$ (1/s) (ForteBio)[1] | $K_D$(M) (MSD)[2] |
|---|---|---|---|---|
| XMT 1517 | $8.7 \times 10^{-8}$ | $2.3 \times 10^5$ | $2.0 \times 10^{-2}$ | $2.4 \times 10^{-8}$ |
| XMT 1518 | $3.3 \times 10^{-9}$ | $2.4 \times 10^5$ | $7.9 \times 10^{-4}$ | $8.5 \times 10^{-10}$ |
| XMT 1519 | $3.5 \times 10^{-8}$ | $2.7 \times 10^5$ | $9.5 \times 10^{-3}$ | $1.4 \times 10^{-8}$ |
| XMT 1520 | $2.1 \times 10^{-9}$ | $1.4 \times 10^5$ | $3.1 \times 10^{-4}$ | $6.1 \times 10^{-10}$ |

[1]Measured on ForteBio instrument. IgG on tip and human HER2 monomer in solution
[2]Measured on Meso Scale Discovery instrument. IgG against biotinylated human HER2 monomer Example 5: Octet Red384 Epitope Binning Epitope binning of the antibodies was performed on a Forte Bio Octet Red384 system (Pall Forte Bio Corporation, Menlo Park, Calif.) using a standard sandwich format binning assay. Control anti-target IgG was loaded onto AHQ sensors and unoccupied Fc-binding sites on the sensor were blocked with a non-relevant human IgG1 antibody. The sensors were then exposed to 100 nM target antigen followed by a second anti-target antibody. Data was processed using ForteBio's Data Analysis Software 7.0. Additional binding by the second antibody after antigen association indicates an unoccupied epitope (non-competitor), while no binding indicates epitope blocking (competitor). This process was iterated for the 4 control antibodies: (i) trastuzumab which binds to Domain IV of HER2 (Cho et al., Nature. 2003 Feb. 13; 421(6924):756-60); (ii) pertuzumab which binds to Domain II of HER2 (Franklin et al., Cancer Cell. 2004 April; 5(4):317-28); (iii) Fab37 which binds to Domain III of HER2 (Fisher et al., J Mol Biol. 2010 Sep. 10; 402(1):217-29); and (iv) chA21 which binds to Domain I of HER2 (Zhou et al., J Biol Chem. 2011 Sep. 9; 286(36): 31676-83; Cheng et al., Cell Res. 2003 February; 13(1):35-48). The sequences for the control antibodies are shown below:

```
>Trastuzumab heavy chain variable region amino acid sequence
                                                              (SEQ ID NO: 40)
1                     15                    30                           45
D I Q M T Q S P S S L S A S V G D R V T I T C R A S Q D V N T A V A W Y Q Q K P G K A P K 46                    60                    75                           90
L L I Y S A S F L Y S G V P S R F S G S R S G T D F T L T I S S L Q P E D F A T Y Y C Q Q 91                    105                   120                          135
H Y T T F P T F G Q G T K V E I K R T V A A P S V F I F P P S D E Q L K S G T A S V V C L 136                   150                   165                          180
L N N F Y P R E A K V Q W K V D N A L Q S G N S Q E S V T E Q D S K D S T Y S L S S T L T 181                   195                   210       214
L S K A D Y E K H K V Y A C E V T H Q G L S S P V T K S F N R G E C >Trastuzumab light chain variable region amino acid sequence
                                                              (SEQ ID NO: 41)
1                     15                    30                           45
E V Q L V E S G G G L V Q P G G S L R L S C A A S G F N I K D T Y I H W V R Q A P G K G L 46                    60                    75                           90
E W V A R I Y P T N G Y T R Y A D S V K G R F T I S A D T S K N T A Y L Q M N S L R A E D 91                    105                   120                          135
T A V Y Y C S R W G G D G F Y A M D Y W G Q G T L V T V S S A S T K G P S V F P L A P S S
```

```
136                  150                  165                  180
K S T S G G T A A L G C L V K D Y F P E P V T V S W N S G A L T S G V H T F P A V L Q S S 181                  195                  210                  225
G L Y S L S S V V T V P S S S L G T Q T Y I C N V N H K P S N T K V D K K V E P K S C D K 226                  240                  255                  270
T H T C P P C P A P E L L G G P S V F L F P P K P K D T L M I S R T P E V T C V V V D V S 271                  285                  300                  315
H E D P E V K F N W Y V D G V E V H N A K T K P R E E Q Y N S T Y R V V S V L T V L H Q D 316                  330                  345                  360
W L N G K E Y K C K V S N K A L P A P I E K T I S K A K G Q P R E P Q V Y T L P P S R E E 361                  375                  390                  405
M T K N Q V S L T C L V K G F Y P S D I A V E W E S N G Q P E N N Y K T T P P V L D S D G 406                  420                  435                  449
S F F L Y S K L T V D K S R W Q Q G N V F S C S V M H E A L H N H Y T Q K S L S L S P G
```

>Pertuzumab heavy chain variable region amino acid sequence (SEQ ID NO: 42)

```
       1         10        20        30        40        50        60
       |         |         |         |         |         |         |
       DIQMTQSPSSLSASVGDRVTITCKASQDVSIGVAWYQQKPGKAPKLLIYSASYRYTGVPS 70        80        90       100       110       120
                |         |         |         |         |         |
       RFSGSGSGTDFTLTISSLQPEDFATYYCQQYYIYPYTFGQGTKVEIKRTVAAPSVFIFPP 130       140       150       160       170       180
                |         |         |         |         |         |
       SDEQLKSGTASVVCLLNNFYPREAKVQWKVDNALQSGNSQESVTEQDSKDSTYSLSSTLT 190       200       210
                |         |         |
       LSKADYEKHKVYACEVTHQGLSSPVTKSFNRGEC
```

>Pertuzumab light chain variable region amino acid sequence (SEQ ID NO: 43)

```
       1         10        20        30        40        50        60
       |         |         |         |         |         |         |
       EVQLVESGGGLVQPGGSLRLSCAASGFTFTDYTMDWVRQAPGKGLEWVADVNFNSGGSIY 70        80        90       100       110       120
                |         |         |         |         |         |
       NQRFKGRFTLSVDRSKNTLYLQMNSLRAEDTAVYYCARNLGPSFYFDYWGQGTLVTVSSA 130       140       150       160       170       180
                |         |         |         |         |         |
       STKGPSVFPLAPSSKSTSGGTAALGCLVKDYFPEPVTVSWNSGALTSGVHTFPAVLQSSG 190       200       210       220       230       240
                |         |         |         |         |         |
       LYSLSSVVTVPSSSLGTQTYICNVNHKPSNTKVDKKVEPKSCDKTHTCPPCPAPELLGGP 250       260       270       280       290       300
                |         |         |         |         |         |
       SVFLFPPKPKDTLMISRTPEVTCVVVDVSHEDPEVKFNWYVDGVEVHNAKTKPREEQYNS 310       320       330       340       350       360
                |         |         |         |         |         |
       TYRVVSVLTVLHQDWLNGKEYKCKVSNKALPAPIEKTISKAKGQPREPQVYTLPPSREEM 370       380       390       400       410       420
                |         |         |         |         |         |
       TKNQVSLTCLVKGFYPSDIAVEWESNGQPENNYKTTPPVLDSDGSFFLYSKLTVDKSRWQ 430       440       448
                |         |         | |
       QGNVFSCSVMHEALHNHYTQKSLSLSPG
```

>Fab37 heavy chain variable region amino acid sequence (SEQ ID NO: 44)

EVQLVESGGGLVQPGGSLRLSCAASGFSIWWSWIHWVRQAPGKGLEWVASISPSSGWTSYADSVKG

RFTISADTSKNTAYLQMNSLRAEDTAVYYCARWWSSAMDYWGQGTLVTVSS

-continued

>Fab37 light chain variable region amino acid sequence
(SEQ ID NO: 45)
DIQMTQSPSSLSASVGDRVTITCRASQSVSSAVAWYQQKPGKAPKLLIYSASSLYSGVPSRFSGSR

SGTDFTLTISSLQPEDFATYYCQQWWWWPSTFGQGTKVEIK

>chA21 heavy chain variable region amino acid sequence
(SEQ ID NO: 46)
EVQLQQSGPEVVKTGASVKISCKASGYSFTGYFINWVKKNSGKSPEWIGHISSSYATSTYNQKFKN

KAAFTVDTSSSTAFMQLNSLTSEDSAVYYCVRSGNYEEYAMDYWGQGTSVIVSS

>chA21 light chain variable region amino acid sequence
(SEQ ID NO: 47)
DIVLTQTPSSLPVSVGEKVTMTCKSSQTLLYSNNQKNYLAWYQQKPGQSPKLLISWAFTRKSGVPD

RFTGSGSGTDFTLTIGSVKAEDLAVYYCQQYSNYPWTFGGGTRLEIK

The antibodies XMT 1519, XMT 1520, XMT 1517, XMT 1518 with highest affinity which did not compete with the four control antibodies were selected.

As shown in FIG. 1A, XMT 1517 and XMT 1518 antibodies and in FIG. 1B, XMT 1519 and XMT 1520 antibodies did not compete with the 4 control antibodies.

Example 6: Antibody Binding Constant Measurements with JIMT-1 Cells

The cell surface binding of the HER2 antibodies to JIMT-1 cells were evaluated using a Macsquant flow cytometer (Miltenyi Biotec, Bergisch Gladbach, Germany). JIMT-1 cells, grown overnight to approximately 90% confluent cultures in DMEM media (ATCC, Manassas, Va.) with 10% FBS (Gibco®, Life Technologies, Grand Island, N.Y.), were released from the plate surface by treatment with Accutase cell detachment solution (Innovative Cell Technologies, San Diego, Calif.). The detached cells were washed once with ice cold media containing 6% goat serum and resuspended in the same media. 100,000 cells were aliquoted per well of a V-bottom, 96-well plate and incubated with a range of HER2 antibody concentrations (0.05-100 nM) in 150 µl DMEM with 6% goat serum on ice for 3 hours. The cells were then washed once with ice cold PBS and resuspended in 100 µl DMEM with 2% goat serum and 6 µg/ml of a secondary fluorescently labeled antibody, Alexa Fluor® 647-labelled goat anti-human IgG (Life Technologies Cat.# A-21445) for 1 hour on ice. The cells were washed once with ice cold PBS (Gibco®, Life Technologies, Cat.#10010049) and suspended in 200 µl of ice cold PBS with 1% paraformaldehyde. The amount of fluorescence bound per cell was determined by running 5000 cells for each treatment on the flow cytometer. The median fluorescence value for each treatment was graphed, and the dissociation constant, $K_d$, was calculated for each antibody with Graphpad Prism software by non-linear regression using the single site, specific binding model. FIG. 2 shows binding of the HER2 antibodies to JIMT-1 cell. The calculated $K_d$ values were 3.4 nM for XMT 1517, 0.4 nM for XMT 1518, 1.2 nM for XMT 1519 and 1.1 nM for XMT 1520.

Example 7: Antibody Affinity Measurements by ELISA

The affinity of the antibodies for recombinant human and cynomolgus monkey HER2 was determined by an ELISA assay. Purified, recombinant HER2 extracellular domain, either human derived (amino acids 23-652, Acro Biosystems Cat.# HE2-H5225) or cynomolgus monkey derived (amino acids 1-652, Sino Biological, Cat.#90295-CO8H) was coated onto the surface of 96 well plates by incubation of each well with 50 µl of a 1 µg/ml solution in 50 mM bicarbonate buffer, pH 9.0, for 2 hours at room temperature. The wells were washed 4 times with TTBS (50 mM Tris-HCl, pH 7.4, 150 mM NaCl, and 0.05% Tween 20). The wells were blocked by incubation with 50 µl of TTBS containing 5% bovine serum albumin for 1 hr. A range of dilutions (0.005 to 10 nM, 3 fold serial dilutions) of each test antibody or Example 16H in 50 µl of TTBS with 3% BSA was then added for 2 hours at room temperature. Unbound test antibodies were removed with TTBS washes (4×). A secondary anti-human IgG conjugated to HRP (Bethyl Laboratories, #A80-115P) at a concentration of 0.2 µg/ml in TTBS with 3% BSA, was incubated in each well for 1 hour. Unbound secondary antibody was removed by 4 TTBS washes. The HRP substrate, TMB Bethyl Laboratories#E102) was added to each well and incubated until a yellow color was visible. The reaction was stopped by the addition of 50 µl of 0.2 N sulfuric acid. The absorbance at 450 nm was measured in a plate reader (Molecular Devices, Spectramax M5). The values were plotted using GraphPad Prism software. $K_d$ was determined by non-linear regression using the one site, specific binding model.

Figure 3A:
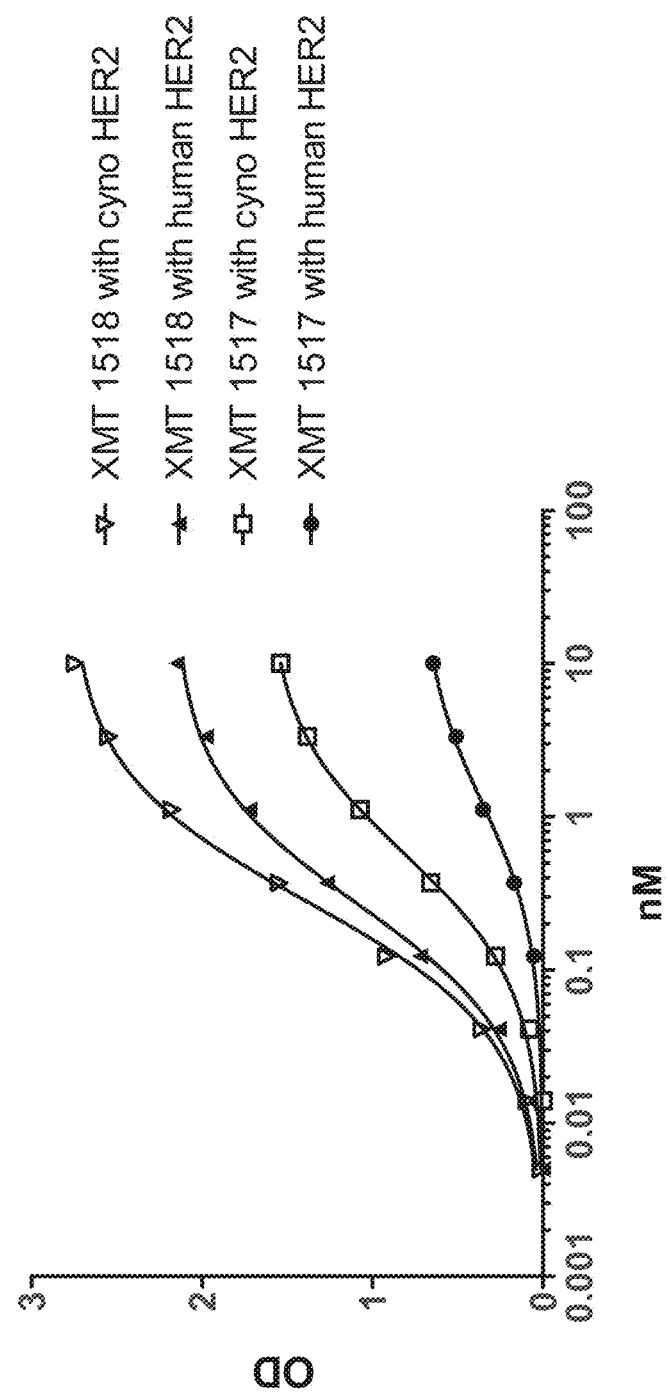
FIG. 3a shows binding affinities of antibodies XMT 1517, XMT 1518 to recombinant human HER2 and cynomolgus monkey HER2.

FIG. 3a gives the results for the binding of the anti-HER2 antibodies XMT 1517, XMT 1518 to human HER2 and cynomolgus monkey HER2. FIG. 3b gives the results for the binding of the anti-HER2 antibodies XMT 1519, XMT 1529 to human HER2 and cynomolgus monkey HER2. The calculated $K_d$ values are given in Table II.

TABLE II

| Test Antibody | Human HER2 $K_d$ (nM) | Cynomolgus monkey HER2 $K_d$ (nM) |
|---|---|---|
| XMT 1517 | 1.2 | 0.6 |
| XMT 1518 | 0.3 | 0.3 |
| XMT 1519 | 0.1 | 0.1 |
| XMT 1520 | 0.1 | 0.1 |

The binding affinities for the 4 test antibodies to human HER2 and cynomolgus monkey HER2 were similar.

Figure 3D:
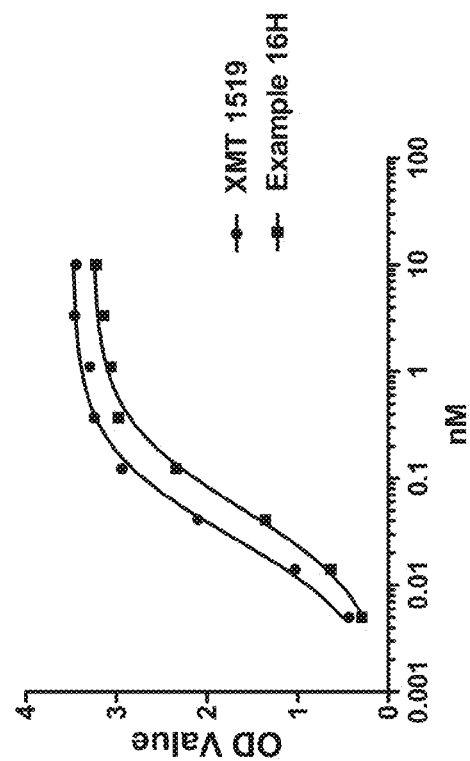
FIG. 3d shows the binding affinities of XMT 1519 and Example 16H to cynomolgus monkey HER2.
Figure 3C:
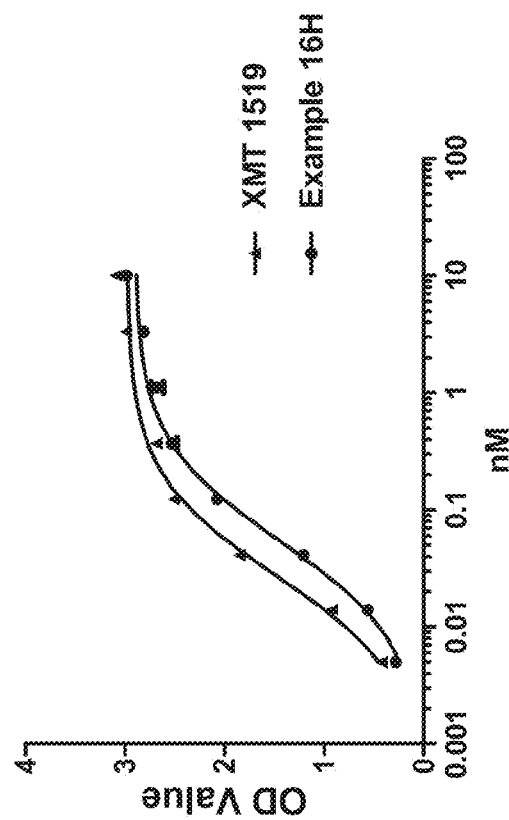
FIG. 3c shows the binding affinities of XMT 1519 and Example 16H to recombinant human HER2.

FIGS. 3c and 3d show the results for the binding of the anti-HER2 antibodies XMT 1519 and Example 16H to human HER2 and cynomolgus monkey HER2 respectively. The calculated $K_d$ values are given in Table IIA below.

TABLE IIA

| Test Article | Human HER2 $K_d$ (nM) | Cynomolgus monkey HER2 $K_d$ (nM) |
|---|---|---|
| XMT 1519 | 0.03 | 0.03 |
| Example 16H | 0.05 | 0.05 |

The binding affinities for XMT 1519 and Example 16H to human HER2 and cynomolgus monkey HER2 were similar.

Example 8: Antibody Competition Assay with JIMT-1 Cells

Figure 4:
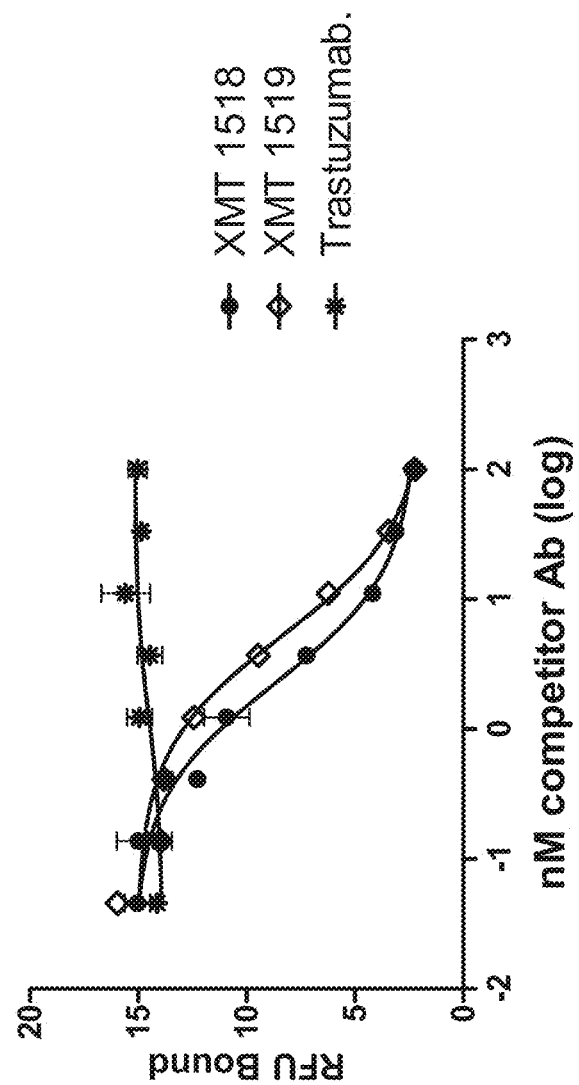
FIG. 4 shows that the antibodies XMT 1518 and XMT 1519 compete for binding to HER2.

To confirm that XMT 1518 and XMT 1519 antibodies bind to overlapping epitopes, the antibodies were analyzed in a competition binding assay on JIMT-1 cells. JIMT-1 cells were grown as described in Example 6. 50,000 cells in 50 µl were aliquoted per well of a V-bottom, 96-well plate. Then 30 nM of antibody XMT 1519 conjugated to Alexa Fluor®-647 in 25 µl of media, was added alone, or mixed with a second, unlabeled antibody (XMT 1518, XMT 1519, or trastuzumab) diluted to a range of concentrations (0.05-100 nM), and incubated on ice for 3 hours. The cells were then washed once with ice cold PBS and resuspended in 100 µl DMEM with 2% goat serum and 6 µg/ml of a goat Alexa Fluor® 647-labelled anti-human IgG (Life Technologies, Cat.# A-21445) for 1 hour on ice. The cells were washed once with ice cold PBS and suspended in 200 µl of ice cold PBS with 1% paraformaldehyde. The amount of fluorescence bound per cell was determined by running 5000 cells for each treatment on a MacsQuant flow cytometer (Miltenyi Biotec, Bergisch Gladbach, Germany). The median fluorescence value for each treatment was graphed, and the dissociation constant $K_D$ calculated for each antibody with GraphPad Prism by non-linear regression using the single site, specific binding model. As shown in FIG. 4, antibody XMT 1518 competed for the binding of Alexa Fluor® 647-labeled XMT 1519 to a similar extent as unlabeled XMT 1519 indicating that both antibodies recognize overlapping epitopes on HER2 whereas trastuzumab did not compete with the binding of Alexa Fluor® 647-labeled XMT 1519.

Example 9: Antibody-Dependent Cell-Mediated Cytotoxicity Assay

The antibody-dependent cell-mediated cytotoxicity (ADCC) activity of anti-HER2 antibodies was quantified on BT474 cells. 5000 cells were plated per well of 96-well plates in DMEM media containing 10% FBS and grown overnight at 37° in 5% $CO_2$. A range of antibody concentrations for XMT 1518, XMT 1519, XMT 1520 or trastuzumab from 0.001 to 100 nM (8 serial, 5-fold dilutions) were added to the cells and the ADCC activity was measured with a bioassay kit from Promega (Cat.# G7018) which uses effector cells engineered to produce luciferase enzyme as a reporter of ADCC activity. Luciferase activity was measured on a spectrophotometer (Molecular Devices, Spectramax M5). The values (expressed as a ratio of the luciferase activity from each sample of antibody treated cells to that of a sample of cells that were not antibody treated) were plotted by non-linear regression using the log of the agonist vs response, variable slope, four parameter model using GraphPad Prism software.

Figure 5:
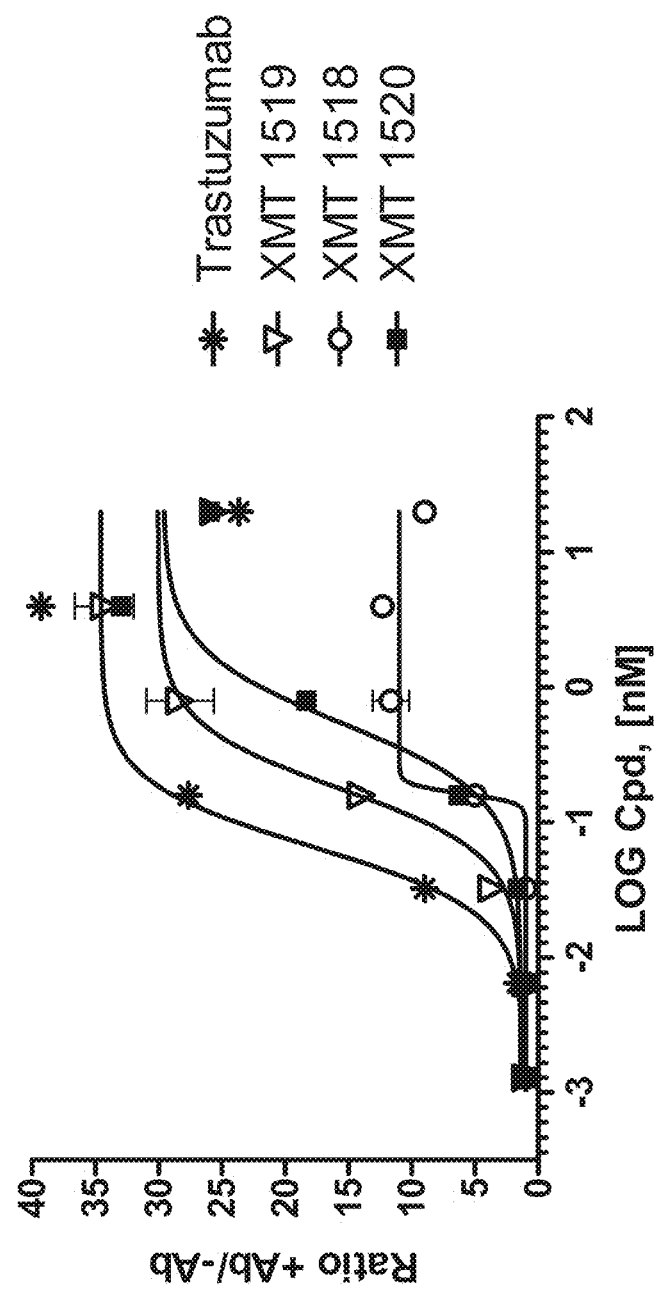
FIG. 5 shows the antibody-dependent cellular cytotoxicity (ADCC) for trastuzumab and antibodies XMT 1518, XMT 1519 and XMT 1520.

FIG. 5 is a graph showing the ADCC values. XMT 1519 and XMT 1520 show maximal activity similar to that of trastuzumab: the ratio of signal with antibody to signal without antibody is 30.1 for XMT 1519 and 29.7 for XMT 1520, while that of trastuzumab is 34.6. XMT 1518 has maximal activity of 11.0. The $EC_{50}$ (half maximal binding) values for the ADCC activity are 0.16 nM for XMT 1518, 0.18 nM for XMT 1519, 0.54 nM for XMT 1520, and 0.07 nM for trastuzumab, respectively.

Example 10: Ligand-Dependent HER2 Signaling in MCF7 Cells

The effect of anti-HER2 antibodies on ligand dependent HER2 signaling in MCF7 cells (ATCC, HTB-22) was determined by measuring the amount of phosphorylated AKT after treatment of the cells with the HER3 ligand, neuregulin-β1. 300,000 MCF7 cells were plated in MEM media with 0.01 mg/ml bovine insulin and 10% FBS in each well of 6 well culture dishes and grown overnight at 37° in 5% $CO_2$ atmosphere. The media was removed and replaced with fresh media containing 10 µg/ml of test antibody and incubated for 1 hour, followed by a 15 minute treatment with 40 pM neuregulin-β 1 (R&D Systems, Minneapolis, Minn., Cat.#377-HB-050). The cells were washed once with ice cold PBS and lysed by addition of 200 µl of buffer containing 50 mM Tris HCl, pH 7.4, 150 mM NaCl, 1% Triton X-100, cOmplete Protease Inhibitor cocktail tablets (Roche, Indianapolis, Ind.) and PhosSTOP phosphatase Inhibitor cocktail tablets (Roche, Indianapolis, Ind.). Lysates were centrifuged at 15,000 rpm for 15 minutes at 4° to remove insoluble debris. The levels of phosphorylated AKT were determined using Cell Signaling Technology PathScan® Phospho-Akt1 (Ser473) Sandwich ELISA Kit, following the manufacturer's instructions.

Table III shows the increase in AKT phosphorylation induced by neuregulin treatment of MCF7 cells, expressed as a percentage of that measured in unstimulated cells.

TABLE III

|  | None | Trastuzumab | Pertuzumab | XMT 1517 | XMT 1518 | XMT 1519 | XMT 1520 |
|---|---|---|---|---|---|---|---|
| AKT | 522 ± 86 | 369 ± 9 | 127 ± 22 | 564 ± 55 | 441 ± 23 | 381 ± 21 | 439 ± 49 |

The treatment with neuregulin increased the levels of phosphorylated AKT five-fold (522% relative to unstimulated cells). XMT 1517, XMT 1518, XMT 1519 and XMT 1520 caused a little or no reduction in the neuregulin induced increase in AKT phosphorylation to 564, 441, 381, and 439% respectively, similar to that caused by trastuzumab (369%). Pertuzumab, which has shown to inhibit ligand-dependent signaling (Franklin et al., Cancer Cell. 2004 Apr. 19; 5:317-28), reduced the neuregulin stimulation to close to that of unstimulated cells (127%). These results suggest that the test antibodies do not act by inhibiting the heterodimerization of HER2 and HER3 that is promoted by neuregulin and is inhibited by pertuzumab.

Example 11: Ligand-Independent HER2 Signaling in MCF7, SKBR3, and JIMT-1 Cells The effect of anti-HER2 antibodies on HER2 signaling in MCF7 (ATCC, HTB-22), SKBR3 (ATCC, HTB-30), JIMT-1 (ATCC, HTB-30) cells was determined by measuring changes in the amount of phosphorylated AKT after a 4 hour antibody treatment. Cells were plated in cell specific media with 10% FBS in each well of 6 well culture dishes and grown overnight at 37° in 5% $CO_2$ atmosphere. The media was removed and replaced with fresh media containing 10 µg/ml of test antibody and incubated for 4 hours. The cells were washed once with ice cold PBS and lysed by addition of 200 µl of buffer containing 50 mM Tris HCl, pH 7.4, 150 mM NaCl, 1% Triton X-100, cOmplete Protease Inhibitor cocktail tablets (Roche, Indianapolis, Ind.) and PhosSTOP phosphatase Inhibitor cocktail tablets (Roche, Indianapolis, Ind.). Lysates were centrifuged at 15,000 rpm for 15 minutes at 4° to remove insoluble debris. The levels of phosphorylated AKT were determined using Cell Signaling Technology PathScan® Phospho-Akt1 (Ser473) Sandwich ELISA Kit, following the manufactures instructions.

Table IV shows the inhibition of ligand independent HER2 signaling in MCF7, SKBR3, and JIMT-1 cells as indicated by the amount of AKT phosphorylation. The results are presented relative to the percentage of untreated cells.

TABLE IV

| Cell Line | Trastuzumab | XMT 1517 | XMT 1518 | XMT 1519 | XMT 1520 |
| --- | --- | --- | --- | --- | --- |
| SKBR3 | 64 ± 1 | 43 ± 5 | 59 ± 2 | 34 ± 2 | 29 ± 5 |
| JIMT-1 | 56 ± 4 | 66 ± 4 | 62 ± 1 | 84 ± 2 | 69 ± 4 |
| MCF7 | 98 ± 4 | 79 ± 5 | 103 ± 17 | 76 ± 3 | 66 ± 3 |

The test anti-HER2 antibodies caused a strong inhibition of HER2 signaling in SKBR3 cells where XMT 1517, XMT 1518, XMT 1519 and XMT 1520 reduced levels of phosphorylated AKT to 43%, 59%, 34%, and 29% of that occurring in untreated cells, compared to a reduction to 64% caused by trastuzumab.

The anti-HER2 antibodies inhibited HER2 signaling in JIMT-1 cells as indicated by a reduction in phosphorylated AKT to 66%, 62%, 84%, and 69% of that occurring in untreated cells for XMT 1517, XMT 1518, XMT 1519 and XMT 1520, respectively, similar to the reduction to 56% caused by trastuzumab.

In MCF7 cells XMT 1518, like trastuzumab, did not inhibit HER2 signaling, however XMT 1517, XMT 1519 and XMT 1520 caused modest reductions in signaling, reducing AKT phosphorylation to 79%, 76%, and 66% of that occurring untreated cells.

Example 12: Ligand-Independent HER2 Signaling in BT474 Cells

The effect of anti-HER2 antibodies on HER2 signaling in BT474 cells (ATCC, HTB-20) was determined by measuring changes in the amount of phosphorylated AKT after a 4 hour antibody treatment. BT474 cells (300,000 cells) were plated in DMEM media with 10% FBS in each well of 6 well culture dishes and grown overnight at 37° in 5% $CO_2$ atmosphere. The media was removed and replaced with fresh media containing 10 µg/ml of test antibody and incubated for 4 hours. The cells were washed once with ice cold PBS and lysed by addition of 200 µl of buffer containing 50 mM Tris HCl, pH 7.4, 150 mM NaCl, 1% Triton X-100, cOmplete Protease Inhibitor cocktail tablets (Roche, Indianapolis, Ind.) and PhosSTOP phosphatase Inhibitor cocktail tablets (Roche, Indianapolis, Ind.). Lysates were centrifuged at 15,000 rpm for 15 minutes at 4° to remove insoluble debris. The levels of phosphorylated AKT were determined by western analysis. 20 µl of each extract was mixed with 7 µl of NUPAGE loading dye (Life Technologies, Cat.# NP0007) and 2 µl of 10× reducing agent (Life Technologies Cat.# NP0004) and loaded onto a 4-12% Bis-Tris polyacrylamide gel (Life Technologies, Cat.# NP0341) which was run in MOPS running buffer (Life Technologies Cat.# NP000102) for 90 min at 120 volts. The separated proteins were transferred to a nitrocellulose membrane on a semi-dry electrophoretic transfer system (Bio-Rad, Transblot system) for 30 minutes at 10 volts in transfer buffer (Life Technologies, Cat.# NP0006) containing 10% methanol. The membrane was incubated for 1 hour in blocking buffer (Li-cor, Cat.#927-40000) and then with a mouse antibody that recognizes the AKT protein (Cell Signaling Technology, #2920) diluted 1:1000, a rabbit antibody that recognizes AKT phosphorylated on serine 473 (Cell Signaling Technology, #4060) and a rabbit antibody that recognizes actin (LiCor, Cat.#926-42210) diluted 1:5,000 in the same blocking buffer for 1 hour. After the incubation the membrane was washed 3 times with 10 ml TTBS and then incubated for 1 hour with secondary antibodies: a goat anti-rabbit IgG conjugated to IRdye® 800CW (Li-Cor, Cat.#926-32211) and a goat anti-mouse IgG conjugated to IRdye® 680RD (Li-Cor, Cat.#926-68070) both diluted 1:10,000 in blocking buffer. The membrane was again washed 3 times with 10 ml TTBS and scanned on a Li-Cor Odyssey scanner. The bands corresponding to AKT, phospho-AKT, and to actin were quantified using the scanner software. Each phospho-AKT band was normalized to the total AKT band and expressed as a percentage of phospho-AKT protein from cells that were not treated with any anti-HER2 antibodies.

The effect of the anti-HER2 antibodies on HER3 phosphorylation was also examined in the same experiment. The above described nitrocellulose blots were also probed with a rabbit antibody that recognizes HER3 phosphorylated on tyrosine 1289 (Cell Signaling Technology, #4791) diluted 1:1000 in blocking buffer for 1 hour. After the incubation the membrane was washed 3 times with 10 ml TTBS and then incubated for 1 hour with a goat anti-rabbit IgG conjugated to IRdye® 800CW (Li-Cor, Cat.#926-32211) diluted 1:10,000 in blocking buffer. The membrane was again washed 3 times with 10 ml TTBS and scanned on a Li-Cor Odyssey scanner. The bands corresponding to phospho-HER3, and to actin were quantified using the scanner software. Each phospho-HER3 band was normalized to the total AKT band and expressed as a percentage of phospho-HER3 protein from cells that were not treated with any anti-HER2 antibodies.

Table V gives the inhibition of ligand independent HER2 signaling in BT474 cells as determined by the amount of AKT phosphorylation or Her3 phosphorylation. The results are presented relative to the percentage of unstimulated cells.

TABLE V

| | Trastuzumab | Pertuzumab | XMT 1519 | XMT 1520 |
|---|---|---|---|---|
| AKT | 31 ± 2 | 44 ± 3 | 21 ± 8 | 30 ± 5 |
| HER3 | 80 | 85 | 71 | 76 |

The anti-HER2 antibodies XMT 1519 reduced AKT phosphorylation to about 21% and HT19B to about 30% of that seen in untreated cells in BT474, compared to trastuzumab that caused a reduction to about 31%, and pertuzumab that caused a reduction to about 44% of untreated cells. HER3 phosphorylation was modestly affected by all antibodies: 71%, 76%, 80%, and 85% of that seen in untreated cells by XMT 1519, XMT 1520, trastuzumab and pertuzumab, respectively.

Example 13: Internalization Rate Measurements

Figure 6:
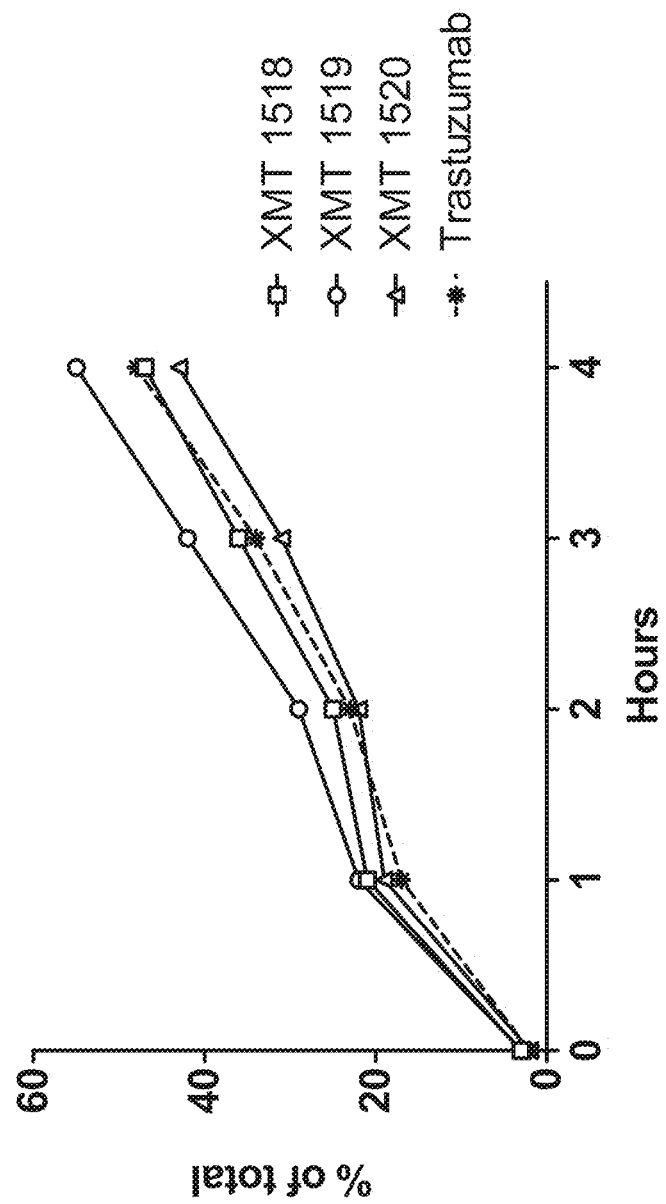
FIG. 6 shows the internalization rate for trastuzumab and antibodies HT XMT 1518, XMT 1519 and XMT 1520.

The rate at which each antibody XMT 1518, XMT 1519, XMT 1520 and trastuzumab, is internalized from the cell surface of SKBR3 cells was determined by fluorescence in a 96-well based assay. SKBR3 cells were seeded in 96 well plates and allowed to attach by overnight growth in DMEM media (ATCC, Manassas, Va., Cat.#30-2002) with 10% fetal bovine serum (FBS) (Gibco®, Life Technologies, Grand Island, N.Y., Cat.#16140-071) at 37° in 5% $CO_2$. The cells were incubated in media containing 10 µg/ml antibody on ice for 1 hour, then washed with ice cold media and incubated one ice with 75 µl of media containing 1 µg/ml of a goat anti-human IgG monovalent Fab fragment (Rockland Immunochemicals, Gilbertsville, Pa., Cat.#809-1102) conjugated to Alexa Fluor®-647 for one hour. After washing the cells were transferred to a 37° incubator to allow internalization for various time points. The plates were scanned on an Odyssey scanner (Li-Cor Biosciences, Lincoln, Neb.) using the 700 nm channel. Then plates were acid-washed by incubation with 100 mM glycine, 20 mM MgSO4, 50 mM KCl, pH 2.2, on ice to remove antibodies bound to the cell surface, washed with ice cold PBS and again scanned to determine the amount of fluorescence internalized by the cells. FIG. 6 shows the rate of internalization of the antibodies over 4 hours. The rate of internalization of all the antibodies is nearly identical to that of trastuzumab, with all having about 50% of the total surface bound at time 0 internalized by 4 hours (FIG. 6).

Example 13A: HER2 Internalization in SKBR3 Cells

Figure 7:
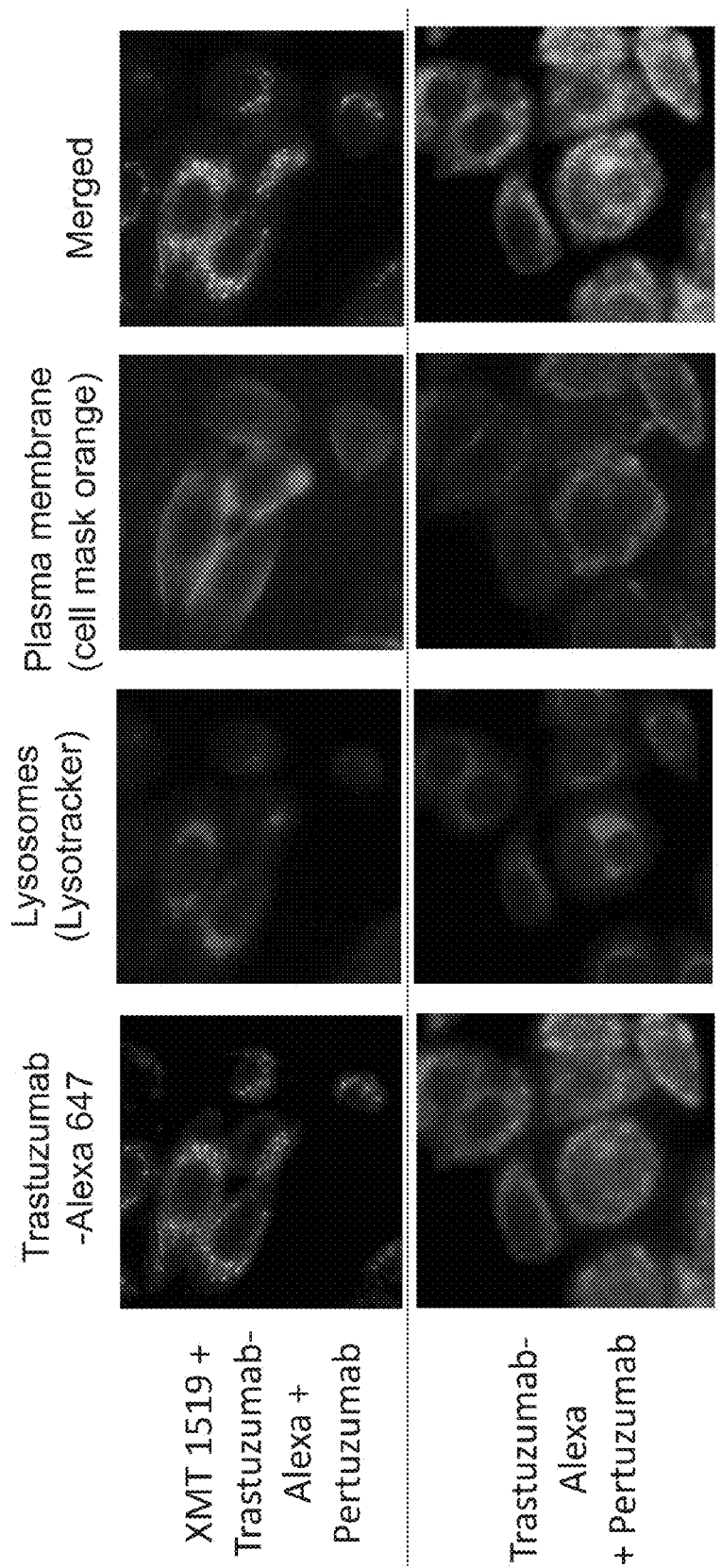
FIG. 7 shows the internalization of HER2 antibodies in SKBR3 cells.

The effect of a combination of anti-HER2 antibodies on the HER2 internalization in SKBR3 cells was investigated by fluorescence microscopy. Trastuzumab was conjugated with Alexa Fluor-647 and was used to visualize the location of trastuzumab and presumably HER2 within the cells. SKBR3 cells were seeded in 4 chamber microscope slides and allowed to attach by overnight growth in DMEM media (ATCC, Manassas, Va., Cat.#30-2002) with 10% fetal bovine serum (FBS) (Gibco®, Life Technologies, Grand Island, N.Y., Cat.#16140-071) at 37° in 5% $CO_2$. SKRB3 cells were incubated for 90 minutes in media containing either (i) a combination of trastuzumab-Alexa-647 and pertuzumab or (ii) a combination of trastuzumab-Alexa-647 and pertuzumab and HER2 antibody XMT 1519. The location of trastuzumab was visualized using fluorescence microscope. As shown in FIG. 7 while most of the trastuzumab-Alexa Fluor-627 in combination with pertuzumab alone was co-localized with cell mask orange, suggesting plasma membrane localization, most of the trastuzumab-Alexa Fluor-647 in combination with both pertuzumab and XMT 1519 co-localized with Lysotracker, suggesting the lysosome localization. This result suggests that the presence of XMT 1519 in combination with trastuzumab and pertuzumab promotes the internalization and trafficking of HER2 to the lysosomes.

Example 13B: Internalization Rate Measurements with Anti-HER2 Antibody Combination The effect of combining multiple anti-HER2 antibodies that recognize different epitopes on the rate of HER2 internalization was determined with a 96 well plate based assay, similar to that described in Example 13. In this experiment cells were treated with a test HER2 antibody alone, in combination with trastuzumab or with trastuzumab and pertuzumab, and the amount of the anti-HER2 antibody internalized at various times was measured.

For the assay, 40,000 SKBR3 cells were plated in DMEM media containing 10% FBS, in each well of three 96 well plates (black colored plates with clear bottomed wells) and allowed to attach overnight at 37° in 5% $CO_2$. The next day the cells were treated with antibodies as follows. Media in each well was replaced with fresh, ice cold media containing 5 µg/ml of one of the test HER2 antibodies, or trastuzumab, and incubated on ice for 1 hr. The unbound antibody was removed by washing the cells two times with ice cold media. For detection, 5 µg/ml of an Alexa 647 labelled anti-human IgG Fab fragment was added to each well in ice cold media and incubated on ice for 1 hr. The unbound secondary antibody was removed by washing each well 2 times with ice cold media. Next, media containing either 5 µg/ml trastuzumab, 5 µg/ml each of trastuzumab and pertuzumab or no additional antibodies was added to each well. Each treatment was carried out in triplicate. One set of wells were treated with the Alexa 647 labelled anti-human IgG monovalent Fab fragment alone, and the fluorescence measured in these wells was used to subtract background fluorescence.

One plate was left on ice to determine the time 0 values for each treatment, and the other plates were incubated at 37° C. After 1.5 hours, one plate from 37° C., and the time 0 plate, were washed 2 times with ice cold PBS and scanned using the 680 nm channel of a Licor Odyssey scanner. The fluorescence measured in each well is used as the total fluorescence for each treatment. The cells were then acid washed 2 times with 100 mM glycine, 50 mM KCl, and 20 mM $MgSO_4$, pH2.2, then washed two times with ice cold PBS to remove the surface bound antibodies. The plates were scanned again to determine the amount of internalized fluorescence in each well. The 24 hour plates were analyzed the same way the next day.

The percentage of each HER2 antibody (or of trastuzumab in the control wells) internalized is calculated by subtracting the background, averaging each of the 3 replicates, then dividing the internalized fluorescence by the total fluorescence for each treatment and multiplying by 100.

As shown in Table VA., 80-90% of XMT 1518, XMT 1519, and XMT 1520 are internalized within one and a half hour when combined with both trastuzumab and pertuzumab. XMT 1517 shows 60% internalization, probably due to its very high off rate, which causes it to diffuse away from the cells during the incubations. When combined with trastuzumab, 20-40% of each test antibody is internalized in an hour and a half and about 15%, is internalized when each test antibody is present alone. Trastuzumab alone shows about 15% internalization in an hour and a half, and about 30% when it is combined with pertuzumab.

Thus, the combination of three HER2 antibodies; any one of the test HER2 antibodies, trastuzumab and pertuzumab, increases the rate of antibody internalization, most likely by increasing the rate of HER2 endocytosis.

TTBS and scanned on a Li-Cor Odyssey scanner. The bands corresponding to full length HER2 protein and to actin were quantified using the scanner software. Each HER2 band was normalized to the actin band and expressed as a percentage of HER2 protein from cells that were not treated with any anti-HER2 antibodies.

TABLE VA

| | | | | Percent internalized | | | | | | | |
|---|---|---|---|---|---|---|---|---|---|---|---|
| | | Trast. | | Alone | | | | with Trastuzumab | | | |
| | | Trast. alone | + Pert. | XMT 1517 | XMT 1518 | XMT 1519 | XMT 1520 | XMT 1517 | XMT 1518 | XMT 1519 | XMT 1520 |
| 0 | hr | 2 | 1 | 4 | 3 | 2 | 2 | 3 | 2 | 2 | 2 |
| 1.5 | hrs | 13 | 28 | 11 | 16 | 14 | 14 | 17 | 41 | 35 | 23 |
| 24 | hrs | 88 | 94 | 83 | 88 | 83 | 78 | 106 | 106 | 107 | 100 |

| | | with Trastuzumab and Pertuzumab | | | |
|---|---|---|---|---|---|
| | | XMT 1517 | XMT 1518 | XMT 1519 | XMT 1520 |
| 0 | hr | 4 | 2 | 2 | 3 |
| 1.5 | hrs | 63 | 90 | 83 | 89 |
| 24 | hrs | 107 | 103 | 88 | 101 |

Example 14: HER2 Degradation

Figure 8:
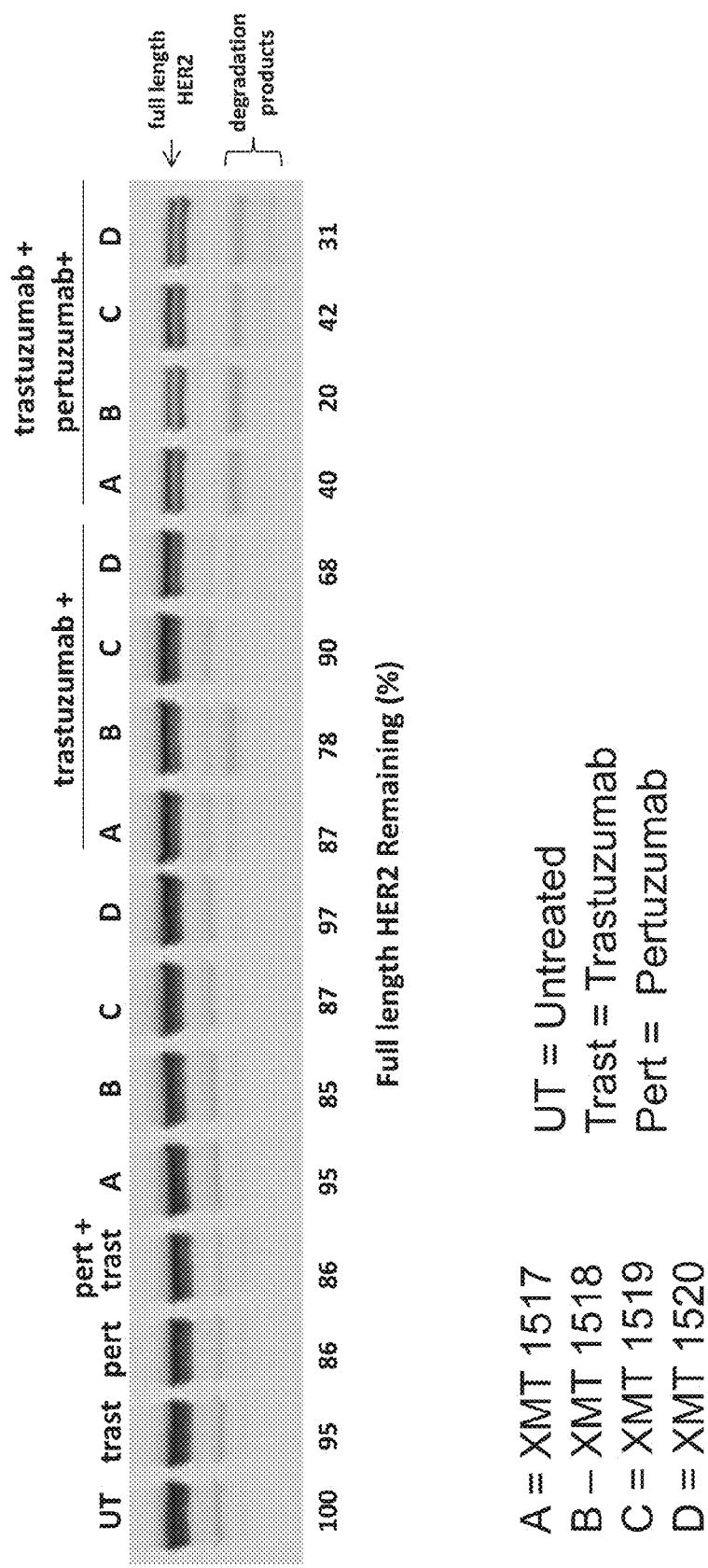
FIG. 8 shows the HER2 degradation induced by a combination of anti-HER2 antibodies.

The effect of anti-HER2 antibodies on HER2 degradation in SKBR3 cells was determined by western analysis after antibody treatment. 300,000 SKBR3 cells were plated in DMEM media with 10% FBS in each well of 6 well culture dishes and grown overnight at 37° in 5% $CO_2$ atmosphere. The media was removed and replaced with fresh media containing 10 μg/ml of each antibody and incubated for 4 hours. The cells were washed once with ice cold PBS and lysed by addition of 200 μl of buffer containing 50 mM Tris HCl, pH 7.4, 150 mM NaCl, 1% Triton X-100, cOmplete Protease Inhibitor cocktail tablets (Roche, Indianapolis, Ind.) and PhosSTOP phosphatase Inhibitor cocktail tablets (Roche, Indianapolis, Ind.). Lysates were centrifuged at 15,000 rpm for 15 minutes at 4° to remove insoluble debris. 20 μl of each extract was mixed with 7 μl of NUPAGE loading dye (Life Technologies, Cat.# NP0007) and 2 μl of 10× reducing agent (Life Technologies Cat.# NP0004) and loaded onto a 4-12% Bis-Tris polyacrylamide gel (Life Technologies, Cat.# NP0341) which was run in MOPS running buffer (Life Technologies Cat.# NP000102) for 90 min at 120 volts. The separated proteins were transferred to a nitrocellulose membrane on a semi-dry electrophoretic transfer system (Bio-Rad, Transblot system) for 30 minutes at 10 volts in transfer buffer (Life Technologies, Cat.# NP0006) containing 10% methanol. The membrane was incubated for 1 hour in blocking buffer (Li-cor, Cat.#927-40000) and then with a rabbit antibody that recognizes the HER2 protein (Cell Signaling Technology, Cat.#2165) diluted 1:1,000, and a rabbit antibody that recognizes actin (LiCor, Cat.#926-42210) diluted 1:5,000 in the same blocking buffer for 1 hour. After the incubation the membrane was washed 3 times with 10 ml TTBS and then incubated for 1 hour with secondary antibodies: a goat anti-rabbit IgG conjugated to IRdye® 800CW (Li-Cor, Cat.#926-32211) and a goat anti-mouse IgG conjugated to IRdye® 680RD (Li-Cor, Cat.#926-68070) both diluted 1:10,000 in blocking buffer. The membrane was again washed 3 times with 10 ml FIG. 8 shows that treatment of SKBR3 cells with the test antibodies alone or in combination with trastuzumab had little or no effect on HER2 levels, with the exception of XMT 1518 and XMT 1520 which caused reductions of full length HER2 to 78 and 68%, respectively, and caused the appearance of lower molecular weight degradation products. However, triple combinations of trastuzumab, pertuzumab and one of the test HER2 antibodies caused extensive degradation of HER2, as well as the appearance of HER2 degradation products. The greatest reductions are seen when XMT 1518, or XMT 1520, is combined with trastuzumab and pertuzumab, with 20%, or 31% HER2 remaining. When the antibody XMT 1517 or XMT 1519 is combined with trastuzumab and pertuzumab, the reduction is 40% or 42% respectively of the normal amount of HER2 remaining.

Example 15: Epitope Mapping

Epitope mapping of antibodies XMT 1517 and XMT 1519 was carried out by Integral Molecular Inc., 3711 Market Street, Suite 900, Philadelphia, Pa., USA, using their Shotgun Mutagenesis Technology. Shotgun Mutagenesis uses a proprietary high throughput cellular expression technology that enables the expression and analysis of large libraries of mutated target proteins within eukaryotic cells. Every residue in a protein is individually mutated, usually to multiple other amino acids, in order to assay changes in function. Proteins are expressed within standard mammalian cell lines, so even difficult proteins that require eukaryotic translational or post-translational processing can be mapped.

Shotgun Mutagenesis Mapping identified six critical amino acids for XMT 1517 binding (C453, H473, N476, R495, H497, and W499) indicating that XMT 1517 binds to regions on C-terminus of Domains III and the N-terminus of Domain IV of HER2. Two secondary critical mutations at H456 and G496 might also be involved in the binding of XMT 1517 to HER2.

Three critical amino acids for XMT1519 binding (E521, L525 and R530) were identified indicating that XMT 1519 binds a region on the N-terminus of Domain IV of Her2.

Example 16: Synthesis of HER2-(EG2-MI-(10 kDa PHF-BA-(AF-HPA-Ala)))

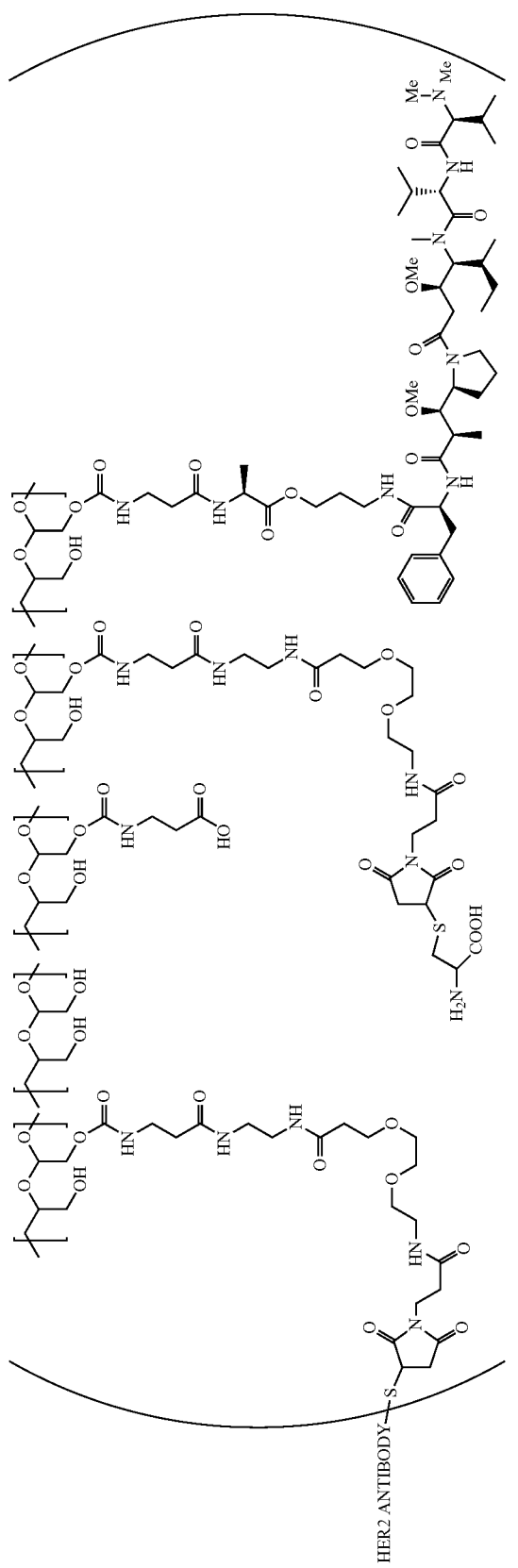

The HER2-(EG2-MI-(10 kDa PHF-BA-(AF-HPA-Ala))) conjugates were prepared using the procedure described in U.S. Ser. No. 14/512,316 filed Oct. 10, 2014. Table VI gives the details of the antibody-polymer drug conjugates.

TABLE VI

| Example No. | Antibody | DAR (Drug:Antibody ratio) |
|---|---|---|
| 16A | Trastuzumab | About 10:1 to about 15:1 |
| 16B | Trastuzumab | About 16:1 to about 21:1 |
| 16C | Trastuzumab | About 5:1 to about 10:1 |
| 16D | XMT 1519 | About 11:1 to about 16.5:1 |
| 16E | XMT 1519 | About 13:1 to about 20:1 |
| 16F | XMT 1519 | About 12:1 to about 18:1 |
| 16G | XMT 1517 | About 7:1 to about 10.5:1 |
| 16H | XMT 1519 | About 11.8:1 to about 17.5:1 |
| 16J | XMT 1519 | About 8.9:1 to about 13.3:1 |

The HER2-(EG2-MI-(10 kDa PHF-BA-(AF-HPA-Ala))) conjugates had a peak molecular weight of about 170 kDa to about 230 kDa. The polymer and polymer conjugates synthesized/measured typically have a polydispersity ≤1.5. The polymer-drug conjugates (i.e., the drug-carrying polymer chain attached to antibody) contained about 27% mol to about 33% mol beta-alanine, about 6.4% mol to about 9.6% mol AF-HPA-Ala and about 1.5% mol to about 4% mol EG2-MI.

Example 17: Synthesis of Rituximab-(EG2-MI-(10 kDa PHF-BA-(AF-HPA-Ala)))

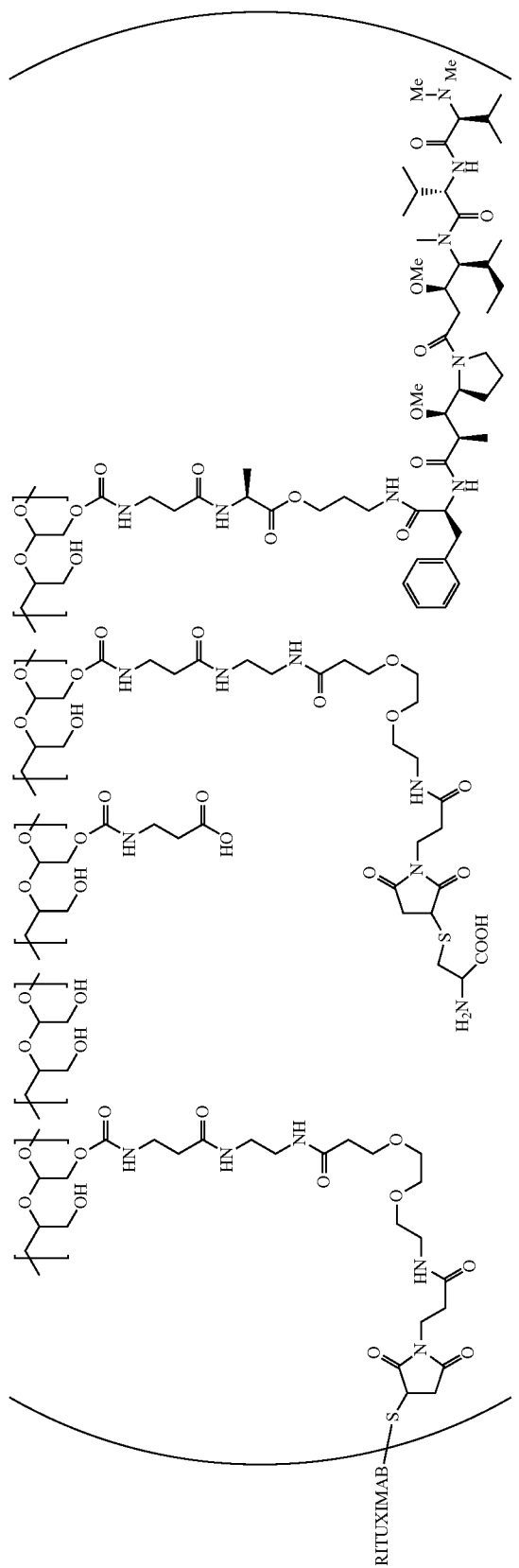

The rituximab-(EG2-MI-(10 kDa PHF-BA-(AF-HPA-Ala))) conjugates (non-binding control) were prepared using the procedure described in U.S. Ser. No. 14/512,316 filed Oct. 10, 2014. Table VII gives the details of the antibody-polymer drug conjugates.

TABLE VII

| Example No. | Antibody | DAR (Drug:Antibody ratio) |
|---|---|---|
| 17A | Rituximab | About 10:1 to about 15:1 |
| 17B | Rituximab | About 16:1 to about 21:1 |
| 17C | Rituximab | About 10:1 to about 15:1 |

The HER2-(EG2-MI-(10 kDa PHF-BA-(AF-HPA-Ala))) conjugates had a peak molecular weight of about 170 kDa to about 230 kDa. The polymer and polymer conjugates synthesized/measured typically have a polydispersity ≤1.5. The polymer-drug conjugates (i.e., the drug-carrying polymer chain attached to antibody) contained about 27% mol to about 33% mol beta-alanine, about 6.4% mol to about 9.6% mol AF-HPA-Ala and about 1.5% mol to about 4% mol EG2-MI.

Example 18: Cytotoxicity Assays for HER2-(EG2-MI-(10 kDa PHF-BA-(AF-HPA-Ala))) Conjugates HER2-(EG2-MI-(10 kDa PHF-BA-(AF-HPA-Ala))) conjugates were evaluated for their antiproliferation properties in tumor cell lines in vitro using Cell Titer-Glo (Promega Corp). JIMT-1(HER2 medium expressing cells, DSMZ, Braunschweig, Germany, Cat.# ACC589), MDA-MB-361 (HER2 medium expressing human breast cancer cells, ATCC, Cat.# HTB-27), MDA-MB-453 cells (triple negative breast cancer cell line, ATCC, Cat.# HTB-131), were cultured in DMEM media (ATCC, Manassas, Va., Cat.#30-2002) with 10% FBS (Gibco®, Life Technologies, Grand Island, N.Y., Cat.#16140-071). NCI-H522 (non-small cell lung carcinoma cell line, not amplified, ATCC, Cat.# CRL-5810), and NCI-H2170 (non-small cell lung carcinoma cell line, ATCC, Cat.# CRL-5928) cells were cultured in RPMI-1640 medium (ATCC, Cat.#30-2001). NCI-H1581 (non-small cell lung carcinoma medium expressing cell line, not amplified, ATCC, Cat.# CRL-5878) cells were cultured in DMEM:F12 medium (ATCC, Cat.#30-2006). SNU5 (gastric carcinoma cell line, not amplified, ATCC, Cat.# CRL-5973) was cultured in Iscove's Modified Dulbecco's Medium (Invitrogen Life Technologies, Cat.#12440053) with 20% FBS. OVCAR3 (ovarian adenocarcinoma cell line, not amplified, ATCC, Cat.# HTB-161) was cultured in RPMI medium with 20% FBS. MDA-MB-175-VII (human breast cancer cell line, not amplified, ATCC, Cat.# HTB-25), was cultured in Leibovitz's L-15 Medium with 20% FBS. CAMA-1 (human breast cancer cell line, not amplified, ATCC, Cat.# HTB-21), was cultured in 90% ATCC-formulated Eagle's Minimum Essential Medium. ZR75-1 (human breast cancer cell line, not amplified, ATCC, Cat.# CRL-1500), was cultured in RPMI-1640 Medium. HCC1187 (human breast cancer cell line, not amplified, ATCC, Cat.# CRL-2322), was cultured in RPMI-1640 Medium. HCC38 (human breast cancer cell line, not amplified, ATCC, Cat.# CRL-2314), was cultured in RPMI-1640 Medium. T47D (human breast cancer cell line, not amplified, ATCC, Cat.# HTB-133), was cultured in RPMI-1640 Medium. HCC70 (human breast cancer cell line, not amplified, ATCC, Cat.# CRL-2315), was cultured in RPMI-1640 Medium. MDA-MB-231 (human breast cancer cell line, not amplified, ATCC, Cat.# HTB-26), was cultured in DMEM Medium. CALU3 (human lung adenocarcinoma cell line, ATCC, Cat.# HTB-55) was cultured in ATCC-formulated Eagle's Minimum Essential Medium. A549 (human lung carcinoma cell line, not amplified, ATCC, Cat.# CCL-185) was cultured in F12K Medium. NCI-H2122 (human lung adenocarcinoma cell line, not amplified, ATCC, Cat.# CRL-5985) was cultured in RPMI-1640 Medium, (ATCC, Cat.#30-2001). NCI-H460 (human lung carcinoma cell line, not amplified, ATCC, Cat.# HTB-177) was cultured in RPMI-1640 Medium, (ATCC, Cat.#30-2001). SHP-77 (human small cell lung cancer cell line, not amplified, ATCC, Cat.# CRL-2195) was cultured in RPMI-1640 Medium, (ATCC, Cat.#30-2001). KATO III (human gastric carcinoma cell line, not amplified, ATCC, Cat.# HTB-103) was cultured in Iscove's Modified Dulbecco's Medium with 20% FBS. MKN-45 III (human gastric adenocarcinoma cell line, not amplified, DSMZ, Braunschweig, Germany, Cat.# ACC409) was cultured in RPMI-1640 Medium, (ATCC, Cat.#30-2001). SKOV3 (human ovary adenocarcinoma cell line ATCC, Cat.# HTB-77), was cultured in McCoy's 5a Medium. TOV-21G (human ovarian adenocarcinoma cell line, not amplified, ATCC, Cat.# CRL-11730 was cultured in 1:1 mixture of MCDB 105 medium containing a final concentration of 1.5 g/L sodium bicarbonate and Medium 199 containing a final concentration of 2.2 g/L sodium bicarbonate. BT474 (HER2 high expressing human breast cancer cells, ATCC, Cat.# HTB-20) was cultured in DMEM Medium with 10% FBS. NCI-N87 (high HER2 expressing gastric cancer cell line, ATCC, Cat.# CRL-5822), was grown in RPMI-1640 Medium 10% FBS.

For the cytotoxicity assay, cells were seeded at a density of 3000 cells per well in 96 well plates and allowed to attach during overnight incubation at 37° C. in the presence of 5% $CO_2$. The media was then replaced with fresh media containing a range of HER2-(EG2-MI-(10 kDa PHF-BA-(AF-HPA-Ala))) conjugates (100 nM to 0.1 pM), or Kadcyla (Genentech) and the cells were incubated for 72 hours or 6 days at 37° in the presence of 5% $CO_2$. Cell survival was measured using CellTiter-Glo® Luminescent Cell Viability Assay (Promega, Madison, Wis.) as described in the kit instructions. Cell viability was normalized to untreated control and expressed as a percentage. The values were plotted and $IC_{50}$ values calculated with Graphpad Prism software (San Diego, Calif.) using 4 parameter, variable slope, dose response curve fitting algorithm. Table VIII gives illustrative results for the cytotoxicity of the HER2-(EG2-MI-(10 kDa PHF-BA-(AF-HPA-Ala))) conjugates and Kadcyla.

TABLE VIII

| Cell Line | HER2 molecules per cell | Her2 expression | Example 16G | Example 16D | Example 16B | Example 16E | Kadcyla |
|---|---|---|---|---|---|---|---|
| | | | IC$_{50}$ (nM) | | | | |
| JIMT-1 | 80,000 | 2+ | 0.1 | 0.6 | 0.3$^b$ | ND | 17.5 |
| MDA-MB-453 | 125,000 | 2+ | ND | 0.04 | 0.04/0.08 | 0.04 | ~100 |
| MDA-MB-361 | 135,000 | 2+ | ND | 0.02 | 0.005/0.001 | ND | 0.27/0.33 |
| MDA-MB-175VII | 51,000 | 1+ | ND | ND | 0.1 | 0.3 | 1.2 |
| CAMA-1 | 50,000 | 1+ | ND | ND | 0.02 | 0.1 | 7.8 |
| ZR75-1 | 40,000 | 1+ | ND | ND | 1.1 | 2.7 | >100 |
| HCC1187 | 38,000 | 2+ | ND | ND | 0.8 | 1.7 | 30 |
| HCC38 | 36,000 | 2+ | ND | ND | 0.8 | 4 | >100 |
| T47D | 20,000 | 1+ | ND | ND | 4.3 | 1.2 | 82.3 |
| HCC70 | 10,000 | 1+ | ND | ND | ND | 4$^c$ | 83.4 |
| MDA-MB-231 | 5400 | 1+ | ND | ND | 11 | 6.3$^c$ | 27 |
| NCI-H522 | 25,000 | 1+ | ND | 0.8 | 0.18 | ND | ~100 |
| NCI-H1581 | 13,000 | 1+ | ND | 5.6 | 2.3 | ND | ~100 |
| NCI-H2170 | 660,000 | 3+ | ND | ND | 0.07 | 0.08 | 0.4 |
| CALU3 | 330,000 | 3+ | ND | ND | 0.25 | 0.15 | >100 |
| NCI-H2122 | 12,000 | 1+ | ND | ND | 0.5 | 2.5 | 19 |
| A549 | 6,000 | 1+ | ND | ND | 20 | 10.8$^c$ | >100 |
| NCI-H460 | 4,000 | 1+ | ND | ND | 16 | 20$^c$ | 68 |
| SHP-77 | 0 | | ND | ND | 67 | 22$^c$ | >100 |
| SNU5 | 22,000 | 1+ | ND | ND | 2.9 | 3.3 | >100 |
| KATOIII | 19,000 | 1+ | ND | ND | 19 | 3.8 | >100 |
| MKN45 | 16,000 | 1+ | ND | ND | ~80 | 5.2 | >100 |
| OVCAR3 | 7,200 | 1+ | ND | ND | 1.6 | 2.4 | ~85 |
| SKOV3 | 220,000 | 3+ | ND | 0.6 | 0.19 | ND | 5.6 |
| TOV21G | 12,000 | 1+ | ND | ND | 0.45 | 8.8 | >100 |
| BT474 | 860,000 | 3+ | ND | 0.03 | 0.1 | 0.06 | 1.3 |
| NCI-N87 | 700,000 | 3+ | ND | 0.03 | 0.03 | 0.08 | 0.3 |

ND = not determined
$^b$Example 16C was used in the assay instead of Example 16B
$^c$equivalent potency to irrelevant antibody control As shown in Table VIII, all the HER2 antibody-polymer-drug conjugates are more potent than Kadcyla in all the tested cell lines.

Example 19: Cytotoxicity Assays for HER2-(EG2-MI-(10 kDa PHF-BA-(AF-HPA-Ala))) Conjugates in a Cell Line with a Mutant HER2

HER2-(EG2-MI-(10 kDa PHF-BA-(AF-HPA-Ala))) conjugates were evaluated for their antiproliferation properties in tumor cell lines in vitro using Cell Titer-Glo (Promega Corp). NCI-H1781 (HER2 mutant expressing human lung cancer cells, ATCC, Cat.# CRL-5894) were cultured in RPMI-1640 medium containing 10% FBS.

For the cytotoxicity assay, cells were seeded at a density of 3000 cells per well in 96 well plates and allowed to attach during overnight incubation at 37° C. in the presence of 5% CO$_2$. The media was then replaced with fresh media containing a range of HER2-(EG2-MI-(10 kDa PHF-BA-(AF-HPA-Ala))) conjugates (100 nM to 0.1 pM), Example 17A (rituximab-(EG2-MI-(10 kDa PHF-BA-(AF-HPA-Ala))), or Kadcyla (Genentech) and the cells were incubated for 72 hours at 37° C. in the presence of 5% CO$_2$. Cell survival was measured using CellTiter-Glo® Luminescent Cell Viability Assay (Promega, Madison, Wis.) as described in the kit instructions. Cell viability was normalized to untreated control and expressed as a percentage. The values were plotted and IC$_{50}$ values calculated with Graphpad Prism software (San Diego, Calif.) using 4 parameter, variable slope, dose response curve fitting algorithm. Table IX gives the results of these assays.

TABLE IX

| Cell Line | HER2 molecules per cell | Example 16E | Example 16J | Example 17A | Kadcyla |
|---|---|---|---|---|---|
| | | IC$_{50}$ (nM) | | | |
| NCI-H1781 | 8,500 | 0.71 | 0.75 | 1.8 | 5.8 |

As shown in Table IX, all the HER2 antibody-polymer-drug conjugates are more potent than the rituximab antibody-polymer-drug conjugate or Kadcyla in the tested cell lines.

Example 20: Tumor Growth Response to Administration of PBRM-Polymer-Drug Conjugates Female CB-17 SCID mice were inoculated subcutaneously with NCI-N87 cells (n=10 for each group), JIMT-1 cells (n=10 for each group), SNU-5 cells (n=10 for each group), H522 cells (n=10 for each group), SKOV3 cells (n=10 for each group), Calu-3 cells (n=10 for each group), NCI-N87 Kadcyla resistant cells (n=10 for each group), NCI-N87-MSA Kadcyla resistant cells (n=10 for each group) or BT474 tumor fragments (n=10 for each group). Female NCr nu/nu were inoculated subcutaneously with TOV-21G cells (n=10 for each group). Test compounds or vehicle were dosed IV as a single dose on day 1 or as indicated. Tumor size was measured at the times indicated in FIGS. 8 to 18 using digital calipers. Tumor volume was calculated and was used to determine the delay in tumor growth. Mice were sacrificed when tumors reached a size of 800 to 1500 mm$^3$. Tumor volumes are reported as the mean±SEM for each group.

Figure 9:
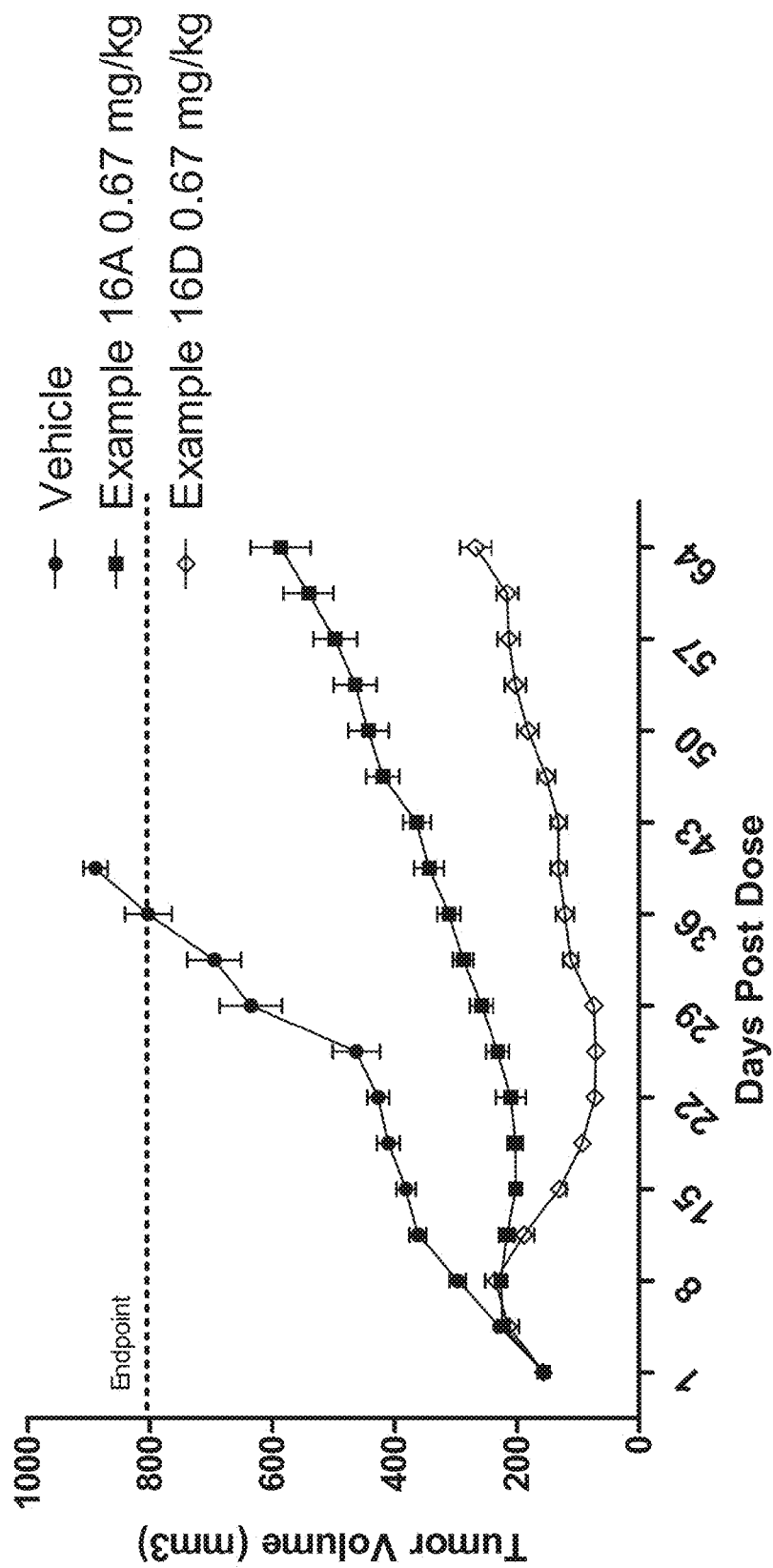
FIG. 9 illustrates the anti-tumor efficacy of Example 16A, trastuzumab-(EG2-MI-(10 kDa PHF-BA-(AF-HPA-Ala))) and Example 16D, XMT 1519-(EG2-MI-(10 kDa PHF-BA-(AF-HPA-Ala))), as measured in a NCI-N87 mouse tumor xenograft model.

FIG. 9 provides the results for the tumor response in mice inoculated subcutaneously with NCI-N87 cells (n=10 for each group) after IV administration of vehicle; Example 16A, trastuzumab-(EG2-MI-(10 kDa PHF-BA-(AF-HPA-Ala))), at 0.67 mg/kg; or Example 16D, XMT 1519-(EG2-MI-(10 kDa PHF-BA-(AF-HPA-Ala))), at 0.67 mg/kg as a single dose at day 1. The vehicle and trastuzumab-(EG2-MI-(10 kDa PHF-BA-(AF-HPA-Ala))), showed an increase of tumor volume. The XMT 1519-(EG2-MI-(10 kDa PHF-BA-(AF-HPA-Ala))) showed 60% partial regressions and resulted in potential therapeutic activity (TGI 88%) based on tumor growth inhibition analysis on Day 29.

Figure 10:
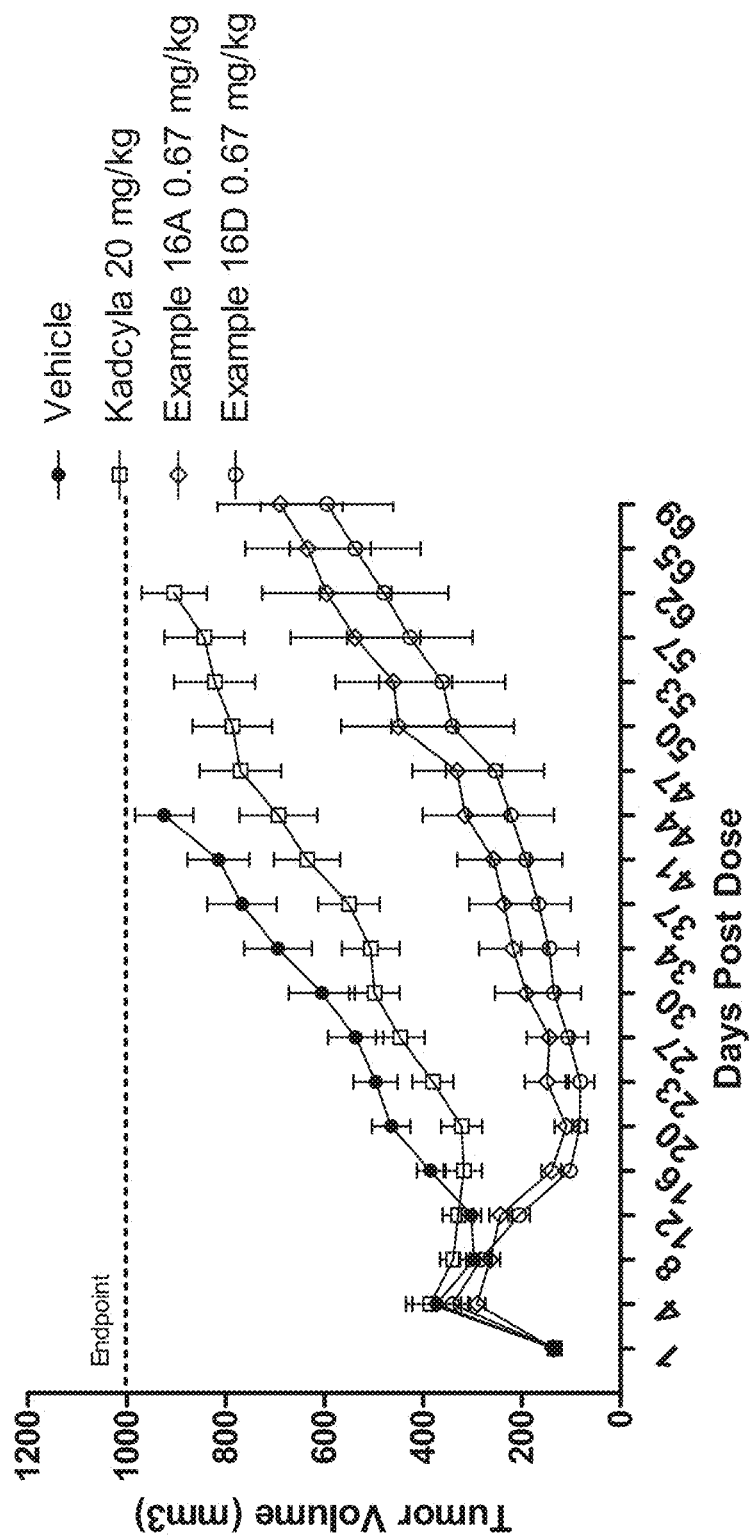
FIG. 10 illustrates the anti-tumor efficacy of Kadcyla; Example 16A, trastuzumab-(EG2-MI-(10 kDa PHF-BA-(AF-HPA-Ala))); and Example 16D, XMT 1519-(EG2-MI-(10 kDa PHF-BA-(AF-HPA-Ala))) as measured in a JIMT-1 mouse tumor xenograft model.

FIG. 10 provides the results for the tumor response in mice inoculated subcutaneously with JIMT-1 cells (n=10 for each group) after IV administration of vehicle; Kadcyla at 20 mg/kg; Example 16A, trastuzumab-(EG2-MI-(10 kDa PHF-BA-(AF-HPA-Ala))), at 0.67 mg/kg; or Example 16D, XMT 1519-(EG2-MI-(10 kDa PHF-BA-(AF-HPA-Ala))), at 0.67 mg/kg as a single dose at day 1. The vehicle and Kadcyla showed an increase of tumor volume. The trastuzumab-(EG2-MI-(10 kDa PHF-BA-(AF-HPA-Ala))) and XMT 1519-(EG2-MI-(10 kDa PHF-BA-(AF-HPA-Ala))) conjugates showed therapeutic potential and had 40% and 70% regressions respectively. XMT 1519-(EG2-MI-(10 kDa PHF-BA-(AF-HPA-Ala))) had 5 partial regressions and 2 complete regressions that remained tumor free survivors at the end of the study at Day 69.

Figure 11:
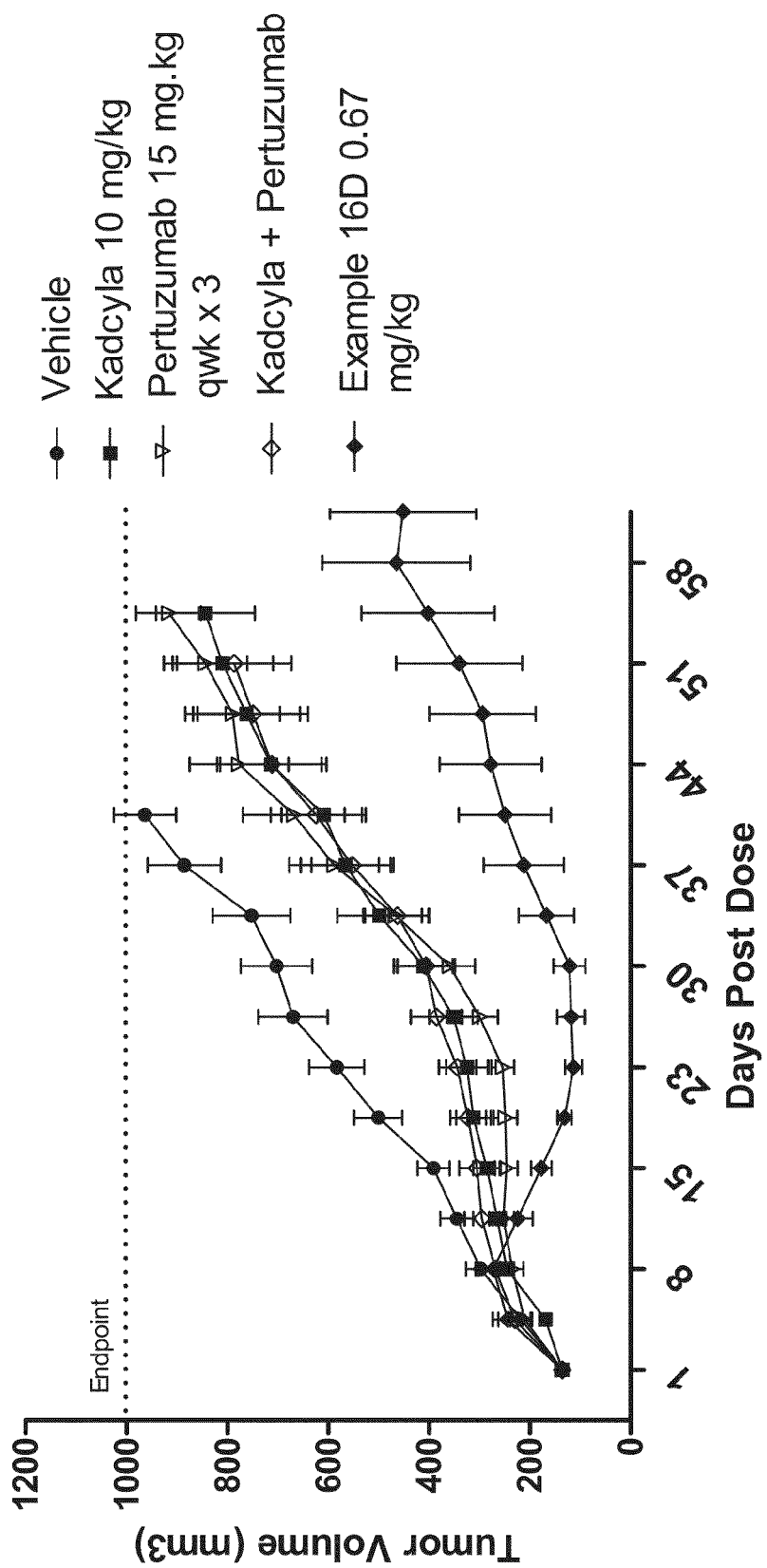
FIG. 11 illustrates the anti-tumor efficacy of Kadcyla; pertuzumab; a combination of Kadcyla and pertuzumab; and Example 16D, XMT 1519-(EG2-MI-(10 kDa PHF-BA-(AF-HPA-Ala))) as measured in a JIMT-1 mouse tumor xenograft model.

FIG. 11 provides the results for the tumor response in mice inoculated subcutaneously with JIMT-1 cells (n=10 for each group) after IV administration of vehicle; Kadcyla at 10 mg/kg as a single dose at day 1; a combination of Kadcyla at 10 mg/kg and pertuzumab at 15 mg/kg dosed weekly for 3 weeks; or Example 16D, XMT 1519-(EG2-MI-(10 kDa PHF-BA-(AF-HPA-Ala))), at 0.67 mg/kg as a single dose at day 1. The vehicle, Kadcyla and the combination of Kadcyla and pertuzumab all showed an increase of tumor volume. The XMT 1519-(EG2-MI-(10 kDa PHF-BA-(AF-HPA-Ala))) conjugate showed 60% partial regressions and was the most efficacious.

Figure 12:
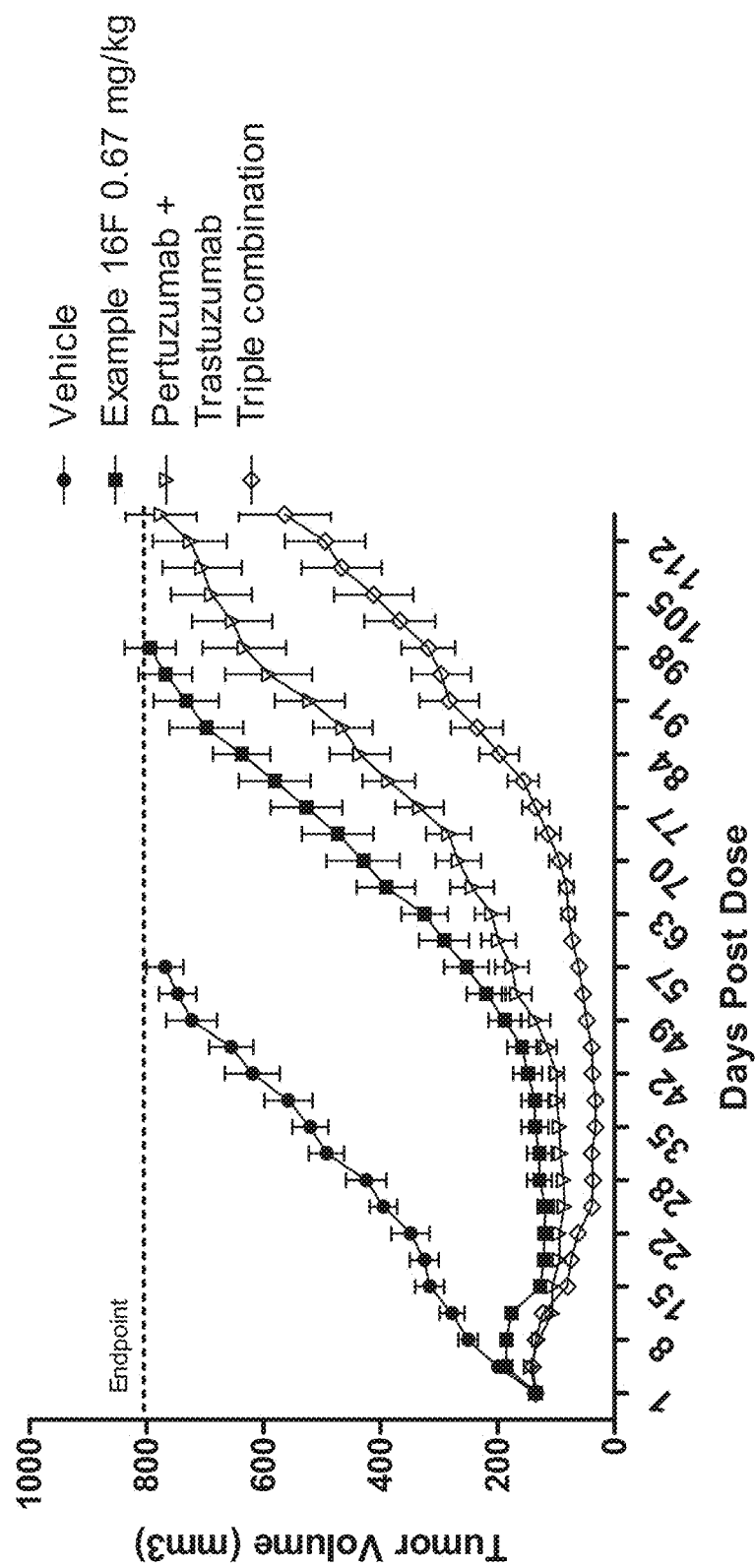
FIG. 12 illustrates the anti-tumor efficacy of Example 16F, XMT 1519-(EG2-MI-(10 kDa PHF-BA-(AF-HPA-Ala))); a combination of trastuzumab and pertuzumab; or a triple combination of trastuzumab; pertuzumab and Example 16F, XMT 1519-(EG2-MI-(10 kDa PHF-BA-(AF-HPA-Ala))) as measured in a NCI-N87 mouse tumor xenograft model.

FIG. 12 provides the results for the tumor response in mice inoculated subcutaneously with NCI-N87 cells (n=10 for each group) after IV administration of vehicle; Example 16F, XMT 1519-(EG2-MI-(10 kDa PHF-BA-(AF-HPA-Ala))), at 0.67 mg/kg as a single dose at day 1; a combination of trastuzumab at 15 mg/kg and pertuzumab at 15 mg/kg dosed weekly for 3 weeks (i.e., at day 1, 8, and 15); or a triple combination of trastuzumab at 15 mg/kg and pertuzumab at 15 mg/kg each dosed weekly for 3 weeks (i.e., at day 1, 8, and 15) together with Example 16F, XMT 1519-(EG2-MI-(10 kDa PHF-BA-(AF-HPA-Ala))) at 0.67 mg/kg as single dose at day 1. The vehicle showed an increase of tumor volume. The XMT 1519-(EG2-MI-(10 kDa PHF-BA-(AF-HPA-Ala))) alone or the combinations all showed a reduction in tumor with the triple combination of trastuzumab; pertuzumab and Example 16F being the most efficacious and resulting in 100% partial regressions, whereas Example 16F alone or the combination of trastuzumab and pertuzumab each resulted in one partial response out of ten. The triplet had a numerically higher rate of partial responses, and led to a significantly greater reduction in tumor volume (p<0.05, Mann-Whitney test) compared to either Example 16F monotherapy or the trastuzumab+pertuzumab doublet. Partial response is defined as regression to less than 50% of baseline tumor volume sustained over at least 3 sequential tumor measurements.

The overall survival benefit for XMT 1519-(EG2-MI-(10 kDa PHF-BA-(AF-HPA-Ala))) in combination with pertuzumab and trastuzumab differed significantly versus the administration of XMT 1519-(EG2-MI-(10 kDa PHF-BA-(AF-HPA-Ala))) alone (P<0.011, logrank test) and was superior to the outcomes achieved by the combination of pertuzumab and trastuzumab (P<0.273, logrank test) or the triple combination of the XMT-1519 antibodies, pertuzumab and trastuzumab (P<0.05, logrank test).

Figure 13:
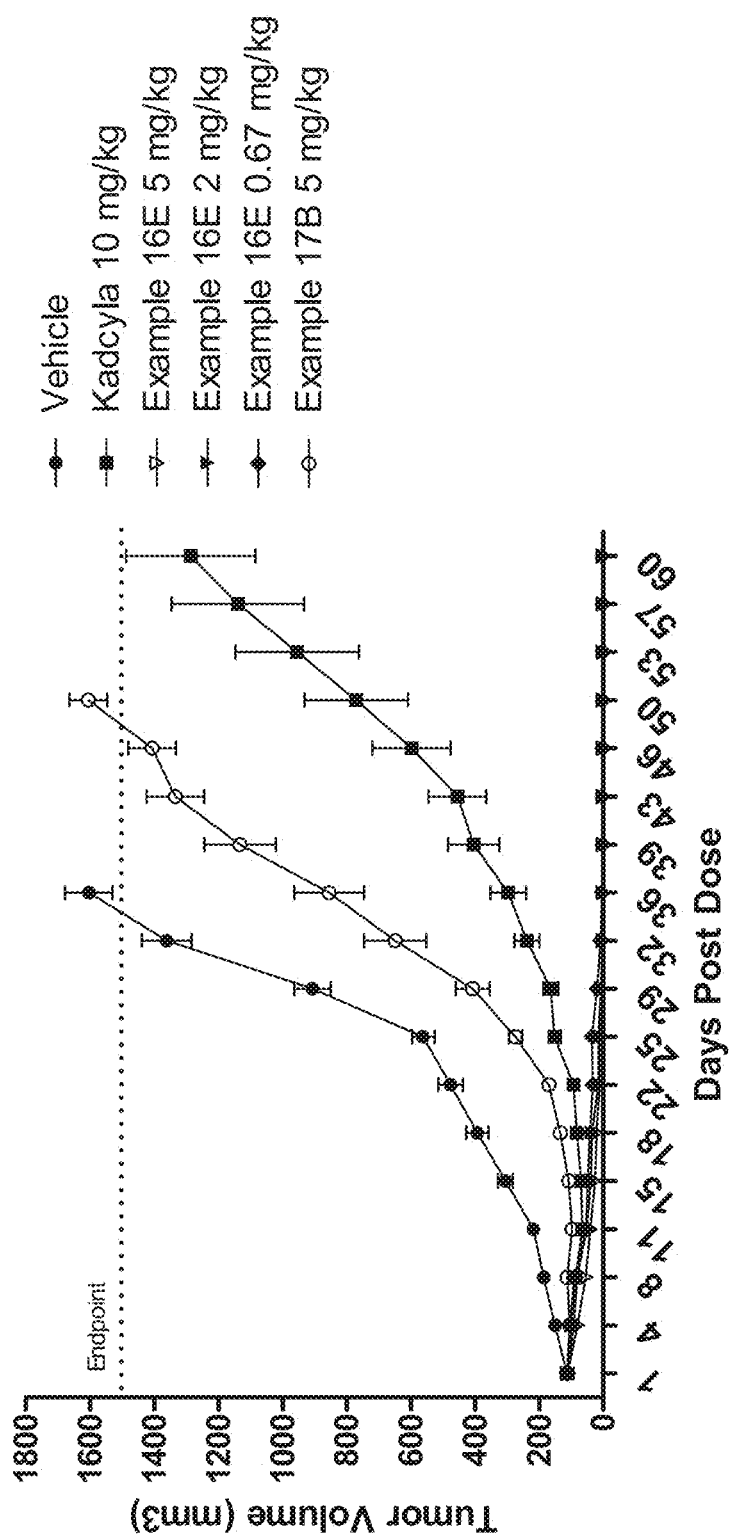
FIG. 13 illustrates the anti-tumor efficacy of Kadcyla, Example 16E, XMT 1519-(EG2-MI-(10 kDa PHF-BA-(AF-HPA-Ala))) and Example 17B, rituximab-(EG2-MI-(10 kDa PHF-BA-(AF-HPA-Ala))) as measured in a SNU5 mouse tumor xenograft model.

FIG. 13 provides the results for the tumor response in mice inoculated subcutaneously with SNU-5 cells (n=10 for each group) after IV administration of vehicle; Kadcyla at 10 mg/kg as a single dose; Example 16E, XMT 1519-(EG2-MI-(10 kDa PHF-BA-(AF-HPA-Ala))) at 5 mg/kg, 2 mg/kg or 0.67 mg/kg as a single dose; or Example 17B, rituximab-(EG2-MI-(10 kDa PHF-BA-(AF-HPA-Ala))) at 5 mg/kg as a single dose at day 1. At day 18 the vehicle showed an increase of tumor volume. The XMT 1519-(EG2-MI-(10 kDa PHF-BA-(AF-HPA-Ala))) conjugate showed tumor reduction and was more efficacious than Kadcyla or rituximab-(EG2-MI-(10 kDa PHF-BA-(AF-HPA-Ala))) and resulted in 100% tumor free survivors at 5 mg/kg and 2 mg/kg doses and 90% tumor free survivors at 0.67 mg/kg dose.

Figure 14:
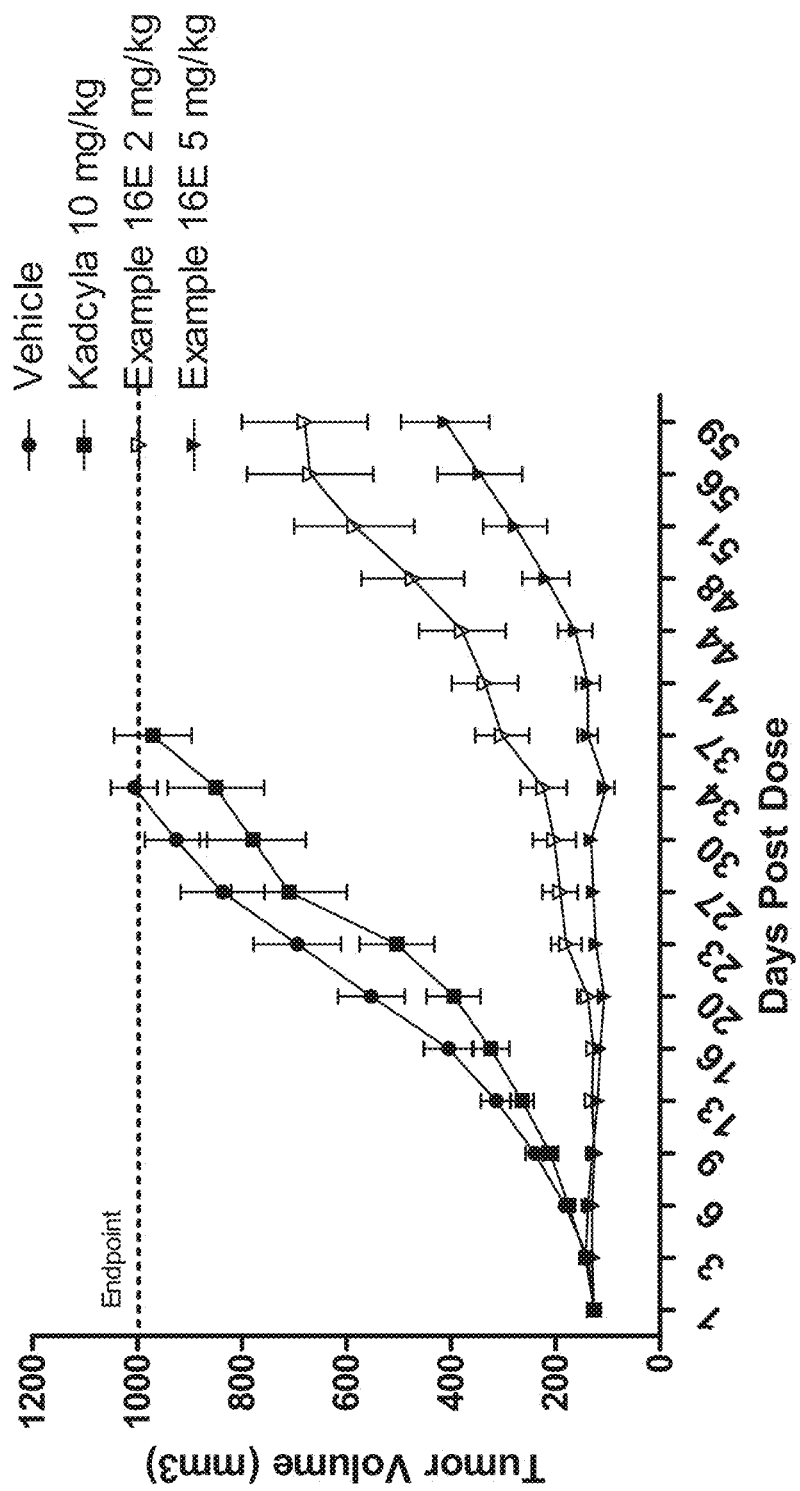
FIG. 14 illustrates the anti-tumor efficacy of Kadcyla and Example 16E, XMT 1519-(EG2-MI-(10 kDa PHF-BA-(AF-HPA-Ala))) as measured in a TOV-21G mouse tumor xenograft model.

FIG. 14 provides the results for the tumor response in mice inoculated subcutaneously with TOV-21G cells (n=10 for each group) after IV administration of vehicle; Kadcyla at 10 mg/kg as a single dose; Example 16E, XMT 1519-(EG2-MI-(10 kDa PHF-BA-(AF-HPA-Ala))) at 5 mg/kg or 2 mg/kg as a single dose at day 1. The XMT 1519-(EG2-MI-(10 kDa PHF-BA-(AF-HPA-Ala))) conjugate showed tumor retardation and was more efficacious than Kadcyla that did not attain the threshold for therapeutic activity.

Figure 15:
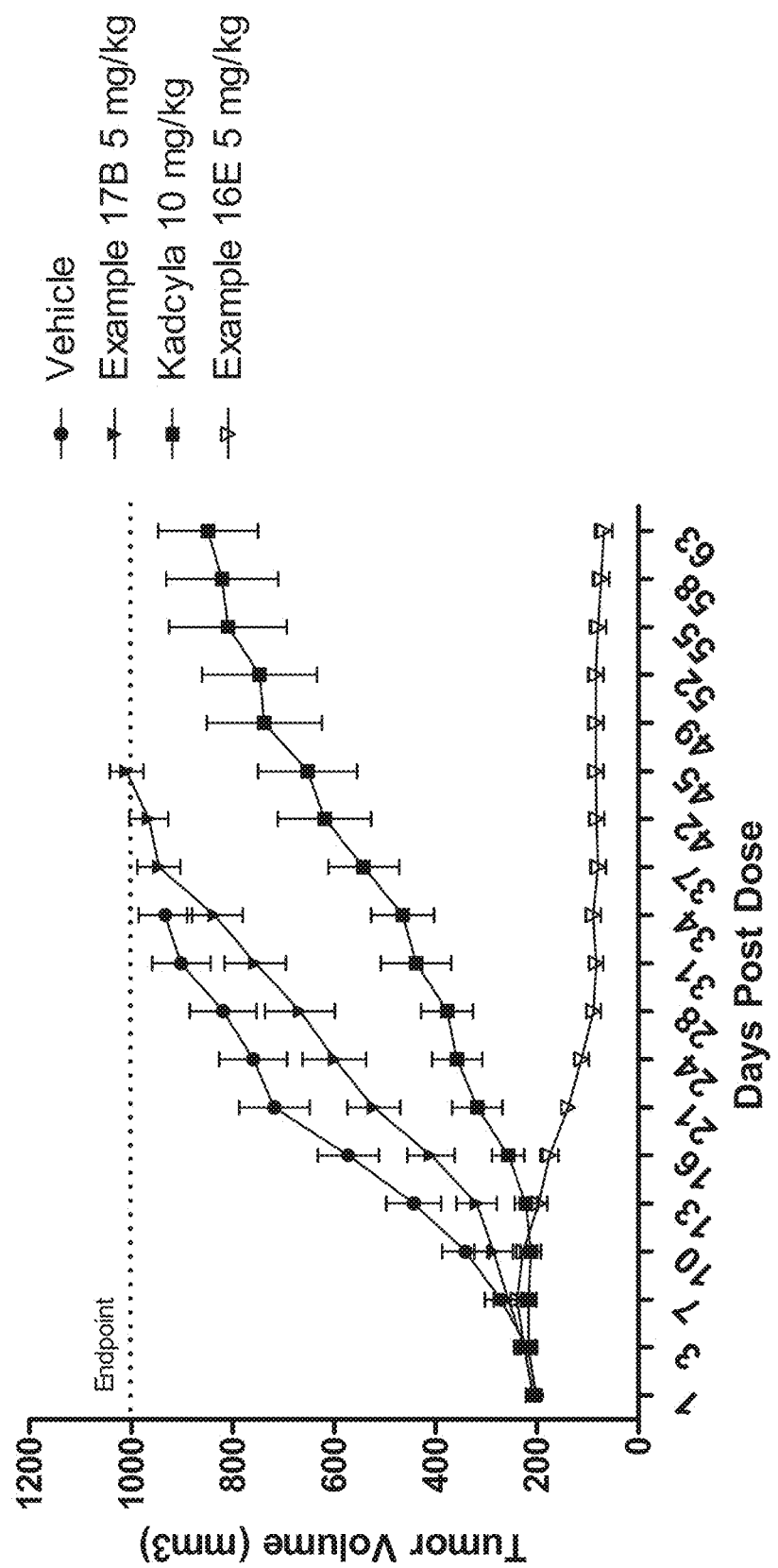
FIG. 15 illustrates the anti-tumor efficacy of Kadcyla, Example 16E, XMT 1519-(EG2-MI-(10 kDa PHF-BA-(AF-HPA-Ala))) and Example 17B, rituximab-(EG2-MI-(10 kDa PHF-BA-(AF-HPA-Ala))) as measured in an H522 mouse tumor xenograft model.

FIG. 15 provides the results for the tumor response in mice inoculated subcutaneously with H522 cells (n=10 for each group) after IV administration of vehicle; Kadcyla at 10 mg/kg as a single dose; Example 16E, XMT 1519-(EG2-MI-(10 kDa PHF-BA-(AF-HPA-Ala))) at 5 mg/kg as a single dose; or Example 17B, rituximab-(EG2-MI-(10 kDa PHF-BA-(AF-HPA-Ala))) at 5 mg/kg as a single dose at day 1. The XMT 1519-(EG2-MI-(10 kDa PHF-BA-(AF-HPA-Ala))) conjugate showed tumor retardation and was more efficacious than Kadcyla and rituximab-(EG2-MI-(10 kDa PHF-BA-(AF-HPA-Ala))) that did not attain the threshold for therapeutic activity.

Figure 16:
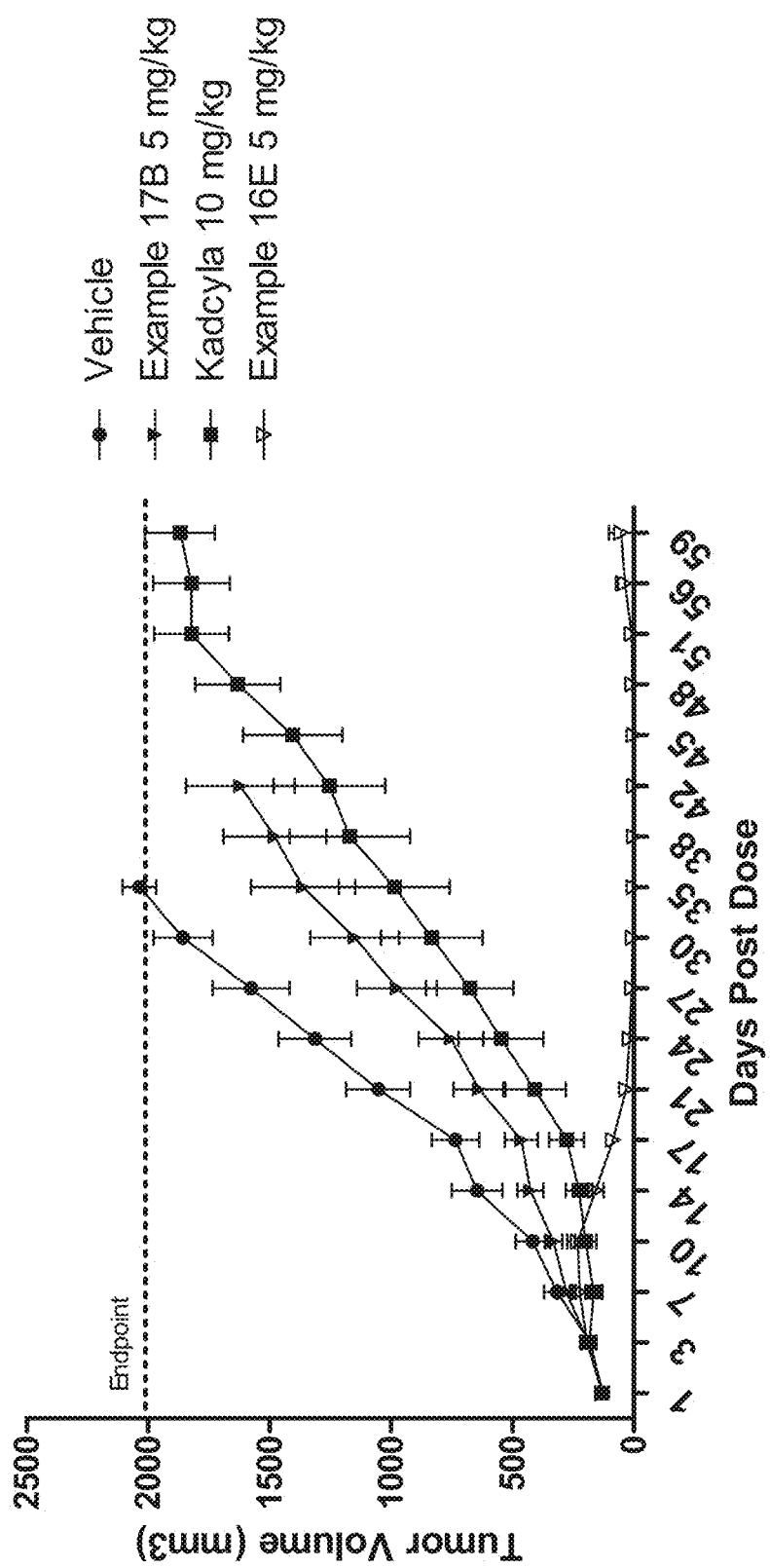
FIG. 16 illustrates the anti-tumor efficacy of Kadcyla, Example 16E, XMT 1519-(EG2-MI-(10 kDa PHF-BA-(AF-HPA-Ala))) and Example 17B, rituximab-(EG2-MI-(10 kDa PHF-BA-(AF-HPA-Ala))) as measured in a SKOV3 mouse tumor xenograft model.

FIG. 16 provides the results for the tumor response in mice inoculated subcutaneously with SKOV3 cells (n=10 for each group) after IV administration of vehicle; Kadcyla at 10 mg/kg as a single dose; Example 16E, XMT 1519-(EG2-MI-(10 kDa PHF-BA-(AF-HPA-Ala))) at 5 mg/kg as a single dose; or Example 17B, rituximab-(EG2-MI-(10 kDa PHF-BA-(AF-HPA-Ala))) at 5 mg/kg as a single dose at day 1. The XMT 1519-(EG2-MI-(10 kDa PHF-BA-(AF-HPA-Ala))) resulted in 100% regressions, consisting of 10 complete responses and was more efficacious than Kadcyla or rituximab-(EG2-MI-(10 kDa PHF-BA-(AF-HPA-Ala) that did not attain the threshold for therapeutic activity.

Figure 17:
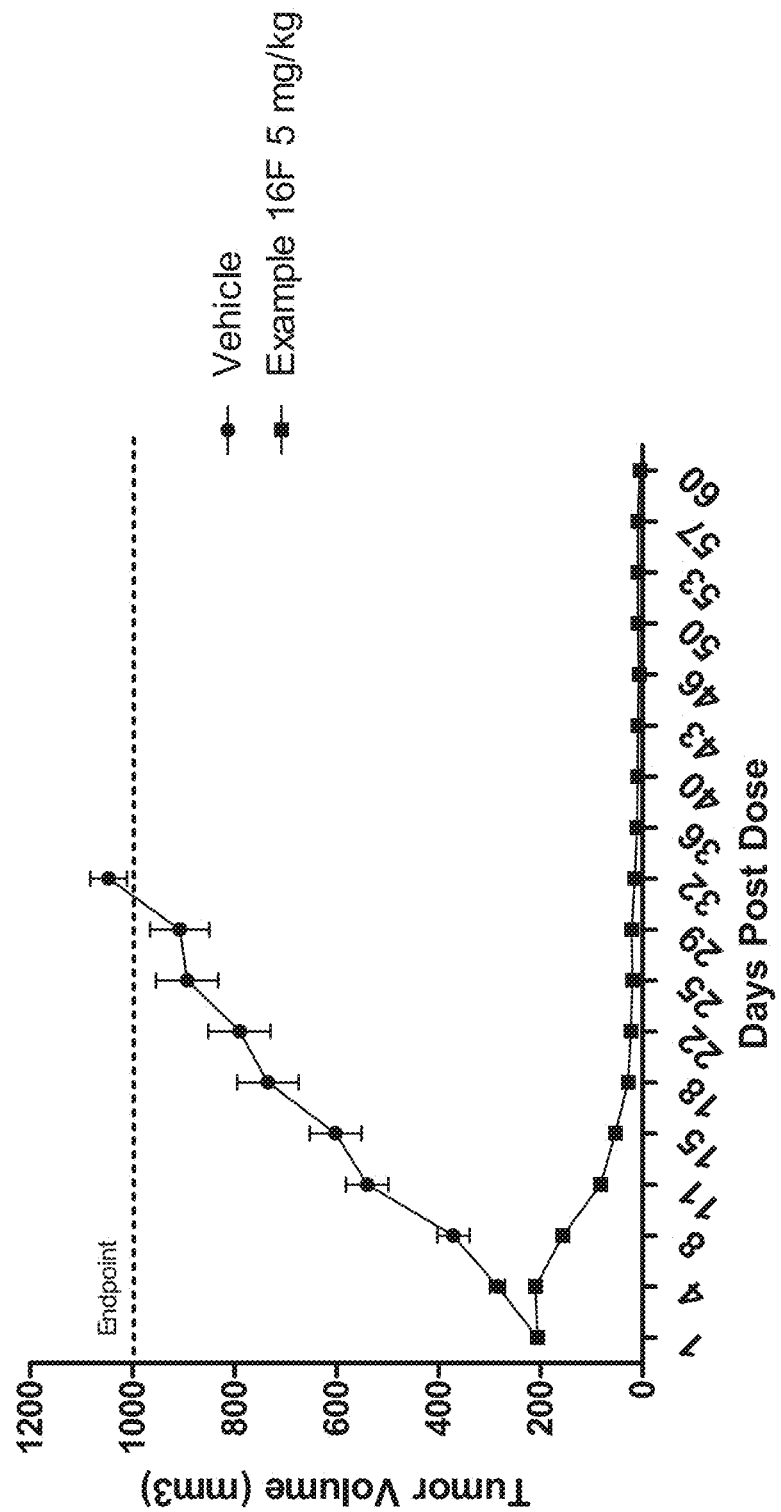
FIG. 17 illustrates the anti-tumor efficacy of Example 16F, XMT 1519-(EG2-MI-(10 kDa PHF-BA-(AF-HPA-Ala))) as measured in a Calu-3 mouse tumor xenograft model.

FIG. 17 provides the results for the tumor response in mice inoculated subcutaneously with Calu-3 cells (n=10 for each group) after IV administration of vehicle; or Example 16F, XMT 1519-(EG2-MI-(10 kDa PHF-BA-(AF-HPA-Ala))) at 5 mg/kg as a single dose at day 1. The XMT 1519-(EG2-MI-(10 kDa PHF-BA-(AF-HPA-Ala))) resulted in 100% regression responses consisting of two partial responses and eight complete responses, six of which remained tumor free on Day 60.

Figure 18:
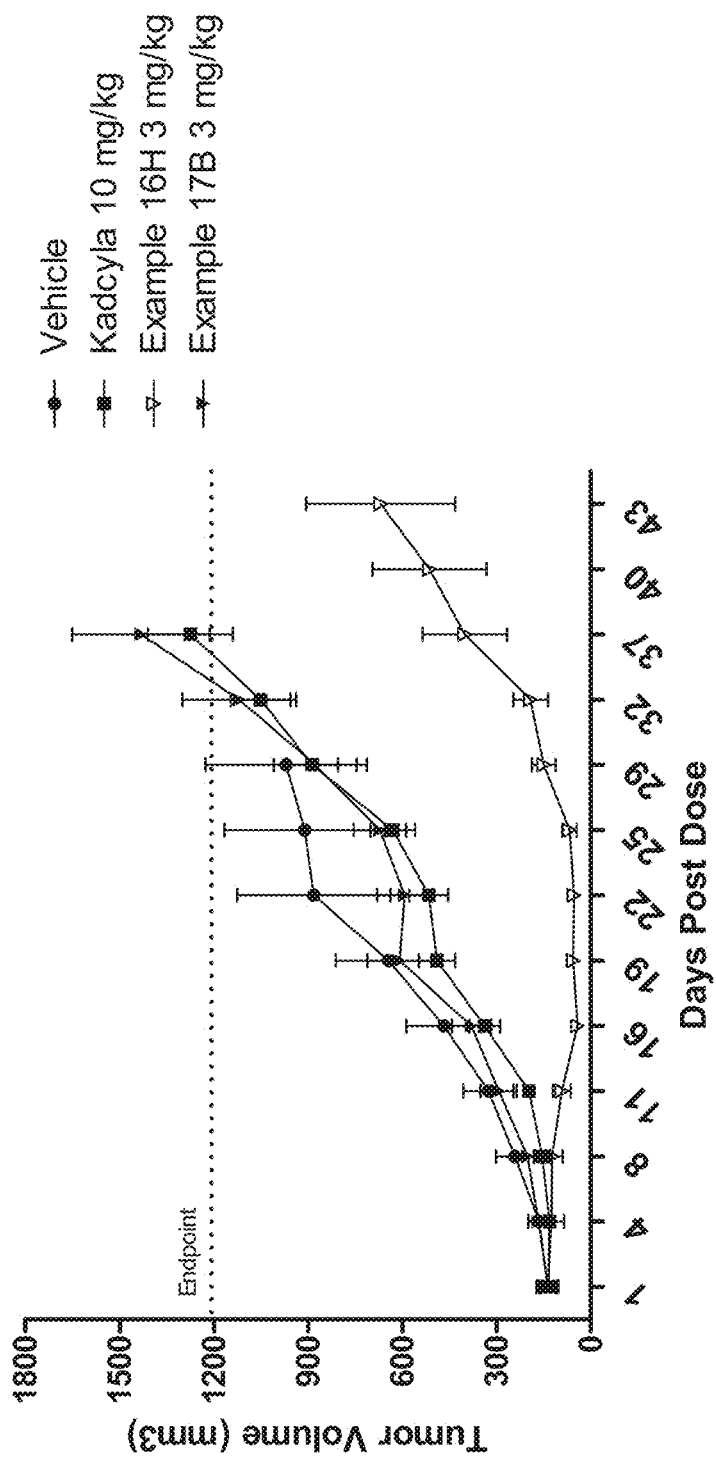
FIG. 18 illustrates the anti-tumor efficacy of Kadcyla, Example 16H, XMT 1519-(EG2-MI-(10 kDa PHF-BA-(AF-HPA-Ala))) and Example 17B, rituximab-(EG2-MI-(10 kDa PHF-BA-(AF-HPA-Ala))) as measured in a BRE-0333 HER2 1+ patient derived xenograft model.

FIG. 18 provides the results for the tumor response in patient derived xenograft model BRE-0333 HER2 1+ (n=8 for each group) after IV administration of vehicle; Kadcyla at 10 mg/kg as a single dose; Example 16H, XMT 1519-(EG2-MI-(10 kDa PHF-BA-(AF-HPA-Ala))) at 3 mg/kg as a single dose or Example 17B, rituximab-(EG2-MI-(10 kDa PHF-BA-(AF-HPA-Ala))) at 3 mg/kg at day 1. The XMT 1519-(EG2-MI-(10 kDa PHF-BA-(AF-HPA-Ala))) conjugate showed tumor retardation and was more efficacious than Kadcyla or rituximab-(EG2-MI-(10 kDa PHF-BA-(AF-HPA-Ala))).

Figure 19:
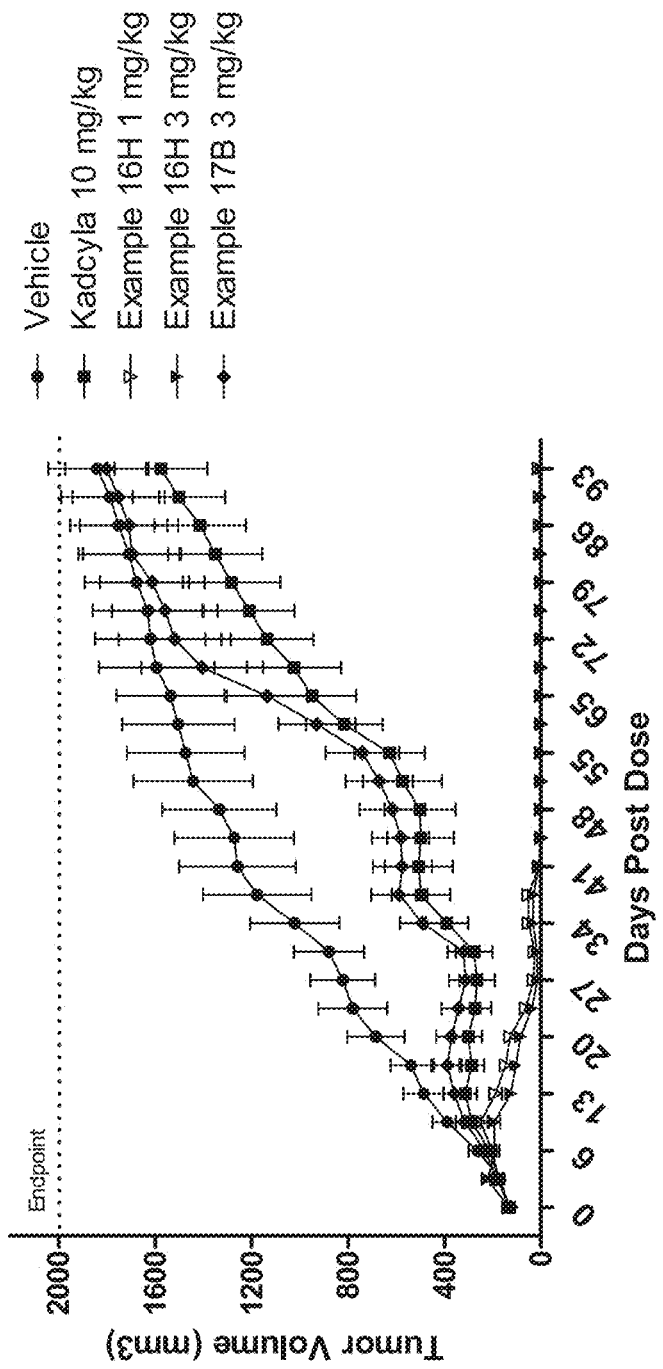
FIG. 19 illustrates the anti-tumor efficacy of Kadcyla, Example 16H, XMT 1519-(EG2-MI-(10 kDa PHF-BA-(AF-HPA-Ala))) and Example 17B, rituximab-(EG2-MI-(10 kDa PHF-BA-(AF-HPA-Ala))) as measured in a MAXF1162 HER2 3+ patient derived xenograft model.

FIG. 19 provides the results for the tumor response in patient derived xenograft model MAXF_1162 HER2 3+ (n=10 for each group) after IV administration of vehicle; Kadcyla at 10 mg/kg as a single dose; Example 16H, XMT 1519-(EG2-MI-(10 kDa PHF-BA-(AF-HPA-Ala))) at 1 or 3 mg/kg or Example 17B, rituximab-(EG2-MI-(10 kDa PHF-BA-(AF-HPA-Ala))) at 3 mg/kg as a single dose at day 1. The XMT 1519-(EG2-MI-(10 kDa PHF-BA-(AF-HPA-Ala))) both at 1 and 3 mg/kg resulted in 100% regression responses and tumor free survivors and was more efficacious than Kadcyla or rituximab-(EG2-MI-(10 kDa PHF-BA-(AF-HPA-Ala))) at 3 mg/kg.

FIG. 20 provides the results for the tumor response in mice inoculated subcutaneously with BT474 tumor fragments (n=10 for each group) after IV administration of vehicle; Kadcyla at 5 mg/kg as a single dose; Example 16H, XMT 1519-(EG2-MI-(10 kDa PHF-BA-(AF-HPA-Ala))) at 5 mg/kg or 2 mg/kg as a single dose at day 1; Example 17C, rituximab-(EG2-MI-(10 kDa PHF-BA-(AF-HPA-Ala))) at 5 mg/kg as a single dose at day 1 or XMT 1519 at 5 mg/kg as a single dose. The XMT 1519-(EG2-MI-(10 kDa PHF-BA-(AF-HPA-Ala))) conjugate showed complete tumor regressions and was more efficacious than Kadcyla, rituximab-(EG2-MI-(10 kDa PHF-BA-(AF-HPA-Ala))) or XMT-1519.

Single doses of 1 mg/kg or 0.67 mg/kg of XMT 1519-(EG2-MI-(PHF-BA-(AF-HPA-Ala))) conjugate showed complete regression in low HER2-expressing breast and gastric cancer models, where ado-trastuzumab emtansine (Kadcyla) was inactive at doses of 10 mg/kg and above. In HER2-driven tumor models, XMT 1519-(EG2-MI-(PHF-BA-(AF-HPA-Ala))) conjugate showed synergistic efficacy in combination with widely used anti-HER2 therapies trastuzumab and pertuzumab. XMT 1519-(EG2-MI-(PHF-BA-(AF-HPA-Ala))) conjugate demonstrated an excellent pharmacokinetic profile and was well tolerated in non-human primates at therapeutic doses.

The preclinical data suggest that XMT 1519-(EG2-MI-(PHF-BA-(AF-HPA-Ala))) conjugate has the potential to greatly expand the number of patients who may benefit from HER2-targeted therapies. The conjugate provides efficient drug delivery in cancers where there are as few as 10,000 HER2 receptors, where other therapies are inactive.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated antibody or antigen binding fragment thereof that specifically binds to an epitope of the human HER2 receptor, wherein the antibody or antigen binding fragment thereof comprises a variable heavy chain complementarity determining region 1 (CDRH1) comprising the amino acid sequence FTFSSYSMN (SEQ ID NO: 25); a variable heavy chain complementarity determining region 2 (CDRH2) comprising the amino acid sequence YISSSSSTI-YYADSVKG (SEQ ID NO: 26); a variable heavy chain complementarity determining region 3 (CDRH3) comprising the amino acid sequence GGHGYFDL (SEQ ID NO: 27); a variable light chain complementarity determining region 1 (CDRL1) comprising the amino acid sequence RASQSVSSSYLA (SEQ ID NO: 28); a variable light chain complementarity determining region 2 (CDRL2) comprising the amino acid sequence GASSRAT (SEQ ID NO: 21); and a variable light chain complementarity determining region 3 (CDRL3) comprising the amino acid sequence QQYHH-SPLT (SEQ ID NO: 29).

2. The isolated antibody or antigen binding fragment thereof of claim 1, wherein the antibody or antigen binding fragment thereof comprises a variable heavy chain comprising the amino acid sequence of SEQ ID NO: 13 and a variable light chain comprising the amino acid sequence of SEQ ID NO: 14.

3. The isolated antibody or antigen binding fragment thereof of claim 1, wherein the antibody or antigen binding fragment thereof comprises a heavy chain comprising the amino acid sequence of SEQ ID NO: 5 and a light chain comprising the amino acid sequence of SEQ ID NO: 6.

4. The isolated antibody or antigen binding fragment thereof of claim 1, wherein the antibody or antigen binding fragment thereof is a monoclonal antibody, a domain antibody, a single chain antibody, a Fab fragment, a F(ab')2 fragment, a single chain variable fragment (scFv), a scFv-Fc fragment, a single chain antibody (scAb), a domain antibody (dAb), a single domain heavy chain antibody, or a single domain light chain antibody.

5. The isolated antibody or antigen binding fragment thereof of claim 1, wherein the antibody or antigen binding fragment thereof is a rabbit, mouse, chimeric, humanized or fully human monoclonal antibody.

6. The isolated antibody or antigen binding fragment thereof of claim 1, wherein the antibody or antigen binding fragment thereof is an IgG isotype.

7. The isolated antibody or antigen binding fragment thereof of claim 1, wherein the antibody or antigen binding fragment thereof is an IgG1 isotype.

8. A conjugate comprising the isolated antibody or antigen binding fragment thereof of claim 1 and one or more therapeutic or diagnostic agents (D), wherein each D is independently connected directly or indirectly to the antibody or antigen binding fragment thereof.

9. The conjugate of claim 8, wherein the antibody or antigen binding fragment thereof comprises a variable heavy chain comprising the amino acid sequence of SEQ ID NO: 13 and a variable light chain comprising the amino acid sequence of SEQ ID NO: 14.

10. The conjugate of claim 8, wherein the antibody or antigen binding fragment thereof comprises a heavy chain comprising the amino acid sequence of SEQ ID NO: 5 and a light chain comprising the amino acid sequence of SEQ ID NO: 6.

11. The conjugate of claim 8, wherein the antibody or antigen binding fragment thereof is a monoclonal antibody, a domain antibody, a single chain antibody, a Fab fragment, a F(ab')2 fragment, a scFv, a scFv-Fc, a scAb, a dAb, a single domain heavy chain antibody, or a single domain light chain antibody.

12. The conjugate of claim 8, wherein the antibody or antigen binding fragment thereof is a rabbit, mouse, chimeric, humanized or fully human monoclonal antibody.

13. The conjugate of claim 8, wherein the antibody or antigen binding fragment thereof is an IgG isotype.

14. The conjugate of claim 8, wherein the antibody or antigen binding fragment thereof is an IgG1 isotype.

15. The conjugate of claim 8, further comprising one or more polymeric scaffolds connected both to the antibody or antigen binding fragment thereof and to one or more D, wherein each of the one or more D is independently connected to the antibody or antigen binding fragment thereof via the one or more polymeric scaffolds.

16. The conjugate of claim 15, wherein each of the one or more polymeric scaffolds independently comprises poly(1-hydroxymethylethylene hydroxymethyl-formal) (PHF) having a molecular weight ranging from about 2 kDa to about 40 kDa.

17. The conjugate of claim 16, wherein each of the one or more polymeric scaffolds independently is of Formula (Ic):

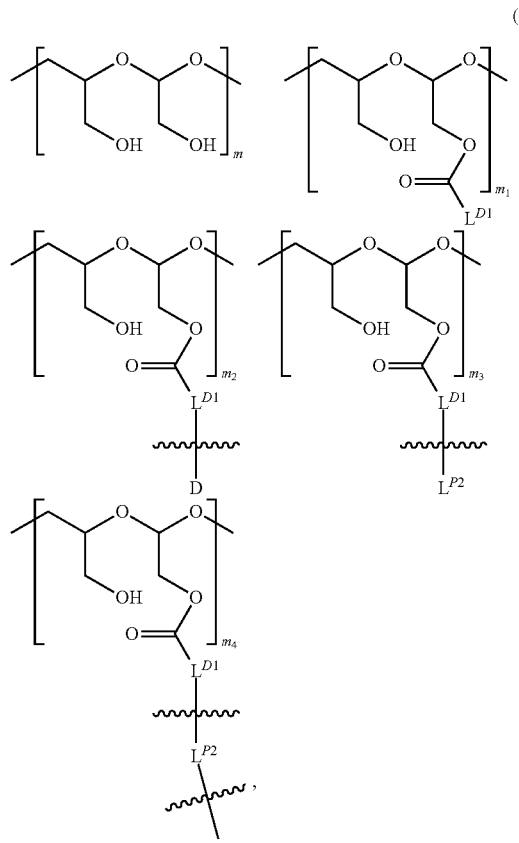

(Ic)

wherein:
$L^{D1}$ is a carbonyl-containing moiety;
each occurrence of

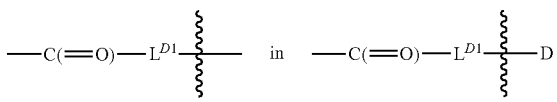

is independently a first linker that contains a biodegradable bond so that when the bond is broken, D is released in an active form for its intended therapeutic effect; and the

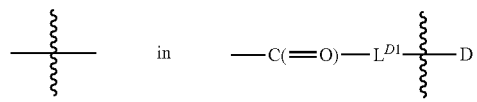

between $L^{D1}$ and D denotes direct or indirect attachment of D to $L^{D1}$;
each occurrence of

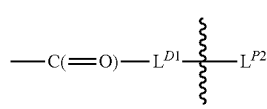

is independently a second linker not yet connected to the isolated antibody or antigen binding fragment thereof, in which $L^{P2}$ is a moiety containing a functional group that is yet to form a covalent bond with a functional group of the isolated antibody or antigen binding fragment thereof, and the

between $L^{D1}$ and $L^{P2}$ denotes direct or indirect attachment of $L^{P2}$ to $L^{D1}$, and each occurrence of the second linker is distinct from each occurrence of the first linker;
each occurrence of

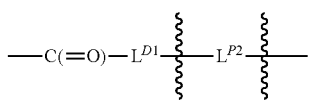

is independently a third linker that connects each D-carrying polymeric scaffold to the isolated antibody or antigen binding fragment thereof, in which the terminal

attached to $L^{P2}$ denotes direct or indirect attachment of $L^{P2}$ to the isolated antibody or antigen binding fragment thereof upon formation of a covalent bond between a functional group of $L^{P2}$ and a functional group of the isolated antibody or antigen binding fragment thereof; and each occurrence of the third linker is distinct from each occurrence of the first linker;
m is an integer from 1 to about 300,
$m_1$ is an integer from 1 to about 140,
$m_2$ is an integer from 1 to about 40,
$m_3$ is an integer from 0 to about 18,
$m_4$ is an integer from 1 to about 10;
the sum of m, $m_1$, $m_2$, $m_3$, and $m_4$ ranges from 15 to 300; and
the total number of $L^{P2}$ connected to the isolated antibody or antigen binding fragment thereof is 10 or less.

18. The conjugate of claim 17, wherein the sum of m, $m_1$, $m_2$, $m_3$ and $m_4$ ranges from 15 to 150, $m_1$ is an integer from 1 to 70, $m_2$ is an integer from 1 to 20, $m_3$ is an integer from 0 to 10, and PHF has a molecular weight ranging from about 2 kDa to about 20 kDa.

19. The conjugate of claim 17, wherein the sum of m, $m_1$, $m_2$, $m_3$ and $m_4$ ranges from 20 to 110, $m_1$ is an integer from 2 to 50, $m_2$ is an integer from 2 to 15, $m_3$ is an integer from 0 to 8; and PHF has a molecular weight ranging from about 3 kDa to about 15 kDa.

20. The conjugate of claim 17, wherein the sum of m, $m_1$, $m_2$, $m_3$ and $m_4$ ranges from 40 to 75, $m_1$ is an integer from 2 to 35, $m_2$ is an integer from 2 to 10, $m_3$ is an integer from 0 to 5; and PHF has a molecular weight ranging from about 5 kDa to about 10 kDa.

21. The conjugate of claim 17, wherein the functional group of $L^2$ is selected from $SR^p$, —S—S-LG,

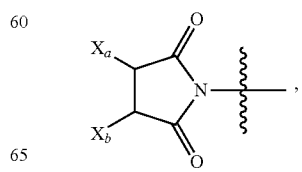

and halo, in which LG is a leaving group, $R^p$ is H or a sulfur protecting group, and one of $X_a$ and $X_b$ is H and the other is a water-soluble maleimido blocking moiety, or $X_a$ and $X_b$, together with the carbon atoms to which they are attached for a carbon-carbon double bond.

22. The conjugate of claim 17, wherein $L^{D1}$ comprises X—$(CH_2)_v$—C(=O)— with X directly connected to the carbonyl group of

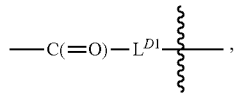

in which X is $CH_2$, O, or NH, and v is an integer from 1 to 6.

23. The conjugate of claim 17, wherein each occurrence of

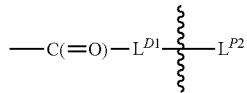

is independently —C(=O)—X—$(CH_2)_v$—C(=O)—NH—$(CH_2)_u$—NHC(=O)—$(CH_2)_w$—$(OCH_2)_x$—NHC(=O)—$(CH_2)_y$-M, in which X is $CH_2$, O, or NH, each of v, u, w, x and y independently is an integer from 1 to 6, and M is

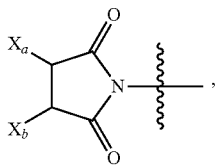

wherein one of $X_a$ and $X_b$ is H and the other is a water-soluble maleimido blocking moiety, or $X_a$ and $X_b$, together with the carbon atoms to which they are attached for a carbon-carbon double bond.

24. The conjugate of claim 23, wherein each of v, u, w, x and y is 2.

25. The conjugate of claim 8, wherein each of the one or more D is a therapeutic agent having a molecular weight of ≤5 kDa, or at least one of the one or more D is a diagnostic agent.

26. The conjugate of claim 24, wherein each of the one or more polymeric scaffolds independently is of Formula (Id):

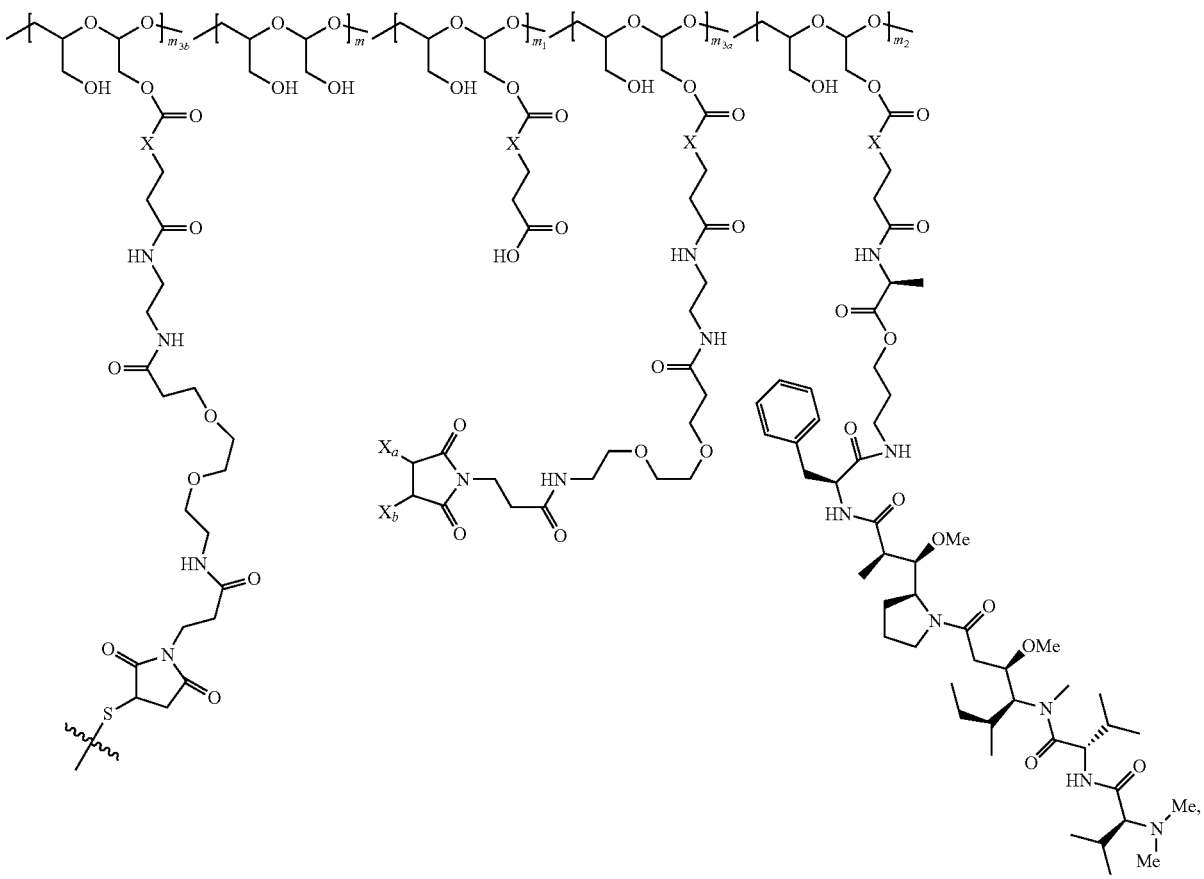

(Id)

wherein:
$m_{3a}$ is an integer from 0 to about 17,
$m_{3b}$ is an integer from 1 to about 8, and
the terminal
denotes the direct attachment of the one or more polymeric scaffolds to the isolated antibody or antigen binding fragment thereof.
27. The conjugate of claim 16, wherein each of the one or more polymeric scaffolds independently is of Formula (If):

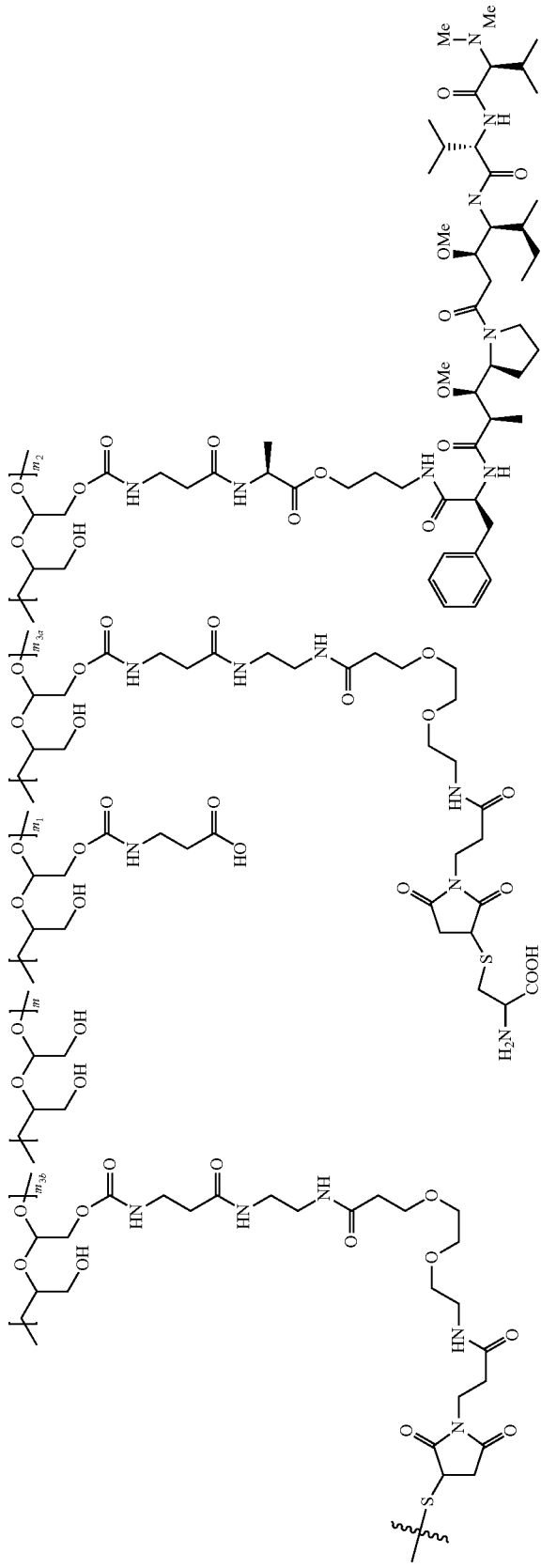
(If)

wherein:

m is an integer from 1 to about 300, $m_1$ is an integer from 1 to about 140, $m_2$ is an integer from 1 to about 40, $m_{3a}$ is an integer from 0 to about 17, $m_{3b}$ is an integer from 1 to about 8;

the sum of $m_{3a}$ and $m_{3b}$ ranges from 1 and about 18; and the sum of m, $m_1$, $m_2$, $m_{3a}$, and $m_{3b}$ ranges from 15 to about 300;

to about 50, $m_2$ is an integer from 2 to about 15, $m_{3a}$ is an integer from 0 to about 7, $m_{3b}$ is an integer from 1 to about 8, the sum of $m_{3a}$ and $m_{3b}$ ranges from 1 and about 8, and the ratio between the PHF and the isolated anti-HER2 antibody or antigen-binding fragment thereof is an integer from 2 to about 8.

30. A method of preparing a conjugate according to claim 8, comprising reacting the isolated antibody or antigen binding fragment thereof that specifically binds to an epitope of the human HER2 receptor with a polymeric scaffold of Formula (Ia) such that the conjugate is formed:

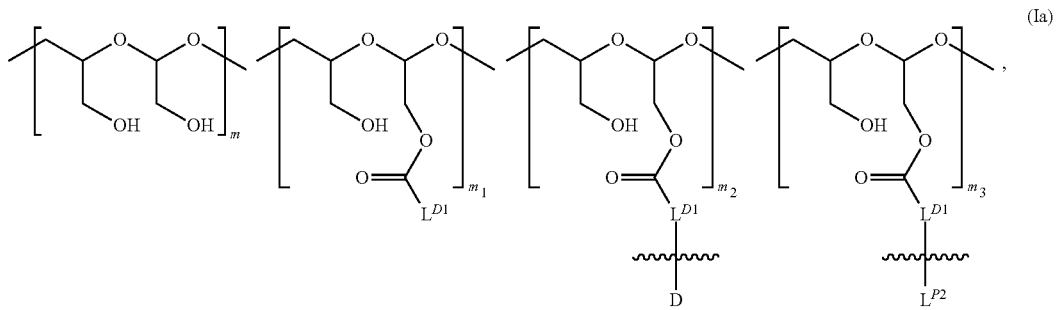

(Ia)

the terminal

denotes the attachment of one or more polymeric scaffolds to the isolated antibody or antigen binding fragment thereof that specifically binds to an epitope of the human HER2 receptor, wherein the isolated antibody or antigen binding fragment thereof is an isolated anti-HER2 antibody that comprises a variable heavy chain complementarity determining region 1 (CDRH1) comprising the amino acid sequence FTFSSYSMN (SEQ ID NO: 25); a variable heavy chain complementarity determining region 2 (CDRH2) comprising the amino acid sequence YISSSSSTIYYADS-VKG (SEQ ID NO: 26); a variable heavy chain complementarity determining region 3 (CDRH3) comprising the amino acid sequence GGHGYFDL (SEQ ID NO: 27); a variable light chain complementarity determining region 1 (CDRL1) comprising the amino acid sequence RASQSVSS-SYLA (SEQ ID NO: 28); a variable light chain complementarity determining region 2 (CDRL2) comprising the amino acid sequence GASSRAT (SEQ ID NO: 21); and a variable light chain complementarity determining region 3 (CDRL3) comprising the amino acid sequence QQYHHSPLT (SEQ ID NO: 29); and the ratio between the PHF and the antibody is 10 or less.

28. The conjugate of claim 27, wherein the PHF in Formula (If) has a molecular weight ranging from about 2 kDa to about 20 kDa, the sum of m, $m_1$, $m_2$, $m_{3a}$ and $m_{3b}$ ranges from about 15 to about 150, $m_1$ is an integer from 1 to about 70, $m_2$ is an integer from 1 to about 20, $m_{3a}$ is an integer from 0 to about 9, $m_{3b}$ is an integer from 1 to about 8, the sum of $m_{3a}$ and $m_{3b}$ ranges from 1 and about 10, and the ratio between the PHF and the isolated anti-HER2 antibody is an integer from 2 to about 8.

29. The conjugate of claim 27, wherein the PHF in Formula (If) has a molecular weight ranging from about 3 kDa to about 15 kDa, the sum of m, $m_1$, $m_2$, $m_{3a}$ and $m_{3b}$ ranges from about 20 to about 110, $m_1$ is an integer from 2 wherein:

$L^{D1}$ is a carbonyl-containing moiety;

each occurrence of

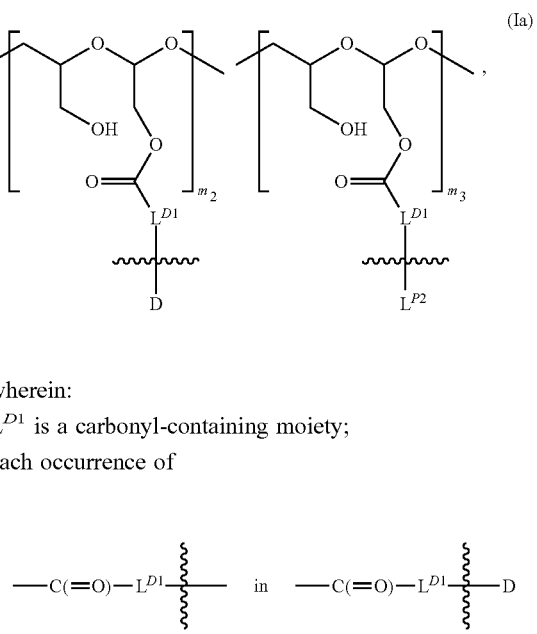

is independently a first linker that contains a biodegradable bond so that when the bond is broken, D is released in an active form for its intended therapeutic effect; and the

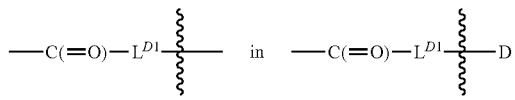

between $L^{D1}$ and D denotes direct or indirect attachment of D to $L^{D1}$;

each occurrence of

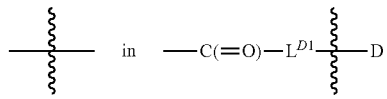

is independently a second linker not yet connected to the isolated antibody or antigen binding fragment thereof, in which $L^{P2}$ is a moiety containing a functional group that is yet to form a covalent bond with a functional group of the isolated antibody or antigen binding fragment thereof, and the

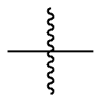
between $L^{D1}$ and $L^{P2}$ denotes direct or indirect attachment of $L^{P2}$ to $L^{D1}$, and each occurrence of the second linker is distinct from each occurrence of the first linker;
m is an integer from 1 to about 300,
$m_1$ is an integer from 1 to about 140,
$m_2$ is an integer from 1 to about 40,
$m_3$ is an integer from 1 to about 18, and
the sum of m, $m_1$, $m_2$ and $m_3$ ranges from 15 to about 300.
* * * * *